US011376285B2

(12) United States Patent
Robinson et al.

(10) Patent No.: US 11,376,285 B2
(45) Date of Patent: Jul. 5, 2022

(54) BACTERIAL BIOMARKER

(71) Applicant: Microbiotica Limited, Cambridge (GB)

(72) Inventors: Matthew Robinson, Cambridge (GB);
Trevor Lawley, Cambridge (GB);
Michael Romanos, Cambridge (GB);
Kevin Vervier, Cambridge (GB);
Simon Harris, Cambridge (GB)

(73) Assignee: Microbiotica Limited, Cambridge (GB)

( * ) Notice: Subject to any disclaimer, the term of this patent is extended or adjusted under 35 U.S.C. 154(b) by 0 days.

(21) Appl. No.: 17/324,899

(22) Filed: May 19, 2021

(65) Prior Publication Data

US 2021/0341458 A1 Nov. 4, 2021

(30) Foreign Application Priority Data

May 19, 2020 (GB) ..................................... 2007452

(51) Int. Cl.
| | |
|---|---|
| *A61K 35/74* | (2015.01) |
| *A61K 45/06* | (2006.01) |
| *C07K 16/28* | (2006.01) |
| *C12N 15/113* | (2010.01) |
| *G01N 33/483* | (2006.01) |

(52) U.S. Cl.
CPC .............. *A61K 35/74* (2013.01); *A61K 45/06* (2013.01); *C07K 16/2818* (2013.01); *C07K 16/2827* (2013.01); *C12N 15/113* (2013.01); *G01N 33/4833* (2013.01); *C07K 2317/73* (2013.01); *G01N 2333/195* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 9,850,225 B2 | 12/2017 | Chupak et al. | |
| 10,064,900 B2* | 9/2018 | Von Maltzahn | A61P 1/12 |
| 10,064,901 B2* | 9/2018 | McKenzie | A61K 9/0053 |
| 10,076,546 B2* | 9/2018 | Henn | A61P 1/12 |
| 10,695,412 B2* | 6/2020 | Honda | A61K 39/39 |
| 10,864,235 B2* | 12/2020 | Henn | A23P 10/30 |
| 10,869,923 B2* | 12/2020 | Lu | A61K 9/0053 |
| 11,026,982 B2 | 6/2021 | Kovarik | |
| 11,141,481 B2 | 10/2021 | Clube | |
| 11,213,552 B2 | 1/2022 | Kovarik | |
| 2017/0354697 A1* | 12/2017 | Schneider | C12N 1/20 |
| 2018/0169157 A1 | 6/2018 | Schneider et al. | |
| 2018/0264056 A1 | 9/2018 | Schneider et al. | |
| 2019/0030098 A1 | 1/2019 | Schneider et al. | |
| 2019/0194740 A1* | 6/2019 | Zhao | G16B 25/20 |
| 2019/0209626 A1 | 7/2019 | Li et al. | |
| 2019/0275090 A1 | 9/2019 | Schneider et al. | |
| 2019/0282632 A1 | 9/2019 | Zitvogel et al. | |
| 2019/0290753 A1 | 9/2019 | Honda et al. | |
| 2020/0027524 A1* | 1/2020 | van der Lelie | G16B 5/00 |
| 2020/0093871 A1 | 3/2020 | Honda et al. | |
| 2020/0129566 A1* | 4/2020 | Carbonnel | A61K 9/0056 |
| 2020/0206284 A1* | 7/2020 | Schneider | A61K 35/742 |
| 2020/0239573 A1* | 7/2020 | Hayes | C12N 15/85 |
| 2020/0353018 A1 | 11/2020 | Ford et al. | |
| 2021/0000885 A1 | 1/2021 | Kovarik | |
| 2021/0069262 A1* | 3/2021 | Allen-Vercoe | A61K 47/38 |
| 2021/0196766 A1* | 7/2021 | Martinez | A61K 47/26 |
| 2021/0341458 A1* | 11/2021 | Robinson | C07K 16/2827 |
| 2021/0361721 A1* | 11/2021 | Wortman | A61K 39/3955 |

FOREIGN PATENT DOCUMENTS

| | | |
|---|---|---|
| EP | 3378949 A1 | 9/2018 |
| EP | 3629023 A1 | 4/2020 |
| WO | 2002007741 A1 | 1/2002 |
| WO | 2013171515 A1 | 11/2013 |
| WO | 2016196605 A1 | 12/2016 |
| WO | 2016203221 A1 | 12/2016 |
| WO | 2017182796 A1 | 10/2017 |
| WO | 2018064165 A2 | 4/2018 |
| WO | 2018081550 A1 | 5/2018 |
| WO | 2018112371 A1 | 6/2018 |
| WO | 2018115519 A1 | 6/2018 |
| WO | 2018171555 A1 | 9/2018 |
| WO | 2018172483 A1 | 9/2018 |
| WO | 2019032572 A1 | 2/2019 |
| WO | 2019051380 A1 | 3/2019 |
| WO | 2019089643 A1 | 5/2019 |
| WO | 2019118515 A2 | 6/2019 |
| WO | 2019136236 A1 | 7/2019 |

(Continued)

OTHER PUBLICATIONS

"International Search Report and Written Opinion corresponding to International Application No. PCT/GB2021/051206 dated Sep. 15, 2021".
"U.S. Appl. No. 17/324,898; office action dated Aug. 4, 2021".
Abhyankar, Dhiraj, et al., "Gut Microbiota and Response to Immunotherapeutic Drugs in Oncology: More Questions Than Answers", Clinical Medicine Insights 14:abstract only (Jul. 28, 2020).
Adachi, Keishi, et al., "Microbial biomarkers for immune checkpoint blockade therapy against cancer", J Gastroenterol, 53:999-1005 (Jul. 12, 2018).
Aghajani, Marra Jai, et al., "Pembrolizumab for anaplastic thyroid cancer: a case study", Cancer Immunology, Immunotherapy, 68:1921-1934 (Oct. 22, 2019).
Ahmed, Yasar, et al., "Antibiotics and response to immunotherapy: Real-world experience", Journal for Immunotherapy of Cancer 8(Suppl 3):A435-A436 Abstract No. 728 (Nov. 9, 2020).

(Continued)

*Primary Examiner* — Nita M. Minnifield
(74) *Attorney, Agent, or Firm* — Myers Bigel, P.A.

(57) ABSTRACT

The invention relates to bacterial compositions useful in the treatment of cancer. In particular, the compositions can be used as a co-therapy with an immune checkpoint therapy. The invention also relates to methods for identifying a subject that will respond to therapy with an immune checkpoint inhibitor comprising determining the abundance of bacteria in a biological sample from said subject.

16 Claims, 29 Drawing Sheets

Specification includes a Sequence Listing.

(56) References Cited

FOREIGN PATENT DOCUMENTS

| WO | 2019178542 | A1 | | 9/2019 | | |
|---|---|---|---|---|---|---|
| WO | 2019191390 | A2 | | 10/2019 | | |
| WO | 2019227085 | A1 | | 11/2019 | | |
| WO | 2020065347 | A1 | | 4/2020 | | |
| WO | 2020077341 | A1 | | 4/2020 | | |
| WO | 2020106983 | A1 | | 5/2020 | | |
| WO | 2020118054 | A1 | | 6/2020 | | |
| WO | 2020118232 | A1 | | 6/2020 | | |
| WO | 2020178720 | A1 | | 9/2020 | | |
| WO | WO-2021234380 | A1 | * | 11/2021 | ............ | A61K 35/74 |
| WO | WO-2021234382 | A1 | * | 11/2021 | ......... | G01N 33/4833 |

OTHER PUBLICATIONS

Bhatt, Aadra P, et al., "The Role of the Microbiome in Cancer Development and Therapy", CACancerJ. Clin 67 (4):326-344 (Jul./Aug. 2017).
Dai, Zhujiang, et al., "Intestinal microbiota: a new force in cancer immunotherapy", Cell Communication and Signaling 18:90 (Jun. 10, 2020) (16 pages).
Derosa, Lisa, et al., "Fecal microbiota transplantation: can it circumvent resistance to PD-1 blockade in melanoma?", Signal Transduction and Targeted Therapy 6:178 (May 8, 2021) (2 pages).
Hakozaki, Taiki, et al., "The gut microbiome associates with immune checkpoint inhibition outcomes in patients with advanced non-small cell lung cancer", Cancer Immunology Research 8(10:1243-1250 (2020 (Abstract only).
Huang, Xuan-Zhang, et al., "Antibiotics use and the efficacy of immune checkpoint inhibitors in cancer patients: a pooled analysis of 2740 cancer patients", OncoImmunology 8(12):arn:e1665973 (abstract only) (Dec. 2, 2019).
Katayama, Yuki, et al., "Impact of bowel movement condition on immune checkpoint inhibitor efficacy in patients with advanced non-small cell lung cancer", Thoracic Cancer 10(3):526-532 (abstract only) (Jan. 21, 2019).
Kim, Esther, et al., "A review on the role of gut microbiota in immune checkpoint blockade therapy for cancer", Mammalian Genome 32:223-231 (Mar. 30, 2021).
Lee, Se-Hoon, et al., "Bifidobacterium bifidum strains synergize with immune checkpoint inhibitors to reduce tumour burden in mice", Nature Microbiology 6:277-288 (abstract only) (Jan. 11, 2021).
Ma, Weijie, et al., "Is chronic refractory colitis from immune checkpoint inhibitor associated with good cancer outcome?", J. Clinical Oncology 35(15):Abstract #e15102 (May 29, 2020).
Nomura, Motoo, et al., "Association of Short-Chain Fatty Acids in the Gut Microbiome With Clinical Response to Treatment With Nivolumab or Pembrolizumab in Patients With Solid Cancer Tumors", JAMA Network Open 3(4): e202895 (Apr. 16, 2020) (12 pages).
Rebeck, Olivia N, et al., "Improving ICI outcomes with a little help from my microbial friends", Cell Host and Microbe 29:155-157 (Feb. 10, 2021).
Riquelme, Erick, et al., "Immunotherapy for Pancreatic Cancer: More Than Just a Gut Feeling", Cancer Discovery 8(4):386-388 (Apr. 2, 2018).
Szczyrek, Michal, et al., "Diet, Microbiome, and Cancer Immunotherapy—A Comprehensive Review", Nutrients 13::2217 (Jun. 28, 2021) (23 pages).
Tanoue, Takeshi, et al., "A defined commensal consortium elicits CD8 T cells and anti-cancer immunity", Nature 31:565:600-605 (Jan. 23, 2019).
Wu, Jianmin, et al., "Modulation of Gut Microbiota to Enhance Effect of Checkpoint Inhibitor Immunotherapy", Frontiers in Immunology 12:Article 669150 (Jun. 29, 2021) (11 pages).
Yi, Ming, et al., "Manipulating Gut Microbiota Composition to Enhance the Therapeutic Effect of Cancer Immunotherapy", Integrative Cancer Therapies 18:abstract only (1 page) (Oct. 21, 2019).
Zhang, Jie, et al., "A new biological triangle in cancer: intestinal microbiota, immune checkpoint inhibitors and antibiotics", Clinical and Transitional Oncology 16 pages (Jun. 14, 2021).
Zipkin, Mark, "Fecal microbiota potentiate checkpoint inhibitors, unleash microbiome startups", Nature Biotechnology 39:529-532 (Apr. 16, 2021).
Zitvogel, Laurence, et al., "The microbiome in cancer immunotherapy: Diagnostic tools and therapeutic strategies", Cancer Immunotherapy 359(6382):1366-1370 (Mar. 23, 2018).
"International Search Report and Written Opinion corresponding to International Application No. PCT/GB2021/051208 dated Jul. 27, 2021".
Gong, Jun, et al., "The gut microbiome and response to immune checkpoint inhibitors: preclinical and clinical strategies", Clinical and Translational Medicine 8:9 (Mar. 18, 2019) (14 pages).
Agata, Yasutoshi, et al., "Expression of the PD-1 antigen on the surface of stimulated mouse T and B lymphocytes", International Immunology 8(5):765-772 (Feb. 6, 1996).
Chang, Hao-Nan, et al., "Blocking of the PD-1/PD-L1 Interaction by a d-Peptide Antagonist for Cancer Immunotherapy", Angew. Chem. Int. Ed. 54:11760-11764 (2015).
Forster, Samuel C, et al., "A human gut bacterial genome and culture collection for improved metagenomic analyses", Nature Biotechnology 37:186-192 (Feb. 2019).
Francisco, Loise M, et al., "The PD-1 Pathway in Tolerance and Autoimmunity", Immunol Rev. 236:219-242 (Jul. 2010).
Frankel, Arthur E, et al., "Metagenomic Shotgun Sequencing and Unbiased Metabolomic Profiling Identify Specific Human Gut Microbiota and Metabolites Associated with Immune Checkpoint Therapy Efficacy in Melanoma Patients", Neoplasia 19(10):848-855 (Oct. 2017).
Gopalakrishnan, V, et al., "Gut microbiome modulates response to anti-PD-1 immunotherapy in melanoma patients", Science 359:97-103 (Jan. 5, 2018).
Green, Michael R, et al., "Molecular Cloning", A Laboratory Manual, 4th ed., Cold Spring Harbor Laboratory Press, Cold Spring Harbor, N.Y. (2012).
Ishida, Yasumasa, et al., "Induced expression of PD-1, a novel member of the immunoglobulin gene superfamily, upon programmed cell death", The EMBO Journal 11(11):3887-3895 (1992).
Koropatkin, Nicole M, et al., "How glycan metabolism shapes the human gut microbiota", Nat Rev Microbiol. 10(5):323-335 (Apr. 11, 2012).
Li, Chunlin, et al., "Peptide Blocking of PD-1/PD-L1 Interaction for Cancer Immunotherapy", Cancer Immunol Res 6(2):178-188 (Feb. 2018).
Li, Yan, et al., "Prebiotic-Induced Anti-tumor Immunity Attenuates Tumor Growth", Cell Reports 30:1753-1766 (Feb. 11, 2020).
Mager, Lukas F, et al., "Microbiome-derived inosine modulates response to checkpoint inhibitor immunotherapy", Science 10.1126/science.abc3421 (Aug. 13, 2020) (17 pages).
Magiera-Mularz, Katarzyna, et al., "Bioactive macrocyclic inhibitors of the PD-1/PD-L1 immune checkpoint", Angew Chem Int Ed Engl. 56(44):13732-13735 (Oct. 23, 2017).
Matson, Vyara, et al., "The commensal microbiome is associated with anti-PD-1 efficacy in metastatic melanoma patients", Science 359:104-108 (Jan. 5, 2018).
Naran, Krupa, et al., "Principles of Immunotherapy: Implications for Treatment Strategies in Cancer and Infectious Diseases", Frontiers in Microbiology 9:3158 (Dec. 2018) (23 pages).
Nishimura, Hiroyuki, et al., "Autoimmune Dilated Cardiomyopathy in PD-1 Receptor-Deficient Mice", Science 291:319-322 (Jan. 12, 2001).
Nishimura, Hiroyuki, et al., "Development of Lupus-like Autoimmune Diseases by Disruption of the PD-1 Gene Encoding an ITIM Motif-Carrying Immunoreceptor", Immunity 11:141-151 (Aug. 1999).
Peters, Brandilyn A, et al., "Relating the gut metagenome and metatranscriptome to immunotherapy responses in melanoma patients", Genome Medicine 11:61 (2019) (14 pages).
Qin, Weiting, et al., "The Diverse Function of PD-1/PD-L Pathway Beyond Cancer", Frontiers in Immunology 10:2298 (Oct. 4, 2019) (16 pages).

(56) References Cited

OTHER PUBLICATIONS

Quince, Christopher, et al., "Shotgun metagenomics, from sampling to sequencing and analysis", Nat Biotechnol 35, 833-844 (2017).

Rao, Martin, et al., "Anti-PD-1/PD-L1 therapy for infectious diseases: learning from the cancer paradigm", International Journal of Infectious Diseases 56:221-228 (2017).

Riley, James L, "PD-1 signaling in primary T cells", Immunol Rev. 229(1):114-125 (May 2009).

Routy, Bertrand, et al., "Gut microbiome influences efficacy of PD-1-based immunotherapy against epithelial tumors", Science 359:91-97 (Jan. 5, 2018).

Sivan, Ayelet, et al., "Commensal Bifidobacterium promotes anti-tumor immunity and facilitates anti-PD-L1 efficacy", Science 350(6264):1084-1089 (Nov. 5, 2015).

Tseng, Su-Yi, et al., "B7-DC, a New Dendritic Cell Molecule with Potent Costimulatory Properties for T Cells", J Exp Med 193(7):839-845 (Apr. 2, 2001).

Wang, Changyu, et al., "In Vitro Characterization of the Anti-PD-1 Antibody Nivolumab, BMS-936558, and In Vivo Toxicology in Non-Human Primates", Cancer Immunol Res; 2(9); 846-856 (May 28, 2014).

Wang, Wenshi, et al., "PD1 blockade reverses the suppression of melanoma antigen-specific CTL by CD4+ CD25Hi regulatory T cells", International Immunology 21(9):1065-1077 (Aug. 3, 2009).

Yu, Sheng, et al., "Nanobodies targeting immune checkpoint molecules for tumor immunotherapy and immunoimaging (Review)", Int. J. Molecular Medicine 47(2):444-454 (2021).

Zhang, Xuewu, et al., "Structural and Functional Analysis of the Costimulatory Receptor Programmed Death-1", Immunity 20:337-347 (Mar. 2004).

Vaddepally et al. "Review of Indications of FDA-Approved Immune Checkpoint Inhibitors per NCCN Guidelines with the Level of Evidence" Cancers, 12:178 2020.

"U.S. Appl. No. 17/324,898; office action dated Mar. 2, 2022".

\* cited by examiner

G

SEQUENCE LISTING

<160> NUMBER OF SEQ ID NOS: 31

<210> SEQ ID NO 1
<211> LENGTH: 1527
<212> TYPE: DNA
<213> ORGANISM: Eisenbergiella sp.

<400> SEQUENCE: 1

```
agagagtttg atcctggctc aggatgaacg ctggcggcgt gcctaacaca tgcaagtcga      60
acggagttat gcagaggaag ttttcggatg gaatcggcgt aacttagtgg cggacgggtg     120
agtaacgcgt gggaaacctg ccctgtaccg ggggataaca cttagaaata ggtgctaata     180
ccgcataagc gcacagcttc acatgaggca gtgtgaaaaa ctccggtggt acaggatggt     240
cccgcgtctg attagccagt tggcaggta acggcctacc aaagcgacga tcagtagccg     300
gcctgagagg gtgaacggcc acattgggac tgagacacgg cccaaactcc tacgggaggc     360
agcagtgggg aatattgcac aatgggggaa accctgatgc agcgacgccg cgtgagtgaa     420
gaagtatttc ggtatgtaaa gctctatcag cagggaagaa aatgacggta cctgactaag     480
aagccccggc taactacgtg ccagcagccg cggtaatacg taggggggcaa gcgttatccg     540 gatttactgg gtgtaaaggg agcgtagacg gcatgacaag ccagatgtga aacccaggg     600 ctcaaccctg ggactgcatt tggaactgcc aggctggagt gcaggagagg taagcggaat     660
tcctagtgta gcggtgaaat gcgtagatat taggaggaac accagtggcg aaggcggctt     720
actggactgt aactgacgtt gaggctcgaa agcgtgggga gcaaacagga ttagatacc     780 tggtagtcca cgcggtaaac gatgattgct aggtgtaggt gggtatggac ccatcggtgc     840
cgcagctaac gcaataagca atccacctgg ggagtacgtt cgcaagaatg aaactcaaag     900
gaattgacgg ggacccgcac aagcggtgga gcatgtggtt taattcgaag caacgcgaag     960
aaccttacca agtcttgaca tcccaatgac gtgtccgtaa cggggcattc tcttcggagc    1020
attggagaca ggtggtgcat ggttgtcgtc agctcgtgtc gtgagatgtt gggttaagtc    1080
ccgcaacgag cgcaacccctt atccttagta gccagcaggt agagctgggc actctaggga    1140
gactgccggg gataacccgg aggaaggcgg ggatgacgtc aaatcatcat gccccttatg    1200
atttgggcta cacacgtgct acaatggcgt aaacaaaggg aagcgagaca gtgatgttga    1260
gcaaatccca gaaataacgt ctcagttcgg attgtagtct gcaactcgac tacatgaagc    1320
tggaatcgct agtaatcgcg aatcagcatg tcgcggtgaa tacgttcccg ggtcttgtac    1380
acaccgcccg tcacaccatg ggagttggaa atgcccgaag cctgtgacct aaccgcaagg    1440
```

| | |
|---|---|
| gaggagcagt cgaaggcagg tctaataact ggggtgaagt cgtaacaagg tagccgtatc | 1500 |
| ggaaggtgcg gctggatcac ctcctttt | 1527 |

<210> SEQ ID NO 2
<211> LENGTH: 1525
<212> TYPE: DNA
<213> ORGANISM: Butyricicoccus sp.

<400> SEQUENCE: 2

| | |
|---|---|
| tttagagagt ttgatcctgg ctcaggatga acgctggcgg cgtgcctaac acatgcaagt | 60 |
| cgaacggagt tattttggaa atctcttcgg ggatggaatt cataacttag tggcggacgg | 120 |
| gtgagtaacg cgtgagcaat ctgcccttag gtggggggata acagccggaa acggctgcta | 180 |
| ataccgcata acacattgaa gccgcatggt tttgatgtca agatttattt gcctttggat | 240 |
| gagctcgcgt ctgattagct ggttggcggg gtaacggccc accaaggcga cgatcagtag | 300 |
| ccggactgag aggttgaacg gccacattgg gactgagaca cggcccagac tcctacggga | 360 |
| ggcagcagtg gggaatattg cgcaatgggg gaaaccctga cgcagcaacg ccgcgtgatt | 420 |
| gaagaaggcc ttcggggttgt aaagatcttt aattggggac gaattttgac ggtacccaaa | 480 |
| gaataagctc cggctaacta cgtgccagca gccgcggtaa tacgtaggga gcaagcgtta | 540 |
| tccggattta ctgggtgtaa agggcgagta ggcgggctgg caagttggga gtgaaatccc | 600 |
| ggggcttaac cccggaactg ctttcaaaac tgctggtctt gagtgatgga gaggcaggcg | 660 |
| gaattccgtg tgtagcggtg aaatgcgtag atatacggag gaacaccagt ggcgaaggcg | 720 |
| gcctgctgga cattaactga cgctgaggag cgaaagcgtg gggagcaaac aggattagat | 780 |
| accctggtag tccacgccgt aaacgatgga tactaggtgt gggaggtatt gacccccttcc | 840 |
| gtgccggagt aacacaaata agtatcccac ctggggagta cggccgcaag gttgaaactc | 900 |
| aaaggaattg acgggggccc gcacaagcag tggagtatgt ggtttaattc gaagcaacgc | 960 |
| gaagaacctt accaggtctt gacatccctc tgaccgccct agagataggg tttcccttcg | 1020 |
| gggcagaggt gacaggtggt gcatggttgt cgtcagctcg tgtcgtgaga tgttgggtta | 1080 |
| agtcccgcaa cgagcgcaac ccttacggtt agttgatacg aaagatcact ctagccggac | 1140 |
| tgccgttgac aaaacggagg aaggtgggga cgacgtcaaa tcatcatgcc ccttatgacc | 1200 |
| tgggctacac acgtactaca atggcagtca tacagaggga agcaaaacag tgatgtggag | 1260 |
| caaatcccta aaagctgtcc cagttcagat tgcaggctgc aactcgcctg catgaagtcg | 1320 |
| gaattgctag taatcgcgga tcagcatgcc gcggtgaata cgttcccggg ccttgtacac | 1380 |
| accgcccgtc acaccatgag agccggtaat acccgaagtc cgtagcctaa ccgcaaggag | 1440 |
| ggcgcggccg aaggtaggac tggtaattag ggtgaagtcg taacaaggta gccgtatcgg | 1500 |
| aaggtgcggc tggatcacct ccttt | 1525 |

<210> SEQ ID NO 3
<211> LENGTH: 1527
<212> TYPE: DNA
<213> ORGANISM: Clostridiales sp.

<400> SEQUENCE: 3

| | |
|---|---|
| tttaagagtt tgatcctggc tcaggacgaa cgctggcggc gtgcctaaca catgcaagtc | 60 |
| gaacgaagct tgatttctga ttttttcgga atgacgaatg atatgactga gtggcggacg | 120 |
| ggtgagtaac gcgtgagcaa cctgcccttc ggaacgggat agtgtctgga acggacagt | 180 |
| aataccgtat aatatatatt gatcgcatgg ttgatatatc aaaactgagg tgccgaagga | 240 |

```
tgggctcgcg tctgattaga tagttggtgg ggtaacggcc taccaagtcg acgatcagta     300
gccggactga gaggttgaac ggccacattg ggactgagac acggcccaga ctcctacggg     360
aggcagcagt ggggaatatt gcacaatggg ggaaaccctg atgcagcaac gccgcgtgaa     420
ggaagacggt tttcggattg taaacttctg ttcttagtga agaataatga cggtagctaa     480
ggagcaagcc acggctaact acgtgccagc agccgcggta atacgtaggt ggcaagcgtt     540
gtccggaatt actgggtgta aagggagcgt aggcgggatg ccaagtcagc tgtgaaaact     600
atgggcttaa cttgtagact gcagttgaaa ctggtattct tgagtgaagt agaggttggc     660
ggaattccga gtgtagcggt gaaatgcgta gatattcgga ggaacaccgg tggcgaaggc     720
ggccaactgg gctttaactg acgctgaggc tcgaaagtgt ggggagcaaa caggattaga     780
taccctggta gtccacactg taaacgatga taactaggtg tgggggtct gacccttcc     840 gtgccgcagc taacgcaata agttatccac ctggggagta cgaccgcaag gttgaaactc     900
aaaggaattg acggggaccc gcacaagcag tggattatgt ggtttaattc gaagcaacgc     960
gaagaacctt accagcactt gacatccgac taacgaagta gagatacatt aggtgccctt    1020
cggggaaagt cgagacaggt ggtgcatggt tgtcgtcagc tcgtgtcgtg agatgttggg    1080
ttaagtcccg caacgagcgc aaccctgcc attagttgct acgcaagagc actctaatgg    1140
gaccgctacc gacaaggtgg aggaaggtgg ggacgacgtc aaatcatcat gccccttatg    1200
tgctgggcta cacacgtaat acaatggcca tcaacaaaga gaagcaatac cgcgaggtgg    1260
agcaaaacta taaaaatggt ctcagttcgg actgcaggct gcaacccgcc tgcacgaagt    1320
tggaattgct agtaatcgtg gatcagcatg ccacggtgaa tacgttcccg ggtcttgtac    1380
acaccgcccg tcacaccatg ggagttggta cacccgaag tcagtagtct aaccgcaagg    1440
aggacgctgc cgaaggtggg attgacgact ggggtgaagt cgtaacaagg tagccgtatc    1500
agaaggtgcg gctggatcac ctccttt                                         1527
```

<210> SEQ ID NO 4
<211> LENGTH: 1539
<212> TYPE: DNA
<213> ORGANISM: Alistipes obesi

<400> SEQUENCE: 4

```
atggagagtt tgatcctggc tcaggatgaa cgctagcggc aggcttaaca catgcaagtc      60
gaggggcagc ataatggtag caatactatt gatggcgacc ggcggacggg tgcgtaacgc     120
gtatgcaacc taccctttac aggggggataa cactgagaaa tcggtactaa taccccataa    180
tattctggga ggcatctttc ggagttgaaa gctttggtgg taaaggatgg gcatgcgttg     240
tattagctag ttggtaaggt aacggcttac caaggcgacg atacataggg ggactgagag     300
gttaaccccc cacattggta ctgagacacg gaccaaactc ctacgggagg cagcagtgag     360
gaatattggt caatggacgg aagtctgaac cagccatgcc gcgtgcagga agacggctct     420
atgagttgta aactgctttt gtacgagggt aaacgcagat acgtgtatct gcctgaaagt     480
atcgtacgaa taaggatcgg ctaactccgt gccagcagcc gcggtaatac ggaggatcca     540
agcgttatcc ggatttattg ggtttaaagg gtgcgtaggc ggtttagtaa gtcagcggtg     600
aaattttggt gcttaacacc aaacgtgccg ttgatactgc tgggctagag agtagttgcg     660
gtaggcggaa tgtatggtgt agcggtgaaa tgcttagaga tcatacagaa caccgattgc     720
gaaggcagct taccaaacta tatctgacgt tgaggcacga aagcgtgggg agcaaacagg     780
```

| | |
|---|---:|
| attagatacc ctggtagtcc acgcagtaaa cgatgatagc tcgttgtcgg cgatacacag | 840 |
| tcggtgacta agagaaatcg ataagctatc cacctgggga gtacgttcgc aagaatgaaa | 900 |
| ctcaaaggaa ttgacggggg cccgcacaag cggaggaaca tgtggtttaa ttcgatgata | 960 |
| cgcgaggaac cttacccggg cttgaaagtt actgacgatt ctggaaacag gatttccctt | 1020 |
| cggggcagga aactaggtgc tgcatggttg tcgtcagctc gtgccgtgag gtgtcgggtt | 1080 |
| aagtcccata acgagcgcaa cccctactga tagttgccat cagagcgttt gagcgatcaa | 1140 |
| acaagctggg cactctatcg ggactgccgg tgtaagccga gaggaaggtg gggatgacgt | 1200 |
| caaatcagca cggcccttac gtccggggcg acacacgtgt acaatggta ggtacagagg | 1260 |
| gcagccaccc agtgatgggg agcgaatctc gaaagcctat ctcagttcgg attggaggct | 1320 |
| gaaactcgcc tccatgaagt tggattcgct agtaatcgcg catcagccat ggcgcggtga | 1380 |
| atacgttccc gggccttgta cacaccgccc gtcaagccat gggagttggg ggtgcctgaa | 1440 |
| gttcgtgacc gaaaggagcg acctagggca aaaccgatga ctgggctaa gtcgtaacaa | 1500 |
| ggtagccgta ccggaaggtg cggctggaac acctccttt | 1539 |

<210> SEQ ID NO 5
<211> LENGTH: 1525
<212> TYPE: DNA
<213> ORGANISM: Alistipes indistinctus

<400> SEQUENCE: 5

| | |
|---|---:|
| atggagagtt tgatcctggc tcaggataaa cgctagcggc aggcctaaca catgcaagtc | 60 |
| gaggggcagc gggtggagta tttcggtact cctgccggcg accggcgcac gggtgcgtaa | 120 |
| cgcgtatgca acctaccttt aacaggggga taatccgaag aaatttggtc taataccca | 180 |
| taatatcatt taaggcatct tagatggttg aaaattccga tggttagaga tgggcatgcg | 240 |
| ttgtattagc tagttggtga ggtaacggct caccaaggct acgatacata gggggactga | 300 |
| gaggttttcc ccccacactg gtactgagac acgaccaga ctcctacggg aggcagcagt | 360 |
| gaggaatatt ggtcaatgga cgcaagtctg aaccagccat gccgcgtgca ggatgaaggt | 420 |
| gctatgcatt gtaaactgct tttgtacgag ggtaaatgca ggtacgtgta cctgtttgaa | 480 |
| agtatcgtac gaataagggt cggctaactc cgtgccagca gccgcggtaa tacgaggac | 540 |
| ccgagcgtta tccggattta ttgggtttaa agggtgcgta ggcggattag taagttagag | 600 |
| gtgaaagctc gatgctcaac atcgaaattg cctctgatac tgttagtcta gagtatagtt | 660 |
| gcggaaggcg aatgtgtgg tgtagcggtg aaatgcttag atatcacaca gaacaccgat | 720 |
| tgcgaaggca gctttccaag ctattactga cgctgatgca cgaaagcgtg gggagcgaac | 780 |
| aggattagat accctggtag tccacgcccgt aaacgatgat aactcgttgc aggcgataca | 840 |
| cagtctgtga cttagcgaaa gcgttaagtt atccacctgg ggagtacgtt cgcaagaatg | 900 |
| aaactcaaag gaattgacgg gggcccgcac aagcggagga acatgtggtt taattcgatg | 960 |
| atacgcgagg aaccttaccc gggcttgaaa gttagcgacg atcctgaaa ggggtcttct | 1020 |
| cttcggagcg cgaaactagg tgctgcatgg ttgtcgtcag ctcgtgccgt gaggtgtcgg | 1080 |
| gttaagtccc ataacgagcg caaccccta ctgttagttac cagcacgtca aggtgggcac | 1140 |
| tctagcagga ctgccggtgt aagccgagag gaaggtgggg atgacgtcaa atcagcacgg | 1200 |
| cccttacgtc cggggcgaca cacgtgttac aatggtcggt acagagggtc gctacccgt | 1260 |
| gagggggatgc caatctcgaa agccgatctc agttcggatt ggaggctgaa actcgcctcc | 1320 |
| atgaagttgg attcgctagt aatcgcgcat cagccatggc gcggtgaata cgttcccggg | 1380 |

| | |
|---|---|
| ccttgtacac accgcccgtc aagccatggg agttgggggt gcctgaagta cgtgaccgca | 1440 |
| aggagcgtcc tagggcaaaa ccgatgactg gggctaagtc gtaacaaggt agccgtaccg | 1500 |
| gaaggtgcgg ctggaacacc tcctt | 1525 |

<210> SEQ ID NO 6
<211> LENGTH: 1506
<212> TYPE: DNA
<213> ORGANISM: Gordonibacter urolithinfaciens

<400> SEQUENCE: 6

| | |
|---|---|
| acggagagtt tgatcctggc tcaggatgaa cgctggcggc gtgcctaaca catgcaagtc | 60 |
| gaacggttaa ggcgccttcg ggcgcgaata gagtggcgaa cgggtgagta acacgtgacc | 120 |
| aacctgcccc cctccccggg ataacgcgag gaaacccgcg ctaataccgg atactccgcc | 180 |
| cctcccgcat gggaggggcg ggaaagcccc gacggagggg gatgggttcg cggcccatta | 240 |
| ggtagacggc ggggcaacgg cccaccgtgc ctgcgatggg tagccgggtt gagagaccga | 300 |
| ccggccacat tgggactgag atacggccca gactcctacg ggaggcagca gtggggaatt | 360 |
| ttgcgcaatg gggggaaccc tgacgcagca acgccgcgtg cgggacgaag gccttcgggt | 420 |
| tgtaaaccgc tttcagcagg gaagaagttg acggtacctg cagaagaagc cccggctaac | 480 |
| tacgtgccag cagccgcggt aatacgtagg gggcgagcgt tatccggatt cattgggcgt | 540 |
| aaagcgcgcg taggcggccc gtcaagcgga acctctaacc cgagggctca accccggcc | 600 |
| gggttccgaa ctgcaggct cgagtttggt agaggaagat ggaattcccg gtgtagcggt | 660 |
| ggaatgcgca gatatcggga agaacaccga tggcgaaggc agtcttctgg gccatcaact | 720 |
| gacgctgagg cgcgaaagct gggggagcga acaggattag ataccctggt agtcccagcc | 780 |
| gtaaacgatg ggtgctaggt gtgggggat catccctccg tgccgcagcc aacgcattaa | 840 |
| gcaccccgcc tggggagtac ggccgcaagg ctaaaactca aaggaattga cggggggccg | 900 |
| cacaagcagc ggagcatgtg gcttaattcg aagcaacgcg aagaaccta ccagggcttg | 960 |
| acatgctggt gaagccgggg aaacccggtg gccgagagga gccagcgcag gtggtgcatg | 1020 |
| gctgtcgtca gctcgtgtcg tgagatgttg ggttaagtcc cgcaacgagc gcaacccctg | 1080 |
| ccatatgttg ccagcattca gttggggact catatgggac tgccggcgtc aagccggagg | 1140 |
| aaggtgggga cgacgtcaag tcatcatgcc ctttatgccc tgggctgcac acgtgctaca | 1200 |
| atggccggta caacgggccg cgacctggcg acaggaagcg aatccctcaa agccggcccc | 1260 |
| agttcggatc ggaggctgca acccgcctcc gtgaagtcgg agttgctagt aatcgcggat | 1320 |
| cagcatgccg cggtgaatac gttcccgggc cttgtacaca ccgcccgtca ccacccga | 1380 |
| gtcgtctgca cccgaagccg ccggccgaac ccgcaagggg cggaggcgtc gaaggtgtgg | 1440 |
| agggtaaggg gggtgaagtc gtaacaaggt agccgtaccg gaaggtgcgg ctggatcacc | 1500 |
| tcctt | 1506 |

<210> SEQ ID NO 7
<211> LENGTH: 1535
<212> TYPE: DNA
<213> ORGANISM: Faecalitalea sp.

<400> SEQUENCE: 7

| | |
|---|---|
| atggagagtt tgatcctggc tcaggatgaa cgctggcggc atgcctaata catgcaagtc | 60 |
| gaacgaagtc tttaggaagc ttgcttccaa agagacttag tggcgaacgg gtgagtaaca | 120 |

```
cgtaggtaac ctgcccatgt gcccgggata actgctggaa acggtagcta aaaccggata      180
ggtatgaggg aggcatcttc ctcatattaa agcaccttcg ggtgtgaaca tggatggacc      240
tgcggcgcat tagctggttg gtgaggtaac ggcccaccaa ggcgatgatg cgtagccgac      300
ctgagagggt gaacggccac attgggactg agacacggcc caaactccta cgggaggcag      360
cagtagggaa ttttcgtcaa tggggggaac cctgaacgag caatgccgcg tgtgtgaaga      420
aggtcttcgg atcgtaaagc actgttgtaa gtgaagaatg ccatatagag gaaatgctat      480
gtgggtgacg gtagcttacc agaaagccac ggctaactac gtgccagcag ccgcggtaat      540
acgtaggtgg caagcgttat ccggaatcat tgggcgtaaa gggtgcgtag gtggcacgat      600
aagtctgaag taaaaggcaa cagctcaact gttgtatgct ttggaaactg tcgagctaga      660
gtgcagaaga gggcgatgga attccatgtg tagcggtaaa atgcgtagat atatggagga      720
acaccagtgg cgaaggcggt cgcctggtct gtaactgaca ctgatgcacg aaagcgtggg      780
gagcaaatag gattagatac cctagtagtc cacgccgtaa acgatgagaa ctaagtgttg      840
gagagattca gtgctgcagt taacgcaata agttctccgc ctggggagta tgcacgcaag      900
tgtgaaactc aaaggaattg acggggggcc cgcacaagcg gtggagtatgt ggtttaattc      960 gaagcaacgc gaagaacctt accaggcctt gacatggata taaatgttct agagataaga      1020
agatagctat atatcacaca ggtggtgcat ggttgtcgtc agctcgtgtc gtgagatgtt      1080
gggttaagtc cgcaacgagc gcaacccctt gtcttctgtt accagcatta agttgggac       1140 tcaggagaga ctgccggtga caaaccggag gaaggtgggg atgacgtcaa atcatcatgc      1200
cccttatggc ctgggctaca cacgtactac aatggcgcct acaaagagca gcgacaccgc      1260
gaggtggagc gaatctcata aagggcgtct cagttcggat tgaagtctgc aactcgactt      1320
catgaagtcg gaatcgctag taatcgcaga tcagcatgct gcggtgaata cgttctcggg      1380
ccttgtacac accgcccgtc aaaccatggg agttggtaat acccgaagcc ggtggcataa      1440
ccgcaaggag tgagccgtcg aaggtaggac cgatgactgg ggttaagtcg taacaaggta      1500
tccctacggg aacgtgggga tggatcacct cctttt                               1535

<210> SEQ ID NO 8
<211> LENGTH: 1530
<212> TYPE: DNA
<213> ORGANISM: Blautia sp.

<400> SEQUENCE: 8
tcagagagtt tgatcctggc tcaggatgaa cgctggcggc gtgcttaaca catgcaagtc       60
gagcgaagca cttaagtgga tctcttcgga ttgaaactta tttgactgag cggcggacgg      120
gtgagtaacg cgtgggtaac ctgcctcata caggggata acagttagaa atggctgcta      180
ataccgcata agcgcacagg accgcatggt ctggtgtgaa aaactccggt ggtatgagat      240
ggacccgcgt ctgattagct agttggaggg gtaacggccc accaaggcga cgatcagtag      300
ccggcctgag agggtgaacg gccacattgg gactgagaca cggcccagac tcctacggga      360
ggcagcagtg gggaatattg cacaatgggg gaaaccctga tgcagcgacg ccgcgtgaag      420
gaagaagtat ctcggtatgt aaacttctat cagcaggaa gaaaatgacg gtacctgact      480
aagaagcccc ggctaactac gtgccagcag ccgcggtaat acgtaggggg caagcgttat      540
ccggatttac tgggtgtaaa gggagcgtag acggaagagc aagtctgatg tgaaaggctg      600
gggcttaacc ccaggactgc attggaaact gtttttctag agtgccggag aggtaagcgg      660
aattcctagt gtagcggtga aatgcgtaga tattaggagg aacaccagtg gcgaaggcgg      720
```

```
cttactggac ggtaactgac gttgaggctc gaaagcgtgg ggagcaaaca ggattagata       780
ccctggtagt ccacgccgta aacgatgaat actaggtgtc gggtggcaaa gccattcggt       840
gccgcagcaa acgcaataag tattccacct ggggagtacg ttcgcaagaa tgaaactcaa       900
aggaattgac ggggacccgc acaagcgtg gagcatgtgt tttaattcga agcaacgcga        960
agaaccttac caagtcttga catccctctg accggcccgt aacggggcct tcccttcggg      1020
gcagaggaga caggtggtgc atggttgtcg tcagctcgtg tcgtgagatg ttgggttaag      1080
tcccgcaacg agcgcaaccc ctatccttag tagccagcag gtagagctgg cactctagg       1140 gagactgccg ggataacccc ggaggaaggc ggggacgacg tcaaatcatc atgcccctta      1200
tgatttgggc tacacacgtg ctacaatggc gtaaacaaag ggaagcgaga cagcgatgtt      1260
gagcaaatcc caaaaataac gtcccagttc ggactgcagt ctgcaactcg actgcacgaa      1320
gctggaatcg ctagtaatcg cgaatcagaa tgtcgcggtg aatacgttcc cgggtcttgt      1380
acacaccgcc cgtcacacca tgggagtcag taacgcccga agtcagtgac ccaaccttac      1440
aggagggagc tgccgaaggc gggaccgata actggggtga agtcgtaaca aggtagccgt      1500
atcggaaggt gcggctggat cacctccttt                                       1530

<210> SEQ ID NO 9
<211> LENGTH: 1528
<212> TYPE: DNA
<213> ORGANISM: Barnesiella intestinihominis

<400> SEQUENCE: 9
cgaagagttt gatcctggct caggatgaac gctagcgaca ggcctaacac atgcaagtcg        60
aggggcagcg gagaggtagc aataccttg ccggcgaccg cgcacgggt gagtaacacg        120 tatgcaatcc acctgtaaca gggggataac ccggagaaat ccggactaat accccataat       180
atgggcgctc cgcatggaga gtccattaaa gagagcaatt ttggttacag acgagcatgc       240
gctccattag ccagttggcg gggtaacggc ccaccaaagc gacgatggat aggggttctg       300
agaggaaggt cccccacatt ggaactgaga cacggtccaa actcctacgg gaggcagcag       360
tgaggaatat tggtcaatgg tcggcagact gaaccagcca agtcgcgtga gggaagacgg       420
ccctacgggt tgtaaacctc ttttgtcgga gagtaaagta cgctacgtgt agtgtattgc       480
aagtatccga agaaaaagca tcggctaact ccgtgccagc agccgcggta atacggagga       540
tgcgagcgtt atccggattt attgggttta aagggtgcgt aggcggcacg ccaagtcagc       600
ggtgaaattt ccgggctcaa cccggactgt gccgttgaaa ctggcgagct agagtgcaca       660
agaggcaggc ggaatgcgtg gtgtagcggt gaaatgcata gatatcacgc agaaccccga       720
ttgcgaaggc agcctgctag ggtgcgacag acgctgaggc acgaaagcgt gggtatcgaa       780
caggattaga taccctggta gtccacgcag taaacgatga atactaactg tttgcgatac       840
aatgtaagcg gtacagcgaa agcgttaagt attccacctg gggagtacgc cggcaacggt       900
gaaactcaaa ggaattgacg ggggcccgca caagcggagg aacatgtggt ttaattcgat       960
gatacgcgag gaaccttacc cgggctcaaa cgcaggggga atgccggtga agtcggcag      1020 ctagcaatag tcacctgcga ggtgctgcat ggttgtcgtc agctcgtgcc gtgaggtgtc      1080
ggcttaagtg ccataacgag cgcaacccct atggacagtt actaacgggt gaagccgagg      1140
actctgtcta gactgccggc gcaagccgcg aggaaggtgg ggatgacgtc aaatcagcac      1200
ggcccttacg tccggggcga cacacgtgtt acaatggcag gtacagaagg cagccagtca      1260
```

```
gcaatgacgc gcgaatcccg aaaacctgtc tcagttcgga ttggagtctg caacccgact    1320
ccatgaagct ggattcgcta gtaatcgcgc atcagccatg gcgcggtgaa tacgttcccg    1380
ggccttgtac acaccgcccg tcaagccatg gaagccggga gtacctgaag catgcaaccg    1440
caaggagcgt acgaaggtaa taccggtaac tggggctaag tcgtaacaag gtagccgtac    1500
cggaaggtgc ggctggaaca cctcctttt                                      1528
```

<210> SEQ ID NO 10
<211> LENGTH: 1525
<212> TYPE: DNA
<213> ORGANISM: Alistipes timonensis

<400> SEQUENCE: 10

```
atggagagtt tgatcctggc tcaggatgaa cgctagcggc aggcctaaca catgcaagtc     60
gaggggcagc gggattgaag cttgcttcaa tcgccggcga ccggcgcacg ggtgcgtaac    120
gcgtatgcaa cctacccaga acaggggat aacactgaga aattggtact aatatcccat     180
aacatcataa ggggcatccc ttttggttga aactccggt ggttctggat gggcatgcgt     240
tgtattagct agttggtgag gtaacggctc accaaggcaa cgatacatag ggggactgag    300
aggttaaccc cccacattgg tactgagaca cggaccaaac tcctacggga ggcagcagtg    360
aggaatattg gtcaatggac gcaagtctga accagccatg ccgcgtgcag gaagacggct    420
ctatgagttg taaactgctt ttgtactagg gtaaactcag atacgtgtat ctgactgaaa    480
gtatagtacg aataaggatc ggctaactcc gtgccagcag ccgcggtaat acggaggatt    540
caagcgttat ccggatttat tgggtttaaa gggtgcgtag gcggtttgat aagttagagg    600
tgaaataccg gtgcttaaca ccggaactgc ctctaatact gttgagctag agagtagttg    660
cggtaggcgg aatgtatggt gtagcggtga atgcttaga gatcatacag aacaccgatt    720
gcgaaggcag cttaccaaac tatatctgac gttgaggcac gaaagcgtgg ggagcaaaca    780
ggattagata ccctggtagt ccacgcagta acgatgata actcgctgtc ggcgatacac    840
agtcggtggc taagcgaaag cgataagtta tccacctggg gagtacgttc gcaagaatga    900
aactcaaagg aattgacggg ggcccgcaca agcggaggaa catgtggttt aattcgatga    960
tacgcgagga accttacccg gcttgaaag ttagtgacgg atctggaaac aggtcttccc    1020
ttcggggcgc gaaactaggt gctgcatggt tgtcgtcagc tcgtgccgtg aggtgtcggg    1080
ttaagtccca taacgagcgc aacccctacc gttagttgcc atcaggtcaa gctgggcact    1140
ctgacgggac tgccggtgta agccgagagg aaggtgggga tgacgtcaaa tcagcacggc    1200
ccttacgtcc ggggccacac acgtgttaca atggtaggta cagagggcag ctacccagcg    1260
atgggatgcg aatctcgaaa gcctatctca gttcggatcg gaggctgaaa cccgcctccg    1320
tgaagttgga ttcgctagta atcgcgcatc agccatggcg cggtgaatac gttcccgggc    1380
cttgtacaca ccgcccgtca agccatggaa gctgggggtg cctgaagttc gtgaccgcaa    1440
ggagcgacct agggcaaaac cggtgactgg ggctaagtcg taacaaggta gccgtaccgg    1500
aaggtgcggc tggaacaccct cctttt                                        1525
```

<210> SEQ ID NO 11
<211> LENGTH: 1528
<212> TYPE: DNA
<213> ORGANISM: Blautia sp.

<400> SEQUENCE: 11

```
tcagagagtt tgatcctggc tcaggatgaa cgctggcggc gtgcttaaca catgcaagtc     60
```

```
gagcgaagca cttgccattg actcttcgga agatttggca tttgactgag cggcggacgg      120
gtgagtaacg cgtgggtaac ctgcctcata caggggaata acagttagaa atggctgcta      180
atgccgcata agcgcacagg accgcatggt ctggtgtgaa aaactgaggt ggtatgagat      240
gggcccgcgt ctgattaggt agttggcggg gtaacggccc accaagccga cgatcagtag      300
ccgacctgag agggtgaccg gccacattgg gactgagaca cggcccagac tcctacggga      360
ggcagcagtg gggaatattg cacaatggag gaaactctga tgcagcgacg ccgcgtgaag      420
gaagaagtat ctcggtatgt aaacttctat cagcagggaa gaaaatgacg gtacctgact      480
aagaagcccc ggctaactac gtgccagcag ccgcggtaat acgtaggggg caagcgttat      540
ccggatttac tgggtgtaaa gggagcgtag acggacgggc aagtctgatg tgaaagcccg      600
gggcttaacc ccgggactgc attggaaact gtccatcttg agtgccggag aggtaagcgg      660
aattcctagt gtagcggtga aatgcgtaga tattaggagg aacaccagtg gcgaaggcgg      720
cttactggac ggtaactgac gttgaggctc gaaagcgtgg ggagcaaaca ggattagata      780
ccctggtagt ccacgccgta acgatgaat actaggtgtc gggttgcaaa gcaatccggt      840
gccgcagcaa acgcagtaag tattccacct ggggagtacg ttcgcaagaa tgaaactcaa      900
aggaattgac ggggacccgc acaagcggtg gagcatgtgg tttaattcga agcaacgcga      960
agaaccttac caagtcttga catctgcctg accgttcctt aaccggaact ttccttcggg     1020
acaggcaaga caggtggtgc atggttgtcg tcagctcgtg tcgtgagatg ttgggttaag     1080
tcccgcaacg agcgcaaccc ctgtccttag tagccagcag tccggctggg cactctaggg     1140
agactgccgg ggataacccg gaggaaggcg gggacgacgt caaatcatca tgccccttat     1200
gatttgggct acacacgtgc tacaatggcg taaacaaagg gaagcggagt ggtgacactg     1260
agcaaatctc aaaaataacg tcccagttcg gactgcagtc tgcaactcga ctgcacgaag     1320
ctggaatcgc tagtaatcgc gaatcagaat gtcgcggtga atacgttccc gggtcttgta     1380
cacaccgccc gtcacaccat gggagtcagt aacgcccgaa gtcagtgacc taaccgcaag     1440
ggaggagctg ccgaaggcgg gaccgataac tggggtgaag tcgtaacaag gtagccgtat     1500
cggaaggtgc ggctggatca cctcctttt                                        1528
```

<210> SEQ ID NO 12
<211> LENGTH: 1530
<212> TYPE: DNA
<213> ORGANISM: Lachnospira sp.

<400> SEQUENCE: 12

```
ttatgagagt ttgatcctgg ctcaggatga acgctggcgg cgtgcttaac acatgcaagt       60
cgaacgaagc atttaagacg gattctttcg ggatgaagac ttttatgact gagtggcgga      120
cgggtgagta acgcgtgggt aacctgcctc acacagggg atagcagttg aaacggctg      180 ataataccgc ataagcgcac agtaccgcat ggtacagtgt gaaaaactcc ggtggtgtga      240
gatggacccg cgtctgatta gcttgttggc agggtaacgg cctaccaagg caacgatcag      300
tagccgacct gagagggtga ccggccacat tgggactgag acacggccca gactcctacg      360
ggaggcagca gtgggggaata ttgcacaatg gaggaaactc tgatgcagcg acgccgcgtg      420
agtgaagaag taattcgtta tgtaaagctc tatcagcagg gaagatagtg acggtacctg      480
actaagaagc tccggctaaa tacgtgccag cagccgcggt aatacgtatg agcaagcgt      540 tatccggatt tactgggtgt aaagggagtg taggtggcat cacaagtcag aagtgaaagc      600
```

| | |
|---|---|
| ccggggctca accccgggac tgcttttgaa actgtggagc tggagtgcag gagaggcaag | 660 |
| tggaattcct agtgtagcgg tgaaatgcgt agatattagg aggaacacca gtggcgaagg | 720 |
| cggcttgctg gactgtaact gacactgagg ctcgaaagcg tggggagcaa acaggattag | 780 |
| atacctggt agtccacgcc gtaaacgatg aatactaggt gtcggggctc ataagagctt | 840 |
| cggtgccgca gcaaacgcaa taagtattcc acctggggag tacgttcgca agaatgaaac | 900 |
| tcaaaggaat tgacgggac ccgcacaagc ggtggagcat gtggtttaat tcgaagcaac | 960 |
| gcgaagaacc ttaccaagtc ttgacatcct cttgaccggt cagtaatgtg acctttctt | 1020 |
| cggaacaaga gtgacaggtg gtgcatggtt gtcgtcagct cgtgtcgtga gatgttgggt | 1080 |
| taagtcccgc aacgagcgca accctattc ttagtagcca gcatttaagg tgggcactct | 1140 |
| aggaagactg ccagggataa cctggaggaa ggtggggatg acgtcaaatc atcatgccc | 1200 |
| ttatgacttg ggctacacac gtgctacaat ggcgtaaaca aagtgaagcg agagtgtgag | 1260 |
| cttaagcaaa tcacaaaaat aacgtctcag ttcggattgt agtctgcaac tcgactacat | 1320 |
| gaagctggaa tcgctagtaa tcgcgaatca gaatgtcgcg gtgaatacgt tcccgggtct | 1380 |
| tgtacacacc gcccgtcaca ccatgggagt cggaaatgcc cgaagtcggt gacctaacga | 1440 |
| aagaaggagc cgccgaaggc aggtctgata actggggtga agtcgtaaca aggtagccgt | 1500 |
| atcggaaggt gcggctggat cacctccttt | 1530 |

<210> SEQ ID NO 13
<211> LENGTH: 1507
<212> TYPE: DNA
<213> ORGANISM: Ruminococcus callidus

<400> SEQUENCE: 13

| | |
|---|---|
| taaagagttt gatcctggct caggacgaac gctggcggca cgcttaacac atgcaagtcg | 60 |
| aacggagaat atcgaagctt gctttgatat tcttagtggc ggacgggtga gtaacacgtg | 120 |
| agtaacctgc ctctgagagt gggatagctt ctggaaacgg atggtaatac cgcatgaaat | 180 |
| catagtatcg catggtacaa tgatcaaaga tttatcgctc agagatggac tcgcgtctga | 240 |
| ttagctagtt ggtaaggtaa cggcttacca aggcgacgat cagtagccgg actgagaggt | 300 |
| tgatcggcca cattgggact gagacacggc ccagactcct acgggaggca gcagtgggga | 360 |
| atattgcaca atgggggaaa ccctgatgca gcgatgccgc gtggaggaag aaggttttcg | 420 |
| gattgtaaac tcctgttgaa gaggacgata atgacggtac tcttttagaa agctccggct | 480 |
| aactacgtgc cagcagccgc ggtaatacgt agggagcgag cgttgtccgg aattactggg | 540 |
| tgtaaaggga gcgtaggcgg gacggcaagt cagatgtgaa aactatgggc tcaacccata | 600 |
| gactgcattt gaaactgttg ttcttgagtg aggtagaggt aagcggaatt cctggtgtag | 660 |
| cggtgaaatg cgtagagatc aggaggaaca tcggtggcga aggcggctta ctgggccttt | 720 |
| actgacgctg aggctcgaaa gcgtggggag caaacaggat tagataccct ggtagtccac | 780 |
| gccgtaaacg atgattacta ggtgtggggg gactgacccc ttccgtgccg cagttaacac | 840 |
| aataagtaat ccacctgggg agtacggccg caaggttgaa actcaaagga attgacgggg | 900 |
| gcccgcacaa gcagtggagt atgtggttta attcgaagca acgcgaagaa ccttaccagg | 960 |
| tcttgacatc gagtgacgta cctagagata ggtattttct tcggaacaca agacaggtg | 1020 |
| gtgcatggtt gtcgtcagct cgtgtcgtga gatgttgggt taagtcccgc aacgagcgca | 1080 |
| acccttacca ttagttgcta cgcaagagca ctctaatggg actgccgttg acaaaacgga | 1140 |
| ggaaggtggg gatgacgtca atcatcatg ccccttatga cctgggctac acacgtacta | 1200 |

```
caatggcaat ataacagagg aagcaatac agcgatgtgg agcaaatccc caaaaattgt    1260
cccagttcag attgcaggct gcaactcgcc tgcatgaagt cggaattgct agtaatcgca    1320
gatcagcatg ctgcggtgaa tacgttcccg ggccttgtac acaccgcccg tcacaccatg    1380
ggagtcggta acacccaaag ccggtcgtct aaccttcggg aggacgccgt ctaaggtggg    1440
attgatgact ggggtgaagt cgtaacaagg tagccgtatc ggaaggtgcg gctggatcac    1500
ctcctttt                                                             1507

<210> SEQ ID NO 14
<211> LENGTH: 1530
<212> TYPE: DNA
<213> ORGANISM: Roseburia faecis

<400> SEQUENCE: 14
atgagagttt gatcctggct caggatgaac gctggcggcg tgcttaacac atgcaagtcg     60
aacgaagcac tctatttgat tttcttcgga aatgaagatt ttgtgactga gtggcggacg    120
ggtgagtaac gcgtgggtaa cctgcctcat acaggggat aacagttgga aacgactgct    180
aataccgcat aagcgcacag gatcgcatgg tccggtgtga aaaactccgg tggtatgaga    240
tggacccgcg tctgattagc cagttggcag ggtaacggcc taccaaagcg acgatcagta    300
gccgacctga gagggtgacc ggccacattg ggactgagac acggcccaaa ctcctacggg    360
aggcagcagt ggggaatatt gcacaatggg ggaaaccctg atgcagcgac gccgcgtgag    420
cgaagaagta tttcggtatg taaagctcta tcagcaggga agaagaatga cggtacctga    480
ctaagaagca ccggctaaat acgtgccagc agccgcggta atacgtatgg tgcaagcgtt    540
atccggattt actgggtgta aagggagcgc aggcggtgcg gcaagtctga tgtgaaagcc    600
cggggctcaa ccccggtact gcattggaaa ctgtcgtact agagtgtcgg aggggtaagt    660
ggaattccta gtgtagcggt gaaatgcgta gatattagga ggaacaccag tggcgaaggc    720
ggcttactgg acgataactg acgctgaggc tcgaaagcgt ggggagcaaa caggattaga    780
taccctggta gtccacgccg taaacgatga atactaggtg tcggggagca ttgctcttcg    840
gtgccgcagc aaacgcaata agtattccac ctggggagta cgttcgcaag aatgaaactc    900
aaaggaattg acggggaccc gcacaagcgg tggagcatgt ggtttaattc gaagcaacgc    960
gaagaacctt accaagtctt gacatcccga tgacagagta tgtaatgtac tttctcttcg   1020
gagcatcggt gacaggtggt gcatggttgt cgtcagctcg tgtcgtgaga tgttgggtta   1080
agtcccgcaa cgagcgcaac ccctgttctt agtagccagc ggttcggccg gcactctag    1140 ggagactgcc agggataacc tggaggaagg cggggatgac gtcaaatcat catgccctt    1200 atgacttggg ctacacacgt gctacaatgg cgtaaacaaa gggaagcgga gccgtgaggc   1260
cgagcaaatc tcaaaaataa cgtctcagtt cggactgtag tctgcaaccc gactacacga   1320
agctggaatc gctagtaatc gcagatcaga atgctgcggt gaatacgttc ccgggtcttg   1380 tacaccgc ccgtcacacc atgggagttg gaaatgcccg aagtcagtga cccaaccgca   1440
aggagggagc tgccgaaggc aggttcgata actggggtga agtcgtaaca aggtagccgt   1500
atcggaaggt gcggctggat cacctccttt                                    1530

<210> SEQ ID NO 15
<211> LENGTH: 1473
<212> TYPE: DNA
<213> ORGANISM: Faecalibacterium prausnitzii
```

<400> SEQUENCE: 15

```
agagtttgat cctggctcag gacgaacgct ggcggcgcgc ctaacacatg caagtcgaac    60
gagagagagg gagcttgctt ccttgatcga gtggcgaacg ggtgagtaac gcgtgaggaa   120
cctgcctcaa agaggggac aacagttgga aacgactgct aataccgcat aagcccacga   180
cccggcatcg ggaagaggga aaaggagcaa tccgctttga gatggcctcg cgtccgatta   240
gctagttggt gaggtaacgg cccaccaagc gacgatcggt agccgactg agaggttgaa    300
cggccacatt gggactgaga cacggcccag actcctacgg gaggcagcag tggggaatat   360
tgcacaatgg gggaaaccct gatgcagcga cgccgcgtgg aggaagaagg tcttcggatt   420
gtaaactcct gttgttgagg aagataatga cggtactcaa caaggaagtg acggctaact   480
acgtgccagc agccgcggta aaacgtaggt cacaagcgtt gtccggaatt actgggtgta   540
aagggagcgc aggcgggcga tcaagttgga agtgaaatcc atgggctcaa cccatgaact   600
gctttcaaaa ctggtcgtct tgagtagtgc agaggtaggc ggaattcccg gtgtagcggt   660
ggaatgcgta gatatcggga ggaacaccag tggcgaaggc ggcctactgg gcaccaactg   720
acgctgaggc tcgaaagtgt gggtagcaaa caggattaga taccctggta gtccacaccg   780
taaacgatga ttactaggtg ttgggagatt gaccctctca gtgccgcagt taacacaata   840
agtaatccac ctgggagta cgaccgcaag gttgaaactc aaaggaattg acggggggccc    900
gcacaagcag tggagtatgt ggtttaattc gacgcaacgc gaagaacctt accaagtctt   960
gacatccctt gacgatgctg gaaacagtat ttctcttcgg agcaaggaga caggtggtgc  1020
atggttgtcg tcagctcgtg tcgtgagatg ttgggttaag tcccgcaacg agcgcaaccc  1080
ttatggtcag ttactacgca agaggactct ggccagactg ccgttgacaa acggaggaa   1140
ggtggggatg acgtcaaatc atcatgccct ttatgacttg gctacacac gtactacaat   1200
ggcgttaaac aaagagaagc aagaccgcga ggtggagcaa aactcagaaa caacgtccca  1260
gttcggactg caggctgcaa ctcgcctgca cgaagtcgga attgctagta atcgtggatc  1320
agcatgccac ggtgaatacg ttcccgggcc ttgtacacac cgcccgtcac accatgagag  1380
ccggggggac ccgaagtcgg tagtctaacc gcaaggagga cgccgccgaa ggtaaaactg  1440
gtgattgggg tgaagtcgta acaaggtagc cgt                                1473
```

<210> SEQ ID NO 16
<211> LENGTH: 1539
<212> TYPE: DNA
<213> ORGANISM: Alistipes obesi

<400> SEQUENCE: 16

```
atggagagtt tgatcctggc tcaggatgaa cgctagcggc aggcttaaca catgcaagtc     60
gaggggcagc ataatggtag taatactatt gatggcgacc ggcggacggg tgcgtaacgc   120
gtatgcaacc taccctttac aggggggataa cactgagaaa tcggtactaa taccccataa   180
tattctggga ggcatctttc ggagttgaaa gctttggtgg taaaggatgg gcatgcgttg   240
tattagctag ttggtaaggt aacggcttac caaggcgacg atacataggg ggactgagag   300
gttaaccccc cacattggta ctgagacacg gaccaaactc ctacgggagg cagcagtgag   360
gaatattggt caatggacgg aagtctgaac cagccatgcc gcgtgcagga agacggctct   420
atgagttgta aactgctttt gtacgagggt aaacgcagat acgtgtatct gcctgaaagt   480
atcgtacgaa taaggatcgg ctaactccgt gccagcagcc gcggtaatac ggaggatcca   540
agcgttatcc ggatttattg ggtttaaagg gtgcgtaggc ggtttagtaa gtcagcggtg   600
```

```
aaattttggt gcttaacacc aaacgtgccg ttgatactgc tgggctagag agtagttgcg      660
gtaggcggaa tgtatggtgt agcggtgaaa tgcttagaga tcatacagaa caccgattgc      720
gaaggcagct taccaaacta tatctgacgt tgaggcacga aagcgtgggg agcaaacagg      780
attagatacc ctggtagtcc acgcagtaaa cgatgatagc tcgttgtcgg cgatacacag      840
tcggtgacta agagaaatcg ataagctatc cacctgggga gtacgttcgc aagaatgaaa      900
ctcaaaggaa ttgacggggg cccgcacaag cggaggaaca tgtggtttaa ttcgatgata      960
cgcgaggaac cttacccggg cttgaaagtt actgacgatt ctggaaacag gatttccctt     1020
cggggcagga aactaggtgc tgcatggttg tcgtcagctc gtgccgtgag gtgtcgggtt     1080
aagtcccata acgagcgcaa cccctactga tagttgccat cagagcgttt gagcgatcaa     1140
acaagctggg cactctatcg ggactgccgg tgtaagccga aggaaggtg  gggatgacgt     1200 caaatcagca cggcccttac gtccggggcg acacacgtgt acaatggta  ggtacagagg     1260 gcagccaccc agtgatgggg agcgaatctc gaaagcctat ctcagttcgg attggaggct     1320
gaaactcgcc tccatgaagt tggattcgct agtaatcgcg catcagccat ggcgcggtga     1380
atacgttccc gggccttgta cacaccgccc gtcaagccat gggagttggg ggtgcctgaa     1440
gttcgtgacc gaaaggagcg acctagggca aaaccgatga ctggggctaa gtcgtaacaa     1500
ggtagccgta ccggaaggtg cggctggaac acctcctttt                           1539

<210> SEQ ID NO 17
<211> LENGTH: 1525
<212> TYPE: DNA
<213> ORGANISM: Butyricicoccus sp.

<400> SEQUENCE: 17
tttagagagt ttgatcctgg ctcaggatga acgctggcgg cgtgcctaac acatgcaagt       60
cgaacggagt tattttggaa atctcttcgg agatggaatt cataactag  tggcggacgg      120 gtgagtaacg cgtgagcaat ctgcccttag gtggggg ata acagccggaa acggctgcta     180
ataccgcata acacattgaa gccgcatggc tttgatgtca agatttatt  gcctttggat      240 gagctcgcgt ctgattagct ggttggcggg gtaacgccc  accaaggcga cgatcagtag      300
ccggactgag aggttgaacg gccacattgg gactgagaca cggcccagac tcctacggga     360
ggcagcagtg gggaatattg cgcaatgggg gaaaccctga cgcagcaacg ccgcgtgatt     420
gaagaaggcc ttcgggttgt aaagatcttt aattggggac gaaaaatgac ggtacccaaa     480
gaataagctc cggctaacta cgtgccagca gccgcggtaa tacgtaggga gcaagcgtta     540
tccggattta ctgggtgtaa agggcgagta ggcgggctgg caagttggga gtgaaatccc     600
ggggcttaac cccggaactg ctttcaaaac tgctggtctt gagtgatgga gaggcaggcg     660
gaattccgtg tgtagcggtg aaatgcgtag atatacggag gaacaccagt ggcgaaggcg     720
gcctgctgga cattaactga cgctgaggag cgaaagcgtg gggagcaaac aggattagat     780
accctggtag tccacgccgt aaacgatgga tactaggtgt gggaggtatt gaccccttcc     840
gtgccggagt taacacaata agtatcccac ctggggagta cggccgcaag gttgaaactc     900
aaaggaattg acggggcccc gcacaagcag tggagtatgt ggtttaattc gaagcaacgc     960
gaagaacctt accaggtctt gacatccctc tgaccgccct agagatagg g tttcccttcg    1020 gggcagaggt gacaggtggt gcatggttgt cgtcagctcg tgtcgtgaga tgttgggtta    1080
agtcccgcaa cgagcgcaac ccttacggtt agttgatacg caagatcact ctagccggac    1140
```

-continued

| | |
|---|---|
| tgccgttgac aaaacggagg aaggtgggga cgacgtcaaa tcatcatgcc ccttatgacc | 1200 |
| tgggctacac acgtactaca atggcagtca tacagaggga agcaaaacag tgatgtggag | 1260 |
| caaatcccta aaagctgtcc cagttcagat tgcaggctgc aactcgcctg catgaagtcg | 1320 |
| gaattgctag taatcgcgga tcagcatgcc gcggtgaata cgttcccggg ccttgtacac | 1380 |
| accgcccgtc acaccatgag agccggtaat acccgaagtc cgtagcctaa ccgcaaggag | 1440 |
| ggcgcggccg aaggtaggac tggtaattag ggtgaagtcg taacaaggta gccgtatcgg | 1500 |
| aaggtgcggc tggatcacct cctt | 1525 |

<210> SEQ ID NO 18
<211> LENGTH: 1506
<212> TYPE: DNA
<213> ORGANISM: Gordonibacter urolithinfaciens

<400> SEQUENCE: 18

| | |
|---|---|
| acggagagtt tgatcctggc tcaggatgaa cgctggcggc gtgcctaaca catgcaagtc | 60 |
| gaacggttaa ggcgccttcg ggcgcgaata gagtggcgaa cggtgagta acacgtgacc | 120 |
| aacctgcccc cctccccggg ataacgcgag gaaacccgcg ctaataccgg atactccgcc | 180 |
| cctcccgcat gggagggggcg ggaaagcccc gacggaggg gatggggtcg cggcccatta | 240 |
| ggtagacggc gaggcaacgg cccaccgtgc ctgcgatggg tagccgggtt gagagaccga | 300 |
| ccggccacat tgggactgag atacggccca gactcctacg ggaggcagca gtggggaatt | 360 |
| ttgcgcaatg gggggaaccc tgacgcagca acgccgcgtg cgggacgaag gccttcgggt | 420 |
| tgtaaaccgc tttcagcagg gaagaagttg acggtacctg cagaagaagc cccggctaac | 480 |
| tacgtgccag cagccgcggt aatacgtagg gggcgagcgt tatccggatt cattgggcgt | 540 |
| aaagcgcgcg taggcggccc gtcaagcgga acctctaacc cgagggctca accccccggcc | 600 |
| gggttccgaa ctgcaggct cgagtttggt agaggaagat ggaattcccg gtgtagcggt | 660 |
| ggaatgcgca gatatcggga agaacaccga tggcgaaggc agtcttctgg gccatcaact | 720 |
| gacgctgagg cgcgaaagct gggggagcga acaggattag ataccctggt agtcccagcc | 780 |
| gtaaacgatg ggtgctaggt gtgggggggat catccctccg tgccgcagcc aacgcattaa | 840 |
| gcacccgcc tggggagtac ggccgcaagg ctaaaactca aaggaattga cgggggcccg | 900 |
| cacaagcagc ggagcatgtg gcttaattcg aagcaacgcg aagaaccta ccagggcttg | 960 |
| acatgctggt gaagccgggg aaacccggtg gccgagagga gccagcgcag gtggtgcatg | 1020 |
| gctgtcgtca gctcgtgtcg tgagatgttg ggttaagtcc cgcaacgagc gcaaccctg | 1080 |
| ccatatgttg ccagcattca gttggggact catatgggac tgccggcgtc aagccggagg | 1140 |
| aaggtgggga cgacgtcaag tcatcatgcc ctttatgccc tgggctgcac acgtgctaca | 1200 |
| atggccggta caacgggccg cgacctggcg acaggaagcg aatccctcaa agccggcccc | 1260 |
| agttcggatc ggaggctgca acccgcctcc gtgaagtcgg agttgctagt aatcgcggat | 1320 |
| cagcatgccg cggtgaatac gttcccgggc cttgtacaca ccgcccgtca caccaccga | 1380 |
| gtcgtctgca cccgaagccg ccggccgaac ccgcaagggg cggaggcgtc gaaggtgtgg | 1440 |
| agggtaaggg gggtgaagtc gtaacaaggt agccgtaccg gaaggtgcgg ctggatcacc | 1500 |
| tcctt | 1506 |

<210> SEQ ID NO 19
<211> LENGTH: 1528
<212> TYPE: DNA
<213> ORGANISM: Blautia sp.

<400> SEQUENCE: 19

```
tcagagagtt tgatcctggc tcaggatgaa cgctggcggc gtgcttaaca catgcaagtc      60
gagcgaagca cttgccattg actcttcgga agatttggca tttgactgag cggcggacgg     120
gtgagtaacg cgtgggtaac ctgcctcata caggggaata acagttagaa atggctgcta     180
atgccgcata agcgcacagg accgcatggt ctggtgtgaa aaactgaggt ggtatgagat     240
gggcccgcgt ctgattaggt agttggcggg gtaacggccc accaagccga cgatcagtag     300
ccgacctgag agggtgaccg gccacattgg gactgagaca cggcccagac tcctacggga     360
ggcagcagtg gggaatattg cacaatggag gaaactctga tgcagcgacg ccgcgtgaag     420
gaagaagtat ctcggtatgt aaacttctat cagcagggaa gaaaatgacg gtacctgact     480
aagaagcccc ggctaactac gtgccagcag ccgcggtaat acgtagggg caagcgttat     540
ccggatttac tgggtgtaaa gggagcgtag acggacgggc aagtctgatg tgaaagcccg     600
gggcttaacc ccgggactgc attggaaact gtccatcttg agtgccggag aggtaagcgg     660
aattcctagt gtagcggtga aatgcgtaga tattaggagg aacaccagtg gcgaaggcgg     720
cttactggac ggtaactgac gttgaggctc gaaagcgtgg ggagcaaaca ggattagata     780
ccctggtagt ccacgccgta aacgatgaat actaggtgtc gggttgcaaa gcaatccggt     840
gccgcagcaa acgcagtaag tattccacct ggggagtacg ttcgcaagaa tgaaactcaa     900
aggaattgac ggggacccgc acaagcggtg gagcatgtgg tttaattcga agcaacgcga     960
agaaccttac caagtcttga catctgcctg accgttcctt aaccggaact ttccttcggg    1020
acaggcaaga caggtggtgc atggttgtcg tcagctcgtg tcgtgagatg ttgggttaag    1080
tcccgcaacg agcgcaaccc ctgtccttag tagccagcag tccggctggg cactctaggg    1140
agactgccgg ggataacccg gaggaaggcg gggacgacgt caaatcatca tgccccttat    1200
gatttgggct acacacgtgc tacaatggcg taaacaaagg gaagcggagt ggtgacactg    1260
agcaaatctc aaaaataacg tcccagttcg gactgcagtc tgcaactcga ctgcacgaag    1320
ctggaatcgc tagtaatcgc gaatcagaat gtcgcggtga atacgttccc gggtcttgta    1380
cacaccgccc gtcacaccat gggagtcagt aacgcccgaa gtcagtgacc taaccgcaag    1440
ggaggagctg ccgaaggcgg gaccgataac tggggtgaag tcgtaacaag gtagccgtat    1500
cggaaggtgc ggctggatca cctcctttt                                      1528
```

<210> SEQ ID NO 20
<211> LENGTH: 1530
<212> TYPE: DNA
<213> ORGANISM: Lachnospira sp.

<400> SEQUENCE: 20

```
ttatgagagt ttgatcctgg ctcaggatga acgctggcgg cgtgcttaac acatgcaagt      60
cgaacgaagc atttaagacg gattctttcg ggatgaagac ttttatgact gagtggcgga    120
cgggtgagta acgcgtgggt aacctgcctc acacaggggg atagcagttg gaaacggctg    180
ataataccgc ataagcgcac agtaccgcat ggtacagtgt gaaaaactcc ggtggtgtga    240
gatgaccccg cgtctgatta gcttgttggc agggtaacgg cctaccaagg caacgatcag    300
tagccgacct gagagggtga ccggccacat tgggactgag acacggccca gactcctacg    360
ggaggcagca gtgggaata ttgcacaatg gaggaaactc tgatgcagcg acgccgcgtg    420
agtgaagaag taattcgtta tgtaaagctc tatcagcagg gaagatagtg acggtacctg    480
```

```
actaagaagc tccggctaaa tacgtgccag cagccgcggt aatacgtatg gagcaagcgt    540
tatccggatt tactgggtgt aaagggagtg taggtggcat cacaagtcag aagtgaaagc    600
ccggggctca accccgggac tgcttttgaa actgtggagc tggagtgcag gagaggcaag    660
tggaattcct agtgtagcgg tgaaatgcgt agatattagg aggaacacca gtggcgaagg    720
cggcttgctg gactgtaact gacactgagg ctcgaaagcg tggggagcaa acaggattag    780 atacccctggt agtccacgcc gtaaacgatg aatactaggt gtcggggctc ataagagctt    840
cggtgccgca gcaaacgcaa taagtattcc acctggggag tacgttcgca agaatgaaac    900
tcaaaggaat tgacggggac ccgcacaagc ggtggagcat gtggtttaat tcgaagcaac    960
gcgaagaacc ttaccaagtc ttgacatcct cttgcccggt cagtaatgtg acctttctct    1020
cggaacaaga gtgacaggtg gtgcatggtt gtcgtcagct cgtgtcgtga tgttgggt     1080 taagtcccgc aacgagcgca accctattc ttagtagcca gcatataagg tgggcactct    1140
aggaagactg ccagggataa cctggaggaa ggtgggatg acgtcaaatc atcatgcccc    1200
ttatgacttg ggctacacac gtgctacaat ggcgtaaaca aagtgaagcg agagtgtgag    1260
cttaagcaaa tcacaaaaat aacgtctcag ttcggattgt agtctgcaac tcgactacat    1320
gaagctggaa tcgctagtaa tcgcgaatca gaatgtcgcg gtgaatacgt tcccgggtct    1380
tgtacacacc gcccgtcaca ccatgggagt cggaaatgcc cgaagtcggt gacctaacga    1440
aagaaggagc cgccgaaggc aggtctgata actggggtga agtcgtaaca aggtagccgt    1500
atcggaaggt gcggctggat cacctccttt                                   1530

<210> SEQ ID NO 21
<211> LENGTH: 1527
<212> TYPE: DNA
<213> ORGANISM: Eisenbergiella sp.
<220> FEATURE:
<221> NAME/KEY: misc_feature
<223> OTHER INFORMATION: R=A or G, Y=C or T

<400> SEQUENCE: 21
agagagtttg atcctggctc aggatgaacg ctggcggcgt gcctaacaca tgcaagtcga    60
acggagttat gcagaggaag ttttcggatg gaatcggcgt aacttagtgg cggacgggtg    120
agtaacgcgt gggaaacctg ccctgtaccg ggggataaca cttagaaata ggtgctaata    180
ccgcataagc gcacagcttc acatgargca gtgtgaaaaa ctccggtggt acaggatggt    240
cccgcgtctg attagccagt tggcagggta ayggcctacc aaagcgacga tcagtagccg    300
gcctgagagg gtgaacggcc acattgggac tgagacacgg cccaaactcc tacgggaggc    360
agcagtgggg aatattgcac aatggggaa accctgatgc agcgacgccg cgtgagtgaa    420
gaagtatttc ggtatgtaaa gctctatcag caggaagaa aatgacgta cctgactaag    480 aagccccggc taactacgtg ccagcagccg cggtaatacg taggggcaa gcgttatccg    540 gatttactgg gtgtaaaggg agcgtagacg gcatgacaag ccagatgtga aacccaggg    600 ctcaaccctg ggactgcatt tggaactgcc aggctggagt gcaggagagg taagcggaat    660
tcctagtgta gcggtgaaat gcgtagatat taggaggaac accagtggcg aaggcggctt    720
actggactgt aactgacgtt gaggctcgaa agcgtgggga gcaaacagga ttagataccc    780
tggtagtcca cgccggtaaac gatgattgct aggtgtaggt gggtatggac ccatcggtgc    840
cgcagctaac gcaataagca atccacctgg ggagtacgtt cgcaagaatg aaactcaaag    900
gaattgacgg ggacccgcac aagcggtgga gcatgtggtt taattcgaag caacgcgaag    960
```

```
aaccttacca agtcttgaca tcccaatgac gtgtccgtaa cggggcattc tcttcggagc      1020
attggagaca ggtggtgcat ggttgtcgtc agctcgtgtc gtgagatgtt gggttaagtc      1080
ccgcaacgag cgcaacccct tatccttagta gccagcaggt aragctgggc actctaggga     1140
gactgccggg gataacccgg aggaaggcgg ggaygacgtc aaatcatcat gccccttatg      1200
atttgggcta cacacgtgct acaatggcgt aaacaaaggg aagcgagaca gtgatgttga      1260
gcaaatccca gaaataacgt ctcagttcgg attgtagtct gcaactcgac tacatgaagc      1320
tggaatcgct agtaatcgcg aatcagcatg tcgcggtgaa tacgttcccg ggtcttgtac      1380
acaccgcccg tcacaccatg ggagttggaa atgcccgaag cctgtgacct aaccgcaagg      1440
gaggagcagt cgaaggcagg tctaataact ggggtgaagt cgtaacaagg tagccgtatc      1500
ggaaggtgcg gctggatcac ctcctttt                                         1527
```

<210> SEQ ID NO 22
<211> LENGTH: 1525
<212> TYPE: DNA
<213> ORGANISM: Butyricicoccus sp.
<220> FEATURE:
<221> NAME/KEY: misc_feature
<223> OTHER INFORMATION: W=A or T

<400> SEQUENCE: 22

```
tttagagagt ttgatcctgg ctcaggatga acgctggcgg cgtgcctaac acatgcaagt       60
cgaacggagt tattttggaa atctcttcgg ggatggaatt cataacttag tggcggacgg      120
gtgagtaacg cgtgagcaat ctgcccttag gtggggata acagccggaa acggctgcta       180
ataccgcata acacattgaa gccgcatggt tttgatgtca aagatttatt gcctttggat      240
gagctcgcgt ctgattagct ggttggcggg gtaacggccc accaaggcga cgatcagtag      300
ccggactgag aggttgaacg gccacattgg gactgagaca cggcccagac tcctacggga      360
ggcagcagtg gggaatattg cgcaatgggg gaaaccctga cgcagcaacg ccgcgtgatt      420
gaagaaggcc ttcggggttgt aaagatcttt aattgggggac gaawwwtgac ggtacccaaa    480
gaataagctc cggctaacta cgtgccagca gccgcggtaa tacgtaggga gcaagcgtta      540
tccggattta ctgggtgtaa agggcgagta ggcgggctgg caagttggga gtgaaatccc      600
ggggcttaac cccggaactg ctttcaaaac tgctggtctt gagtgatgga gaggcaggcg      660
gaattccgtg tgtagcggtg aaatgcgtag atatacggag gaacaccagt ggcgaaggcg      720
gcctgctgga cattaactga cgctgaggag cgaaagcgtg gggagcaaac aggattagat      780
accctggtag tccacgccgt aaacgatgga tactaggtgt gggaggtatt gaccccttcc      840
gtgccggagt taacacaata agtatcccac ctggggagta cggccgcaag gttgaaactc      900
aaaggaattg acgggggccc gcacaagcag tggagtatgt ggtttaattc gaagcaacgc      960
gaagaacctt accaggtctt gacatccctc tgaccgccct agagataggg tttcccttcg     1020
gggcagaggt gacaggtggt gcatggttgt cgtcagctcg tgtcgtgaga tgttgggtta     1080
agtcccgcaa cgagcgcaac ccttacggtt agttgatacg aaagatcact ctagccggac     1140
tgccgttgac aaaacggagg aaggtgggga cgacgtcaaa tcatcatgcc cttatgacc      1200 tgggctacac acgtactaca atggcagtca tacagaggga agcaaaacag tgatgtggag     1260
caaatcccta aaagctgtcc cagttcagat gcaggctgc aactcgcctg catgaagtcg      1320
gaattgctag taatcgcgga tcagcatgcc gcggtgaata cgttcccggg ccttgtacac     1380
accgcccgtc acaccatgag agccggtaat acccgaagtc cgtagcctaa ccgcaaggag     1440
```

```
ggcgcggccg aaggtaggac tggtaattag ggtgaagtcg taacaaggta gccgtatcgg    1500
aaggtgcggc tggatcacct cctttt                                        1525

<210> SEQ ID NO 23
<211> LENGTH: 1506
<212> TYPE: DNA
<213> ORGANISM: Gordonibacter urolithinfaciens
<220> FEATURE:
<221> NAME/KEY: misc_feature
<223> OTHER INFORMATION: R=A or G, Y=C or T

<400> SEQUENCE: 23
acggagagtt tgatcctggc tcaggatgaa cgctggcggc gtgcctaaca catgcaagtc      60
gaacggttaa ggcgccttcg ggcgcgaata gagtggcgaa cgggtgagta acacgtgacc     120
aacctgcccc cctccccggg ataacgcgag gaaacccgcg ctaataccgg atactccgcc     180
cctcccgcat gggaggggcg ggaaagcccc gacggagggg gatggggtcg cggcccatta     240
ggtagacggc gggggcaacgg cccaccgtgc ctgcgatggg tagccgggtt gagagaccga     300
ccggccacat tgggactgag atacggccca gactcctacg ggaggcagca gtggggaatt     360
ttgcgcaatg gggggaaccc tgacgcagca acgccgcgtg cgggacgaag gccttcgggt     420
tgtaaaccgc tttcagcagg gaagaagttg acggtacctg cagaagaagc cccggctaac     480
tacgtgccag cagccgcggt aatacgtagg gggcgagcgt tatccggatt cattgggcgt     540
aaagcgcgcg taggcggccc gtcaagcgga acctctaacc cgagggctca accccggcc     600 gggttccgaa ctgcaggct cgagtttggt agaggaagat ggaattcccg gtgtagcggt     660
ggaatgcgca gatatcggga agaacaccga tggcgaaggc agtcttctgg gccatcaact     720
gacgctgagg cgcgaaagct gggggagcga acaggattag ataccctggt agtcccagcc     780
gtaaacgatg ggygctaggt gtgggggggat catccctccg tgccgcagcc aacgcattaa     840
gcrccccgcc tggggagtac ggccgcaagg ctaaaactca aaggaattga cgggggcccg     900
cacaagcagc ggagcatgtg gcttaattcg aagcaacgcg aagaacctta ccagggcttg     960
acatgctggt gaagccgggg aaacccggtg gccgagagga gccagcgcag gtggtgcatg    1020
gctgtcgtca gctcgtgtcg tgagatgttg ggttaagtcc cgcaacgagc gcaacccctg    1080
ccatatgttg ccagcattca gttggggact catatgggac tgccggcgtc aagccggagg    1140
aaggtgggga cgacgtcaag tcatcatgcc ctttatgccc tgggctgcac acgtgctaca    1200
atggccggta caacgggccg cgacctggcg acaggaagcg aatccctcaa agccggcccc    1260
agttcggatc ggaggctgca acccgcctcc gtgaagtcgg agttgctagt aatcgcggat    1320
cagcatgccg cggtgaatac gttcccgggc cttgtacaca ccgcccgtca ccacccga     1380 gtcgtctgca cccgaagccg ccggccgaac ccgcaagggg cggaggcgtc gaaggtgtgg    1440
agggtaaggg gggtgaagtc gtaacaaggt agccgtaccg gaaggtgcgg ctggatcacc    1500
tcctttt                                                             1506

<210> SEQ ID NO 24
<211> LENGTH: 1535
<212> TYPE: DNA
<213> ORGANISM: Faecalitalea sp.

<400> SEQUENCE: 24
atggagagtt tgatcctggc tcaggatgaa cgctggcggc atgcctaata catgcaagtc      60
gaacgaagtc tttaggaagc ttgcttccaa agagacttag tggcgaacgg gtgagtaaca     120
```

```
cgtaggtaac ctgcccatgt gcccgggata actgctggaa acggtagcta aaaccggata      180
ggtatgaggg aggcatcttc ctcatattaa agcaccttcg ggtgtgaaca tggatggacc      240
tgcggcgcat tagctggttg gtgaggtaac ggcccaccaa ggcgatgatg cgtagccgac      300
ctgagagggt gaacggccac attgggactg agacacggcc caaactccta cgggaggcag      360
cagtagggaa ttttcgtcaa tggggggaac cctgaacgag caatgccgcg tgtgtgaaga      420
aggtcttcgg atcgtaaagc actgttgtaa gtgaagaatg ccatatagag gaaatgctat      480
gtgggtgacg gtagcttacc agaaagccac ggctaactac gtgccagcag ccgcggtaat      540
acgtaggtgg caagcgttat ccggaatcat tgggcgtaaa gggtgcgtag gtggcacgat      600
aagtctgaag taaaaggcaa cagctcaact gttgtatgct ttggaaactg tcgagctaga      660
gtgcagaaga gggcgatgga attccatgtg tagcggtaaa atgcgtagat atatggagga      720
acaccagtgg cgaaggcggt cgcctggtct gtaactgaca ctgatgcacg aaagcgtggg      780
gagcaaatag gattagatac cctagtagtc cacgccgtaa acgatgagaa ctaagtgttg      840
gagagattca gtgctgcagt taacgcaata agttctccgc ctggggagta tgcacgcaag      900
tgtgaaactc aaaggaattg acgggggccc gcacaagcgg tggagtatgt ggtttaattc      960
gaagcaacgc gaagaacctt accaggcctt gacatggata taaatgttct agagatagaa     1020
agatagctat atatcacaca ggtggtgcat ggttgtcgtc agctcgtgtc gtgagatgtt     1080
gggttaagtc ccgcaacgag cgcaaccctt gtcttctgtt accagcatta agttgggac      1140 tcaggagaga ctgccggtga caaaccggag gaaggtgggg atgacgtcaa atcatcatgc     1200
cccttatggc ctgggctaca cacgtactac aatggcgcct acaaagagca gcgacaccgc     1260
gaggtggagc gaatctcata aagggcgtct cagttcggat tgaagtctgc aactcgactt     1320
catgaagtcg gaatcgctag taatcgcaga tcagcatgct gcggtgaata cgttctcggg     1380
ccttgtacac accgcccgtc aaaccatggg agttggtaat acccgaagcc ggtggcataa     1440
ccgcaaggag tgagccgtcg aaggtaggac cgatgactgg ggttaagtcg taacaaggta     1500
tccctacggg aacgtgggga tggatcacct ccttt                                 1535
```

<210> SEQ ID NO 25
<211> LENGTH: 1530
<212> TYPE: DNA
<213> ORGANISM: Blautia sp.
<220> FEATURE:
<221> NAME/KEY: misc_feature
<223> OTHER INFORMATION: M=A or C, R=A or G, Y=C or T, K=G or T, W=A or T

<400> SEQUENCE: 25

```
tcagagagtt tgatcctggc tcaggatgaa cgctggcggc gtgcttaaca catgcaagtc       60
gagcgaagcr cttraryggd tctcttcgga ttgaaryttw tktgactgag cggcggacgg      120
gtgagtaacg cgtgggtaac ctgcctcata caggggdata acagttagaa atggctgcta     180
ataccgcata agcgcacagg accgcatggt ctggtgtgaa aaactccggt ggtatgagat     240
ggacccgcgt ctgattagct agttggaggg gtaacggccc accaaggcga cgatcagtag     300
ccggcctgag agggtgaacg gccacattgg gactgagaca cggcccagac tcctacggga     360
ggcagcagtg gggaatattg cacaatgggg gaaaccctga tgcagcgacg ccgcgtgaag     420
gaagaagtat ctcggtatgt aaacttctat cagcagggaa gaaaatgacg gtacctgact     480
aagaagcccc ggctaactac gtgccagcag ccgcggtaat acgtaggggg caagcgttat     540
ccggatttac tgggtgtaaa gggagcgtag acggaagagc aagtctgatg tgaaaggctg     600
```

```
gggcttaacc ccaggactgc attggaaact gttttctag agtgccggag aggtaagcgg        660
aattcctagt gtagcggtga aatgcgtaga tattaggagg aacaccagtg gcgaaggcgg        720
cttactggac ggtaactgac gttgaggctc gaaagcgtgg ggagcaaaca ggattagata       780
ccctggtagt ccacgccgta aacgatgaat actaggtgtc gggtggcaaa gccattcggt        840
gccgcagcaa acgcaataag tattccacct ggggagtacg ttcgcaagaa tgaaactcaa        900
aggaattgac ggggacccgc acaagcggtg gagcatgtgg tttaattcga agcaacgcga        960
agaaccttac caagtcttga catccctctg accggcccgt aacggggcct cccttcggg       1020 gcagaggaga caggtggtgc atggttgtcg tcagctcgtg tcgtgagatg ttgggttaag       1080
tcccgcaacg agcgcaaccc ctatccttag tagccagcag gtrragctgg gcactctagg       1140
gagactgccg gggataaccc ggaggaaggc ggggacgacg tcaaatcatc atgcccctta       1200
tgatttgggc tacacacgtg ctacaatggc gtaaacaaag ggaagcgaga cagcgatgtt       1260
gagcaaatcc caaaaataac gtcccagttc ggactgcagt ctgcaactcg actgcacgaa       1320
gctggaatcg ctagtaatcg cgaatcagaa tgtcgcggtg aatacgttcc cgggtcttgt       1380
acacaccgcc cgtcacacca tgggagtcag taacgcccga agtcagtgac ccaaccttay       1440
aggagggagc tgccgaaggc gggaccgata actggggtga agtcgtaaca aggtagccgt       1500
atcggaaggt gcggctggat cacctccttt                                        1530

<210> SEQ ID NO 26
<211> LENGTH: 1528
<212> TYPE: DNA
<213> ORGANISM: Barnesiella intestinihominis
<220> FEATURE:
<221> NAME/KEY: misc_feature
<223> OTHER INFORMATION: R=A or G, Y=C or T

<400> SEQUENCE: 26
cgaagagttt gatcctggct caggatgaac gctagcgaca ggcctaacac atgcaagtcg         60
aggggcagcg grgaggyagc aataccttg ccggcgaccg gcgcacgggt gagtaacacg        120
tatgcaatcc acctgtaaca gggggataac ccggagaaat ccggactaat accccataat       180
atgggcgctc cgcatggagr gtccattaaa gagagcaatt ttggttacag acgagcatgc        240
gctccattag ccagttggcg gggtaacggc ccaccaaagc gacgatggat aggggttctg       300
agaggaaggt cccccacatt ggaactgaga cacggtccaa actcctacgg gaggcagcag        360
tgaggaatat tggtcaatgg tcggcagact gaaccagcca agtcgcgtga gggaagacgg        420
ccctacgggt tgtaaacctc ttttgtcgga gagtaaagtr cgctacgtgt agygtattgc        480
aagtatccga agaaaaagca tcggctaact ccgtgccagc agccgcggta atacggagga       540
tgcgagcgtt atccggattt attgggttta aagggtgcgt aggcggcacg ccaagtcagc        600
ggtgaaattt ccgggctcaa cccggactgt gccgttgaaa ctggcgagct agagtgcaca        660
agaggcaggc ggaatgcgtg gtgtagcggt gaaatgcata gatatcacgc agaacccga        720 ttgcgaaggc agcctgctag ggtgcgacag acgctgaggc acgaaagcgt gggtatcgaa        780
caggattaga taccctggta gtccacgcag taaacgatga atactaactg tttgcgatac       840
aatgtaagcg gtacagcgaa agcgttaagt attccacctg gggagtacgc cggcaacggt       900
gaaactcaaa ggaattgacg ggggcccgca caacggagg acatgtggt ttaattcgat       960 gatacgcgag gaaccttacc cgggctcaaa cgcaggggga atgccggtga agtcggcag       1020 ctagcaatag tcacctgcga ggtgctgcat ggttgtcgtc agctcgtgcc gtgaggtgtc       1080
```

```
ggcttaagtg ccataacgag cgcaacccct atggacagtt actaacgggt gaagccgagg   1140
actctgtcta gactgccggc gcaagccgcg aggaaggtgg ggatgacgtc aaatcagcac   1200
ggcccttacg tccggggcga cacacgtgtt acaatggcag gtacagaagg cagccagtca   1260
gcaatgacgc gcgaatcccg aaaacctgtc tcagttcgga ttggagtctg caacccgact   1320
ccatgaagct ggattcgcta gtaatcgcgc atcagccatg gcgcggtgaa tacgttcccg   1380
ggccttgtac acaccgcccg tcaagccatg gaagccggga gtacctgaag catgcaaccg   1440
caaggagcgt acgaaggtaa taccggtaac tggggctaag tcgtaacaag gtagccgtac   1500
cggaaggtgc ggctggaaca cctcctttt                                    1528
```

<210> SEQ ID NO 27
<211> LENGTH: 1528
<212> TYPE: DNA
<213> ORGANISM: Blautia sp.
<220> FEATURE:
<221> NAME/KEY: misc_feature
<223> OTHER INFORMATION: M=A or C, R=A or G, Y=C or T, K=G or T, S=G or C

<400> SEQUENCE: 27

```
tcagagagtt tgatcctggc tcaggatgaa cgctggcggc gtgcttaaca catgcaagtc   60
gagcgaagca cttryyattg amtcttcgga rgatttrgca tktgactgag cggcggacgg   120
gtgagtaacg cgtgggtaac ctgcctcata caggggaata acagttagaa atggctgcta   180
atgccgcata agcgcacagg rccgcatggt cyggtgtgaa aaactsmggt ggtatgagat   240
ggrcccgcgt ctgattaggt agttggcggg gtaacggccc accaagccga cgatcagtag   300
ccgacctgag agggtgaccg gccacattgg gactgagaca cggcccagac tcctacggga   360
ggcagcagtg gggaatattg cacaatggag gaaactctga tgcagcgacg ccgcgtgaag   420
gaagaagtat ctcggtatgt aaacttctat cagcagggaa gaaaatgacg gtacctgact   480
aagaagcccc ggctaactac gtgccagcag ccgcggtaat acgtaggggg caagcgttat   540
ccggatttac tgggtgtaaa gggagcgtag acggacgggc aagtctgatg tgaaagcccg   600
gggcttaacc ccgggactgc attggaaact gtccatcttg agtgccggag aggtaagcgg   660
aattcctagt gtagcggtga aatgcgtaga tattaggagg aacaccagtg gcgaaggcgg   720
cttactggac ggtaactgac gttgaggctc gaaagcgtgg ggagcaaaca ggattagata   780
ccctggtagt ccacgccgta aacgatgaat actaggtgtc gggttgcaaa gcaatccggt   840
gccgcagcaa acgcagtaag tattccacct ggggagtacg ttcgcaagaa tgaaactcaa   900
aggaattgac ggggacccgc acaagcggtg gagcatgtgg tttaattcga agcaacgcga   960
agaaccttac caagtcttga catctgcctg accgttcctt aaccggaact tccttcggg    1020 acaggcaaga caggtggtgc atggttgtcg tcagctcgtg tcgtgagatg ttgggttaag   1080
tcccgcaacg agcgcaaccc ctgtccttag tagccagcag tccggctggg cactctaggg   1140
agactgccgg ggataacccg gaggaaggcg gggacgacgt caaatcatca tgccccttat   1200
gatttgggct acacacgtgc tacaatggcg taaacaaagg gaagcggagt ggtgacactg   1260
agcaaatctc aaaaataacg tcccagttcg gactgcagtc tgcaactcga ctgcacgaag   1320
ctggaatcgc tagtaatcgc gaatcagaat gtcgcggtga atacgttccc gggtcttgta   1380
cacaccgccc gtcacaccat gggagtcagt aacgcccgaa gtcagtgacc taaccgcaag   1440
ggaggagctg ccgaaggcgg gaccgataac tggggtgaag tcgtaacaag gtagccgtat   1500
```

```
cggaaggtgc ggctggatca cctcctttt                                      1528
```

<210> SEQ ID NO 28
<211> LENGTH: 1530
<212> TYPE: DNA
<213> ORGANISM: Lachnospira sp.
<220> FEATURE:
<221> NAME/KEY: misc_feature
<223> OTHER INFORMATION: M=A or C, R=A or G, Y=C or T, W=A or T

<400> SEQUENCE: 28

```
ttatgagagt ttgatcctgg ctcaggatga acgctggcgg cgtgcttaac acatgcaagt      60
cgaacgaagc atttgmgacr gattyyttcg grwtgaagac ttttatgact gagtggcgga     120
cgggtgagta acgcgtgggt aacctgcctc acacaggggg atagcagttg aaacggctg      180
ataataccgc ataagcgcac agtaccgcat ggtacagtgt gaaaaactcc ggtggtgtga     240
gatggacccg cgtctgatta gcttgttggc rgggtaacgg ccyaccaagg caacgatcag     300
tagccgacct gagagggtga ccggccacat tgggactgag acacggccca gactcctacg     360
ggaggcagca gtggggaata ttgcacaatg gaggaaactc tgatgcagcg acgccgcgtg     420
agtgaagaag taattcgtta tgtaaagctc tatcagcagg gaagatagtg acggtacctg     480
actaagaagc tccggctaaa tacgtgccag cagccgcggt aatacgtatg gagcaagcgt     540
tatccggatt tactgggtgt aaagggagtg taggtggcat cacaagtcag aagtgaaagc     600
ccggggctca accccgggac tgcttttgaa actgtggagc tggagtgcag gagaggcaag     660
tggaattcct agtgtagcgg tgaaatgcgt agatattagg aggaacacca gtggcgaagg     720
cggcttgctg gactgtaact gacactgagg ctcgaaagcg tggggagcaa acaggattag     780
ataccctggt agtccacgcc gtaaacgatg aatactaggt gtcggggctc ataagagctt     840
cggtgccgca gcaaacgcaa taagtattcc acctggggag tacgttcgca agaatgaaac     900
tcaaaggaat tgacgggac ccgcacaagc ggtggagcat gtggtttaat tcgaagcaac     960
gcgaagaacc ttaccaagtc ttgacatcct cttgrccggt cagtaatgtg rycttttctt    1020
cggaacaaga gtgacaggtg gtgcatggtt gtcgtcagct cgtgtcgtga gatgttgggt    1080
taagtcccgc aacgagcgca acccctattc ttagtagcca gcatttaagr tgggcactct    1140
aggaagactg ccagggataa cctggaggaa ggtgggatg acgtcaaatc atcatgcccc    1200
ttatgacttg ggctacacac gtgctacaat ggcgtaaaca aagtgaagcg agagtgtgag    1260
cttaagcaaa tcacaaaaat aacgtctcag ttcggattgt agtctgcaac tcgactacat    1320
gaagctggaa tcgctagtaa tcgcgaatca gaatgtcgcg gtgaatacgt tcccgggtct    1380
tgtacacacc gcccgtcaca ccatgggagt cggaaatgcc cgaagtcggt gacctaacga    1440
aagaaggagc cgccgaaggc aggtctgata actggggtga agtcgtaaca aggtagccgt    1500
atcggaaggt gcggctggat cacctccttt                                    1530
```

<210> SEQ ID NO 29
<211> LENGTH: 1530
<212> TYPE: DNA
<213> ORGANISM: Roseburia faecis
<220> FEATURE:
<221> NAME/KEY: misc_feature
<223> OTHER INFORMATION: R=A or G, Y=C or T, S=G or C

<400> SEQUENCE: 29

```
atgagagttt gatcctggct caggatgaac gctggcggcg tgcttaacac atgcaagtcg      60
aacgaagcac tctatttgat tttcttcggr aatgaagatt ttgtgactga gtggcggacg     120
```

```
ggtgagtaac gcgtgggtaa cctgcctcat acagggggat aacagttgga aacgactgct    180
aataccgcat aagcgcacag gatygcatgr tccggtgtga aaaactccgg tggtatgrga    240
tggacccgcg tctgattagc cagttggcag ggtaacggcc taccaaagcg acgatcagta    300
gccgacctga gagggtgacc ggccacattg ggactgagac acggcccaaa ctcctacggg    360
aggcagcagt ggggaatatt gcacaatggg ggaaaccctg atgcagcgac gccgcgtgag    420
cgaagaagta tttcggtatg taaagctcta tcagcaggga agaagaatga cggtacctga    480
ctaagaagca ccggctaaat acgtgccagc agccgcggta atacgtatgg tgcaagcgtt    540
atccggattt actgggtgta aagggagcgc aggcggtgcg gcaagtctga tgtgaaagcc    600
cggggctcaa ccccggtact gcattggaaa ctgtcgtact agagtgtcgg aggggtaagt    660
ggaattccta gtgtagcggt gaaatgcgta gatattagga ggaacaccag tggcgaaggc    720
ggcttactgg acgataactg acgctgaggc tcgaaagcgt ggggagcaaa caggattaga    780
taccctggta gtccacgccg taaacgatga atactaggtg tcggggagca ttgctcttcg    840
gtgccgcagc aaacgcaata agtattccac ctggggagta cgttcgcaag aatgaaactc    900
aaaggaattg acggggaccc gcacaagcgg tggagcatgt ggtttaattc gaagcaacgc    960
gaagaacctt accaagtctt gacatcccga tgacagagta tgtaatgtas yytcycttcg   1020
grgcatcggt gacaggtggt gcatggttgt cgtcagctcg tgtcgtgaga tgttgggtta   1080
agtcccgcaa cgagcgcaac ccctgtyctt agtagccagc ggttcggccg ggcactctag   1140
ggagactgcc agggataacc tggaggaagg cggggatgac gtcaaatcat catgccctt    1200 atgacttggg ctacacacgt gctacaatgg cgtaaacaaa gggaagcrra gccgtgaggc   1260
cgagcaaatc tcaaaaataa cgtctcagtt cggactgtag tctgcaaccc gactacacga   1320
agctggaatc gctagtaatc gcagatcaga atgctgcggt gaatacgttc ccgggtcttg   1380
tacacaccgc ccgtcacacc atgggagttg gaaatgcccg aagtcagtga cccaaccgca   1440
aggagggagc tgccgaaggc aggttcgata actggggtga agtcgtaaca aggtagccgt   1500
atcggaaggt gcggctggat cacctccttt                                    1530
```

```
<210> SEQ ID NO 30
<211> LENGTH: 20
<212> TYPE: DNA
<213> ORGANISM: Artificial Sequence
<220> FEATURE:
<223> OTHER INFORMATION: primer sequence
<220> FEATURE:
<221> NAME/KEY: misc_feature
<223> OTHER INFORMATION: M=A or C

<400> SEQUENCE: 30
agagtttgat ymtggctcag                                                20

<210> SEQ ID NO 31
<211> LENGTH: 21
<212> TYPE: DNA
<213> ORGANISM: Artificial Sequence
<220> FEATURE:
<223> OTHER INFORMATION: primer sequence

<400> SEQUENCE: 31
acggytacct tgttacgact t                                              21
```

BACTERIAL BIOMARKER

STATEMENT REGARDING ELECTRONIC FILING OF A SEQUENCE LISTING

A Sequence Listing in ASCII text format, submitted under 37 C.F.R. § 1.821, entitled 1553-11 Sequence_ST25.txt, 62,305 bytes in size, generated on May 18, 2021 and flied via EFS-Web, Is provided in lieu of a paper copy. This Sequence Listing is hereby incorporated herein by reference into the specification for its disclosure.

INTRODUCTION

Immune suppression and evasion by malignant cancer cells is known as one of the hallmarks of cancer. A number of co-inhibitory receptors and their ligands, known as immune checkpoints, contribute to this process. Immune checkpoint inhibitor cancer immunotherapies have been transformational in cancer management in that they can lead to long-term remission and they can be effective across many cancers. Among these checkpoints are programmed cell death 1 (PD-1), PD-L1 and CTLA-4. The introduction of PD-1 inhibitors into clinical practice has had a revolutionary effect on cancer treatment, but consistent responses and favourable long-term outcomes are only observed in a fraction of patients. The majority of patients do not respond to therapy. The highest proportion is for melanoma (reaching 40%), but it is much lower for the other cancers. Moreover, a significant number of patients develop immune-related adverse events and have to stop therapy.

Accordingly, there is a need for (a) biomarkers to predict response to immune checkpoint inhibitors and (b) approaches to increase the proportion of cancer patients that respond to therapy.

PD-1 (UniProt Accession No. Q15116, GenBank Accession No. U6488) protein is encoded by the PDCD1 gene and expressed as a 55 kDa type I transmembrane protein (Agata 1996 Int Immunol 8(5):785-72). PD-1 is an immunoglobulin superfamily member (Ishkia 1992 EMBO 11(11):3887-95) and it is an inhibitory member of the extended CD28/CTLA-4 family of T cell regulators. Other members of this family include CD28, CTLA-4, ICOS and BTLA. PD-1 exists as a monomer, lacking the unpaired cysteine residue characteristic of other CD28 family members (Zhang 2004 Immunity 20:337-47). Its cytoplasmic domain contains an immunoreceptor tyrosine-based inhibitory motif (ITIM) and an immunoreceptor tyrosine-based switch motif (ITSM) that are phosphorylated during signal transduction (Riley 2009 Immunol Rev 229(1):114-25).

PD-1 is expressed on B cells, T cells, and monocytes (Agata 1996). The role of PD-1 in maintaining immunologic self-tolerance was demonstrated in PDCD1−/− mice, which develop autoimmune disorders (Nishimura 1999 Immunity 11:141-51, Nishimura 2001 Science 291(5502):319-22). The PD-1 pathway therefore regulates antigen responses, balancing autoimmunity and tolerance.

There are two ligands for PD-1 that mediate its regulatory function. PD-L1 (B7-H1) is normally expressed on dendritic cells, macrophages, resting B cells, bone marrow-derived mast cells and T cells as well as non-hematopoietic cell lineages (reviewed in Francisco 2010 Immunol Rev 236:219-42). PD-L2 (B7-DC) Is largely expressed on dendritic cells and macrophages (Tseng 2001 J Exp Med 193(7):839-45). Ligand expression is influenced by local mediators and can be upregulated by inflammatory cytokines.

PD-1 is known as an immunoinhibitory protein that negatively regulates TCR signals. The interaction between PD-1 and PD-L1 can act as an immune checkpoint, which can lead to, e.g., a decrease in tumour infiltrating lymphocytes, a decrease in T-cell receptor mediated proliferation, and/or immune evasion by cancerous cells. Immune suppression can be reversed by inhibiting the local interaction of PD-1 with PD-L1 or PD-L2; the effect is additive when the interaction of PD-1 with both PD-L1 and PD-L2 is blocked.

The PD-1 pathway can be exploited in cancer or infection, whereby tumours or viruses can evade effective immune recognition and T cells demonstrate an 'exhausted' phenotype.

Disruption of the PD-1:PD-L1 interaction enhances T cell activity. Inhibitory anti-PD-1 monoclonal antibodies demonstrate blockade of the interaction between PD-1 and its ligands (Wang 2014 Cancer Immunol Res 2(9):846-56). T cell function in vitro can be enhanced by PD-1 blockade, as demonstrated by improved proliferation and cytokine responses in mixed lymphocyte reactions of T cells and dendritic cells. Cytotoxic T Lymphocytes (CTLs) derived from melanoma patients have also been shown to be enhanced by PD-1 blockade in vitro using the antibody nivolumab, and can become resistant to suppression by regulatory T cells (Wang 2009 Int Immunol 21(9):1065-1077). This antibody has been shown to be efficacious in melanoma and in non-small-cell lung carcinoma (NSCLC) patients. Another PD-1 blocking antibody, pembrolizumab, demonstrates responses in NSCLC patients refractory to CTLA-4 blockade. Nivolumab and pembrolizumab both functionally block the interaction of human PD-1 with its ligands.

The gut microbiome of cancer patients is a major driver of response to immune checkpoint therapy.

Previous studies have analysed clinical datasets to identify gut microbiota associated with treatment efficacy (Frankel *Neoplasia* (2017) 19:848; Gopalakrishnan *Science* (2018) 359:97; Matson *Science* (2018) 359:104; Routy *Science* (2018) 359:91). However, the major challenge in the field has been that the microbiome signatures identified in the independent studies are very different. The published studies vary in response criteria and cancer indication, but also factors that are known to impact microbiome analysis such as sample collection, storage and processing and geographical location. Therefore, it has been difficult to understand what the true signature is amongst the inter-study noise.

Thus, there is a need to provide efficacious treatments of cancer as well as biomarkers that are predictive for response to treatment and the present invention is aimed at addressing this need.

SUMMARY OF THE INVENTION

The Invention Is based on the finding that the gut microbiome in subjects that respond to treatment with an immune checkpoint inhibitor is different to the gut microbiome in subjects that do not respond to treatment with the immune checkpoint inhibitor, and that the gut microbiome may therefore be employed either as a diagnostic for immune checkpoint inhibitor treatment or as the source of a therapy.

The invention is therefore aimed at a number of aspects, including, but not limited to the following:

A composition comprising certain bacteria as defined herein which have been identified in patients who respond to treatment with an immune checkpoint inhibitor and which can be used as a treatment of disease, including treatment of cancer, an infectious disease or use as a vaccine adjuvant;

A co-therapy comprising a composition having certain bacteria as defined herein and an immune checkpoint inhibitor treatment and Provision of certain bacteria as defined herein as a diagnostic for immune checkpoint inhibitor treatment to identify patients that benefit from immune checkpoint inhibitor treatment and also to identify patients which may receive bacterial or other therapy, e.g. before administration of the checkpoint inhibitor therapy.

These aspects as well as other related aspects of the invention and embodiments are further described herein.

The inventors have identified a microbiome biomarker signature associated with and highly predictive of response to treatment with an immune checkpoint inhibitor. This is of great significance in the field, providing the basis for the following: a predictive biomarker for checkpoint inhibitor therapy; a live bacterial therapeutic (LBT) therapy; a live bacterial therapeutic co-therapy with an immune checkpoint inhibitor, for example anti-PD-1, anti-PD-L1 or anti-CTLA-4 drugs for the treatment of cancer, to increase the proportion of patients responding to checkpoint inhibitors. In particular, the inventors have identified a number of bacterial species present in the gut microbiome that exhibit modulated abundance indicative of a response to treatment with an immune checkpoint inhibitor. Detecting modulated abundance of these bacteria may therefore be employed to discriminate responders to checkpoint inhibitor therapy from non-responders. In addition, the administration of such live bacteria as a medicine is predicted to convert patients not responding to checkpoint inhibitors to responders.

The bacteria identified and described herein may be employed individually to determine response and/or provide treatment, or combinations of the bacteria may be provided to increase the discriminatory power of the diagnostic method and provide non-invasive methods of diagnosis for response versus non-response as well as methods of treatment.

The inventors have identified specific gut bacteria associated with checkpoint inhibitor response. The invention thus provides gut bacteria that can be used to modulate the microbiome to improve the therapeutic response to immune checkpoint inhibitors patients, for example cancer patients. Studies in the present disclosure used a cohort of patients with melanoma undergoing therapy with anti-PD-1 drugs or combination therapy with anti-PD-1 plus anti-CTLA-4 drugs. Gut microbiome samples taken prior to immune checkpoint therapy were characterized in these patients via metagenomic whole genome shotgun sequencing. Significant differences were observed in the composition of the gut microbiome in responders versus non-responders to immune checkpoint blockade therapy (e.g., to PD-1-based therapy), with an increase or decrease in abundance of specific bacteria in the gut microbiome of responders versus non-responders pre-treatment. In particular, the bacteria as described herein were found to be more abundant in responders. Therefore, these bacteria and subsets thereof find use in a composition which can be employed for the treatment of disease, including cancer, either alone or in combination with an immune checkpoint inhibitor treatment. Furthermore, these bacteria can be used as biomarkers, i.e. as a diagnostic to distinguish responders to checkpoint inhibitor, e.g. PD-1 inhibitor, therapy from non-responders for immune checkpoint inhibitor treatment.

The present studies show that patients with a "favourable" gut microbiome (with modulated, e.g. high relative abundance of one or more of bacteria as described herein) have enhanced anti-tumour immune responses. In contrast, patients with an "unfavourable" gut microbiome (with low relative abundance of the species B1-B15 as defined herein) have impaired anti-tumour immune responses. These findings highlight the potential for parallel modulation of the gut microbiome to significantly enhance checkpoint blockade treatment efficacy. Based on these findings, methods of disease management, e.g. cancer treatment and diagnosis are provided herein. Also provided herein are methods to use the compositions described herein as predictive biomarker compositions to identify patients who will have a favourable response to immune checkpoint blockade. Moreover, the compositions described herein have immunostimulatory properties. Therefore, treatment of disease is not limited to cancer, but the compositions provides treatment of other diseases, e.g. diseases that benefit form immunostimulatory treatment, e.g. non-cancer immunotherapies.

In a first aspect, the invention thus relates to a composition comprising one or more bacterial isolate, in particular a bacterial population, belonging to one or more bacterial species selected from Table 1. Thus, the invention relates to a composition comprising a bacterium selected from one or more bacteria selected from Table 1. Specifically, the invention thus relates to a composition comprising one or more bacterial isolate having a 16SrDNA selected from SEQ ID. Nos 1 to 15.

The composition may comprise or consists of 2, 3, 4, 5, 6, 7, 8, 9, 10, 11, 12, 13, 14 or 15 isolated bacteria. These are different bacteria selected from different species, that is bacteria having a 16SrDNA of selected from SEQ ID. Nos 1 to 29 or a sequence having at least 95%, 97%, 98% 98.7%, 99% or 100% sequence identity with a nucleic acid sequence selected from SEQ ID. Nos 1 to 29, e.g. selected from SEQ ID. Nos 1 to 15 or a sequence having at least 95%, 97%, 98% 98.7% or 99% sequence identity with a nucleic acid sequence selected from SEQ ID. Nos 1 to 15.

In one embodiment, the composition thus comprises or consists of isolated bacteria selected from at least 2, 3, 4, 5, 6, 7, 5, 9, 10, 11, 12, 13, 14 or 15 bacterial species wherein the bacteria comprise a 16S rDNA sequence selected from SEQ ID. Nos 1 to 29, e.g. 1 to 15, or a sequence having at least 95%, 97%, 98% 98.7%, 99% or 100% sequence identity with a nucleic acid sequence selected from SEQ ID. Nos 1 to 15.

In one embodiment, the composition comprises or consists of isolated bacteria selected from at least two species wherein the bacteria from the first species comprise a 16S rDNA sequence having least 95%, 97%, 98%, 98.7%, 99% or 100% sequence identity with a nucleic acid sequence according to SEQ ID NO: 1, and the bacteria from the second species comprise a 16S rDNA sequence having at least 95%, 97%, 98%, 98.7%, 99% or 100% sequence identity with a nucleic acid sequence according to SEQ ID NO: 2.

In one embodiment, the composition comprises or consists of isolated bacteria selected from at least 9 species wherein the bacteria comprise a 16S rDNA sequence selected from SEQ ID. Nos 1 to 29, e.g. 1 to 15 or a sequence having at least 95%, 97%, 98%, 98.7%, 99% or 100% sequence identity with a sequence selected from SEQ ID. Nos 1 to 29, e.g. 1 to 15. In one embodiment, the 9 species include bacteria comprising a 16S rDNA sequence according to SEQ ID NO: 1, or a sequence having at least 95%, 97%, 98% 98.7%, 99% or 100% sequence identity thereto and bacteria comprising a 16S rDNA sequence according to SEQ ID NO: 2 or a sequence having at least 95%, 97%, 98%, 98.7%, 99% or 100% sequence identity thereto.

In another aspect, the invention relates to a pharmaceutical composition as described herein, a pharmaceutical carrier and optionally an immune checkpoint inhibitor.

In another aspect, the invention relates to a composition as described herein for use in the treatment of disease, such as particular cancer or an infectious disease. The composition can also be used as a vaccine adjuvant. This is used to enhance vaccine response and administration may be together with the vaccine.

In another aspect, the invention relates to a composition as described herein in increasing efficacy of an anti-cancer treatment with an immune checkpoint inhibitor.

In another aspect, the invention relates to a method for treating cancer comprising modulating the level/abundance of one or more bacteria selected from those of Table 1 in a subject.

In another aspect, the invention relates to a kit comprising a composition as described herein and optionally an anti-cancer treatment that includes an immune checkpoint inhibitor.

In another aspect, the invention relates to a method for identifying a subject that will respond to therapy with an immune checkpoint inhibitor comprising determining the abundance of one or more bacteria selected from those of Table 1 in a biological sample from said subject that comprises gut intestinal flora wherein an increase in the abundance of one or more of bacteria selected from those of Table 1 is indicative that the subject will respond to therapy with an immune checkpoint inhibitor.

In another aspect, the invention relates to a use of a bacterium selected from one or more bacteria selected from those of Table 1 in identifying a patient that will respond to therapy with an immune checkpoint inhibitor.

In another aspect, the invention relates to a kit comprising;
a sealable container configured to receive a biological sample;
polynucleotide primers for amplifying a 16S rDNA polynucleotide sequence from at least one gut associated bacterium to form an amplified 16S rDNA polynucleotide sequence, wherein the amplified 16S rDNA sequence has at least 95%, 97%, 98%, 98.7%, 99% or 100% sequence identity to a polynucleotide sequence selected from SEQ ID NOs 1 to SEQ ID NO 29; e.g. 1 to 15, a detecting reagent to detect the amplified 16S rDNA sequence; and instructions for use.

In another aspect, the invention relates to a food product or a vaccine co-therapy to boost vaccine response comprising the composition as described herein.

In another aspect, the invention relates to a method for identifying a faecal donor, e.g. for treatment of cancer, comprising assessing a faecal sample of a subject for the presence of one or more bacteria selected from Table 1 and identifying the faecal donor based on the presence and/or abundance of one or more bacteria selected from Table 1.

In another aspect, the invention relates to a use of one or more bacteria selected from Table 1 in a method for identifying a donor for FMT therapy, e.g. for treatment of cancer.

In another aspect, the invention relates to a method for treating a faecal transplant prior to administration to a subject comprising supplementing the faecal transplant with one or more isolated bacteria selected from Table 1.

In another aspect, the invention relates to a method for screening/identifying a faecal donor comprising assessing a faecal sample of a subject for the presence of one or more bacteria associated with response to cancer; and identifying the faecal donor based on the presence and/or abundance of one or more bacteria.

Figure 1:
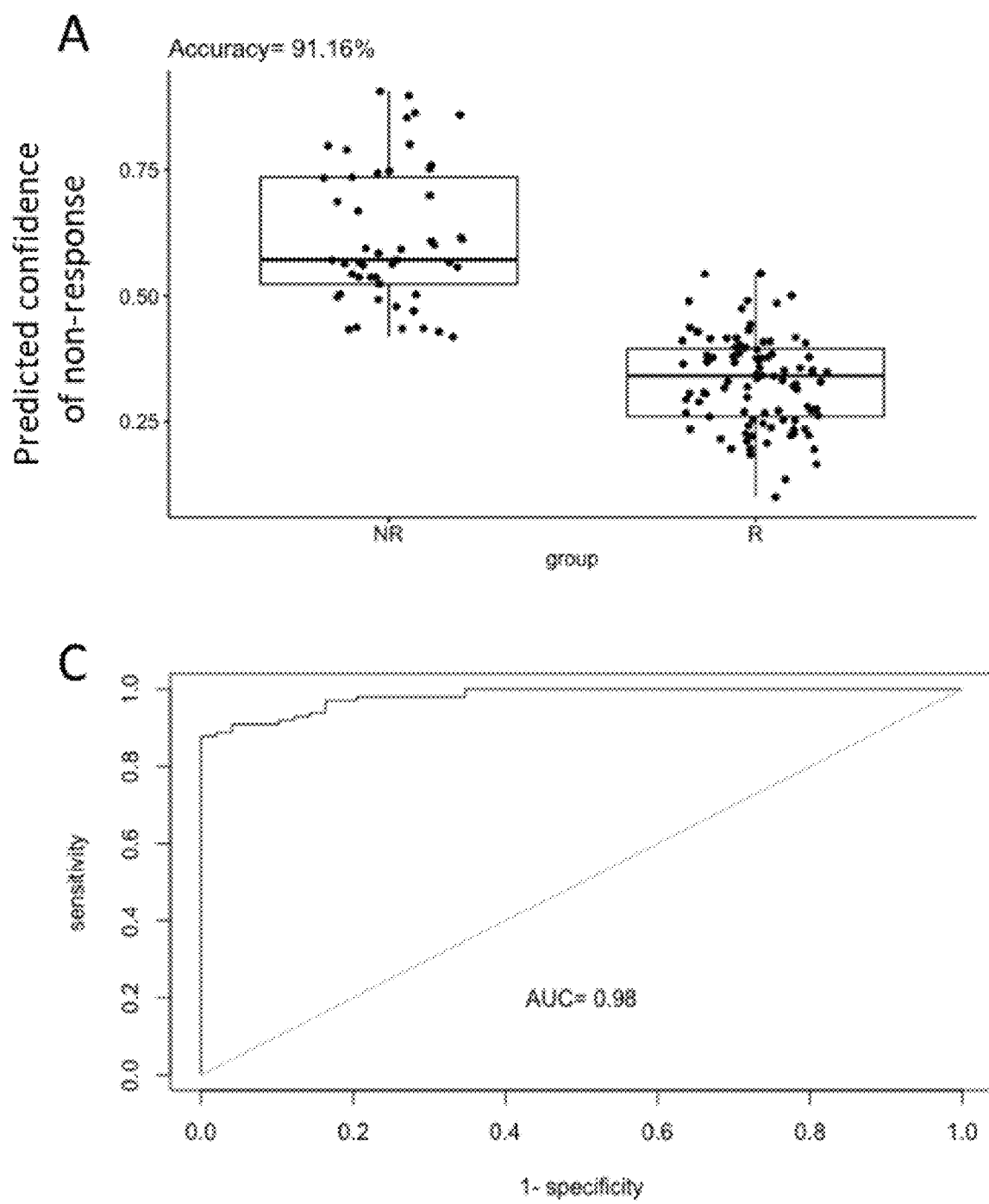
FIG. 1. A) All 147 patients from the four melanoma studies were divided into responders and non-responders according to clinical outcome. The probability of not responding to immunotherapy was predicted from the baseline faecal sample based on machine learning predictions that used the abundance of bacteria in a defined signature. A cut off of 0.5 was used to determine the accuracy of the prediction. Accuracy was 91.16%. x axis is group. B) As A except each study is considered separately. frankel accuracy 84.62%; gajewski accuracy 89.74%; melresist accuracy 93.18%; wargo accuracy 100%. X axis is group. C) Receiver Operating Characteristic (ROC) curve of the combined melanoma dataset showing False Positive Rate as a function of True Positive Rate based on machine learning predictions based the same microbiome signature. AUC=0.98. X axis is 1-specificity, y axis is sensitivity. D) As C but each study is considered separately. Random forest out-of-bag error was used to prevent overoptimistic performance and improve generalizability. AUC frankel 0.958; AUC gajewski 0.978; AUC melresist 0.983; AUC wargo 1. X axis is 1-specificity, y axis is sensitivity.
Figure 1:
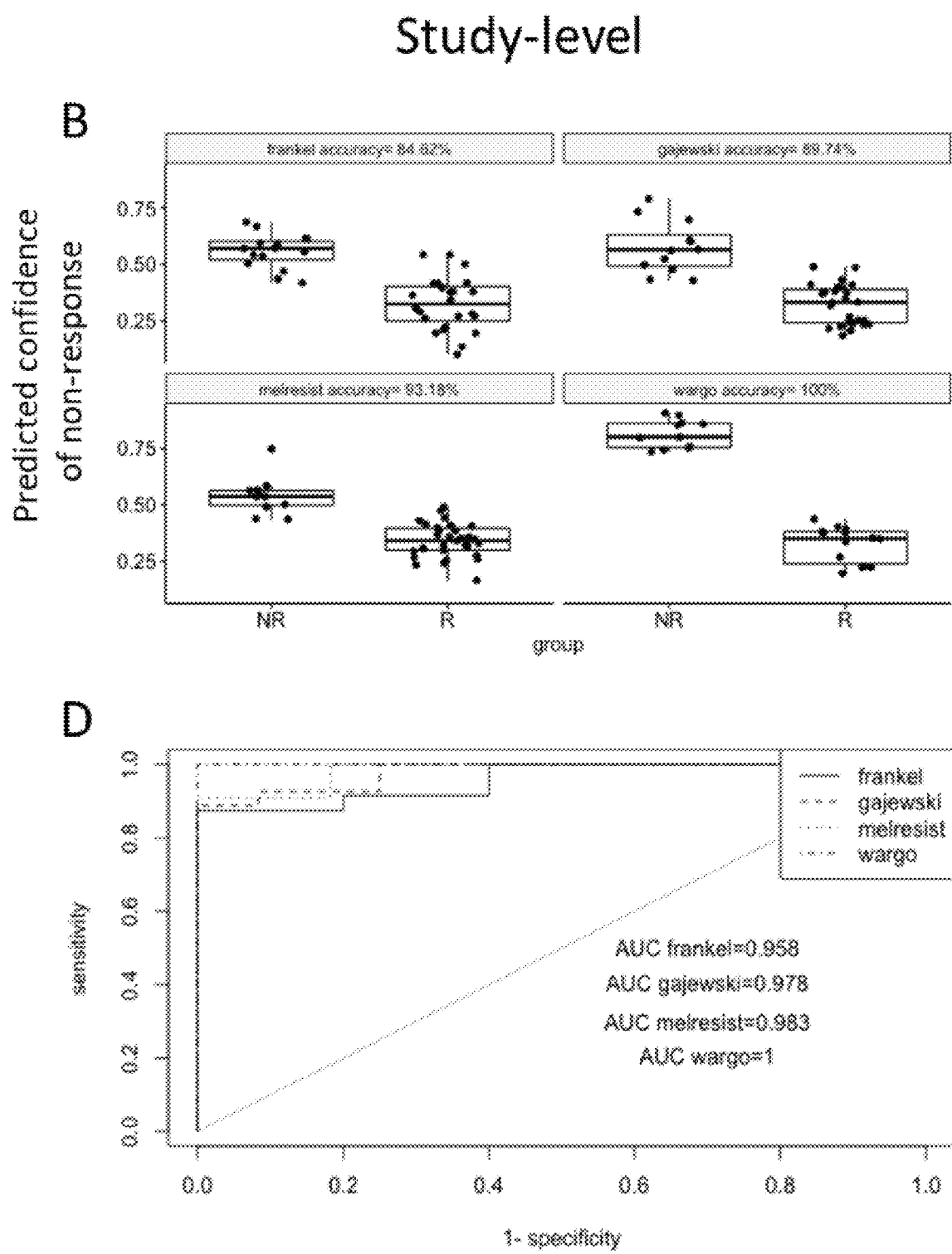

In the figures, Con stands for consortium. Consortia are shown in Table 3.

DETAILED DESCRIPTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Generally, nomenclatures used in connection with, and techniques of microbiology, cell and tissue culture, pathology, molecular biology, immunooncology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g., Green and Sambrook et al., Molecular Cloning: A Laboratory Manual, 4th ed., Cold Spring Harbor Laboratory Press, Cold Spring Harbor, N.Y. (2012).

The nomenclatures used in connection with, and the laboratory procedures and techniques of analytical chemistry, microbiology, bioinformatics and medicinal and pharmaceutical chemistry described herein are those well-known and commonly used in the art.

The invention relates to bacterial compositions each comprising or consisting of one or more bacterial isolate from one or more species as disclosed herein, e.g., a consortium of defined bacterial isolates. The compositions have immunostimulatory properties and are thus therapeutic compositions useful in the treatment of disease. In some embodiments, the compositions are mixtures of bacterial isolates selected from more than one species as identified in Table 1.

The compositions are not faecal microbiota transplants (FMT) and do not contain faecal material, but contain defined mixtures of bacterial isolates free of faecal material. Therefore, preparations that contain a defined bacterial mixture are generally accepted to be a safer treatment than FMT. An advantage of the present composition is that it comprises only fully defined and characterised bacteria and no undefined or unwanted components, which may be present in donor stools, thereby allowing the therapeutic composition to be standardised and increasing safety of the composition.

FMT relies on a stool sample from a human donor which is administered directly to the recipient, e.g. via colonoscopy, without bacteria present in the stool sample being isolated prior to the administration of the FMT to the recipient. While FMT is widely used, there are some disadvantages associated with FMT. The composition of the FMT material is very donor dependant and therefore is inconsistent. Despite screening of donors, it is difficult to determine the bacterial load of the samples. Donors also have to be screened for pathogens and to assess the risk of colonization with drug-resistant bacteria. In certain aspects described below, the invention also relates to augmenting FMT therapy with one or more bacterial isolate from one or more species as disclosed herein and methods for screening/identifying a faecal donor.

The compositions as described herein include isolated bacteria. The term "isolated" refers to bacteria that are isolated from the natural environment. The isolated bacteria, e.g. isolated bacterial strains, are substantially free of other cellular material, chemicals and/or faecal material. Thus, as used herein, the term "isolated" bacteria refers to bacteria that have been separated from one or more undesired component, such as another bacterium or bacterial strain, one or more component of a growth medium, and/or one or more component of a sample, such as a faecal sample. In some embodiments, the bacteria are substantially isolated from a source such that other components of the source are not detected. As used herein, the term "species" refers to a taxonomic entity as conventionally defined by genomic sequence and/or phenotypic characteristics. A "strain" is a particular instance of a species that has been isolated and purified according to conventional microbiological techniques. It will be understood that the terms bacteria and bacterial isolates refer to a plurality of bacteria, that is a bacterial population.

In one embodiment, the bacteria of the composition are metabolically inactive prior to administration. For example, the bacteria are lyophilised. In one embodiment, the composition includes vegetative bacterial cells and does not include bacterial spores. In one embodiment, the composition includes vegetative bacterial cells and/or bacterial spores. In one embodiment, the composition includes vegetative bacterial cells and does not include bacterial spores or is substantially devoid of spores. In one embodiment, the composition includes fewer than about 0.5%, 1%, 2%, 3%, 4% or 5% spores.

The composition is preferably a live bacterial therapeutic, bacteriotherapy or a live biotherapeutic product. As described herein, a live bacterial product (also referred to as a bacterial composition, live bacterial consortium, mixture of bacteria or bacterial consortium) comprises one or more bacterial strain from one or more bacterial species as described herein. The term live bacterial therapy is interchangeably used with bacteriotherapy herein and defines a therapy using live bacteria to restore health or alleviate disease/disease symptoms or increase response to a therapy.

The bacterial compositions of the invention provide an immunostimulatory effect. In some embodiments, the bacterial composition induces or stimulates an immunotherapeutic effect, for example an anti-cancer effect (e.g., inhibition or cytotoxicity of cancer cells), when administered to the subject. In some embodiments, the bacterial composition induces or stimulates an immune response that provides an anti-cancer or other beneficial therapeutic effect when administered to the subject as further explained herein.

As described herein, the composition may comprise one or more bacterial species selected from those listed in Table 1. The ability of the specific bacteria or the combination of bacterial species of the live bacterial product to induce a beneficial effect, i.e. an immunostimulatory effect, such as an anti-cancer effect, can be assessed using any of method known in the art, e.g., in vitro assays for example using cell culture, or in vivo studies. Suitable assays are shown in the examples.

In some embodiments, the anticancer live bacterial product induces a specific immune cell population (e.g., CD8+ T-cells, Th17, Th1 cells). The abundance of a specific population of cells (e.g., CD8+ T-cells, Th17. Th1 cells) can be assessed by any method known in the art, for example by detecting a cellular marker indicative of the cell type, assessing a direct or indirect activity of the cell type, and/or by measuring the production of one or more cytokines produced by the specific cell type. In some embodiments, the anti-cancer live bacterial product induces CD8+ T-cells (or "CD8+ T cells"). As will be appreciated by one of ordinary skill in the art, a combination of bacterial species and/or multiple strains from one or more species as described herein may be selected and combined to produce an anti-cancer live bacterial product that induces CD8+ T-cells.

In one embodiment, the isolated bacteria, e.g. isolated bacterial strains from the species listed herein, can be viable bacteria that are capable of colonising the gastrointestinal gut of a subject when administered to said subject.

The inventors have shown that by combining bacteria from different species, a therapeutic composition can be provided which finds use as a co-therapy with a checkpoint inhibitor. In a first aspect, the invention relates to a composition comprising isolated bacteria, e.g. a bacterial strain, selected from one or more of the bacterial species B1, B2, B3, B4, B5, B6, B7, B8, B9, B10, B11, B12, B13, B14 and/or B15 as shown in Table 1 or subsets thereof. The invention thus relates to a composition comprising one or more bacterial isolate, e.g. bacterial population, having a 16SrDNA selected from SEQ ID. Nos 1 to 19, e.g. 1 to 15. The invention thus relates to a composition comprising or consisting of bacterial isolates of one or more of the species as shown in Table 1.

Table 1 below lists the 15 different bacterial species from which the isolated bacteria present in the composition are selected. Reference to exemplary 16S rDNA sequence characterising each species is also provided in Table 1. The terms 16S rDNA sequence or 16S rDNA as used herein refer to DNA nucleic acid sequences, i.e. a nucleic acid molecule, which encodes 16S rRNA nucleic acid sequence i.e. a nucleic acid molecule. Nucleic acid sequences referenced below are listed in Table 2. Also, as explained further below, the bacteria of the composition and of other aspects as described herein may have a 16S rDNA sequence with certain sequence identity to the SEQ ID Nos. as listed below.

sequences) having similar or the same biological properties can also be included. In some embodiments, bacterial strains provided herein can be replaced with bacterial strains with similar or the same biological properties.

In some embodiments, the anticancer/live bacterial composition comprises one or more bacterial strain of one or more of the 15 recited species shown in Table 1. In some

TABLE 1

Bacterial species of the composition and biomarker signature

| No | Taxonomy | 16S rDNA sequence-sequence identifier | Possible alternative taxonomy: name and/or closely related species based on closely related bacteria identified from public databases |
|---|---|---|---|
| B1 | *Eisenbergiella* sp. | SEQ ID No. 1; SEQ ID No. 21 | *Eisenbergiella tayi* |
| B2 | *Butyricicoccus* sp. | SEQ ID No. 2; SEQ ID No. 17; SEQ ID No. 22 | *Butyricicoccus pullicaecorum*, bacterium NLAE-zl-H41, bacterium NLAE-zl-H55, bacterium NLAE-zl-H60 |
| B3 | *Clostridiales* sp. | SEQ ID No. 3 | n/a |
| B4 | *Alistipes obesi* | SEQ ID No. 4; SEQ ID No. 16 | n/a |
| B5 | *Alistipes indistinctus* | SEQ ID No. 5 | n/a |
| B6 | *Gordonibacter urolithinfaciens* | SEQ ID No. 6; SEQ ID No. 18; SEQ ID No. 23 | n/a |
| B7 | *Faecalitalea* sp. | SEQ ID No. 7; SEQ ID No. 24 | *Longicatena caecimuris* |
| B8 | *Blautia* sp. | SEQ ID No. 8; SEQ ID No. 25 | *Blautia producta, Blautia coccoides, Blautia marasmi, Blautia stercoris* |
| B9 | *Barnesiella intestinihominis* | SEQ ID No. 9; SEQ ID No. 26 | n/a |
| B10 | *Alistipes timonensis* | SEQ ID No. 10 | n/a |
| B11 | *Blautia* sp. | SEQ ID No. 11; SEQ ID No. 19; SEQ ID No. 27 | n/a |
| B12 | *Lachnospira* sp. | SEQ ID No. 12; SEQ ID No. 20; SEQ ID No. 28 | *Lactobacillus rogosae* |
| B13 | *Ruminococcus callidus* | SEQ ID No. 13 | n/a |
| B14 | *Roseburia faecis* | SEQ ID No. 14; SEQ ID No. 29 | n/a |
| B15 | *Faecalibacterium prausnitzii* | SEQ ID No. 15 | n/a |

The aspects and embodiments of the invention described herein are defined by reference to the species name and/or SEQ ID NO. as shown in Table 1. In some cases, different exemplary sequences are provided in Table 1 for the same species, e.g. corresponding to different exemplary strains which belong to the same species. Where multiple sequences are provided for a species, these sequences share a high sequence identity, e.g. the different strains defined by SEQ ID No. 2 and SEQ ID No. 17 have at least 99% sequence identity, SEQ ID No. 4 and SEQ ID No. 16 have at least 99% sequence identity. SEQ ID No. 6 and SEQ ID No. 18 have at least 99% sequence identity and SEQ ID No. 12 and SEQ ID No. 20 have at least 99% sequence identity.

In the aspects and embodiments described herein, for each of B1 to B15, any of the sequences defined above (SEQ ID. Nos 1 to 29) can be used. Thus, where multiple sequences are provided for a single species, any of these sequences can be used.

It will be appreciated that the inventors provide compositions with certain bacterial species that have immunostimulatory effects, e.g. anti-cancer effects. It will also be appreciated that for each species, different strains can be used, i.e. strains identified above or other strains that belong to the same species. It should be appreciated that closely related bacterial strains (e.g., as defined by 16S rDNA embodiments, the anticancer/live bacterial composition comprises one or more bacterial strain of more than one of the 15 recited species; e.g. 2, 3, 4, 5, 6, 7, 8, 9, 10, 11, 12, 13, 14 or 15 species.

In one embodiment, the composition comprises or consists of 15 isolated bacteria. e.g. bacteria from each of the 15 bacterial species listed in Table 1, for example with reference to the 16S rDNA sequences as shown in the Table or a sequence with certain percentage identity thereto as explained below or with reference to the species name as shown above.

The invention also relates to compositions that comprise or consist of bacteria selected from a subset of the bacterial species listed in Table 1; e.g. compositions that comprise or consist of different bacteria selected from 1, 2, 3, 4, 5, 6, 7, 8, 9, 10, 11, 12, 13, 14 or 15 of the bacterial species listed in Table 1, with reference to the 16S rDNA sequences as shown in the Table 1 or a sequence with certain percentage identity thereto as explained below or with reference to the species name as shown above. All combinations are envisaged.

Thus, in one embodiment, the composition comprises or consists of at least one isolated bacterial population belonging to one or more of the species in Table 1. For example, the composition comprises or consists of bacteria selected from 2, 3, 6, 9 or 12 bacterial species listed in Table 1. These may be selected from the consortia shown in Table 3, for example consortia 2, 4, 5, 6 and 10. The bacteria may be defined by reference to their 16S rDNA as shown in the sequence identifiers Table 1. Thus, different bacteria selected from those listed in Table 1 can be combined in a single composition.

For example, the composition comprises or consists of isolated bacteria selected from at least 2, e.g. up to 3, up to 4, up to 5, up to 6, up to 7, up to 8, up to 9, up to 10, up to 11, up to 12, up to 13, up to 14 or up to 15 species shown in Table 1, for example with reference to the sequences as shown in the Table. For example, the composition comprises or consists of isolated bacteria from 9 bacterial species listed in Table 1. In one example, the composition comprises or consists of isolated bacteria from 9 species as shown in Table 3, i.e. consortia 2, 4, 5, 6 and 10. The bacteria may be defined by reference to their 16S rDNA as shown in the sequence identifiers in Table 1.

In one embodiment, the composition comprises or consists of isolated bacteria selected from 2, 3, 4, 5, 6, 7, 8, 9, 10, 11, 12, 13, 14 or 15 species listed in Table 1, for example with reference to the sequence IDs as shown in Table 1. In one embodiment, the composition comprises or consists of isolated bacteria selected from the consortia in Table 3. In one embodiment, the composition comprises or consists of isolated bacteria having a 16S rDNA selected from the SEQ ID NOs. as shown in Table 1. The bacteria may be defined by reference to their 16S rDNA as shown in the sequence identifiers in Table 1. Sequences with certain percentage sequence identify as shown herein are also within the scope of the invention.

In one embodiment, the composition comprises isolated bacteria selected from at least 2, at least 3, at least 4, at least 5, at least 6, at least 7, at least 8, at least 9, at least 10, at least 11, at least 12, at least 13, at least 14 or at least 15 species listed in table 1, for example with reference to the sequences as shown in table 1, for example with reference to the sequence IDs as shown in Table 1. In one embodiment, the composition comprises isolated bacteria selected from at least 9 species as shown in Table 1. Sequences with certain percentage sequence identify as shown herein are also within the scope of the invention.

In one embodiment, the composition comprises or consists of isolated bacteria selected from no more than 2, no more than 3, no more than 4, no more than 5, no more than 6, no more than 7, no more than 8, no more than 9, no more than 10, no more than 11, no more than 12, no more than 13, no more than 14 or no more than 15 species listed in Table 1, for example with reference to the sequences as shown in table 1, for example with reference to the sequence IDs as shown in Table 1. Sequences with certain percentage sequence identify as shown herein are also within the scope of the invention.

In one embodiment, the composition comprises or consists of isolated bacteria selected from 2 to 4, 2 to 5, 2 to 6, 2 to 7, 2 to 8, 2 to 9, 2 to 10, 2 to 11, 2 to 12, 2 to 13, 2 to 14 or 2 to 15 species shown in table 1, for example with reference to the sequences as shown in Table 1, for example with reference to the sequence IDs as shown in Table 1. Sequences with certain percentage sequence identify as shown herein are also within the scope of the invention.

In one embodiment, the composition comprises an isolated bacterial mixture comprising or consisting of 2 to 15 bacterial strains having at least 90%, 95%, 97%, 98%, 98.7% or 99% sequence identity to 16s rDNA sequences selected from SEQ ID Nos 1 to 15, e.g. SEQ ID Nos. 16 to 29. Exemplary compositions are set out herein, e.g. In Table 3.

A skilled person would appreciate that that bacterial species selected from Table 1 and for use in the composition and methods of the invention can have the sequence shown in Tables 1 and 2 or a sequence that has certain percentage identity thereto and retains biological activity; i.e. activity against cancer/efficacy in enhancing the effect of a therapy using an immune checkpoint inhibitor.

In one embodiment, the composition may be as described above, but does not comprise bacteria of any other species, i.e. species not listed in Table 1 or the composition comprise only de minimis or biologically irrelevant amounts of bacteria from another species. By biologically irrelevant is meant bacteria that do not have an effect on the treatment of cancer. Thus, in one embodiment, the composition consists of the recited bacteria.

In one embodiment, the composition does not comprise other bacterial species that fall within a genus listed in Table 1.

In one embodiment, the composition may comprise other bacterial species that fall within a genus listed in Table 1, but does not comprise bacterial species of a genus not listed in Table 1. In one embodiment, the composition may comprise other bacterial species that fall within a different genus.

Methods of determining sequence identity are known in the art. It is known that clades, operational taxonomic units (OTUs), species, and strains are, in some embodiments, Identified by their 16S rDNA sequence. The relatedness can be determined by the percent identity and this can be determined using methods known in the art.

Bacterial species and strains used in a composition as described herein can be identified based on the 16S nucleic acid sequence (full length or part thereof, such as V regions). The 16S ribosomal DNA gene codes for the DNA component of the 30S subunit of the bacterial ribosome. It is widely present in all bacterial species. Different bacterial species have one to multiple copies of the 16S rRNA gene. 16S rRNA gene sequencing is by far one of the most common methods targeting housekeeping genes to study bacterial phylogeny and genus/species classification. Thus, bacteria can be taxonomically classified based on the sequence of the gene encoding the 16S nucleic acid sequence, e.g. ribosomal DNA (rDNA) in the bacterium. This gene sequence is also referred to as the ribosomal DNA sequence (rDNA). The bacterial 16S rDNA is approximately 1500 nucleotides in length and is used in reconstructing the evolutionary relationships and sequence similarity of one bacterial isolate to another using phylogenetic approaches. 16S rDNA sequences are used for phylogenetic reconstruction as they are in general highly conserved, but contain specific hypervariable regions that harbor sufficient nucleotide diversity to differentiate genera and species of most microbes.

Using well known techniques to determine a full 16S rDNA sequence or the sequence of any hypervariable region of the 16S rDNA sequence, genomic DNA is extracted from a bacterial sample, the 16S rDNA (full region or specific hypervariable regions) amplified using polymerase chain reaction (PCR), the PCR products cleaned, and nucleotide sequences delineated to determine the genetic composition of the 16S rDNA gene or subdomain of the gene. If full 16S rDNA sequencing is performed, the sequencing method used may be, but is not limited to, Sanger sequencing. If one or more hypervariable regions are used, such as the V4 region, the sequencing may be, but is not limited to being, performed using the Sanger method or using a next-generation sequencing method, such as an Illumina (sequencing by synthesis) method using barcoded primers allowing for multiplex reactions. The V1-V9 regions of the 16S rDNA refer to the first nine hypervariable regions of the 16S rDNA gene that are often used for genetic typing of bacterial samples. In some embodiments, at least one of V1 to V9 is used to characterise the bacterial isolate.

In some embodiments, bacterial species identified as described herein are identified by sequence identity to 16S rDNA sequences as known in the art and described herein. In some embodiments, the selected species are identified by sequence identity to full length 16S rDNA sequences as shown in Table 2. In some embodiments, the selected species are identified by sequence identity to a part of the 16S rDNA sequences as shown in Table 2, for example V3 and/or V4.

As used herein, the term "homology" or "identity" generally refers to the percentage of nucleic acid residues in a sequence that are identical with the residues of the reference sequence with which it is compared, after aligning the sequences and in some embodiments after introducing gaps, if necessary, to achieve the maximum percentage homology, and not considering any conservative substitutions as part of the sequence identity. Thus, the percentage homology between two nucleic acid sequences is equivalent to the percentage identity between the two sequences. Methods and computer programs for the alignment are well known. The percentage identity between two sequences can be determined using well known mathematical algorithms.

In one embodiment, the degree of sequence identity between a query sequence and a reference sequence can be determined with the aid of a commercially available sequence comparison program.

This typically involves aligning the two sequences using the default scoring matrix and default gap penalty, identifying the number of exact matches, and dividing the number of exact matches with the length of the reference sequence. Suitable computer programs useful for determining identity include, for example, BLAST (blast.ncbi.nlm.nih.gov).

In the various embodiments as set out herein when reference is made to a SEQ ID NO., sequences that have certain percentage sequence identity to the full length sequence are also within the scope of the invention.

Thus, the full length or partial 16S rDNA of the bacterial species listed in Table 2 with reference to the sequence identifier in Table 1 and which is used in the compositions and methods of the invention has at least 90%, e.g. at least 91%, 92%, 93%, 94%, 95%, 96%, 97%, 98%, 98.7%, 99%, 99.5% or 100% sequence identity to the corresponding reference 16S rDNA (i.e. SEQ IDs 1 to 29). In some embodiments, the threshold sequence identity is at least 94.5%. In one embodiment, said sequence identity is at least 95%. In one embodiment, said sequence identity is at least 96%. In one embodiment, said sequence identity is at least 97%. In one embodiment, said sequence identity is at least 98%. In one embodiment, said sequence identity is at least 98.7%. In one embodiment, said sequence identity is at least 99%.

In one aspect, the composition therefore comprises two or more bacteria, that is bacterial species, comprising a 16S rDNA sequence selected from SEQ ID NO. 1 to 15 or comprising a 16S rDNA sequence having at least 90% e.g. at least 91%, 92%, 93%, 94%, 95%, 96%, 97%, 98%, 99%; e.g. 97% or 98.7% identity to a nucleic acid sequence selected from SEQ ID NOs. 1 to 15. Such sequences include SEQ ID. Nos 16 to 29, for example SEQ ID. Nos 16 to 20.

In some embodiments, the threshold sequence identity is 94.5%, 94.6%, 94.7%, 94.8%, 94.9%, 95.0%, 95.1%, 95.2%, 95.3%, 95.4%, 95.5%, 95.6%, 95.7%, 95.8%, 95.9%, 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9% 99.0%, 99.1%, 99.2%, 99.3%, 99.4%, 99.5%, 99.6%, 99.7%, 99.8%, 99.9% or 100%.

In one embodiment, a bacterium present in the composition belongs to the same species as a bacterium disclosed herein, has at least 90% e.g. at least 91%, 92%, 93%, 94%, 95%, 96%, 97%, 98%, 99%; e.g. 97% or 98.7% identity to a nucleic acid sequence selected from SEQ ID NOs. 1 to 15 and retains activity against cancer/efficacy in enhancing the effect of a therapy using an immune checkpoint inhibitor. Such sequences include SEQ ID. Nos 16 to 29, for example SEQ ID. Nos 16 to 20.

In one embodiment, the composition comprises or consists of one or more of the following 15 bacteria having a 16sDNA of the following SEQ ID Nos.:

SEQ ID No. 1 or a 16S rDNA sequence having at least 90% e.g. at least 91%, 92%, 93%, 94%, 95%, 96%, 97%, 98%, 99%; e.g. 97% or 98.7% identity thereto, SEQ ID No. 2 or a 16S rDNA sequence having at least 90% e.g. at least 91%, 92%, 93%, 94%, 95%, 96%, 97%, 98%, 99%; e.g. 97% or 98.7% identity thereto, SEQ ID No. 3 or a 16S rDNA sequence having at least 90% e.g. at least 91%, 92%, 93%, 94%, 95%, 96%, 97%, 98%, 99%; e.g. 97% or 98.7% identity thereto, SEQ ID No. 4 or a 16S rDNA sequence having at least 90% e.g. at least 91%, 92%, 93%, 94%, 95%, 96%, 97%, 98%, 99%; e.g. 97% or 98.7% identity thereto, SEQ ID No. 5 or a 16S rDNA sequence having at least 90% e.g. at least 91%, 92%, 93%, 94%, 95%, 96%, 97%, 98%, 99%; e.g. 97% or 98.7% identity thereto, SEQ ID No. 6 or a 16S rDNA sequence having at least 90% e.g. at least 91%, 92%, 93%, 94%, 95%, 96%, 97%, 98%, 99%; e.g. 97% or 98.7% identity thereto, SEQ ID No. 7 or a 16S rDNA sequence having at least 90% e.g. at least 91%, 92%, 93%, 94%, 95%, 96%, 97%, 98%, 99%; e.g. 97% or 98.7% identity thereto, SEQ ID No. 8 or a 16S rDNA sequence having at least 90% e.g. at least 91%, 92%, 93%, 94%, 95%, 96%, 97%, 98%, 99%; e.g. 97% or 98.7% identity thereto, SEQ ID No. 9 or a 16S rDNA sequence having at least 90% e.g. at least 91%, 92%, 93%, 94%, 95%, 96%, 97%, 98%, 99%; e.g. 97% or 98.7% Identity thereto, SEQ ID No. 10 or a 16S rDNA sequence having at least 90% e.g. at least 91%, 92%, 93%, 94%, 95%, 96%, 97%, 98%, 99%; e.g. 97% or 98.7% identity thereto, SEQ ID No. 11 or a 16S rDNA sequence having at least 90% e.g. at least 91%, 92%, 93%, 94%, 95%, 96%, 97%, 98%, 99%; e.g. 97% or 98.7% identity thereto, SEQ ID No. 12 or a 16S rDNA sequence having at least 90% e.g. at least 91%, 92%, 93%, 94%, 95%, 96%, 97%, 98%, 99%; e.g. 97% or 98.7% identity thereto, SEQ ID No. 13 or a 16S rDNA sequence having at least 90% e.g. at least 91%, 92%, 93%, 94%, 95%, 96%, 97%, 98%, 99%; e.g. 97% or 98.7% Identity thereto, SEQ ID No. 14 or a 16S rDNA sequence having at least 90% e.g. at least 91%, 92%, 93%, 94%, 95%, 96%, 97%, 98%, 99%; e.g. 97% or 98.7% Identity thereto, SEQ ID No. 15 or a 16S rDNA sequence having at least 90% e.g. at least 91%, 92%, 93%, 94%, 95%, 96%, 97%, 98%, 99%; e.g. 97% or 98.7% identity thereto.

Examples of the above are SEQ ID Nos. 16-29.

Thus, the composition comprises or consists of a population of bacteria that belong to one or more of the 15 bacterial having a 16sDNA as shown above.

In one embodiment, the composition does not include *Faecalibacterium prausnitzii* (e.g. SEQ ID No. 15). In one embodiment, the composition does not include *Alistipes indistinctus* (e.g. SEQ ID No. 5), *Alistipes obesi* (e.g. SEQ ID No. 4 or 16) and/or *Alistipes timonensis* (e.g. SEQ ID No. 10).

In one embodiment, the composition comprises a consortium as shown in Table 3.

Thus, in one embodiment, the composition comprises or consists of bacteria having SEQ ID No. 1 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 2 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 3 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 4 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 5, or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 6 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 7 or a 16S rDNA sequence having at least 90% e.g. at least 91%, 92%, 93%, 94%, 95%, 96%, 97%, 98%, 99%; e.g. 97% or 98.7% identity thereto; bacteria having SEQ ID No. 8 or a 16S rDNA sequence having at least 90% e.g. at least 91%, 92%, 93%, 94%, 95%, 96%, 97%, 98%, 99%; e.g. 97% or 98.7% identity thereto or a 16S rDNA sequence having at least 90% e.g. at least 91%, 92%, 93%, 94%, 95%, 96%, 97%, 98%, 99%; e.g. 97% or 98.7% identity thereto and bacteria having SEQ ID No. 9 or a 16S rDNA sequence having at least 90% e.g. at least 91%, 92%, 93%, 94%, 95%, 96%, 97%, 98%, 99%; e.g. 97% or 98.7% identity thereto or a 16S rDNA sequence having at least 90% e.g. at least 91%, 92%, 93%, 94%, 95%, 96%, 97%, 98%, 99%; e.g. 97% or 98.7% identity thereto (consortium 2 in Table 3).

In one embodiment, the composition comprises or consists of bacteria having SEQ ID No. 1 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 2 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 3 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 6 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 7, or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 8 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 9 or a 16S rDNA sequence having at least 90% e.g. at least 91%, 92%, 93%, 94%, 95%, 96%, 97%, 98%, 99%; e.g. 97% or 98.7% identity thereto; bacteria having SEQ ID No. 11 or a 16S rDNA sequence having at least 90% e.g. at least 91%, 92%, 93%, 94%, 95%, 96%, 97%, 98%, 99%; e.g. 97% or 98.7% identity thereto or a 16S rDNA sequence having at least 90% e.g. at least 91%, 92%, 93%, 94%, 95%, 96%, 97%, 98%, 99%; e.g. 97% or 98.7% identity thereto; bacteria having SEQ ID No. 12 or a 16S rDNA sequence having at least 90% e.g. at least 91%, 92%, 93%, 94%, 95%, 96%, 97%, 98%, 99%; e.g. 97% or 98.7% identity thereto or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 13 or a 16S rDNA sequence having at least 90% e.g. at least 91%, 92%, 93%, 94%, 95%, 96%, 97%, 98%, 99%; e.g. 97% or 98.7% identity thereto or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 14 or a 16S rDNA sequence having at least 90% e.g. at least 91%, 92%, 93%, 94%, 95%, 96%, 97%, 98%, 99%; e.g. 97% or 98.7% identity thereto or a 16S rDNA sequence having at least 90% e.g. at least 91%, 92%, 93%, 94%, 95%, 96%, 97%, 98%, 99%; e.g. 97% or 98.7% identity thereto and bacteria having SEQ ID No. 15 or a 16S rDNA sequence having at least 90% e.g. at least 91%, 92%, 93%, 94%, 95%, 96%, 97%, 98%, 99%; e.g. 97% or 98.7% identity thereto or a 16S rDNA sequence having at least 90% e.g. at least 91%, 92%, 93%, 94%, 95%, 96%, 97%, 98%, 99%; e.g. 97% or 98.7% identity thereto (consortium 3 in Table 3).

In another embodiment, the composition comprises or consists of bacteria having SEQ ID No. 1 or a 16S rDNA sequence having at least 90% e.g. at least 91%, 92%, 93%, 94%, 95%, 96%, 97%, 98%, 99%; e.g. 97% or 98.7% identity thereto, SEQ ID No. 2 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 3 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 6 or a 16S rDNA sequence having at least 90% e.g. at least 91%, 92%, 93%, 94%, 95%, 96%, 97%, 98%, 99%; e.g. 97% or 98.7% Identity thereto, bacteria having SEQ ID No. 7 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 8 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 9 or a 16S rDNA sequence having at least 90% e.g. at least 91%, 92%, 93%, 94%, 95%, 96%, 97%, 98%, 99%; e.g. 97% or 98.7% Identity thereto, bacteria having SEQ ID No. 11 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 14 or a 16S rDNA sequence having at least 90% e.g. at least 91%, 92%, 93%, 94%, 95%, 96%, 97%, 98%, 99%; e.g. 97% or 98.7% identity thereto (consortium 4 in Table 3).

In another embodiment, the composition comprises or consists of bacteria having SEQ ID No. 1 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 7 or a 16S rDNA sequence having at least 90% e.g. at least 91%, 92%, 93%, 94%, 95%, 96%, 97%, 98%, 99%; e.g. 97% or 98.7% Identity thereto, bacteria having SEQ ID No. 8 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 9 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 13 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 16 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 17 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 18 or a 16S rDNA sequence having at least 90% e.g. at least 91%, 92%, 93%, 94%, 95%, 96%, 97%, 98%, 99%; e.g. 97% or 98.7% identity thereto and bacteria having SEQ ID No. 20 or a 16S rDNA sequence having at least 90% e.g. at least 91%, 92%, 93%, 94%, 95%, 96%, 97%, 98%, 99%; e.g. 97% or 98.7% identity thereto (consortium 5 in Table 3).

In another embodiment, the composition comprises or consists of bacteria having SEQ ID No. 1 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 2 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 7 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 9 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 13 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 16 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 18 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 19 or a 16S rDNA sequence having at least 90% e.g. at least 91%, 92%, 93%, 94%, 95%, 96%, 97%, 98%, 99%; e.g. 97% or 98.7% identity thereto and bacteria having SEQ ID No. 20 or a 16S rDNA sequence having at least 90% e.g. at least 91%, 92%, 93%, 94%, 95%, 96%, 97%, 98%, 99%; e.g. 97% or 98.7% identity thereto (consortium 6 in Table 3).

In another embodiment, the composition comprises or consists of bacteria having SEQ ID No. 1 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 2 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 7 or a 16S rDNA sequence having at least 90% e.g. at least 91%, 92%, 93%, 94%, 95%, 96%, 97%, 98%, 99%; e.g. 97% or 98.7% Identity thereto, bacteria having SEQ ID No. 9 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 18 or a 16S rDNA sequence having at least 90% e.g. at least 91%, 92%, 93%, 94%, 95%, 96%, 97%, 98%, 99%; e.g. 97% or 98.7% identity thereto and bacteria having SEQ ID No. 19 or a 16S rDNA sequence having at least 90% e.g. at least 91%, 92%, 93%, 94%, 95%, 96%, 97%, 98%, 99%; e.g. 97% or 98.7% Identity thereto (consortium 7 in Table 3).

In another embodiment, the composition comprises or consists of bacteria having SEQ ID No. 1 or a 16S rDNA sequence having at least 90% e.g. at least 91%, 92%, 93%, 94%, 95%, 96%, 97%, 98%, 99%; e.g. 97% or 98.7% Identity thereto, bacteria having SEQ ID No. 2 or a 16S rDNA sequence having at least 90% e.g. at least 91%, 92%, 93%, 94%, 95%, 96%, 97%, 98%, 99%; e.g. 97% or 98.7% Identity thereto and, bacteria having SEQ ID No. 7 or a 16S rDNA sequence having at least 90% e.g. at least 91%, 92%, 93%, 94%, 95%, 96%, 97%, 98%, 99%; e.g. 97% or 98.7% Identity thereto (consortium 8 in Table 3).

In another embodiment, the composition comprises or consists of bacteria having SEQ ID No. 1 or a 16S rDNA sequence having at least 90% e.g. at least 91%, 92%, 93%, 94%, 95%, 96%, 97%, 98%, 99%; e.g. 97% or 98.7% identity thereto and bacteria having SEQ ID No. 2 or a 16S rDNA sequence having at least 90% e.g. at least 91%, 92%, 93%, 94%, 95%, 96%, 97%, 98%, 99%; e.g. 97% or 98.7% identity thereto (consortium 9 in Table 3).

Thus, in one embodiment, the composition comprises or consists of bacteria having SEQ ID No. 1 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 2 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 3 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 5 or a 16S rDNA sequence having at least 90% e.g. at least 91%, 92%, 93%, 94%, 95%, 96%, 97%, 98%, 99%; e.g. 97% or 98.7% Identity thereto, bacteria having SEQ ID No. 7, or a 16S rDNA sequence having at least 90% e.g. at least 91%, 92%, 93%, 94%, 95%, 96%, 97%, 98%, 99%; e.g. 97% or 98.7% Identity thereto, bacteria having SEQ ID No. 10 or a 16S rDNA sequence having at least 90% e.g. at least 91%, 92%, 93%, 94%, 95%, 96%, 97%, 98%, 99%; e.g. 97% or 98.7% identity thereto, bacteria having SEQ ID No. 11 or a 16S rDNA sequence having at least 90% e.g. at least 91%, 92%, 93%, 94%, 95%, 96%, 97%, 98%, 99%; e.g. 97% or 98.7% identity thereto; bacteria having SEQ ID No. 13 or a 16S rDNA sequence having at least 90% e.g. at least 91%, 92%, 93%, 94%, 95%, 96%, 97%, 98%, 99%; e.g. 97% or 98.7% Identity thereto or a 16S rDNA sequence having at least 90% e.g. at least 91%, 92%, 93%, 94%, 95%, 96%, 97%, 98%, 99%; e.g. 97% or 98.7% Identity thereto and bacteria having SEQ ID No. 14 or a 16S rDNA sequence having at least 90% e.g. at least 91%, 92%, 93%, 94%, 95%, 96%, 97%, 98%, 99%; e.g. 97% or 98.7% Identity thereto or a 16S rDNA sequence having at least 90% e.g. at least 91%, 92%, 93%, 94%, 95%, 96%, 97%, 98%, 99%; e.g. 97% or 98.7% Identity thereto (consortium 10 In Table 3).

With reference to the percentage identities recited for the embodiments of the compositions above, in one embodiments sequence identity is at least 98.7% or 99%. It will be understood that where Table 1 provides multiple sequences for a single species, any of these sequences can be used according to the above embodiments.

In one example, species used in the composition are identified based on their 16S rDNA sequence (e.g., full-length sequence, or partial sequence). In some cases, strains of bacterial species useful in an invention, e.g., strains of the species disclosed herein, can be obtained from a public biological resource center such as the ATCC, the DSMZ, or the Riken BioResource Center. 16s rDNA sequences useful for identifying species or other aspects of the invention can be obtained from public databases, e.g., the Human Microbiome Project (HMP) web site or GenBank.

A skilled person would appreciate that the compositions may include one or more than one strain of a particular bacterial species as listed in Table 1. For example, the composition of the invention comprises more than one bacterial strain for a species. For example, in some embodiments, the composition of the invention comprises more than one strain from within the same species (e.g. more than 1, 2, 3, 4, 5, 6, 7, 8, 9, 10, 15, 20, 25, 30, 35, 40 or 45 strains). In another embodiment, the composition of the invention comprises one bacterial strain for each species.

In one embodiment, the bacteria of the composition are capable of colonising the gastrointestinal tract of a subject. In one embodiment, the bacteria of the composition are capable of sustained engraftment in the gastrointestinal tract of a subject.

In one embodiment, the composition has one or more of the following characteristics:
The composition has an immunostimulatory effect;
The composition is effective in treating and/or preventing cancer in a subject, tissue or cell, e.g. when used together with a checkpoint inhibitor therapy;
The composition is effective in treating and/or preventing an infectious disease in a subject, tissue or cell;
Administration of the composition to a subject, tissue or cell induces an immune response in a subject and/or increases the efficacy according to an anti-cancer therapy that includes an immune checkpoint inhibitor,
Administration of the composition to a subject, tissue or cell enhances CD8+ response;
Administration of the composition to a subject, tissue or cell enhances immune checkpoint blockade;
Administering of the composition maintains or induces responsiveness of a tumour an immune checkpoint;
Administration of the composition to a subject, tissue or cell increases the number or activity of a cell type of the immune system, e.g. T cells, B cells, dendritic cells, macrophages, neutrophils, NK cells, plasmacytoid dendritic cells and combinations thereof;
Administration of the composition to a subject, tissue or cell shifts a ratio of immune cells in the subject in favor of a cell type capable of suppressing growth of a tumour e.g. T cells, cytotoxic T lymphocytes, T helper cells, natural killer (NK) cells, natural killer T (NKT) cells, plasmacytoid dendritic cells, anti-tumour macrophages, B cells, dendritic cells, and combinations thereof and/or
Administration of the composition to a subject, tissue or cell shifts a ratio of immune cells in the subject against a cell type capable of protecting a tumour e.g. myeloid-derived suppressor cells (MDSCs), regulatory T cells (Tregs), tumour associated neutrophils (TANs), M2 macrophages, tumour associated macrophages (TAMs), and a combination thereof;
Administration of the composition to a subject, tissue or cell increases the abundance/level of bacteria in the subject which discourages cancer/tumour growth, spread, and/or evasion of treatment/immune response;
Administration of the composition to a subject, tissue or cell increases the abundance of bacteria in the subject tissue or cell which creates an environment or microenvironment (e.g., metabolome) that is conducive to the treatment of cancer and/or inhibits cancer/tumour growth.

The subject may be a human or an animal in an animal model, for example a mouse model. In vitro models can also be used for testing efficacy, e.g. tissue or cell-based models. Suitable models and assays are also shown in the examples.

As used herein, an "immune response" refers to the action of a cell of the immune system (e.g., T lymphocytes, B lymphocytes, natural killer (NK) cells, macrophages, eosinophils, mast cells, dendritic cells, neutrophils, etc.) and soluble macromolecules produced by any of these cells or the liver (including antibodies, cytokines, and complement) that results in selective targeting, binding to, damage to, destruction of, and/or elimination from a subject of invading pathogens, cells or tissues infected with pathogens, or cancerous or other abnormal cells. This can be measured by assessing suitable markers or cell types.

As used herein, the term "immunotherapy" refers to the treatment or prevention of cancer by a method comprising inducing, enhancing, suppressing or otherwise modifying an immune response.

The bacterial isolates can be isolated and cultured as described in WO2013/171515 or WO2017/182796, both incorporated herein by reference. In one embodiment, bacterial strains are cultured and grown individually and then combined in the composition.

A bacterial isolate used in the composition is preferably a non-pathogenic strain. In other words, the bacterium preferably does not cause a disease in a healthy human individual when administered to said individual.

In one embodiment, each bacterium present in the composition is susceptible to treatment with one or more antibiotics. In other words, the bacterium is not resistant to treatment with at least one antibiotic. This allows antibiotic treatment of an individual in the event that one or more of the bacteria included in a therapeutic composition administered to the individual cause disease in the individual, contrary to expectations. Thus, in one embodiment, the bacterium is susceptible to treatment with one or more antibiotics selected from the group consisting of: a beta-lactam, fusidic acid, elfamycin, aminoglycoside, fosfomycin, tunicamycin metronidazole and/or vancomycin. In vitro and in silico methods for screening bacteria for antibiotic resistance are known in the art.

In one embodiment, the isolated bacterium included in the compositions may not comprise one or more genes encoding one or more virulence factors and/or preferably does not produce one or more virulence factors. Virulence factors in this context are properties which enhance the potential of a bacterium to cause disease in an individual. Virulence factors include the production of bacterial toxins, such as endotoxins and exotoxins by a bacterium, as well as the production of hydrolytic enzymes that may contribute to the pathogenicity of the bacterium. Methods for screening bacteria for genes encoding virulence factors are known in the art.

In some embodiments, one or more of the bacterial strains are human-derived bacteria, meaning the one or more bacterial strains were obtained from or identified from a human or a sample therefrom (e.g., a human donor). In some embodiments of the compositions provided herein, all of the bacterial strains are human-derived bacteria. In some embodiments of the compositions provided herein, the bacterial strains are derived from more than one human donor.

The bacterial strains used in the live bacterial products provided herein generally are isolated from the microbiome of healthy individuals, e.g. from human faeces, but in some cases may not be from healthy individuals. In some embodiments, the live bacterial products include strains originating from a single individual. In some embodiments, the live bacterial products include strains originating from multiple individuals. In some embodiments, the bacterial strains are obtained from multiple individuals, isolated and grown up individually. The bacterial compositions that are grown up individually may subsequently be combined to provide the compositions of the disclosure. It should be appreciated that the origin of the bacterial strains of the live bacterial products provided herein is not limited to the human microbiome from a healthy individual.

Isolation and characterisation can be achieved using standard methods in the art. For example, the V4-V5 region of the 16S rRNA encoding gene can be amplified and sequenced. Sequences can then be aligned and compared to the 16S sequences provided herein for the bacterial isolates. Sequence protocols and alignment software are well known in the art.

In some cases, strains of bacterial species useful in an invention, e.g., strains of the species disclosed herein, can be obtained from a public biological resource centre as described above.

In some embodiments in which the composition of the invention comprises more than one bacterial strain or species as listed herein, the individual bacterial strains or species may be for separate, simultaneous or sequential administration. For example, the composition may comprise bacteria from all or a subset of the species listed in Table 1, or the bacterial strains or species are selected from those listed in Table 1, but may be stored separately and be administered separately, simultaneously or sequentially. In some embodiments, the more than one bacterial strain or species are stored separately, but are mixed together prior to use.

As explained herein, the bacterial compositions of the invention have therapeutic effects when administered to a subject and can be used in the treatment or prevention of cancer. Thus, the compositions as described herein are therapeutic compositions. Thus, the invention also extends to pharmaceutical compositions comprising a composition of bacteria as described herein. This may include further ingredients, for example a vaccine.

In one embodiment, the composition may comprise a pharmaceutically acceptable excipient, carrier, buffer, stabilizer or other materials well known to those skilled in the art. Such materials should be non-toxic and should not interfere with the efficacy of the isolated bacteria present in the therapeutic composition. The precise nature of the pharmaceutically acceptable excipient or other material will depend on the route of administration, which may be oral or rectal. Many methods for the preparation of therapeutic compositions are known to those skilled in the art.

The bacterial compositions of the invention may comprise a prebiotic, a pharmaceutically acceptable carrier, insoluble fibre, a buffer, an osmotic agent, an anti-foaming agent and/or a preservative. Particular examples of excipients included in the composition are disclosed below.

Prebiotics may provide nutrients for the isolated bacteria present in the bacterial composition to assist their early growth and colonisation after administration to the individual. Any prebiotic known in the art may be used. Non-limiting examples of prebiotics include oligosaccharides, e.g., fructooligosaccharides such as oligofructose and inulin, mannan oligosaccharides and galactooligosaccharides, soluble, oligofructose-enriched inulin and soluble fibre. Insoluble fibre may be included in the therapeutic composition as a carrier, e.g., to provide protection during transit or storage. A buffer may be included in the bacterial composition to promote the viability of the isolated bacteria present. An anti-fungal agent may be included in the bacterial composition as a preservative.

In one embodiment, the therapeutic bacterial compositions may comprise no other active ingredient other than the bacterial isolates as described herein, including no other isolated bacterium, and optionally a prebiotic. Thus, the active ingredient of the therapeutic composition may consist of the group of bacterial isolates as described herein, and optionally a prebiotic.

The bacterial compositions of the invention can be administered to a subject in a variety of ways as described in more detail elsewhere herein, including in the form of a capsule, tablet, gel or liquid.

The bacterial compositions of the invention may be for oral or rectal administration to the subject. Where the composition is for oral administration, the composition may be in the form of a capsule, or a tablet. Where the therapeutic composition is for rectal administration, the therapeutic composition may be in the form of an enema, tablet or capsule. The preparation of suitable capsules, tablets and enemas is well-known in the art. The capsule or tablet may comprise an enteric coating to protect the capsule or tablet from stomach acid. For example, the capsule or tablet may be enteric-coated, pH defendant, slow-release, and/or gastro-resistant. Such capsules and tablets are used, for example, to minimize dissolution of the capsule or tablet in the stomach but allow dissolution in the small intestine. When intended for oral administration, the composition can be in solid or liquid form, where semi-solid, semi-liquid, suspension and gel forms are included within the forms considered herein as either solid or liquid.

As a solid composition for oral administration, the compostions can be formulated into a powder, granule, compressed tablet, pill, capsule, chewing gum, wafer or the like. Such a solid composition typically contains one or more inert diluents. In addition, one or more of the following can be present: binders such as carboxymethylcellulose, ethyl cellulose, microcrystalline cellulose, or gelatin, excipients such as starch, lactose or dextrins, disintegrating agents such as alginic acid, sodium alginate, corn starch and the like; lubricants such as magnesium stearate, glidants such as colloidal silicon dioxide, sweetening agents such as sucrose or saccharin, a flavoring agent such as peppermint, methyl salicylate or orange flavoring; and a coloring agent. When the composition is in the form of a capsule (e. g. a gelatin capsule), it can contain, in addition to materials of the above type, a liquid carrier such as polyethylene glycol, cyclodextrin or a fatty oil.

When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

The bacterial composition may include a pharmaceutically acceptable carrier or vehicle that can be particulate, so that the compositions are, for example, in tablet or powder form. The term "carrier" refers to a diluent, adjuvant or excipient, with which the composition is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, the composition and pharmaceutically acceptable carriers are sterile. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions can take the form of one or more dosage units. In an embodiment, the dose unit comprises at least $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$ or greater than $1 \times 10^{13}$ colony forming units (cfu) of vegetative bacterial cells. In an embodiment, the dose unit comprises a pharmaceutically acceptable excipient, an enteric coating or a combination thereof. The bacterial isolates or composition may be provided at a suitable dose.

Treatments or specific processes can be applied to improve the stability or viability of the bacterial isolates in the composition. The bacterial composition can be applied in a dry form or in a wet from. The bacterial composition may be lyophilized. The lyophilized therapeutic composition may comprise one or more stabilisers and/or cryoprotectants. The lyophilized bacterial composition may be reconstituted using a suitable diluent prior to administration to the individual.

Then invention also relates to a pharmaceutical composition comprising one or more bacteria of selected from the bacterial species of Table 1 or comprising a composition as described herein and further comprising an effective amount of an immune checkpoint inhibitor.

Immune checkpoints are regulatory pathways within the immune system that are involved in maintaining immune homeostasis (e.g., self-tolerance, modulating the duration and extent of an immune response) to minimize cellular damage due to aberrant immune responses. Inhibitors of immune checkpoints, herein referred to as "immune checkpoint inhibitors," specifically inhibit immune checkpoints and may have a stimulatory or inhibitory effect on the immune response.

In one embodiment, the immune checkpoint inhibitor is an antibody or fragment thereof, an interfering nucleic acid molecule or another chemical entity.

A number of checkpoint inhibitors are known in the art and a number of treatments have been approved by regulatory authorities, including antibody treatments, whilst others, including treatments with monoclonal antibodies or antibody fragments, such as single domain antibodies, have shown efficacy across a wide range of cancers.

In one embodiment, the immune checkpoint inhibitor inhibits PD-1 activity, i.e. acts as PD-1 antagonist.

"PD-1 antagonist" or "PD-1 inhibitor" means any chemical compound or biological molecule that blocks binding of PD-L1 expressed on a cancer and or immune cell to PD-1 expressed on an immune cell (T cell, B cell or NKT cell) and preferably also blocks binding of PD-L2 expressed on a cancer and or immune cell to the immune-cell expressed PD-1.

In one embodiment, the immune checkpoint inhibitor is a PD-1 inhibitor, PD-L1 inhibitor or PD-L2 inhibitor, e.g. an anti PD-1 antibody or anti PD-L1 or anti PD-L2 antibody. In one embodiment, the immune checkpoint inhibitor is an anti PD-1 antibody. In one embodiment, the immune checkpoint inhibitor is an anti PD-1 or PD-L1 antibody optionally selected from nivolumab (MDX-1106, MDX-1106-04, ONO-4538, or BMS-936558), pembrolizumab (Trade name KEYTRUDA® formerly lambrolizumab, also known as Merck 3745, MK-3475 or SCH-900475), cemiplimab, avelumab, durvalumab, atezolizumab, spartalizumab, camrelizumab, sintilimab, tislelizumab, pidilizumab or toripalimab.

In one embodiment, the immune checkpoint inhibitor is an anti-cytotoxic T-lymphocyte-associated protein 4 (CTLA-4 inhibitor), i.e. inhibits the activity of CTLA-4. CTLA-4 (CD152) is a B7/CD28 family member that inhibits T cell functions with NCBI Gene ID: 1493. CTLA-4 mAbs or CTLA-4 ligands can prevent CTLA-4 from binding to its native ligands, thereby blocking the transduction of the T-cell negative regulating signal by CTLA-4 and enhancing the responsiveness of T-cells to various antigens. In this aspect, results from in vivo and in vitro studies are substantially in concert.

The CTLA4 inhibitor can be a CTLA4 antibody, optionally Ipilimumab or Tremellmumab.

In one embodiment, the immune checkpoint inhibitor Is an anti-TGIT, anti-LAG3 or anti-TIM3 agent, e.g. and antibody. The checkpoint targets listed herein are not limiting and a skilled person would understand that other checkpoint targets are also within the scope of the invention and may be inhibited.

It should further be appreciated that multiple immune checkpoint inhibitors may be used in the methods, compositions, and kits disclosed herein.

In some embodiments, the cancer immunotherapy agent comprises an anticancer vaccine (also referred to herein as a cancer vaccine). Cancer vaccines generally act to increase an immune response to cancer cells. For example, cancer vaccines include cancer antigen(s) that act to induce or stimulate an immune response against cells bearing the cancer antigen(s). The immune response induced or stimulated can include an antibody (humoral) immune response and/or a T-cell (cell-mediated) immune response.

Unless otherwise specified, the term PD-1 as used herein refers to human PD-1. The terms "Programmed Death 1", "Programmed Cell Death 1". "Protein PD-1", "PD-1", PD1," "PDCD1", "hPD-1" and "hPD-1" are used interchangeably, and include variants, isoforms, species homologs of human PD-1. The term PD-1 antibody or antibody fragment refers to a molecule capable of specifically binding to the human PD-1 antigen and antagonising PD-1 action. Human PD-1 amino acid sequences can be found in NCBI Locus No.: NP_005009. Human PD-L1 and PD-L2 amino acid sequences can be found in NCBI Locus No.: NP_054862 and NP_079515, respectively.

The term "antibody" as used herein broadly refers to any immunoglobulin (Ig) molecule, or antigen binding portion thereof, comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. The antibody may be mono or multispecific, e.g. bispecific. The antibody may be administered in combination with another antibody therapy, e.g. another antibody that targets a checkpoint inhibitor or in combination with another anti-cancer therapy, e.g. chemotherapy and targeted therapies, surgery and/or radiotherapy.

In a full-length antibody, each heavy chain is comprised of a heavy chain variable region or domain (abbreviated herein as HCVR) and a heavy chain constant region. The heavy chain constant region is comprised of three domains, CH1, CH2 and CH3. Each light chain is comprised of a light chain variable region or domain (abbreviated herein as LCVR) and a light chain constant region. The light chain constant region is comprised of one domain, CL.

The heavy chain and light chain variable regions can be further subdivided into regions of hypervariability, termed complementarity determining regions (CDR), Interspersed with regions that are more conserved, termed framework regions (FR). Each heavy chain and light chain variable region is composed of three CDRs and four FRs, arranged from amino-terminus to carboxy-terminus in the following order: FR1, CDR1, FR2, CDR2, FR3, CDR3, FR4.

Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term antibody as used herein includes antibody fragments, such as F(ab')2, Fab, Fv, scFv, a heavy chain only antibody, single domain antibodies ($V_H$, $V_L$, $V_{HH}$) or an antibody mimetic protein. Various antibody formats have been shown to show efficacy against checkpoint inhibitors, including single domain antibodies (e.g. Yu S et al. Nanobodies targeting immune checkpoint molecules for tumor immunotherapy and immunoimaging. Int J Mol Med. 2021; 47(2):444-454).

scFv fragments (~25 kDa) consist of the two variable domains, $V_H$ and $V_L$. Naturally, $V_H$ and $V_L$ domain are non-covalently associated via hydrophobic interaction and tend to dissociate. However, stable fragments can be engineered by linking the domains with a hydrophilic flexible linker to create a single chain Fv (scFv). The smallest antigen binding fragment is the single variable fragment, namely the $V_H$ or $V_L$ domain. Binding to a light chain/heavy chain partner respectively is not required for target binding. Such fragments are used in single domain antibodies. A single domain antibody (~12 to 15 kDa) therefore has either the $V_H$ or $V_L$ domain.

The antibody may be human, humanised or chimeric. A chimeric antibody is a recombinant protein that contains the variable domains including the complementarity determining regions (CDRs) of an antibody derived from one species, preferably a rodent antibody, while the constant domains of the antibody molecule are derived from those of a human antibody.

A humanized antibody is a recombinant protein in which the CDRs from an antibody from one species; e.g., a rodent antibody, are transferred from the heavy and light variable chains of the rodent antibody into human heavy and light variable domains (e.g., framework region sequences). The constant domains of the antibody molecule are derived from those of a human antibody. In certain embodiments, a limited number of framework region amino acid residues from the parent (rodent) antibody may be substituted into the human antibody framework region sequences.

Checkpoint inhibitors are not limited to antibodies. In one embodiment, the immune checkpoint inhibitor is an interfering nucleic acid molecule, optionally wherein the interfering nucleic acid molecule is an siRNA molecule, an shRNA molecule or an antisense RNA molecule.

In one embodiment, the immune checkpoint inhibitor is a small molecule or PROteolysis TArgeting Chimera (PROTAC), alternative scaffold protein, biologics or other immune checkpoint inhibitor. In one embodiment, the immune checkpoint inhibitor is an interfering nucleic acid molecule. In one embodiment, the interfering nucleic acid molecule is an siRNA molecule, an shRNA molecule or an antisense RNA molecule. In one embodiment, the immune checkpoint inhibitor is a small molecule or a PROteolysis TArgeting Chimera (PROTAC) or other immune checkpoint inhibitor. Examples that small molecules can be used as checkpoint inhibitors is provided by research on sulfamonomethoxine and sulfamethizole. Exemplary small molecule compounds that inhibit PD-L1 are disclosed in U.S. Pat. No. 9,850,225 incorporated herein by reference. A small molecule currently in human clinical trials is a molecule called Ca-170, which inhibits both the PD-L1 pathway and the V-domain Ig suppressor of the T-cell activation (VISTA) pathway.

In one embodiment, the immune checkpoint inhibitor is a peptide inhibitor. An example is the peptide antagonist. (D)PPA-1, which blocks the PD-1/PD-L1 interaction and decreases tumor growth in vivo (Chang H. N et al. Blocking of the PD-1/PD-L1 Interaction by a D-Peptide Antagonist for Cancer Immunotherapy. Angew. Chem. Int. Ed. 2015; 54:11760-11764). Another peptide inhibitor is PL120131, shown to act as a competitive inhibitor of PD-L1 (Magiera-Mularz K. et al Bioactive Macrocyclic Inhibitors of the PD-1/PD-L1 Immune Checkpoint. Angew. Chem. Int. Ed. 2017; 56:13732-13735) and TPP-1 (Li C., Zhang N et al, Peptide Blocking of PD-1/PD-L1 Interaction for Cancer Immunotherapy. Cancer Immunol. Res. 2018; 6:178-188).

In another aspect, there is provided a bacterial composition described herein for use in the treatment of disease. e.g. cancer. In another aspect, there is provided the use of a bacterial composition described herein in the manufacture of a medicament for the treatment or prevention of a disease, e.g. cancer.

In another aspect, there is provided a method for treating or preventing a disease comprising administering a bacterial composition described herein to a subject. In another aspect, there is provided a method for treating or preventing a disease in a subject comprising modulating the level of, e.g. Increasing the level/relative abundance of one or more bacterium selected from B1, B2, B3, B4, B5, B8, B7, B8, B9, B10, B11, B12, B13, B14 and/or B15 as shown in Table 1 or a subset thereof in a subject. In one embodiment, the subset comprises or consists of bacteria selected from 1, 2, 3, 4, 5, 8, 7, 8, 9, 10, 11, 12, 13, 14 or 15 bacterial species shown in Table 1. Modulating the level according to one or more bacterium in the subject enhances an immune response by the subject and/or inhibits immune evasion by the cancer and/or increases efficacy according to an anti-cancer treatment with an immune checkpoint inhibitor. In one embodiment, the method comprises administering a composition as described herein.

As explained below, the level/abundance can be compared to a reference value from a reference subject or population of subjects.

In one embodiment, the disease is cancer. In one embodiment, the cancer is melanoma. "Melanoma" Is taken to mean a tumour arising from the melanocytic system of the skin and other organs. Non-limiting examples of melanomas are Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma, subungual melanoma, Cutaneous melanoma, uveal/intraocular melanoma and superficial spreading melanoma.

The compositions of the present invention are particularly useful for the treatment of cancers that are treatable by checkpoint inhibitors.

In one embodiment, the cancer is associated with cells (e.g., exhausted T cells, B cells, monocytes, etc.) that express abnormally high levels of PD-1. Other cancers include those characterized by elevated expression of PD-1 and/or its ligands PD-L1 and/or PD-L2.

In one embodiment, the cancer is selected from a cancer that has high levels of cancer-associated genetic mutations and/or high levels of expression of tumour antigens. In another embodiment, the cancer is selected from a cancer known to be immunogenic or that is able to become immunogenic upon treatment with other cancer therapies. In a further embodiment the cancer can be selected from a cancer generally treated by non-immunological therapies, such as chemotherapy, in which the patient's immune system is likely to have a role.

The cancer can be selected from a solid or non-solid tumour. For example, in addition to melanoma, the cancer may be selected from another skin cancer or from bone cancer, pancreatic cancer, cancer of the head or neck, cutaneous or intraocular malignant melanoma, uterine cancer, ovarian cancer, rectal cancer, cancer of the anal region, stomach cancer, testicular cancer, breast cancer, brain cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, kidney cancer, sarcoma of soft tissue, cancer of the urethra, cancer of the bladder, renal cancer, lung cancer, non-small cell lung cancer, thymoma, urothelial carcinoma leukemia, prostate cancer, mesothelioma, adrenocortical carcinoma, lymphomas, such as such as Hodgkin's disease, non-Hodgkin's, gastric cancer, and multiple myelomas.

In one embodiment, the tumour is a solid tumour. Examples of solid tumours which may be accordingly treated include breast carcinoma, lung carcinoma, colorectal carcinoma, pancreatic carcinoma, glioma and lymphoma. Some examples of such tumours include epidermoid tumours, squamous tumours, such as head and neck tumours, colorectal tumours, prostate tumours, breast tumours, lung tumours, including small cell and non-small cell lung tumours, pancreatic tumours, thyroid tumours, ovarian tumours, and liver tumours. Other examples include Kaposi's sarcoma, CNS, neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma. Examples of vascularized skin cancers for which the antagonists of this invention are effective include squamous cell carcinoma, basal cell carcinoma and skin cancers that can be treated by suppressing the growth of malignant keratinocytes, such as human malignant keratinocytes. In one embodiment, the cancer is NSCL.

In one embodiment, the tumour is a non-solid tumour. Examples of non-solid tumours include leukemia, multiple myeloma and lymphoma.

In one aspect, the cancer is identified as a PD-1 and/or PD-L1 positive cancer or a cancer positive for another checkpoint protein. In one aspect, the cancer is locally advanced, unresectable, metastatic, or recurrent cancer.

Preferred cancers whose growth may be inhibited using the agents of the invention include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer).

As used herein, "treat", "treating" or "treatment" means inhibiting or relieving a disease or disorder. For example, treatment can include a postponement of development of the symptoms associated with a disease or disorder, and/or a reduction in the severity of such symptoms that will, or are expected, to develop with said disease. The terms include ameliorating existing symptoms, preventing additional symptoms, and ameliorating or preventing the underlying causes of such symptoms. Thus, the terms denote that a beneficial result is being conferred on at least some of the mammals, e.g., human patients, being treated. Many medical treatments are effective for some, but not all, patients that undergo the treatment.

The term "subject" or "patient" refers to an animal, e.g. a human, which is the object of treatment, observation, or diagnosis. By way of example only, a subject includes, but is not limited to, a mammal, Including, but not limited to, a human or a non-human mammal, such as a non-human primate, murine, bovine, equine, canine, ovine, or feline. In one embodiment, the subject is a cancer patient that has received prior anti-cancer treatment or is receiving anti-cancer treatment. In one embodiment, the anti-cancer treatment is treatment with an immune checkpoint inhibitor. Exemplary immune checkpoint inhibitors are described herein.

The term "anti-cancer therapy" refers to any therapeutic regimen that aims to reduce or eliminate cancer, slow the progression of cancer, prevent or reduce the risk of cancer metastasis, and/or reduce or prevent any one or more symptoms associated with cancer. The anti-cancer therapies described herein involve administering anti-cancer therapies to a subject, e.g., a subject having cancer or at risk of having cancer.

Administration according to the method and uses above includes oral administration or rectal administration.

In one embodiment, the subject has received prior anti-cancer therapy with an immune checkpoint inhibitor. In one embodiment, an anti-cancer therapy comprising an immune checkpoint inhibitor is administered to the subject. This can be administered at the same time as the composition of the invention, either as part of the same medicament or as a second medicament. It can also be administered prior or after the administration of the composition of the invention. Other treatment schedules are also within the scope of the invention.

In one embodiment, the immune checkpoint inhibitor is administered before, after or at the same time as the bacterial composition. In one embodiment, checkpoint therapy is initiated, and then supplemented with treatment using the bacterial composition described herein if no response is seen after 3-6 months.

In one embodiment, the immune checkpoint inhibitor is administered after the bacterial composition. In one embodiment the immune checkpoint inhibitor is administered by injection/Infusion. In one embodiment the injection is an intravenous, Intramuscular, intratumoural or subcutaneous injection.

Checkpoint Inhibitors that can be used in accordance with the treatment aspects are defined above. For example, the immune checkpoint inhibitor inhibits PD-1, CTLA-4 or PD-L1 activity. In one embodiment the immune checkpoint inhibitor is an anti PD-1, CTLA-4 or PD-L1 antibody. In one embodiment, the anti PD-1, CTLA-4 or PD-L1 antibody is selected from nivolumab, pembrolizumab, cemiplimab, avelumab, durvalumab, atezolizumab, Spartalizumab, Camrelizumab, Sintilimab, Tislelizumab, Pidilizumab or Toripalimab, Ipilimumab or Tremelimumab.

The amount of the antibody that is effective/active in the treatment of a particular disorder or condition will depend on the nature of the disorder or condition and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances. Factors like age, body weight, sex, diet, time of administration, rate of excretion, condition of the host, drug combinations, reaction sensitivities and severity of the disease shall be taken into account.

Typically, the amount is at least about 0.01% of an anti-PD-1, CTL-4 or PD-L1 antibody by weight of the composition. When intended for oral administration, this amount can be varied to range from about 0.1% to about 80% by weight of the composition. Oral compositions can comprise from about 4% to about 50% of the antibody by weight of the composition.

Antibody compositions can be prepared so that a parenteral dosage unit contains from about 0.01% to about 2% by weight of the antibody.

For administration by injection, the composition can comprise from about typically about 0.1 mg/kg to about 250 mg/kg of the animal's body weight, preferably, between about 0.1 mg/kg and about 20 mg/kg of the animals body weight, and more preferably about 1 mg/kg to about 10 mg/kg of the animals body weight. In one embodiment, the composition is administered at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks.

In one embodiment, the immune checkpoint inhibitor is an interfering nucleic acid molecule. In one embodiment, the interfering nucleic acid molecule is an siRNA molecule, an shRNA molecule or an antisense RNA molecule. In one embodiment, the immune checkpoint inhibitor is a small molecule or a PROteolysis TArgeting Chimera (PROTAC) or other immune checkpoint inhibitor, for example as described above.

In one embodiment, the method and uses further comprise administration of an anti-cancer therapy, e.g. a second anti-cancer therapeutic in addition to an immune checkpoint inhibitor. The anti-cancer therapy may include a therapeutic agent or radiation therapy and includes gene therapy, viral therapy, RNA therapy bone marrow transplantation, nanotherapy, targeted anti-cancer therapies or oncolytic drugs or a combination thereof. Examples of other therapeutic agents include other checkpoint inhibitors, antineoplastic agents, immunogenic agents, attenuated cancerous cells, tumour antigens, antigen presenting cells such as dendritic cells pulsed with tumour-derived antigen or nucleic acids, Immune stimulating cytokines (e.g., IL-2, IFNa2, GM-CSF), targeted small molecules and biological molecules (such as components of signal transduction pathways, e.g. modulators of tyrosine kinases and inhibitors of receptor tyrosine kinases, and agents that bind to tumour-specific antigens, including EGFR antagonists), an anti-inflammatory agent, a cytotoxic agent, a radiotoxic agent, or an immunosuppressive agent and cells transfected with a gene encoding an immune stimulating cytokine (e.g., GM-CSF), chemotherapy. In one embodiment, the composition is used in combination with surgery. In one embodiment, the composition is used in combination with a stem-cell transplant therapy comprising a peripheral blood transplant, a bone marrow transplant, a cord blood transplant, or a skin-derived stem cell transplant.

In one embodiment, the composition is used in combination with adoptive cell transfer (ACT). In general, adoptive cell transfer therapy involves harvesting cells from a subject, specifically producing or expanding a specific cell population, optionally activating the cells, and administering the expanded cells to the subject. In some embodiments, the desired cells are immune cells capable of killing or eliminating cancer cells.

In some embodiments, the adoptive cell transfer therapy uses engineered T-cell receptors or chimeric antigen receptors, which may be referred to as CAR-T therapy. CAR-T cells include T-cells taken from a subject that are genetically engineered to express chimeric antigen receptors (CARs) on the cell surface. The CAR-T cell receptors are designed to recognize a specific antigen on cancer cells (e.g., a cancer antigen). After the CAR-T cells are infused Into the subject, the CAR-T cells recognize and kill cancer cells that express the specific antigen on their surfaces. In some embodiments, the CAR-T cells are autologous cells, meaning the T cells were harvested and re-administered to the same subject. In some embodiments, the CAR-T cells are CD8+ T cells. In some embodiments, the CAR-T cells are allogeneic cells, meaning the T cells were harvested from one subject (e.g., the donor) and administered to a different subject (e.g., the recipient).

Examples of cancer antigens that may be targeted by CAR-T cells are known in the art, and selection of a cancer antigen for targeting will depend on factors such as the cancer that is being targeted.

In some embodiments, the anticancer therapy involves administering one or more costimulatory agents. In some embodiments, the costimulatory agent is a molecule that targets one or more costimulatory molecules, thereby modulating the immune response. In some embodiments, the costimulatory agent enhances an anticancer immune response, for example, by preventing the downregulation of an immune response. A costimulatory agent may be administered alone in a cancer therapy or in combination with one or more cancer therapies to enhance the therapeutic effect of the cancer therapy. In some embodiments, the costimulatory agent is an antibody that targets CD-28, OX-40, 4-1BB, or CD40.

In one embodiment of the present invention, the composition is administered concurrently with a chemotherapeutic agent and/or with radiation therapy. In another specific embodiment, the chemotherapeutic agent and/or radiation therapy is administered prior or subsequent to administration of the composition of the present invention, preferably at least an hour, five hours, 12 hours, a day, a week, a month, more preferably several months (e. g. up to three months), prior or subsequent to administration of composition of the present invention.

As used herein, a chemotherapy agent refers to a molecule (e.g., drug) that specifically or preferentially kills cancer cells or prevents the proliferation of cancer cells. Chemotherapy agents can generally be categorized based on the molecular target of the chemotherapy agent, the mechanism of action, and/or the structure of the agent. In some embodiments, the chemotherapy agent is an alkylating agent, a plant alkaloid, an antitumor antibiotic, an antimetabolite, a topoisomerase inhibitor, or other antineoplastic agent.

In one embodiment, the chemotherapeutic agent is selected from the group consisting of alkylating agents, alkyl sulfonates, aziridines, an ethylenimine, a methylamelamine, an acetogenin, a camptothecin bryostatin, cally statin, CC-1065, a cryptophycin, dolastatin, duocarmycin, eleutherobin, pancratistatin, a sarcodictyin, spongistatin, a nitrogen mustard, a nitrosurea, an antibiotic, a dynemicin; a bisphosphonate, an esperamicin, neocarzinostatin chromophore and related chromoprotein enedlyne antibiotic chromophores, an aclacinomysin, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin, epirubicin, esorubicin, idarubicin, marcellomycin, a mitomycin, mycophenolic acid, nogalamycin, an olivomycin, peplomycin, potfiromycin, puromycin, quelamycin, rodorubicin, streptonigrin, streptozocin, tubercidin, ubenimex, zinostatin, zorubicin an antimetabolite, a folic acid analogue, a purine analog, a pyrimidine analog, an androgen, an anti-adrenal, a folic acid replenishes aceglatone, aldophosphamide glycoside, aminolevulinic acid, eniluracil, amsacrine, bestrabucil, bisantrene, edatrexate, demecolcine, diaziquone, elformithine, elliptinium acetate, an epothilone, etoglucid, gallium nitrate, hydroxyurea, lentinan, lonidainine, a maytansinold, mitoguazone, mitoxantrone, mopidanmol, nitraerine, pentostatin, phenamet, pirarubicin, losoxantrone, podophyllinic acid, 2-ethylhydrazide, procarbazine, PSK polysaccharide complex, razoxane, rhizoxin, sizofuran, spirogermanium, tenuazonic acid, triaziquone, 2,2',2"-trichlorotriethylamine, a trichothecene, urethan, vindesine, dacarbazine, mannomustine, mitobronitol, mitolactol, pipobroman, gacytosine, arabinoside ("Ara-C"), cyclophosphamide, thiotepa, a taxoid, ABRAXANE Cremophor-free, an albumin-engineered nanoparticle formulation of paclitaxel and TAXOTERE doxetaxel, chlorambucil, GEMZAR gemcitabine, 6-thioguanine, mercaptopurine, methotrexate, a platinum analog, vinblastine, platinum, etoposide (VP-16), ifosfamide, mitoxantrone, vincristine, NAVELBINE, vinorelbine, novantrone, teniposide, edatrexate, daunomycin, aminopterin, xeloda, ibandronate, irinotecan (Camptosar, CPT-11), topoisomerase inhibitor RFS 2000; difluoromethylomithine (DMFO), a retinoid, capecitabine, combretastatin, leucovorin (LV), oxaliplatin, Binimetinib (Mektovi), Encorafenib (Braftovi), Iapatinib (TYKERB), an inhibitor of PKC-a, an inhibitor of Raf, an inhibitor of H-Ras, an inhibitor of EGFR, an inhibitor of VEGF-A, pharmaceutically acceptable salt, acid or derivative thereof, and combinations thereof.

In some embodiments, the composition of the invention may be administered with two or more (e.g., 2, 3, 4, 5, or more) therapeutic agents.

In one embodiment, administration is together with an agent involved in T-cell activation, a tumour microenvironment modifier (TME) or a tumour-specific target.

In one embodiment, the method and uses further comprise administering an antibiotic to the subject.

In yet another aspect, the invention provides a method of modulating an immune response in a subject comprising administering to the subject a composition of the invention.

In some embodiments, the individual has cancer that is resistant (has been demonstrated to be resistant) to one or more anti-cancer therapies. In some embodiments, resistance to anti-cancer therapy includes recurrence of cancer or refractory cancer. Recurrence may refer to the reappearance of cancer, in the original site or a new site, after treatment. In some embodiments, resistance to anti-cancer therapy includes progression of the cancer during treatment with the anti-cancer therapy. In some embodiments, the cancer is at early stage or at late stage.

The composition of the invention has immunostimulatory properties. Therefore, use of the composition is not limited to the treatment of cancer. Thus, due to the immunostimulatory properties, the composition finds use in the treatment of any disease which requires immunostimulation, e.g. non-cancer immunotherapies. Immunotherapy is collectively defined as a therapeutic approach that targets or manipulates the immune system. Ultimately, immunotherapy aims to harness the host's adaptive and innate immune response to effectuate long-lived elimination of diseased cells and can be categorized broadly into passive (including adoptive and antibody-based) and active (including vaccine therapy and allergen-specific) approaches. Passive-mediated immunotherapy involves the administration of ex vivo-generated immune elements (antibodies, immune cells) to patients and does not stimulate the host immune response, while active immunotherapy induces the patient's immune response and results in the development of specific immune effectors (antibodies and T cells). Immunotherapy offers a possible modality to improve the ability to prevent or treat infectious diseases (Naran et al, Front Microbiol. 2018; 9: 3158). Thus, in some embodiments, the disease is an infectious disease.

The recent success of PD-1 and PD-L1 blockade in cancer therapy illustrates the important role of the PD-1/PD-L1 pathway in the regulation of antitumor immune responses. However, signaling regulated by the PD-1/PD-L pathway is also associated with substantial inflammatory effects that can resemble those in autoimmune responses, chronic infection, and sepsis, consistent with the role of this pathway in balancing protective immunity and immunopathology, as well as in homeostasis and tolerance (Qin et al, Front Immunol. 2019; 10: 2298; Rao et al, Int. J. Infect. Dis. 2017; 56: 223). Thus, in another aspect, the invention provides a composition as described herein; e.g. comprising one or more of B1 to B15 as in table 1, e.g. a composition with one or more bacterial isolate having a 16SrDNA having a sequence selected from SEQ ID Nos. 1 to 15 or a sequence with at least 97%, 98%, 98.7% or 99% sequence identity thereto. e.g. SEQ ID Nos. 16-29, for use in the treatment of an infectious disease. Also provided is a method for the treatment of an infectious disease comprising administering a composition of the invention to a subject. Also covered is a composition as described herein for use in the manufacture of a medicament for the treatment of an infectious disease.

An infectious disease may be a viral, fungal and bacterial infection. The infectious disease may be a chronic infectious disease. Non-limiting examples include human immunodeficiency virus (HIV), hepatitis B (HBV), hepatitis C (HCV), JC (John Cunningham) virus/progressive multifocal leukoencephalopathy and tuberculosis.

Treatment of infections with the composition of the invention can be as co-therapy with an immunotherapy, for example an immune checkpoint inhibitor, other anti-viralS or anti-infectives.

In another aspect, the invention provides a composition as described herein, e.g. comprising one or more of B1 to B15 as in table 1, e.g. a composition with one or more bacterial isolate having a 16S rDNA having a sequence selected from SEQ ID Nos. 1 to 15 or a sequence with at least 97%, 98%, 98.7% or 99% sequence identity thereto, for use as a vaccine adjuvant. Also provided is a method for increasing vaccine efficacy comprising administering a composition as described herein, e.g. comprising one or more of B1 to B15 as in Table 1, e.g. a composition with one or more bacterial isolate having a 16S rDNA having a sequence selected from SEQ ID Nos. 1 to 15 or a sequence with at least 97%, 98%, 98.7%, 99% or 100% sequence identity thereto, e.g. SEQ ID Nos. 16-29, to a subject. Said subject may receive a vaccine before, after or concurrently with administration of the bacterial composition.

Administration may be in a "therapeutically effective amount", this being sufficient to show benefit to the individual. Such benefit may be at least amelioration of at least one symptom. Thus "treatment" of a specified disease refers to amelioration of at least one symptom. The actual amount administered, and rate and time-course of administration, will depend on the nature and severity of what is being treated, the particular patient being treated, the clinical condition of the individual patient, the site of delivery of the composition, the type of therapeutic composition, the method of administration, the scheduling of administration and other factors known to medical practitioners. Prescription of treatment, e.g. decisions on dosage etc., is within the responsibility of general practitioners and other medical doctors and may depend on the severity of the symptoms and/or progression of a disease being treated. A therapeutically effective amount or suitable dose of a therapeutic composition of the invention can be determined by comparing its in vitro activity and in vivo activity in an animal model. Methods for extrapolation of effective dosages in mice and other test animals to humans are known. The precise dose will depend upon a number of factors, including whether the therapeutic composition is for prevention or for treatment.

In one embodiment of the methods which require administration of the composition, the method includes the further step of detecting the presence of one or more of the bacterial strain that has been administered in the subject subsequent to administration. Methods for detection include for example detecting a 16S nucleic acid sequence as defined herein of at least one administered bacterial isolate in said subject.

The composition of the present invention may be prepared by a method comprising culturing the two or more isolated bacteria present in the composition in a suitable medium or media. Media and conditions suitable for culturing the bacteria to be included in the therapeutic composition of the present invention are described in detail elsewhere herein. For example, a method of preparing a therapeutic composition according to the present invention may comprise the steps of:
(i) culturing a first isolated bacterium;
(ii) culturing a second and optionally a further isolated bacterium; and
(iii) mixing the bacteria obtained in (i) and (ii) to prepare the therapeutic composition.

The isolated bacteria to be included in the composition may be cultured in separate steps. In other words, a separate culture of each bacterium to be included in the therapeutic composition is preferably prepared. This allows the growth of each bacterium to be evaluated and the amount of each bacterium to be included in the pharmaceutical composition to be controlled as desired. The bacteria cultured in steps (i) and (ii) preferably have distinct 16S nucleic acid sequences, that is 16S nucleic acid sequences that share less than 99%, 98%, 97%, 96% or 95% sequence identity.

The above method may include steps of culturing each isolated bacterium which is to be included in the composition.

The method may optionally comprise one or more further steps in which the bacteria are mixed with one or more additional ingredients, such as a pharmaceutically acceptable excipient, prebiotic, carrier, insoluble fibre, buffer, osmotic agent, antifoaming agent, and/or preservative. In addition, or alternatively, the method may comprise suspending the bacteria obtained in (i) and optionally (ii) in a chemostat medium, or saline, e.g. 0.9% saline. The bacteria obtained in (i) and optionally (ii) may be provided under a reduced atmosphere, such as $N_2$, $CO_2$, $H_2$, or a mixture thereof, e.g. $N_2:CO_2:H_2$. The gases may be present in appropriate ratios for the preservation of the bacteria present in the therapeutic composition. For example, the reduced atmosphere may comprise 80% $N_2$, 10% $CO_2$ and 10% $H_2$. In addition, or alternatively, the method may comprise a step of lyophilising the bacteria obtained in (i) and optionally (ii), optionally in the presence of a stabiliser and/or cryproptectant. The method may also comprise a step of preparing a capsule, tablet, or enema comprising the bacteria obtained in (i) and optionally (ii). The capsule or tablet may be enteric-coated, pH dependant, slow-release, and/or gastro-resistant.

The composition of the invention may also be provided in the form of a food supplement, beverage or other food stuff. The invention thus also relates to a food product or a vaccine comprising a composition of the invention.

Also provided is an immunogenic composition comprising fragments of bacteria selected from the those listed in Table 1, for use as an adjuvant to an anti-PD-1/PD-L1/PD-L2 antibody-based therapy administered to a cancer patient.

Biomarker

The invention provides microbiome biomarkers that are predictive of tumor response to therapy in a cancer patient with an immune checkpoint inhibitor. In particular, the invention provides a microbiome biomarker signature that is predictive of tumor response therapy with an immune checkpoint inhibitor.

As used herein, a microbiome biomarker signature is a composite biomarker signature that comprises bacteria from at least 2, 3, 4, 5, 6, 7, 8, 9, 10, 11, 12, 13, 14 or 15 bacterial species as shown in Table 1 which each have increased abundance in subjects that are responsive to therapy with an immune checkpoint inhibitor. In one embodiment, the signature comprises bacteria from at least 9, 10, 11, 12, 13, 14 or 15 bacterial species selected from Table 1 which each have increased abundance in a population of subjects that are responsive to therapy with an immune checkpoint inhibitor. The biomarker signature is described in more detail below.

Another aspect provides a method of treating cancer in a subject comprising administering a therapeutically effective amount of an immune checkpoint inhibitor to said subject, wherein the subject has been determined to have a favorable microbial profile in the gut microbiome. A favorable microbial profile is characterised by the presence of the biomarkers/biomarker signature described herein.

Another aspect provides a method of treating cancer in a subject, wherein the subject has been determined to have an unfavorable microbial profile in the gut microbiome. A unfavorable microbial profile is characterised by the absence of the biomarkers/biomarker signature described herein. The method may further comprise administration of an anti-cancer therapy that is not an immune checkpoint inhibitor therapy. In another embodiment, the method comprises administration of a therapeutic bacterial composition described herein and co-therapy with an immune checkpoint inhibitor therapy, e.g. a PD-1 inhibitor.

Thus, the invention also relates to a method for identifying a subject that will respond to therapy with an immune checkpoint inhibitor, e.g. PD-1, comprising determining the abundance of one or more of the bacteria identified as B1, B2, B3, B4, B5, B6, B7, B8, B9, B10, B11, B12, B13, B14 and/or B15 in Table 1 in a biological sample from said subject that comprises gut (i.e. intestinal) flora wherein an increase in the abundance of one or more of B1, B2, B3, B4, B5, B8, B7, B8, B9, B10, B11, B12, B13, B14 and/or B15, e.g. one or more of B1, B2, B3, B4, B5, B6, B7, B8 and/or B9, is indicative that the subject will respond to therapy with an immune checkpoint inhibitor, e.g. PD-1. B1 to B15 are listed in Table 1 and this includes references to sequence identifiers to define the bacteria. Corresponding sequences are listed in Table 2. In one embodiment, the subject is a patient that has been diagnosed with a cancer, e.g. melanoma.

In particular, the invention also relates to a method for predicting a response to an immune checkpoint inhibitor therapy in a subject having cancer/a method for identifying a subject that will respond to therapy with an immune checkpoint inhibitor, the method comprising:
a) determining the abundance of one or more of the bacteria selected from B1, B2, B3, B4, B5, B6, B7, B8, B9, B10, B11, B12, B13, B14 and/or B15 in Table 1 in a biological sample obtained from the subject and
b) comparing the abundance to a reference level from cancer patients that do not respond to therapy with an immune checkpoint inhibitor; or comparing the abundance to a reference level from cancer patients that respond to therapy with an immune checkpoint inhibitor;
wherein if the reference level is from cancer patients that do not respond to therapy with an immune checkpoint inhibitor, then an increase in the abundance of one or more of B1, B2, B3, B4, B5, B6, B7, B8, B9, B10, B11, B12, B13, B14 and/or B15 compared to the reference level, is indicative that the subject will respond to therapy with an immune checkpoint inhibitor or
wherein if the reference level is from patients that do respond to therapy with an immune checkpoint inhibitor, then the same, substantially the same or an increase in the abundance of one or more of B1, B2, B3, B4, B5, B6, B7, B8, B9, B10, B11, B12, B13, B14 and/or B15, is indicative that the subject will respond to therapy with an immune checkpoint inhibitor.

An additional step may include identifying the subject that will respond to therapy.

In particular, the invention also relates to a method for predicting a response to an immune checkpoint inhibitor therapy in a subject having cancer/a method for identifying a subject that will respond to therapy with an immune checkpoint inhibitor, the method comprising:
a) determining the abundance of one or more of the bacteria selected from B1, B2, B3, B4, B5, B6, B7, B8, B9, B10, B11, B12, B13, B14 and/or B15 in Table 1 in a biological sample obtained from the subject and;
b) comparing the abundance to a reference level from cancer patients or healthy subjects and
c) applying random forest analysis. In this embodiment, the reference level is from cancer patients, that is a pool of cancer patients. These may include responders and non-responders.

An additional step may include identifying the subject that will respond to therapy or prediction a response.

Thus, the abundance of bacteria from 1, 2, 3, 4, 5, 6, 7, 8, 9, 10, 11, 12, 13, 14 or 15 different species selected from B1, B2, B3, B4, B5, B6, B7, B8, B9, B10, B11, B12, B13, B14 and B15 in Table 1 is determined. Respective sequences characterising the species are provided as SEQ IDs 1 to 15. As explained elsewhere, SEQ IDs 16-29 can also be used. In some embodiments, the abundance of bacteria selected from at least 9, 10, 11, 12, 13, 14 or 15 different species identified as B1, B2, B3, B4, B5, B6, B7, B8, B9, B10, B11, B12, B13, B14 and B15 in Table 1 is determined. Thus, the abundance of bacteria having sequences IDs selected from at least 9 of the following SEQ IDs is determined: SEQ ID NO. 1, 2, 3, 4, 5, 6, 7, 8, 9, 10, 11, 12, 13, 14 or 15 or sequences with at least 97%, 98%, 98.7% or 99% sequence identity thereto, such as, for example SEQ IDs 16 to 29.

Also provided is a method for predicting relapse in a patient who is treated or who has been treated for a cancer, comprising assessing, in faeces samples from said patient obtained e.g. at different time-points, the presence/relative abundance of one or more bacteria selected from B1, B2, B3, B4, B5, B6, B7, B8, B9, B10, B11, B12, B13, B14 and/or B15.

When abundance is determined, an abundance score is obtained for each of the bacteria, i.e. bacterial species, and measured. According to the method, an increase in the abundance, i.e. the abundance score, of one or more of the bacteria listed in Table 1 is indicative that the subject will respond to therapy with an immune checkpoint inhibitor. An increase refers to an increase of abundance, i.e. the abundance score, compared to a reference value. Therefore, the method may also comprise comparing the abundance one or more of the bacteria listed in Table 1 to one or more reference value. For example, the abundance of one or more of the bacteria listed in Table 1 can be compared to a reference value for one or more of the bacteria listed in Table 1. Alternatively, the arithmetic mean of the abundance of one or more of the bacteria listed in Table 1 can be compared to a single reference value which is the reference arithmetic mean of the abundance of one or more of the bacteria listed in Table 1. In one embodiment, the method determines the abundance of at least 9, 10, 11, 12, 13, 14 or 15 different bacteria selected from B1 to B15, thus determining a microbiome biomarker signature, i.e. a microbiome biomarker signature score, that is based on the composite signature.

In one embodiment of the methods, the abundance of all of the bacteria listed in Table 1 is determined. In another embodiment, the abundance of a subset the bacteria listed in Table 1 is determined. For example, the subset comprises or consists of 1, 2, 3, 4, 5, 6, 7, 8, 9, 10, 11, 12, 13, 14 or 15 different bacteria selected from Table 1. In one embodiment, the subset comprises or consists of 9 bacteria, e.g. *Eisenbergiella* sp., *Butyriccoccus* sp., *Clostridiales* sp., *Alistipes obesi*, *Alistipes Indistinctus*, *Gordonibacter urolithinfaciens*, *Faecalitalea* sp., *Blautia* sp. (B8), and *Barnesiella intestinihominis*. In one embodiment, the subset comprises or consists of 9 or 12 bacteria, e.g. one of the bacterial consortia in Table 3. In one embodiment, the biomarker does not comprise an *Alistipes* species.

The reference value may be a predetermined value from a reference sample. For example, the reference value can be the average abundance of each of the bacteria or their composite signature, respectively, in a pool of reference subjects.

For example, the reference value is a predetermined value, e.g. a predetermined threshold value. Such a value can be predetermined from a reference sample. A predetermined threshold value relating to abundance of one or more bacteria of B1 to B15 refers to the abundance of the bacteria in the sample as a proportion of the total microbiota in the sample, for example a stool sample, above or below which the sample is scored as being positive for the signature and thus responsive to therapy with an immune checkpoint inhibitor. For example, if the abundance score for the test sample is at or above a predetermined threshold, then the sample is considered to be positive for the signature and the subject is responsive to therapy with an immune checkpoint inhibitor.

For example, abundance scores of the tested bacteria levels in a sample pool are stored on a computer, or on computer-readable media, to be used as reference levels in comparisons to the abundance of the tested bacteria from the test sample when needed. Machine learning algorithms and/or models commonly used in the identification of biomarkers, such as a Cox model, trained using training data comprising information on a plurality of biomarkers in a set of subjects or other models may be used to establish reference values and or to correlate abundance of the bacteria selected from one or more of the bacteria listed in Table 1 in the sample with the subject's responsiveness to treatment with an immune checkpoint inhibitor.

The term "correlating" is used herein to determine or calculate responsiveness to treatment status based on modulated abundance of one or more bacteria should be understood to mean any methods of correlation, e.g. algorithmic methods. The methodology described herein employs a mathematical modelling technique known as Random Forest Classification, but other modelling techniques may be employed. Therefore, in one embodiment, a Random Forest Classification Model or similar model is used to correlate abundance of the bacteria selected from one or more of the bacteria listed in Table 1 in the sample with the subject's responsiveness to treatment with an immune checkpoint inhibitor. Thus, in one embodiment, the methods of the invention may employ a computer program to correlate modulated abundance of the bacteria with immune checkpoint inhibitor treatment response.

Alternatively, the reference value is not predetermined, but it is established as part of a single experiment. Thus, the abundance of the one or more tested bacteria in the test sample may be compared to the abundance of the one or more tested bacteria in the pool of samples, where abundance of the tested bacteria from the test sample and abundance of the tested bacteria from the pool are determined during the course of a single experiment.

In the various embodiments, the reference sample/sample pool may be a population of cancer patients that have been shown to be responsive or non-responsive to therapy with an immune checkpoint inhibitor. In other embodiments, the reference sample/sample pool may be a population of cancer patients that have not yet received therapy with a checkpoint inhibitor.

In one embodiment, the reference sample used to establish a reference value may be from non-responders to immune checkpoint inhibitor therapy. If the test sample shows an increased abundance of the one or more bacteria selected from B1 to B15 compared to the reference sample, then the test subject is likely to respond to therapy with a checkpoint immune inhibitor. The increase may be at least 10%, 20%, 30%, 40%, 50%, 60%, 70%, 80%, 90% or more.

In one embodiment, the reference sample used to establish a reference value may be from responders to immune checkpoint inhibitor therapy. If the test sample shows the same, substantially the same or an increase in the abundance of the one or more bacteria selected from B1 to B15 than the reference sample, then the test subject is likely to respond to therapy with a checkpoint immune inhibitor.

As a skilled person would understand, a reference value or reference gene signature score as used herein means the score for a bacterial abundance signature that has been determined to divide at least the majority of responders from at least the majority of non-responders in a reference population of subjects.

As used herein, a "good responder to a treatment", also called a "responder" or "responsive" patient or in other words a patient who "benefits from" this treatment, refers to a patient who is affected with a cancer and who shows or will show a clinically significant relief in the cancer after receiving this treatment. Conversely, a "bad responder" or "non-responder" is one who does not or will not show a clinically significant relief in the cancer after receiving this treatment. The response to treatment may be assessed according to the standards recognized in the art, such as immune-related response criteria (irRC), WHO or RECIST criteria.

A signature biomarker described herein is useful to identify cancer patients who are most likely to achieve a clinical benefit from treatment with an immune checkpoint inhibitor. This utility supports the use of these biomarkers in a variety of research and commercial applications. Including but not limited to, clinical trials of PD-1 antagonists in which patients are selected on the basis of their microbiome gene signature score, diagnostic methods and products for determining a patients microbiome gene signature score or for classifying a patient as positive or negative for a microbiome signature biomarker, personalized treatment methods which involve tailoring a patient's drug therapy based on the patient's microbiome signature score, as well as pharmaceutical compositions and drug products comprising a PD-1 antagonist for use in treating patients who test positive for a microbiome signature biomarker.

A skilled person would also understand that the utility of any of the applications claimed herein does not require that 100% of the patients who test positive for a biomarker of the invention achieve an anti-tumor response to an immune checkpoint inhibitor, nor does it require a diagnostic method or kit to have a specific degree of specificity or sensitivity in determining the presence or absence of a biomarker in every subject, nor does it require that a diagnostic method claimed herein be 100% accurate in predicting for every subject whether the subject is likely to have a beneficial response to a PD-1 antagonist. Thus, the inventors herein intend that the terms "determine", "determining" and "predicting" should not be interpreted as requiring a definite or certain result; instead these terms should be construed as meaning either that a claimed method provides an accurate result for at least the majority of subjects or that the result or prediction for any given subject is more likely to be correct than incorrect. Preferably, the accuracy of the result provided by a diagnostic method of the invention is one that a skilled artisan or regulatory authority would consider suitable for the particular application in which the method is used.

As used herein, the sample is a biological sample from the gut, i.e. one that comprises gut intestinal flora. This refers to a sample obtained from the gut of a subject, for example a faecal sample. Methods of isolating bacteria from a faecal sample are known. In some cases, the microbiome sample is obtained by mucosal biopsy. A test sample is sample obtained from a subject that is being assessed.

In one embodiment of the method, the abundance is relative abundance. As used herein, the term "relative abundance" as applied to a bacterium in a sample should be understood to mean the abundance of the bacterium in the sample as a proportion of the total microbiota in the sample or a reference sample. In one embodiment, the relative abundance is the abundance of the bacterium in the sample as a proportion of the total microbiota in the sample.

In one embodiment, the modulated abundance is a difference in relative abundance of the bacterium in the sample compared with the relative abundance in the same sample from a reference subject.

In one embodiment, the abundance of the bacterium in the sample as a proportion of the total microbiota in the sample is measured to determine the relative abundance of the bacterium. Then, in such embodiments, the relative abundance of the bacterium in the sample is compared with the relative abundance In the same sample from a reference individual (also referred to herein as the "reference relative abundance"). A difference in relative abundance of the bacterium in the sample, e.g. an increase, compared to the reference relative abundance is a modulated relative abundance. Detection of modulated abundance can also be performed in an absolute manner by comparing sample abundance values with absolute reference values.

Any suitable method of detecting bacterial presence/abundance may be employed, including, for example, agar plate quantification assays, fluorimetric sample quantification, PCR methods, 16S rRNA/rDNA gene amplicon sequencing, Shotgun metagenomic sequencing and dye-based metabolite depletion or metabolite production assays. The PCR technique used can quantitatively measure starting amounts of DNA, cDNA, or RNA. Examples of PCR-based techniques according to the invention include techniques such as, but not limited to, quantitative PCR (Q-PCR), reverse-transcriptase polymerase chain reaction (RT-PCR), quantitative reverse-transcriptase PCR (QRT-PCR), rolling circle amplification (RCA) or digital PCR. These techniques are well known and easily available and do not need a precise description. In a particular embodiment, the determination of the copy number of the bacterial genes of the invention is performed by quantitative PCR.

In one embodiment, the sample is analysed using a nucleic acid amplification reaction. Analysing may include detecting family, order-, class- and/or genus-specific 16S rRNA/rDNA or other sequences in the bacterial genome. In one embodiment, full length 16S rDNA may be detected. In one embodiment, partial 16S rDNA may be detected, for example one of the V regions. In one embodiment, analysing includes hybridizing bacterial nucleic acid in the sample to beads or to an array, e.g. a nucleic acid microarray.

The PCR-based techniques are performed with amplification primers designed to be specific for the sequences which are measured. The present invention hence also pertains to a set of primers suitable for performing the above method, i.e., a set of primers comprising primer pairs for amplifying sequences specific for each of the microorganism species to be detected (i.e., at least one more species selected amongst those recited in Tables 1 and 2 and 3).

16S rDNA sequence is provided herein for B1-B15 and this can be used to generate primers for such an analysis. In one embodiment, a plurality of the bacteria is detected. In one embodiment, the sample is analysed for nucleic acid of the bacteria using genome sequencing.

In one embodiment, the subject is a cancer patient, such as melanoma patient. The cancer patient may or may not have received anti-cancer treatment. Thus, the subject may be one that is in need of treatment with an immune checkpoint inhibitor. In one embodiment, the subject is a healthy individual, for example a healthy individual with a family history of cancer, such as melanoma.

In one embodiment, if the subject is a cancer patient and has been identified as a subject that will respond to therapy with an immune checkpoint inhibitor, then the method may include the further step of administering an immune checkpoint inhibitor to said patient.

In one embodiment, the method also comprises the prior step of obtaining the biological sample that comprises gut flora.

In one embodiment, the method also includes the initial step of identifying a subject in need of treatment with the immune checkpoint inhibitor.

In one embodiment of the methods, if the subject is identified as a responder, e.g. If one or more of the bacteria listed in Table 1 has been shown to have an increased abundance in the sample, an anti-cancer therapy comprising an immune checkpoint inhibitor is administered to the subject.

Checkpoint inhibitors are as defined herein. In one embodiment of the methods, the immune checkpoint inhibitor inhibits PD-1 activity, i.e. acts as a PD-1 antagonist. In one embodiment of the methods, the immune checkpoint inhibitor inhibits PD-L1 activity, i.e. acts as a PD-L1 antagonist. In one embodiment of the methods, the immune checkpoint inhibitor inhibits CTLA-4 activity, i.e. acts as a CTLA-4 antagonist. In one embodiment of the methods, the immune checkpoint inhibitor inhibits LAG3, TIGIT or TIM3-activity.

In one embodiment the immune checkpoint inhibitor is an anti PD-1, PD-L1 or CTLA-4 antibody. In one embodiment, the anti PD-1 antibody is selected from nivolumab, pembrolizumab, cemiplimab, avelumab, durvalumab, atezolizumab, Spartalzumab, Camrelizumab, Sintilimab, Tislelizumab, Pidilizumab or Toripalimab, Ipilimumab or Tremelimumab.

In one embodiment, the immune checkpoint inhibitor is an interfering nucleic acid molecule. In one embodiment, the interfering nucleic acid molecule is an siRNA molecule, an shRNA molecule or an antisense RNA molecule.

In one embodiment, the immune checkpoint inhibitor is a small molecule or PROteolysis TArgeting Chimera (PROTAC) or another immune checkpoint inhibitor as defined above.

In one embodiment, in a further step of the method, surgical, radiation, and/or chemotherapeutic cancer intervention is carried out or a second anti-cancer therapeutic is administered to said subject.

In another aspect, the invention relates to a method of detecting the risk that a subject will not respond to therapy with an immune checkpoint inhibitor. The method comprising determining the abundance of one or more of the bacteria listed in Table 1 In a biological sample from said subject that comprises gut intestinal flora wherein a decrease in the abundance or an abundance below a reference level of one or more of the bacteria listed in Table 1 is indicative that the subject will not respond to therapy with an immune checkpoint inhibitor. The method may also comprise comparing the abundance of one or more of the bacteria listed in Table 1 to one or more reference value. A reference value is as described above. The abundance that is determined is relative abundance. In a further step, if the subject has been identified as a subject that will not respond to therapy with an immune checkpoint inhibitor, alternative anti-cancer treatment is administered. Alternatively, in a further step, if the subject has been identified as a subject that will not respond to therapy with an immune checkpoint inhibitor, a therapeutic bacterial composition as described herein is administered together with a checkpoint inhibitor therapy, e.g. an anti PD-1 therapy.

In another aspect, the invention relates to a method of discriminating between subjects that respond to therapy with an immune checkpoint inhibitor and subjects that do not respond to therapy with an immune checkpoint inhibitor. The method comprising determining the abundance of one or more of the bacteria listed in Table 1 in a biological sample from said subject that comprises gut intestinal flora wherein a decrease in the abundance or a abundance below a reference level of one or more of the bacteria listed in Table 1 is indicative that the subject will not respond to therapy with an immune checkpoint inhibitor and an increase in the abundance of one or more of the bacteria listed in Table 1 is indicative that the subject will respond to therapy with an immune checkpoint inhibitor. The method may also comprise comparing the abundance one or more of the bacteria fisted in Table 1 to one or more reference value. A reference value is as described above. The abundance that is determined is relative abundance. In a further step, if the subject has been identified as a subject that will not respond to therapy with an immune checkpoint inhibitor, alternative anti-cancer treatment is administered.

In one embodiment of the biomarker methods above, modulated abundance of at least 1, 2, 3, 4, 5, 6, 7, 8, 9, 10, 11, 12, 13, 14 or 15 different bacteria selected from Table 1 is indicative of a response to treatment. In another embodiment of the biomarker methods above, modulated abundance of at least 9, 10, 11, 12, 13, 14 or 15 different bacteria selected from Table 1 is indicative of a response to treatment. Thus, establishing a composite signature that includes abundance of at least 9, 10, 11, 12, 13, 14 or 15 different bacteria is a particular embodiment of the methods. It is the totality of the bacteria, i.e. the biomarker signature, that provides a particularly powerful discriminatory tool.

In one embodiment of the various methods above, the abundance of at least 9 bacterial species/a population of 9 bacterial species selected from those in Table 1 is assessed, i.e. 9 species selected from SEQ ID Nos. 1, 2, 3, 4, 5 6, 7, 8, 9, 10, 11, 12, 13, 14 and 15. In one embodiment, the subset of 9 corresponds to a consortium as shown in Table 3, i.e. consortia 2, 4, 5, 6 or 10. In one embodiment, the 9 species comprise bacteria as defined by SEQ ID NO. 1 or a sequence with at least 97%, 98%, 98.7% or 99% sequence identity thereto. In one embodiment, the 9 species comprise bacteria as defined by SEQ ID NO. 2 or a sequence with at least 97%, 98%, 98.7% or 99% sequence identity thereto. =In one embodiment, the 9 species comprise bacteria as defined by SEQ ID NO. 3 or a sequence with at least 97%, 98%, 98.7% or 99% sequence identity thereto. In one embodiment, the 9 species comprises bacteria as defined by SEQ ID NO. 4 or a sequence with at least 97%, 98%, 98.7% or 99% sequence identity thereto. In one embodiment, the 9 species comprise bacteria as defined by SEQ ID NO. 5 or a sequence with at least 97%, 98%, 98.7% or 99% sequence identity thereto. In one embodiment, the 9 species comprise bacteria as defined by SEQ ID NO. 6 or a sequence with at least 97%, 98%, 98.7% or 99% sequence identity thereto. In one embodiment, the 9 species comprise bacteria as defined by SEQ ID NO. 7 or a sequence with at least 97%, 98%, 98.7% or 99% sequence identity thereto. In one embodiment, the 9 species comprise bacteria as defined by SEQ ID NO. 8 or a sequence with at least 97%, 98%, 98.7% or 99% sequence identity thereto. In one embodiment, the 9 species comprise bacteria as defined by SEQ ID NO. 9 or a sequence with at least 97%, 98%, 98.7% or 99% sequence identity thereto. In one embodiment, the 9 species comprise bacteria as defined by SEQ ID NO. 10 or a sequence with at least 97%, 98%, 98.7% or 99% sequence identity thereto. In one embodiment, the 9 species comprise bacteria as defined by SEQ ID NO. 11 or a sequence with at least 97%, 98%, 98.7% or 99% sequence identity thereto. In one embodiment, the 9 species comprise bacteria as defined by SEQ ID NO. 12 or a sequence with at least 97%, 98%, 98.7% or 99% sequence identity thereto. In one embodiment, the 9 species comprise bacteria as defined by SEQ ID NO. 13 or a sequence with at least 97%, 98%, 98.7% or 99% sequence identity thereto. In one embodiment, the 9 species comprise bacteria as defined by SEQ ID NO. 14 or a sequence with at least 97%, 98%, 98.7% or 99% sequence identity thereto. In one embodiment, the 9 species comprise bacteria as defined by SEQ ID NO. 15 or a sequence with at least 97%, 98%, 98.7% or 99% sequence identity thereto. In one embodiment, the 9 species do not comprise an *Alistipes* species.

In one embodiment, the biomarker methods above may comprise a further step of determining another biomarker that is predictive of tumor response with an immune checkpoint inhibitor, for example a PD-1, PD-L1 or CTLA-4 antagonist. For example, the biomarker may be a Programmed Death Ligand 1 (PD-L1) or Programmed Death Ligand 1 (PD-L2) gene signature. Thus, the method may comprise the step of obtaining a sample from the tumor of a test subject, measuring RNA expression level in the tumor sample of one or more gene in a PD-1 and/or PD-L1 gene signature and comparing the RNA expression level to a reference level. Expression can be measured by any appropriate methods, including immunohistochemistry.

In another aspect, the invention relates to one or more of the bacteria listed in Table 1 for use as a predictive biomarker in determining the efficacy of therapeutic intervention with checkpoint inhibitor, e.g. PD-1 therapy. The term predictive biomarker as used herein is to describe a biomarker that gives information about the effect of a therapeutic intervention, i.e. responsiveness to treatment with an immune checkpoint inhibitor. Thus, the invention also relates to the use of one or more bacterium: e.g. 1, 2, 3, 4, 5, 6, 7, 8, 9, 10, 11, 12, 13, 14 or 15 different bacteria selected from one or more of the bacterial species listed in Table 1 in identifying a patient that will respond to therapy with an immune checkpoint inhibitor.

The invention also relates to a biomarker signature, that is a consortium of one or more of the bacteria listed in Table 1, e.g. as in Table 3, which can be used to predict the efficacy of therapeutic intervention with checkpoint inhibitor therapy, e.g. with a PD-1 inhibitor or with another checkpoint inhibitor therapy.

Systems and Computer Readable Media

Embodiments of the invention also provide for systems (and computer readable media for causing computer systems) to perform a method for determining responsiveness to treatment with an immune checkpoint inhibitor in a subject. In another aspect, a computer-implemented method is provided for indicating a likelihood that a subject responds to treatment with an immune checkpoint inhibitor. The method comprises: retrieving on a computer biomarker information for an individual, wherein the biomarker information comprises biomarker values that each correspond to the abundance of one or more bacteria selected from the group of bacteria set forth in Table 1; performing with the computer a classification of each of the biomarker values; and indicating a likelihood that the subject responds to treatment with an immune checkpoint inhibitor based upon a plurality of classifications.

In another aspect, a computer program product is provided for indicating a likelihood that a subject responds to treatment with an immune checkpoint inhibitor. The computer program product includes a computer readable medium embodying program code executable by a processor of a computing device or system, the program code comprising: code that retrieves data attributed to a biological sample from an individual, wherein the data comprises biomarker values that each correspond to the abundance of one or more bacteria selected from the group of bacteria set forth in Table 1; and code that executes a classification method that indicates a likelihood that the individual responds to treatment with an immune checkpoint inhibitor as a function of the biomarker values.

In one embodiment the reference data stored in the storage device to be read by the comparison module is compared, e.g., relative abundance of a particular bacterium in a reference sample as described herein. The "comparison module" can use a variety of available software programs and formats for the comparison operative to compare bacteria abundance information data determined in the determination system to reference samples and/or stored reference data, e.g. a predetermined threshold value. In one embodiment, the comparison module is configured to use pattern recognition techniques to compare information from one or more entries to one or more reference data patterns.

The comparison module may be configured using existing commercially-available or freely-available software for comparing patterns and may be optimized for particular data comparisons that are conducted. The comparison module provides computer readable information related to the response-associated bacteria.

The comparison module provides a computer readable comparison result that can be processed in computer readable form by predefined criteria, or criteria defined by a user, to provide a content based in part on the comparison result that may be stored and output.

The methods described herein therefore provide for systems (and computer readable media for causing computer systems) to perform methods for determining responsiveness to treatment with an immune checkpoint inhibitor in a subject.

FMT

Implantation or administration of human microbiota into the bowel of a sick patient is called Faecal Microbiota Transplantation (FMT), also commonly known as faecal bacteriotherapy. FMT is believed to repopulate the gut with a diverse array of microbes that bring missing beneficial functions or microbiota to the resident gut bacteria, displace harmful microbiota or control key pathogens by creating an unfavourable ecological environment.

In another aspect, the invention relates to a method for screening/Identifying a faecal donor comprising assessing a faecal sample of a subject for the presence of one or more bacteria associated with response to cancer; e.g. response to cancer when a patient is treated with an immune checkpoint inhibitor and identifying the faecal donor based on the presence and/or abundance of one or more bacteria.

For example, in such a method, the one or more bacteria selected from Table 1 and the faecal donor is identified based on the presence and/or abundance of one or more bacteria selected from Table 1.

In another aspect, the invention relates to a method for screening/identifying a faecal donor comprising assessing a faecal sample of a subject for the presence of one or more bacteria selected from Table 1 and identifying the faecal donor based on the presence and/or abundance of one or more bacteria selected from Table 1. The method may also comprise obtaining a faecal sample from a donor. Assessing a faecal sample of a subject for the presence of one or more bacteria can be done by methods known in the art, e.g. sequence analysis of bacterial genomes, e.g. using a shotgun sequencing approach. For example, one or more of the bacteria is present above a predetermined threshold, the donor is selected as a donor for bacteriotherapy purposes. The predetermined threshold may be based on the average abundance of the one or more bacteria in faecal samples obtained from a donor population. A higher than average abundance indicates that the faeces are suitable for FMT therapy.

The invention also relates to a use of one or more bacteria selected from Table 1 in a method for identifying a donor for FMT therapy.

The Invention relates to a method for treating a faecal transplant prior to administration to a subject comprising supplementing the faecal transplant with one or more bacterial isolates selected from Table 1 or with a faecal sample obtained from a donor by the method described above.

According to another aspect of the present invention, an individual in need of a treatment with an immune checkpoint inhibitor therapy is treated by FMT, using faecal microbiota from healthy individual(s) that has been shown to be abundant in one or more of the species in table 1, and/or faecal microbiota from one or several individual(s) treated with an immune checkpoint inhibitor therapy and who proved to respond to this therapy, and/or faecal microbiota from one or several individual(s) exhibiting a gut microbiota profile that identifies him/her/them as likely to respond to the envisioned treatment or from a responding patient.

In the aspects above, the FMT therapy is for the treatment of a disease as mentioned herein, e.g. a cancer such as melanoma.

Composition and Methods for Increasing Abundance of Bacteria in a Host

In another aspect of the invention, a subject's microbiome may be altered to increase the abundance of bacteria listed in Table 1 or a subset thereof. Glycan metabolism has been shown to influence the human gut microbiota and prebiotics can enrich bacterial taxa that promote anti-tumor immunity (Koropatkin et al, Nature Reviews Microbiology volume 10, pages 323-335 (2012); Li et al, Cell Report, Volume 30. ISSUE 6, P1753-1766.e6, Feb. 11, 2020). Thus, there is provided a method for increasing the abundance of bacteria listed in table 1 in a subject or a subset thereof by administration of a composition comprising oligosaccharides, such as glycans. Compositions comprising oligosaccharides, such as glycans for use in such a method are also envisaged.

Kits

In a further aspect, the invention relates to a kit. The kit includes a composition described herein and optionally an anti-cancer treatment that includes an immune checkpoint inhibitor as described herein. In an example, the kit can include materials to ship the collected material without harming the samples (e.g., packaged in lyophilized form, or packaged in an aqueous medium etc.). The kit may include the processed material or treatment in a sterile container, such as a nasogastric (NG) tube, a vial (e.g., for use with a retention enema), a gastro-resistant capsule (e.g., acid-bio resistant to reach the intestinal tract, having a sterile outside), etc. The kit may also comprise instructions for use.

In an alternative aspect, the kit comprises
a sealable container configured to receive a biological sample, such as a faecal sample;
polynucleotide primers for amplifying a 16S rDNA polynucleotide sequence from at least one gut associated bacterium to form an amplified 16S rDNA polynucleotide sequence, wherein the amplified 16S rDNA sequence has at least 97%, 98%, 98.7% or 99% homology to a polynucleotide sequence selected from SEQ ID NOs 1 to SEQ ID NO 15, e.g. SEQ ID NOs 16 to 29;
a detecting reagent to detect the amplified 16S rDNA sequence; and
instructions for use.

The invention also relates to as kit comprising a composition comprising oligosaccharides, such as glycans for use in a method for increasing the abundance of bacteria listed in table 1 in a subject or a subset thereof by administration of the composition.

The invention also relates to the use of a composition of the invention, i.e. comprising or consisting of one or more a bacterial isolate as shown in Table 1 with reference to a SEQ ID NO. shown therein, in increasing efficacy of an anti-cancer treatment with an immune checkpoint inhibitor. The invention also relates to the use of a composition of the invention, i.e. comprising or consisting of one or more a bacterial isolate as shown in Table 1 with reference to a SEQ ID NO. as shown in the Table, in enhancing immune checkpoint blockade. The invention also relates to a method for increasing efficacy of an anti-cancer treatment with an immune checkpoint inhibitor comprising administering a composition of the invention, i.e. comprising or consisting of one or more bacterial isolate as shown in Table 1 with reference to a SEQ ID NO., to a subject. The invention also relates to a method for enhancing immune checkpoint blockade comprising administration of a composition of the invention, i.e. comprising or consisting of one or more bacterial isolate as shown in Table 1 with reference to a SEQ ID NO. as shown in the Table to a subject.

The invention also relates to the use of a composition of the invention in providing an immunostimulatory effect.

The invention also relates to a method for determining if a cancer patient needs a bacterial composition of the invention, i.e. comprising or consisting of one or more a bacterial isolate as shown in Table 1 with reference to a SEQ ID NO. as shown therein, before administration of an immune checkpoint inhibitor comprising assessing, in a faeces sample from said patient, the presence or absence or one or more bacterial isolates selected from the species in Table 1.

Aspects

The Invention is further described in the following aspects.

1. A composition comprising isolated bacteria selected from at least two species wherein the bacteria from the first species comprise a 16S rDNA sequence having at least 98.7% sequence identity with a nucleic acid sequence according to SEQ ID NO: 1, and the bacteria from the second species comprise a 16S rDNA sequence having at least 98.7% sequence identity with a nucleic acid sequence according to SEQ ID NO: 2.
2. The composition according to aspect 1, further comprising isolated bacteria from at least 1, 2, 3, 4, 5, 6, 7, 8, 9, 10, 11, 12 or 13 different species wherein the bacteria comprise a 16S rDNA sequence selected from a sequence having at least 98.7% sequence identity with a nucleic acid sequence according to SEQ ID NO: 3 to 15.
3. The composition according to aspect 1 further comprising isolated bacteria from at least 4 different species wherein the bacteria comprise a 16S rDNA sequence selected from a sequence having at least 98.7% sequence identity with a nucleic acid sequence according to SEQ ID NO: 3 to 15.
4. The composition according to aspect 1, further comprising isolated bacteria from at least 7 different species wherein the bacteria comprise a 16S rDNA sequence selected from a sequence having at least 98.7% sequence identity with a nucleic acid sequence according to SEQ ID NO: 3 to 15.
5. The composition according to aspect 1, further comprising a bacterial isolate comprising a 16S rDNA sequence selected from a sequence having at least 98.7% sequence identity with a nucleic acid sequence according to SEQ ID NO: 7.
6. The composition according to aspect 1 comprising a consortium selected from consortia 1 to 4 or 6 to 10 as shown in Table 3.
7. The composition according to any preceding aspect, wherein said composition is formulated for oral or rectal administration.
8. The composition according to aspect 7, wherein said composition is in the form of a capsule, tablet, gel or liquid.
9. The composition according to aspect 8, wherein said composition is encapsulated in an enteric coating.
10. The composition according to any preceding aspect, wherein the composition comprises live, attenuated or killed bacteria.
11. The composition according to any preceding aspect, wherein the composition comprises bacterial spores.
12. The composition according to any of aspects 1 to 11, wherein the composition does not comprise bacterial spores.
13. The composition according to any preceding aspect, wherein the composition comprises bacterial strains that originate from one or more human donor.
14. The composition according to any preceding aspect, wherein the bacteria are lyophilized.
15. The composition according to any preceding aspect, wherein the composition comprises at least about $1 \times 10^3$ to $1 \times 10^{13}$ CFU of bacteria.
16. The composition according to any preceding aspect, wherein administration of the composition induces an immune response in a subject and/or increases the efficacy of an anti cancer therapy that includes an immune checkpoint inhibitor.
17. A pharmaceutical composition comprising a composition of any of aspects 1 to 16 and a pharmaceutical carrier.
18. The pharmaceutical composition according to aspect 17, further comprising an effective amount of an immune checkpoint inhibitor or a vaccine.
19. The pharmaceutical composition according to aspect 18, wherein the immune checkpoint inhibitor inhibits PD-1, PDL-1, CTLA-4, LAG3 or TIM-3 activity.
20. The pharmaceutical composition according to aspect 19 wherein the immune checkpoint inhibitor is an anti PD-1, PDL-1 or CTLA-4 antibody or fragment thereof.
21. The pharmaceutical composition according to aspect 20 wherein the anti PD-1, PDL-1 or CTLA4 antibody is selected from nivolumab, pembrolizumab, cemiplimab, avelumab, durvalumab, atezolizumab, spartalizumab, camrelizumab, sintilimab, tislelizumab, pidilizumab toripalimab, Ipilimumab or Tremelimumab.

22. The pharmaceutical composition according to aspect 18, wherein the immune checkpoint inhibitor is an interfering nucleic acid molecule, a small molecule or PROteolysis TArgeting Chimera (PROTAC), alternative protein scaffold or other immune checkpoint inhibitor.

23. The pharmaceutical composition according to aspect 22, wherein the interfering nucleic acid molecule is an siRNA molecule, an shRNA molecule or an antisense RNA molecule.

24. A composition according to any of aspects 1 to 16, or a pharmaceutical composition of any of aspects 17 to 23 for use in the treatment of disease.

25. A composition according to any of aspects 1 to 16, or a pharmaceutical composition of any of aspects 17 to 23 for use in the treatment of cancer or an infectious disease or for use as a vaccine adjuvant or for increasing the efficacy of a cancer treatment.

26. A method for treating cancer or an infectious disease in a subject in need thereof, comprising administering a composition according to any of aspects 1 to 17 or a pharmaceutical composition of aspect 17, to said subject.

27. The method of aspect 26 wherein said subject is receiving, has received or will receive therapy with an immune checkpoint inhibitor, thereby treating the cancer or infectious disease.

28. A method for treating cancer in a subject in need thereof comprising administering a composition according to aspect 18 to said subject.

29. The method according to aspect 26 or 27, wherein administration of the composition enhances an immune response by the subject and/or inhibits immune evasion by the cancer and/or increases efficacy of an anti cancer treatment with an immune checkpoint inhibitor.

30. The composition for use according to aspect 25, or the method according to any of aspects 26 to 29 wherein the cancer is selected from melanoma melanoma, such as Harding-Passey melanoma, juvenile melanoma, lentigo maligna melanoma, malignant melanoma, acral-lentiginous melanoma, amelanotic melanoma, benign juvenile melanoma, Cloudman's melanoma. S91 melanoma, nodular melanoma, subungual melanoma, Cutaneous melanoma, uveal/intraocular melanoma and superficial spreading melanoma or bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, breast cancer, brain cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, kidney cancer, sarcoma of soft tissue, cancer of the urethra, cancer of the bladder, renal cancer, lung cancer, non-small cell lung cancer, thymoma, urothelial carcinoma leukemia, prostate cancer, mesothelioma, adrenocortical carcinoma, lymphomas, such as such as Hodgkin's disease, non-Hodgkin's, gastric cancer, and multiple myelomas.

31. The composition for use according to aspect 25 or the method according to any of aspects 26 to 29, wherein the composition or pharmaceutical composition is administered by oral administration or rectal administration.

32. The composition for use according to aspect 25 or the method according to any of aspects 26 to 29, wherein said subject has received prior anti cancer therapy with an immune checkpoint inhibitor.

33. The composition for use according to aspect 25 or the method according to any of aspects 26 or 29 further comprising administering an anti cancer therapy with an immune checkpoint inhibitor.

34. The composition for use or method according to aspect 33, wherein the immune checkpoint inhibitor is administered before, after or at the same time as the bacterial formulation.

35. The composition for use or method according to aspect 33 or 34, wherein the immune checkpoint inhibitor is administered by injection.

36. The composition for use or method according to any of aspects 33 to 35, wherein the injection is an intravenous, intramuscular, intratumoural or subcutaneous injection.

37. The composition for use or method according to any of aspects 33 to 36 wherein the immune checkpoint inhibitor inhibits PD-1, PDL-1 or CTLA-4 activity.

38. The composition for use or method according to aspect 37, wherein the immune checkpoint inhibitor is an anti PD-1, PDL-1 or CTLA-4 antibody.

39. The composition for use method according to aspect 38, wherein the anti PD-1. PDL-1 or CTLA4 antibody is selected from nivolumab, pembrolizumab, cemiplimab, avelumab, durvalumab, atezolizumab, Spartalizumab, Camrelizumab, Sintilimab, Tislelizumab, Pidilizumab, Toripalimab, Ipilimumab or Tremelimumab.

40. The composition for use or method according to any of aspects 33 to 37, wherein the immune checkpoint inhibitor is an interfering nucleic acid molecule, a small molecule or PROteolysis TArgeting Chimera (PROTAC) or other immune checkpoint inhibitor.

41. The composition for use or method according to aspect 40, wherein the interfering nucleic acid molecule is an siRNA molecule, an shRNA molecule or an antisense RNA molecule or a small molecule or peptide.

42. The composition for use according to aspect 25 or 30 to 41, or the method according to any of aspects 26 to 41, further comprising surgical, radiation, and/or chemotherapeutic cancer intervention or administration of a second anti cancer therapeutic.

43. The composition for according to aspect 25 or 30 to 42 or method according to any of aspects 26 to 42, further comprising administering to the subject an antibiotic.

44. The composition for use according to aspect 25 or 30 to 43 or method according to any of aspects 26 to 43, wherein the subject is identified as at risk of developing a cancer.

45. A kit comprising a composition according to any of aspects 1 to 17, and optionally an anti cancer treatment that includes an immune checkpoint inhibitor.

46. A food product or a vaccine adjuvant comprising the composition of any of aspects 1 to 17.

47. A method for treating faecal transplant prior to administration to a subject comprising supplementing the faecal transplant with isolated bacteria selected from at least two species wherein the bacteria from the first species comprise a 16S rDNA sequence having at least 98.7% sequence identity with a nucleic acid sequence according to SEQ ID NO: 1, and the bacteria from the second species comprise a 16S rDNA sequence having at least 98.7% sequence identity with a nucleic acid sequence according to SEQ ID NO: 2.
48. A use of a composition of any of aspects 1 to 17 or a pharmaceutical composition of aspect 18, in increasing efficacy of an anti cancer treatment with an immune checkpoint inhibitor.
49. A use of a composition of any of aspects 1 to 17 or a pharmaceutical composition of aspect 18, in enhancing immune checkpoint blockade.
50. A method for enhancing immune checkpoint blockade comprising administering a composition of any of aspects 1 to 17 or a pharmaceutical composition of aspect 18.
51. A composition comprising a bacterium selected from one or more bacteria selected from Table 1.
52. A method for treating or preventing cancer comprising modulating the level of one or more bacteria selected from those of Table 1 in a subject.

The invention is also further described in the following additional aspects.

1. A method for identifying a subject that will respond to therapy with an immune checkpoint inhibitor comprising determining the abundance of bacteria from at least 9 different species in a biological sample from said subject that comprises gut flora wherein said bacteria comprise a 16S rDNA sequence selected from SEQ ID NOs: 1 to 15 or a sequence having at least 98.7% sequence identity with a nucleic acid sequence selected from SEQ ID NOs: 1 to 15 wherein said abundance is indicative of a response of a subject to therapy with an immune checkpoint inhibitor.
2. The method for identifying a subject that will respond to therapy with an immune checkpoint inhibitor according to aspect 1, the method comprising:
    a) determining the abundance of the bacteria in a biological sample obtained from the subject and
    b) comparing the abundance to a reference level from cancer patients that do not respond to therapy with an immune checkpoint inhibitor or cancer patients that respond to therapy with an immune checkpoint inhibitor;
    wherein if the reference level is from patients that do not respond to therapy with an immune checkpoint inhibitor, then an increase in the abundance of each of the bacteria compared to the reference level, is indicative that the subject will respond to therapy with an immune checkpoint inhibitor or
    wherein if the reference level is from patients that do respond to therapy with an immune checkpoint inhibitor, then the same or substantially the same or an increase in abundance of each of the bacteria, is indicative that the subject will respond to therapy with an immune checkpoint inhibitor.
3. The method for identifying a subject that will respond to therapy with an immune checkpoint inhibitor according to aspect 1, the method comprising:
    a) determining the abundance of the bacteria in a biological sample obtained from the subject;
    b) comparing the abundance to a reference level from cancer patients and
    c) applying random forest analysis.
4. The method according to a preceding aspect, wherein the bacterial species comprise a 16S rDNA sequence selected from SEQ ID NO: 1 or 2 or a 16S rDNA sequence having at least 98.7% sequence identity thereto.
5. The method according to a preceding aspect, wherein the method comprises determining the abundance of bacteria from 10, 11, 12, 13, 14 or 15 species wherein said bacteria comprise a 16S rDNA sequence selected from SEQ ID NOs: 1 to 15 or a sequence having at least 98.7% sequence identity with a nucleic acid sequence selected from SEQ ID NOs: 1 to 15.
6. The method according to a preceding aspect wherein said subject is a cancer patient.
7. The method according to aspect 6, wherein the cancer is selected from melanoma, bone cancer, pancreatic cancer, cancer of the head or neck, cutaneous or intraocular malignant melanoma, uterine cancer, ovarian cancer, rectal cancer, cancer of the anal region, stomach cancer, testicular cancer, breast cancer, brain cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, kidney cancer, sarcoma of soft tissue, cancer of the urethra, cancer of the bladder, renal cancer, lung cancer, non-small cell lung cancer, thymoma, urothelial carcinoma leukemia, prostate cancer, mesothelioma, adrenocortical carcinoma, lymphomas, such as such as Hodgkin's disease, non-Hodgkin's, gastric cancer, and multiple myelomas.
8. The method according to aspect 7, wherein the melanoma is selected from Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma, subungual melanoma, Cutaneous melanoma, uveal/intraocular melanoma and superficial spreading melanoma.
9. The method according to a preceding aspect, further comprising the step of identifying a subject in need of treatment with the immune checkpoint inhibitor.
10. The method according to a preceding aspect, further comprising administering an immune checkpoint inhibitor to said subject.
11. The method according to a preceding aspect wherein the immune checkpoint inhibitor inhibits PD-1, PD-L1 or CTLA-4 activity.
12. The method according to aspect 11, wherein the immune checkpoint inhibitor is an anti PD-1, PDL-1 or CTLA-4 antibody.
13. The method according to aspect 12, wherein the anti PD-1, PDL-1 or CTLA-4 antibody is selected from nivolumab, pembrolizumab, cemiplimab, avelumab, durvalumab, atezolizumab, Spartalizumab, Camrelizumab, Sintilimab, Tislelizumab, Pidilizumab, Toripalimab, Ipilimumab or Tremelimumab.
14. The method according to any of aspects 1 to 11, wherein the immune checkpoint inhibitor is an interfering nucleic acid molecule, a small molecule or a PROteolysis TArgeting Chimera (PROTAC) or other immune checkpoint inhibitor.
15. The method according to aspect 14, wherein the interfering nucleic acid molecule is an siRNA molecule, an shRNA molecule or an antisense RNA molecule or a small molecule or peptide.

16. The method according to a preceding aspect, wherein the abundance is the abundance of the bacteria in the sample as a proportion of the total microbiota in the sample.
17. The method according to a preceding aspect, further comprising the step of obtaining a biological sample that comprises gut flora from said subject.
18. The method according to a preceding aspect, wherein the sample is a faecal sample.
19. Use of bacteria selected from at least 9 different bacterial species wherein said bacteria comprise a 16S rDNA sequence selected from SEQ ID NOs: 1 to 15 or a sequence having at least 98.7% sequence identity with a nucleic acid sequence selected from SEQ ID NOs: 1 to 15 in identifying a patient that will respond to therapy with an immune checkpoint inhibitor.
20. A kit comprising
    a sealable container configured to receive a biological sample;
    polynucleotide primers for amplifying a 16S rDNA polynucleotide sequence from at least 9 different bacterial species wherein said bacteria comprise a 16S rDNA sequence selected from SEQ ID NOs: 1 to 15 or a sequence having at least 98.7% sequence identity with a nucleic acid sequence selected from SEQ ID NOs: 1 to 15;
    a detecting reagent to detect the amplified 16S rDNA sequence; and
    instructions for use.
21. A method for identifying a faecal donor comprising assessing a faecal sample of a subject for the presence of bacteria from at least 9 different bacterial species wherein said bacteria comprise a 16S rDNA sequence selected from SEQ ID NOs: 1 to 15 or a sequence having at least 98.7% sequence identity with a nucleic acid sequence selected from SEQ ID NOs: 1 to 15 and identifying the faecal donor based on the presence and/or abundance of the bacteria.
22. The use of bacteria from at least 9 different bacterial species wherein said bacteria comprise a 16S rDNA sequence selected from SEQ ID NOs: 1 to 15 or a sequence having at least 98.7% sequence identity with a nucleic acid sequence selected from SEQ ID NOs: 1 to 15 in a method for identifying a donor for FMT therapy.
23. A method for determining if a cancer patient needs a bacterial compensation before administration of an immune checkpoint inhibitor comprising assessing, in a faeces sample from said patient, the presence or absence of bacteria from at least 9 different bacterial species wherein said bacteria comprise a 16S rDNA sequence selected from SEQ ID NOs: 1 to 15 or a sequence having at least 98.7% sequence identity with a nucleic acid sequence selected from SEQ ID NOs: 1 to 15.
24. A method for predicting a response to an immune checkpoint inhibitor therapy in a subject having cancer comprising determining the abundance of bacteria from at least 9 different species wherein said bacteria comprise a 16S rDNA sequence selected from SEQ ID NOs: 1 to 15 or a sequence having at least 98.7% sequence identity with a nucleic acid sequence selected from SEQ ID NOs: 1 to 15 in a biological sample from said subject that comprises gut flora wherein said abundance is indicative of a response or non-response of a subject to therapy with an immune checkpoint inhibitor.
25. A method for predicting a response to an immune checkpoint inhibitor therapy in a subject having cancer according to aspect 24, the method comprising:
    a) determining the abundance of the bacteria a biological sample obtained from the subject;
    b) comparing the abundance to a reference level from patients that do not respond to immune checkpoint inhibitor therapy; or patients that respond to immune checkpoint inhibitor therapy; wherein if the reference level is from patients that do not respond to immune checkpoint inhibitor therapy, then an increase in the abundance of each of the bacteria compared to the reference level, is indicative that the subject will respond to therapy with an immune checkpoint inhibitor or
    wherein if the reference level is from patients that do respond to immune checkpoint inhibitor therapy, then the same or substantially the same or an increase in abundance of each of the bacteria, Is indicative that the subject will respond to therapy with an immune checkpoint inhibitor.
26. The method according to aspect 24, the method comprising:
    a) determining the abundance of the bacteria a biological sample obtained from the subject and;
    b) comparing the abundance to a reference level from cancer patients or healthy subjects and
    c) applying random forest analysis.
27. The method according to any of aspects 24 to 26, the method comprising the step of predicting a response.
28. The method according to any of aspects 24 to 27, where if the subject is predicted to be a non-responder, an anti cancer therapy is administered which is not an immune checkpoint inhibitor.
29. The method according to any of aspects 24 to 28, where if the subject is predicted to be a non-responder, a composition comprising isolated bacteria from one or more species is administered wherein the bacteria comprise a sequence selected from SEQ ID 1 to 15 or a sequence having at least 98.7% sequence identity with a nucleic acid sequence selected from SEQ ID NOs: 1 to 15.
30. A method according to aspect 29, where if the subject is predicted to be a non-responder, a composition comprising isolated bacteria selected from at least two species is administered wherein the bacteria from the first species comprise a 16S rDNA sequence having at least 98.7% sequence identity with a nucleic acid sequence according to SEQ ID NO: 1, and the bacteria from the second species comprise a 16S rDNA sequence having at least 98.7% sequence identity with a nucleic acid sequence according to SEQ ID NO: 2.
31. A method according to aspect 29 or 31, wherein the composition further comprises isolated bacteria from at least 1, 2, 3, 4, 5, 6, 7, 8, 9, 10, 11, 12 or 13 different species wherein the bacteria comprise a 16S rDNA sequence selected from a sequence having at least 98.7% sequence identity with a nucleic acid sequence according to SEQ ID NO: 3 to 15.
32. The method according to any of aspects 24 to 27, where if the subject is predicted to be a responder, an immune checkpoint inhibitor therapy is administered.

Further aspects and embodiments of the invention will be apparent to those skilled in the art given the present disclosure including the following experimental exemplification.

Unless otherwise defined herein, scientific and technical terms used in connection with the present disclosure shall have the meanings that are commonly understood by those of ordinary skill in the art. While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification are incorporated herein by reference in their entirety, including any references to gene accession numbers and references to patent publications.

"and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein. Unless context dictates otherwise, the descriptions and definitions of the features set out above are not limited to any particular aspect or embodiment of the invention and apply equally to all aspects and embodiments which are described.

The invention is further described in the non-limiting examples.

Example 1 Identification of Gut Bacteria and Isolates Driving Response to Immunotherapy The inventors have analysed how the microbiome of melanoma patients impacts response to immune checkpoint inhibitor therapy in the MELRESIST study. This study was conducted at Cambridge University Hospitals and was performed with the best standards in sample collection and processing. The study involved 69 patients many of which had longitudinal faecal sampling. The inventors analysed the relative abundance of gut bacteria in the baseline MELRESIST faecal samples by performing shotgun metagenomic sequencing. The metagenomic sequencing was analysed using a comprehensive and highly curated reference genome database primarily built on reference-quality genomes from cultured isolates. This reference-based metagenomic analysis gives highly sensitive and accurate identification of bacteria (Forster et al Nat Biotechnol. 2019; 37: 188). To support this analysis, the inventors re-analysed three additional shotgun metagenomic datasets from melanoma patients about to receive immune checkpoint inhibitor therapy using the same analysis platform.

The microbiome was examined by machine teaming approaches to select the specific bacterial species most predictive of response to immune checkpoint inhibitor therapy. For the first time in the field, a consistent microbiome signature associated with and highly predictive of response across multiple studies was identified. The size and quality of the MELRESIST dataset, the comprehensive and accurate identification of bacteria by reference-based metagenomic analysis and machine learning analysis all contributed to the discovery of this cross-study microbiome signature. The signature also further validates the central importance of the gut microbiome as a primary driver of immune checkpoint inhibitor response. This provides the basis for both a predictive biomarker and Live Bacterial Therapeutic co-therapy to increase the proportion of patients responding to checkpoint inhibitors. Using feature reduction steps, this microbiome signature was reduced to small consortia of bacteria comprising species more abundant in patients that response to immunotherapy. These smaller consortia are still predictive of response across studies, so can act as a biomarker. In addition, these consortia can form a live bacterial therapeutic for the co-administration with immune checkpoint inhibitors in the treatment of cancer.

This analysis enabled the identification of strains isolates representing thirteen species in the consortia. Dendritic cells stimulated with these strains, individually or as consortia of up to nine, potently activated Cytotoxic T Lymphocytes. Two consortia of nine were also tested in a syngeneic mouse model of cancer and both consortia demonstrated tumour growth inhibition. These results validate the bacteria as drivers of anti-tumour response.

1.1 Discovery Based on MELRESIST Clinical Study

MELRESIST is a study performed at Cambridge University Hospitals in which 69 advanced melanoma patients gave a faecal sample prior to and/or following treatment with anti-PD1 based immunotherapy. Complete clinical metadata, Including response to therapy, antibiotic use and toxicities, was also recorded. A rigorous sample collection protocol was used to ensure the highest possible standards. The DNA was extracted in a single batch at Microbiotica, and shotgun metagenomics performed. Shotgun metagnomics sequencing is well known in the art and for example described in Quince, C. et al, Shotgun metagenomics, from sampling to analysis. Nat Biotechnol 35, 833-844 (2017).

Reference-based metagenomics was used to analysis the sequences of the baseline stool samples to give more sensitive and specific identification of bacteria. The accuracy is further improved by a bioinformatic tool to mask mobile elements thereby reducing spurious signals caused by horizontal gene transfer. Suitable methods are also described in WO2020065347 Incorporated by reference. Additional classification filtering removes mis-assigned reads caused by contamination and gene duplication. The platform can accurately classify over 95% of the metagenomic reads leading to a precise mapping of the abundance of almost every bacterium in the sample.

To support and validate the analysis, three additional datasets from melanoma patients about to undergo immune checkpoint inhibitor therapy were reanalysed using the Microbiotica high-precision platform. These were:

Frankel *Neoplasia* (2017) 19:848, Advanced melanoma, 39 patients

Gopalakrishnan et al and Wargo *Science* (2018) 359:97, Metastatic melanoma, 25 patients (referenced as Wargo in figures)

Matson et al and Gajewski *Science* (2018) 359:104, Metastatic melanoma, 39 patients (referenced as Gajewski in figures)

1.2 Bioinformatic Analysis to Derive Microbiome-Signatures Predictive of Response to Immunotherapy The baseline samples from MELRESIST were used to define a signature of response by linking the relative abundance of each bacteria in a sample to the clinical outcome data. In the primary analysis stable disease, partial response and complete response at 6 months were all determined to be a response and progressive disease was considered nonresponse. Machine learning approaches, including Random Forest models, were used to select species providing the most power as part of a signature to predict response.

The random forest classifier is an algorithm based on the results of many decision trees. In a single decision tree, features are selected iteratively that best separate samples into responder and non-responder categories, until all features are utilized. In the case of prevalence data, these features could be presence or absence of a given species, where presence of a single species might be preferentially associated with responder samples, or vice versa. Alternatively, relative abundance of a given species might be predictive of response, in which it could be either more or less abundant in responder samples. Since a single decision tree typically overfits data and does not produce robust results, random forests are often used instead. A random forest classifier is based on many different decision trees, where each tree only uses a subset of the available data, for example randomly leaving out 20% of the observed species for each tree. In some cases, a subset of the samples is used for training the random forest. The random forest classifier thus learns which signals are strongest across all possible features and samples. For all random forest models, out-of-bag error was used to prevent overoptimistic performance and improve generalizability.

The inventors expanded the analysis by including the additional melanoma datasets to identify the bacteria linked to response across multiple studies. First, the data from the different studies was standardised, for example the response criteria was changed to be consistent with the MELRESIST study where necessary. A signature was then generated using the machine learning process on the combined dataset of all four melanoma datasets. The ability of this signature to function as a biomarker was then tested on the combined dataset, and it predicted whether a patient would respond to therapy with an accuracy of 91% (FIG. 1A). The Receiver Operating Characteristic (ROC) curve of this analysis gave an area under the curve (AUC) of 0.98 (FIG. 1C) thereby confirming how highly predictive this signature is. Importantly, the signature was 83-100% accurate when tested against the studies individually (FIG. 1B), and the ROC curves gave AUCs from 0.96 to 1 (FIG. 1D). This is the first demonstration of a microbiome based predictive biomarker that accurately predicts response across studies.

To progress the signature as a biomarker and select bacteria for inclusion in a Live Bacterial Therapeutic, the inventors identified the bacteria most robustly associated with response. The species that were consistently increased in abundance in responding patients from three or all four studies were selected to be advanced. Subsequently, a filtering step was applied to choose the bacteria with the cleanest signal by excluding species where the metagenomic reads did not broadly and evenly cover the genome.

Figure 2:
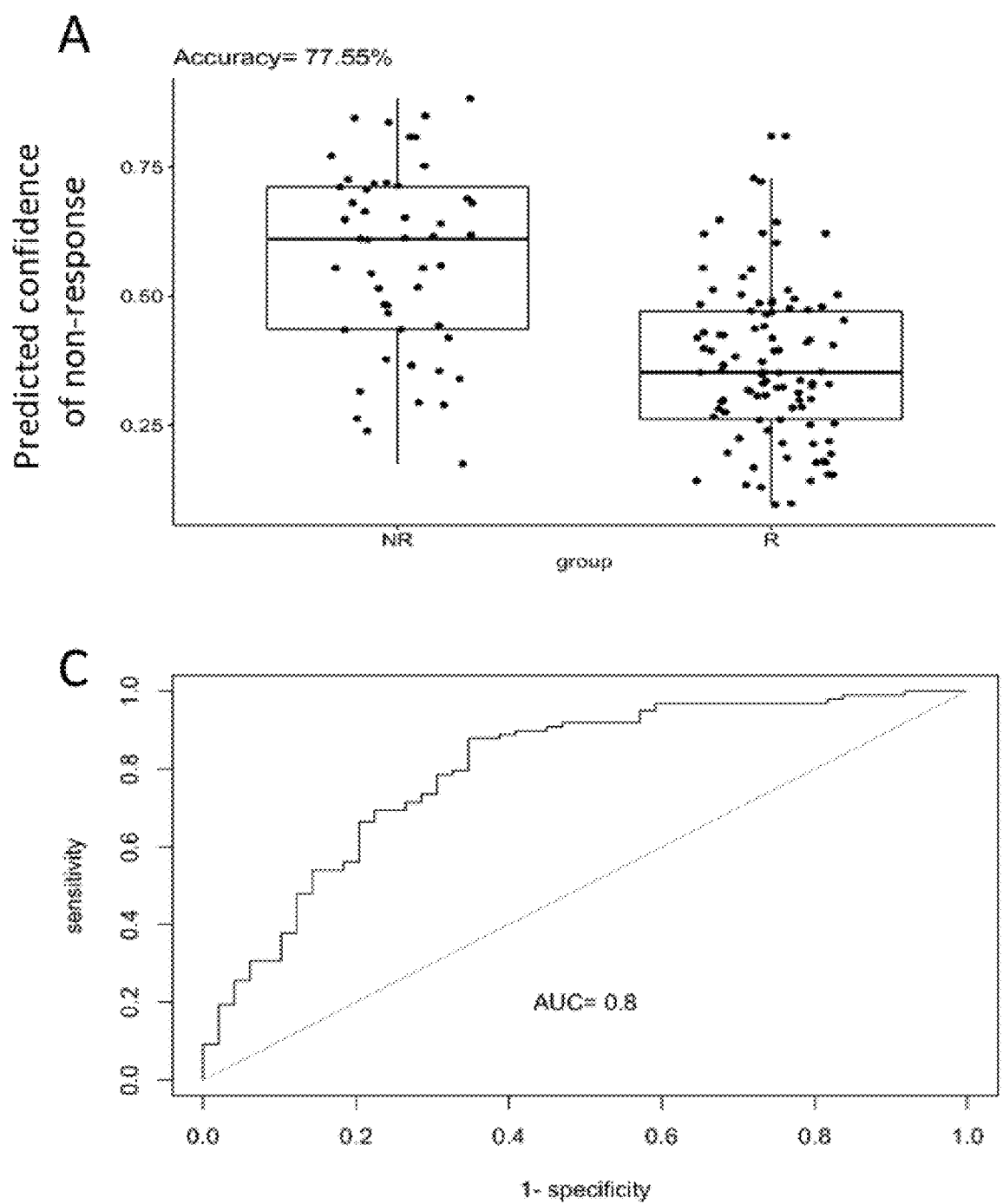
FIG. 2. A) All 147 patients from the four melanoma studies were divided into responders and non-responders according to clinical outcome. The probability of not responding to immunotherapy was predicted from the baseline faecal sample based on machine learning predictions that used the abundance of the 15 bacteria in consortium 1. A cut off of 0.5 was used to determine the accuracy of the prediction. Accuracy was 77.55%. B) As A except each study is considered separately. frankel accuracy 79.49%; gajewski accuracy 66.67%; melresist accuracy 81.82%; wargo accuracy 84%. C) Receiver Operating Characteristic (ROC) curve of the combined melanoma dataset showing False Positive Rate as a function of True Positive Rate based on machine learning predictions based on consortium 1. AUC=0.8. D) As C but each study is considered separately. Random forest out-of-bag error was used to prevent overoptimistic performance and improve generalizability. AUC frankel 0.867; AUC gajewski 0.725; AUC melresist 0.879; AUC wargo 0.773.
Figure 2:
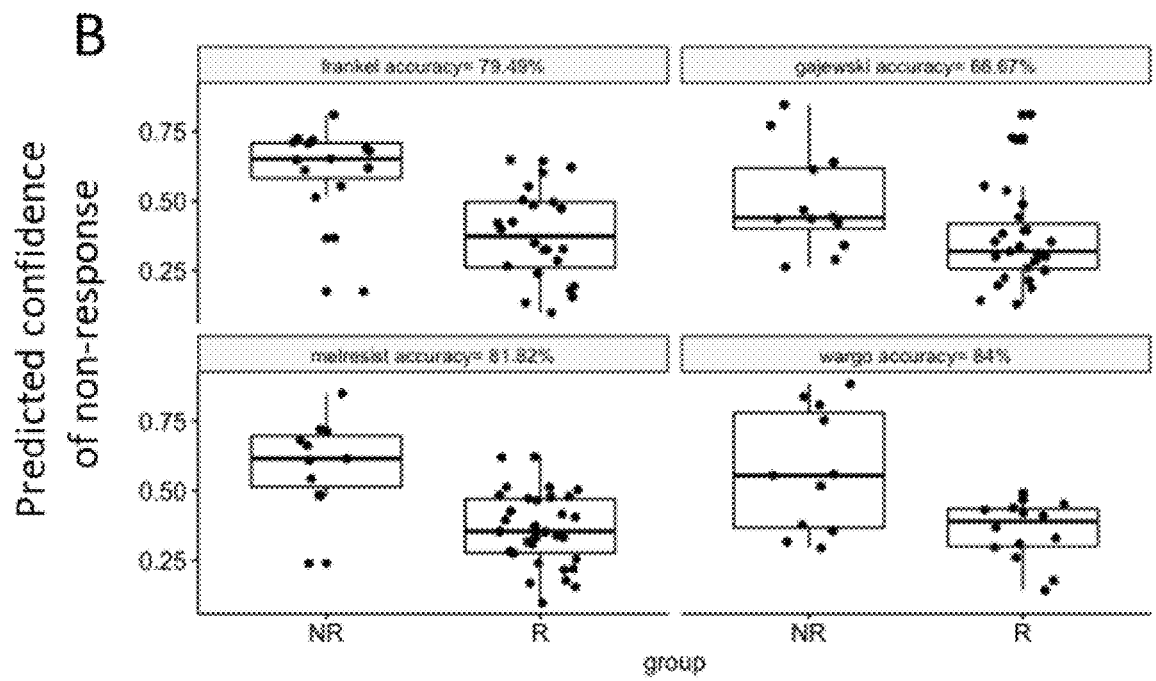
Figure 2:
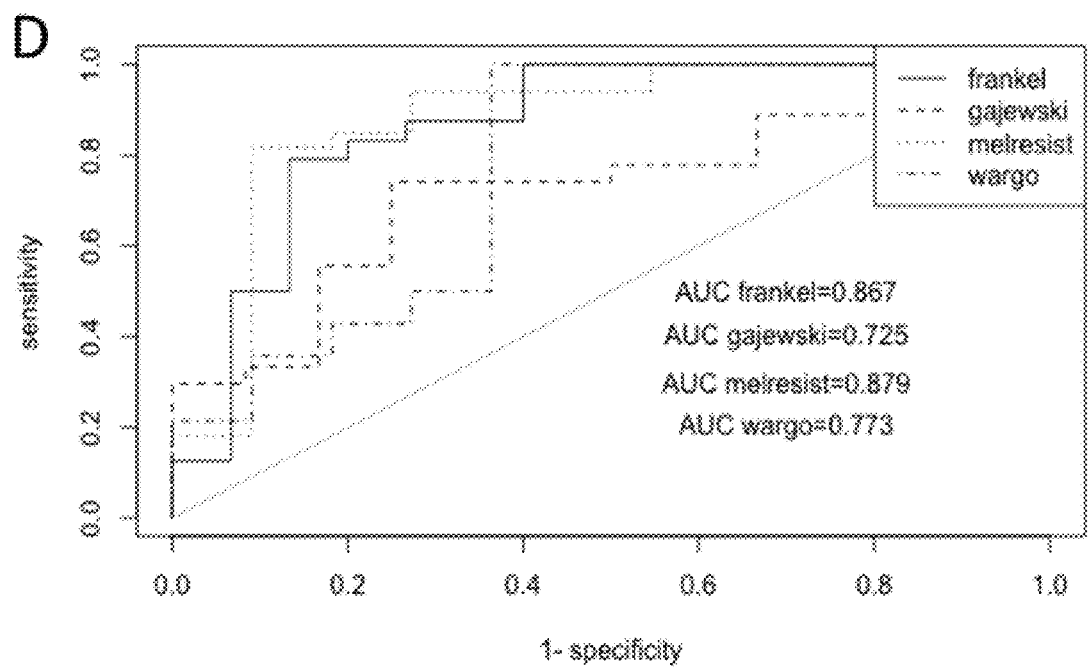
Figure 3:
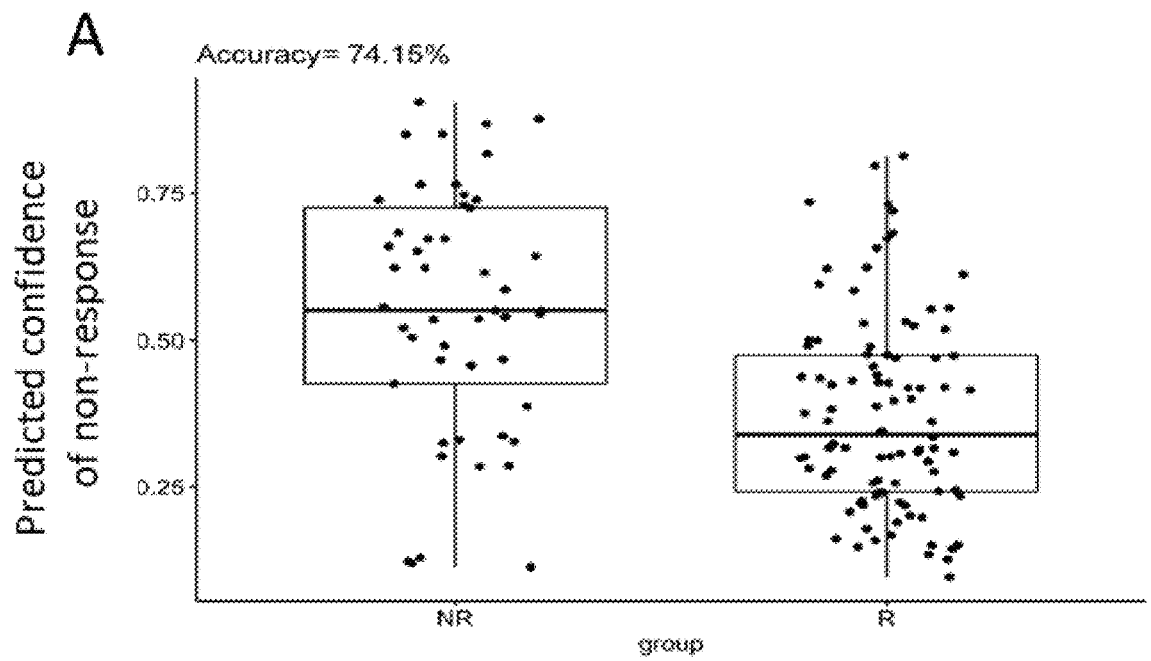
FIG. 3. A) All 147 patients from the four melanoma studies were divided into responders and non-responders according to clinical outcome. The probability of not responding to immunotherapy was predicted from the baseline faecal sample based on machine learning predictions that used the abundance of the 9 bacteria in consortium 2. A cut off of 0.5 was used to determine the accuracy of the prediction. Accuracy was 74.15%. B) As A except each study is considered separately. frankel accuracy 76.92%; gajewski accuracy 69.23%; melresist accuracy 75%; wargo accuracy 76%. C) Receiver Operating Characteristic (ROC) curve of the combined melanoma dataset showing False Positive Rate as a function of True Positive Rate based on machine learning predictions based on consortium 2. AUC=0.75. D) As C but each study is considered separately. Random forest out-of-bag error was used to prevent overoptimistic performance and improve generalizability. AUC frankel 0.831; AUC gajewski 0.676; AUC melresist 0.788; AUC wargo 0.734.
Figure 3:
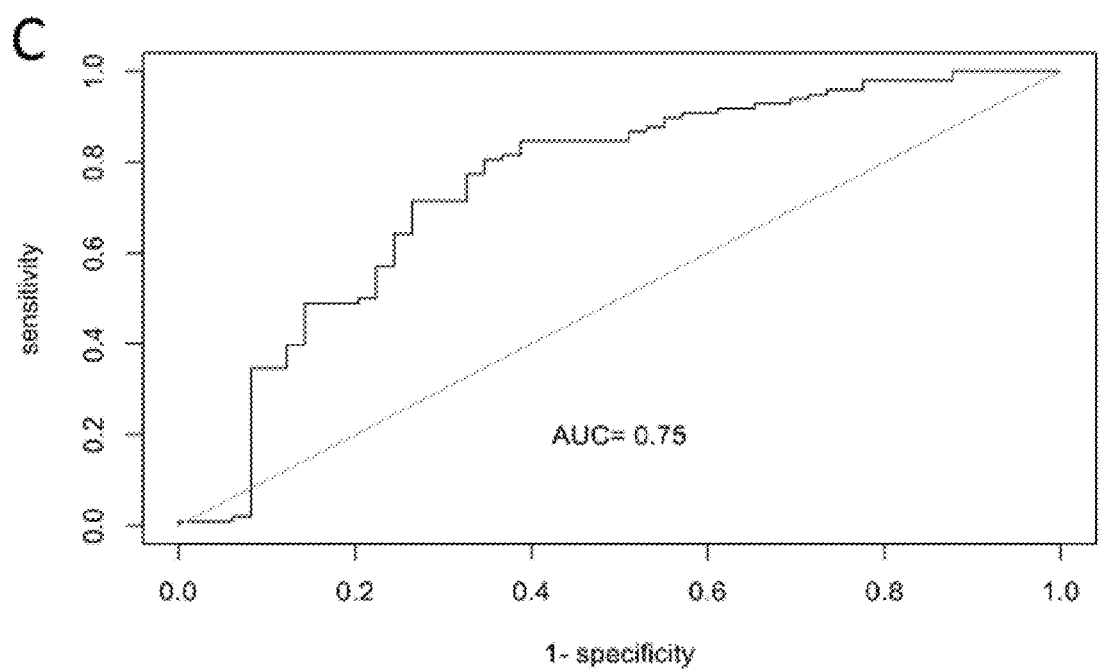
Figure 3:
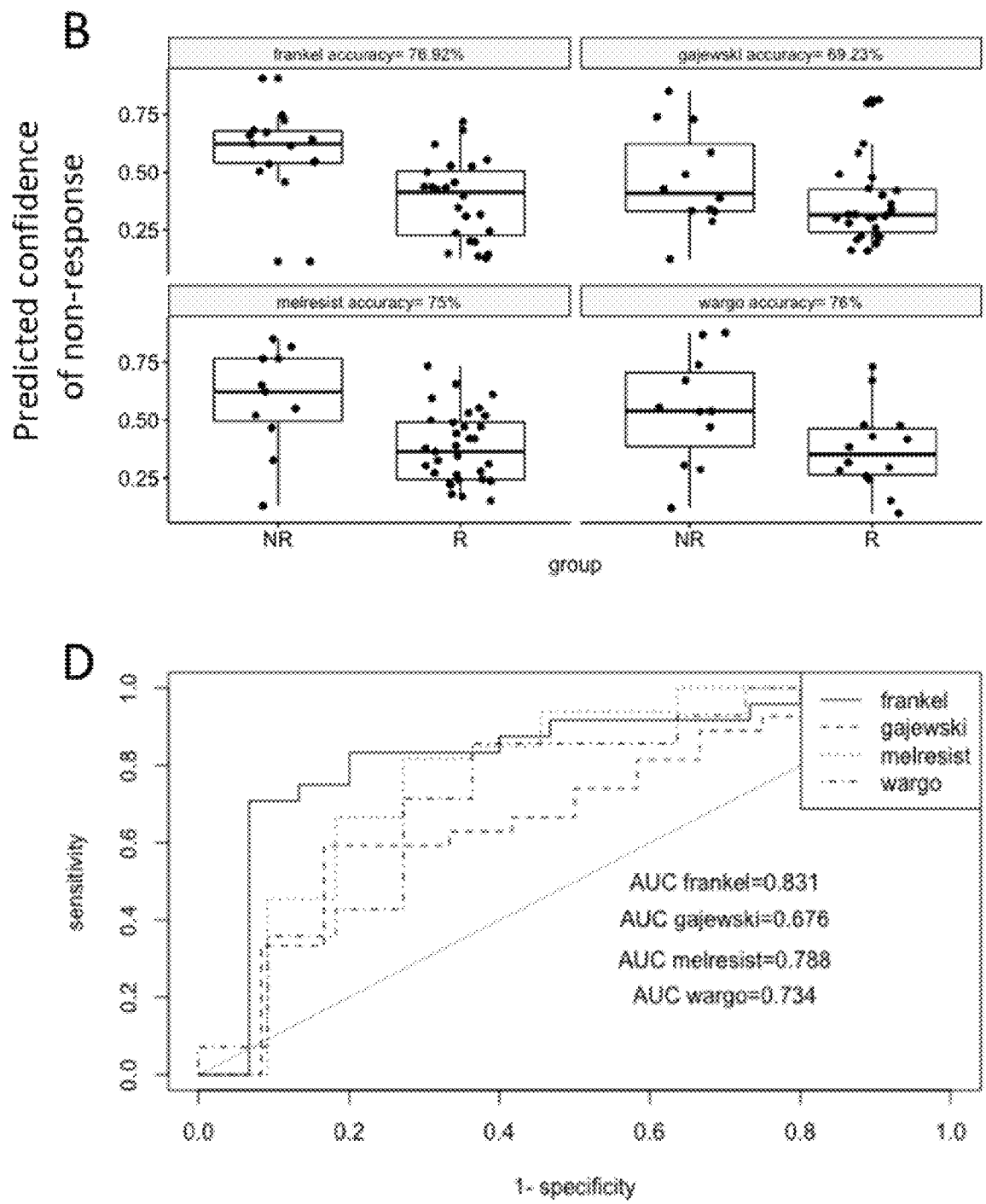
Figure 4:
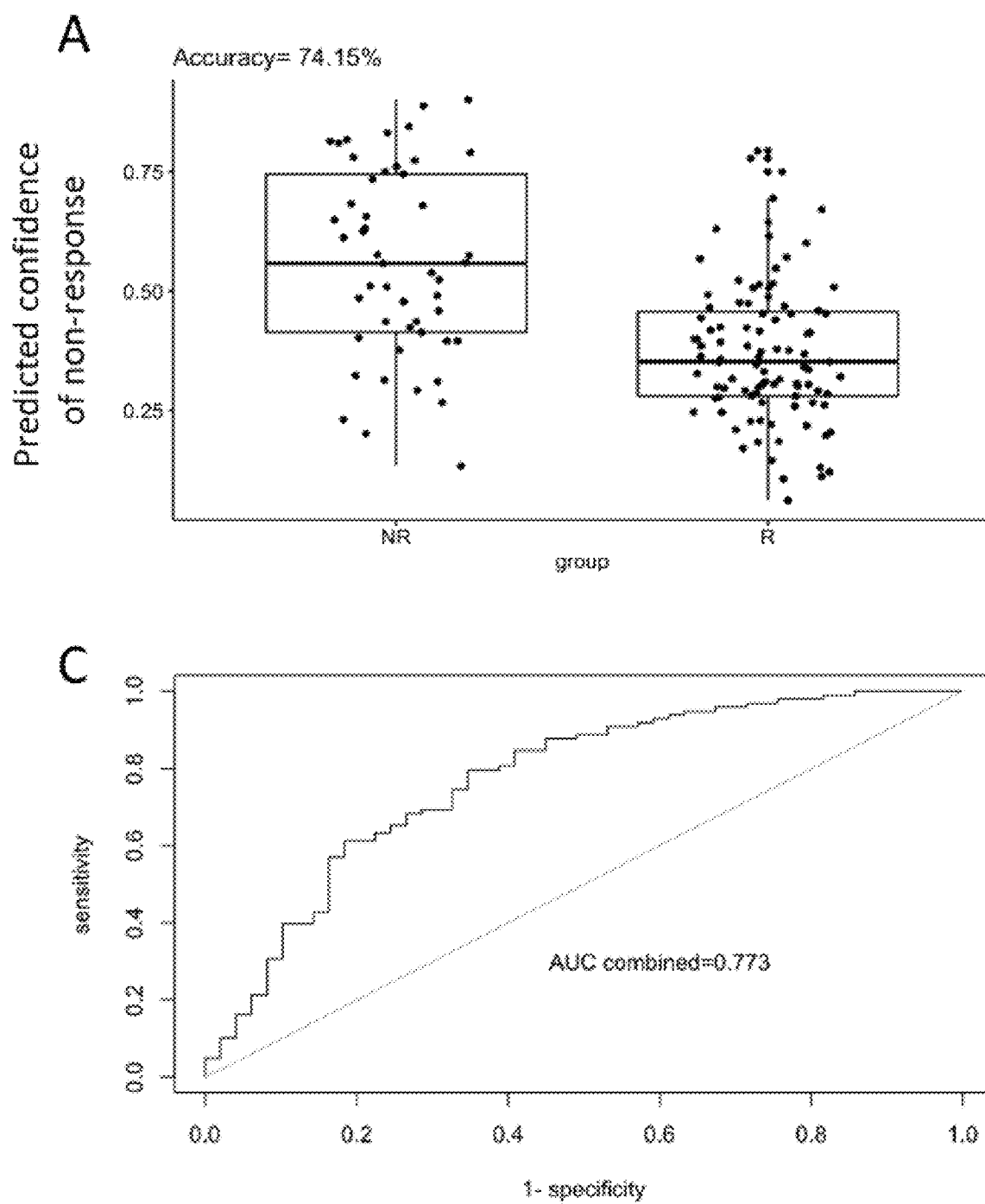
FIG. 4. A) All 147 patients from the four melanoma studies were divided into responders and non-responders according to clinical outcome. The probability of not responding to immunotherapy was predicted from the baseline faecal sample based on machine learning predictions that used the abundance of the 12 bacteria in consortium 3. A cut off of 0.5 was used to determine the accuracy of the prediction. Accuracy was 74.15%. B) As A except each study is considered separately. frankel accuracy 76.92%; gajewski accuracy 66.67%; melresist accuracy 81.82%; wargo accuracy 68%. C) Receiver Operating Characteristic (ROC) curve of the combined melanoma dataset showing False Positive Rate as a function of True Positive Rate based on machine learning predictions based on consortium 3. AUC=0.773. D) As C but each study is considered separately. Random forest out-of-bag error was used to prevent overoptimistic performance and improve generalizability. AUC frankel 0.844; AUC gajewski 0.685; AUC melresist 0.862; AUC wargo 0.76.
Figure 4:
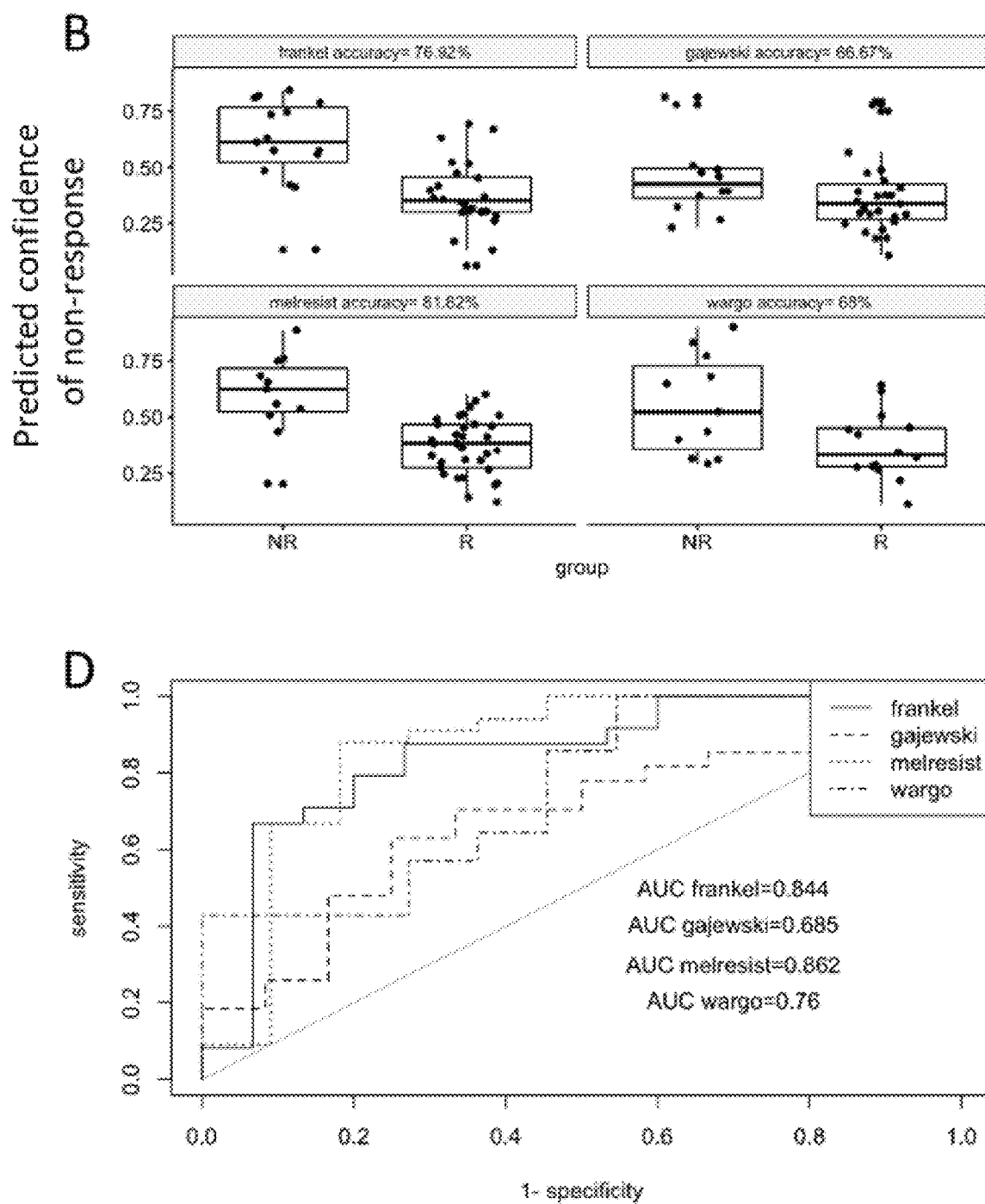
Figure 5:
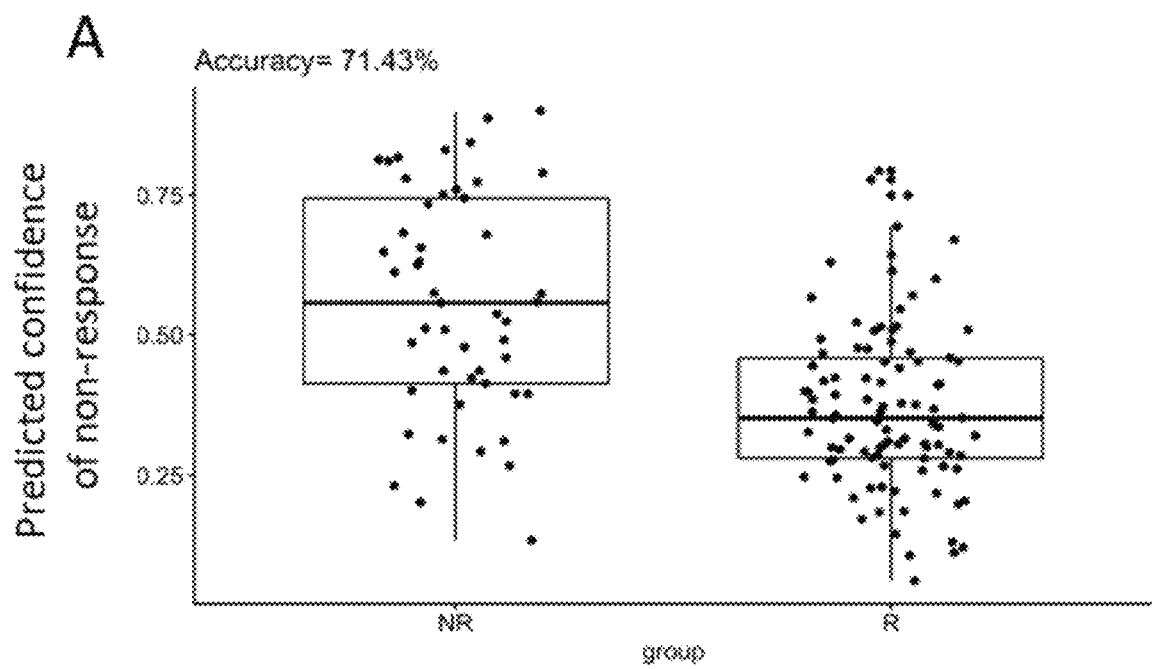
FIG. 5. A) All 147 patients from the four melanoma studies were divided into responders and non-responders according to clinical outcome. The probability of not responding to immunotherapy was predicted from the baseline faecal sample based on machine learning predictions that used the abundance of the 9 bacteria in consortium 4. A cut off of 0.5 was used to determine the accuracy of the prediction. Accuracy was 71.43%. B) As A except each study is considered separately. frankel accuracy 76.92%; gajewski accuracy 64.1%; melresist accuracy 77.27%; wargo accuracy 64%. C) Receiver Operating Characteristic (ROC) curve of the combined melanoma dataset showing False Positive Rate as a function of True Positive Rate based on machine learning predictions based on consortium 4. AUC=0.737. D) As C but each study is considered separately. Random forest out-of-bag error was used to prevent overoptimistic performance and improve generalizability. AUC frankel 0.781; AUC gajewski 0.667; AUC melresist 0.791; AUC wargo 0.708.
Figure 5:
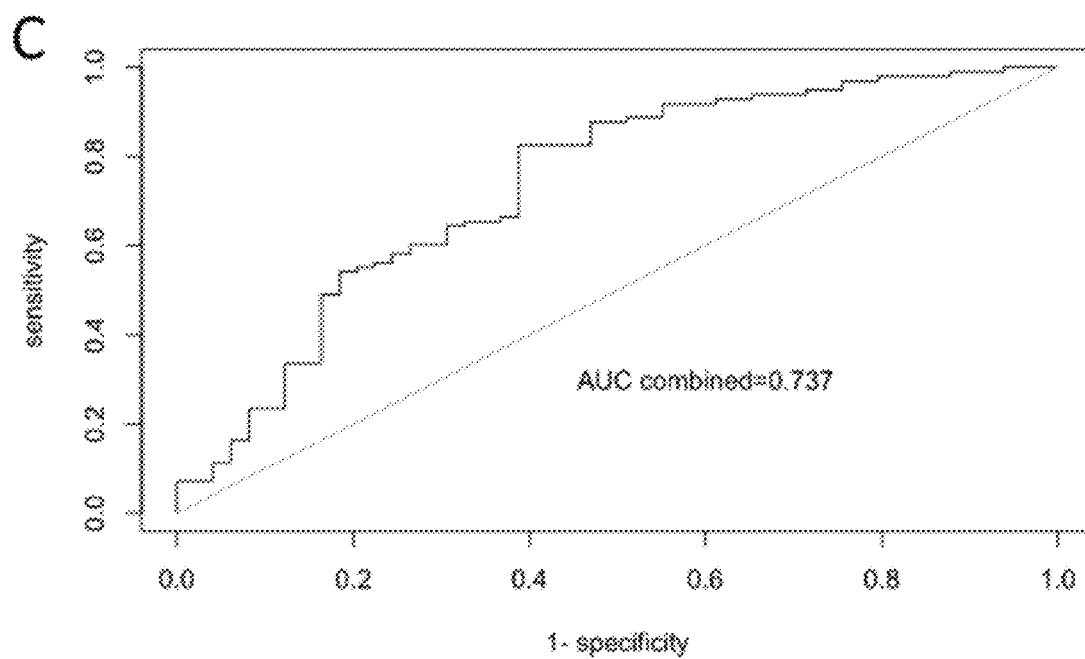
Figure 5:
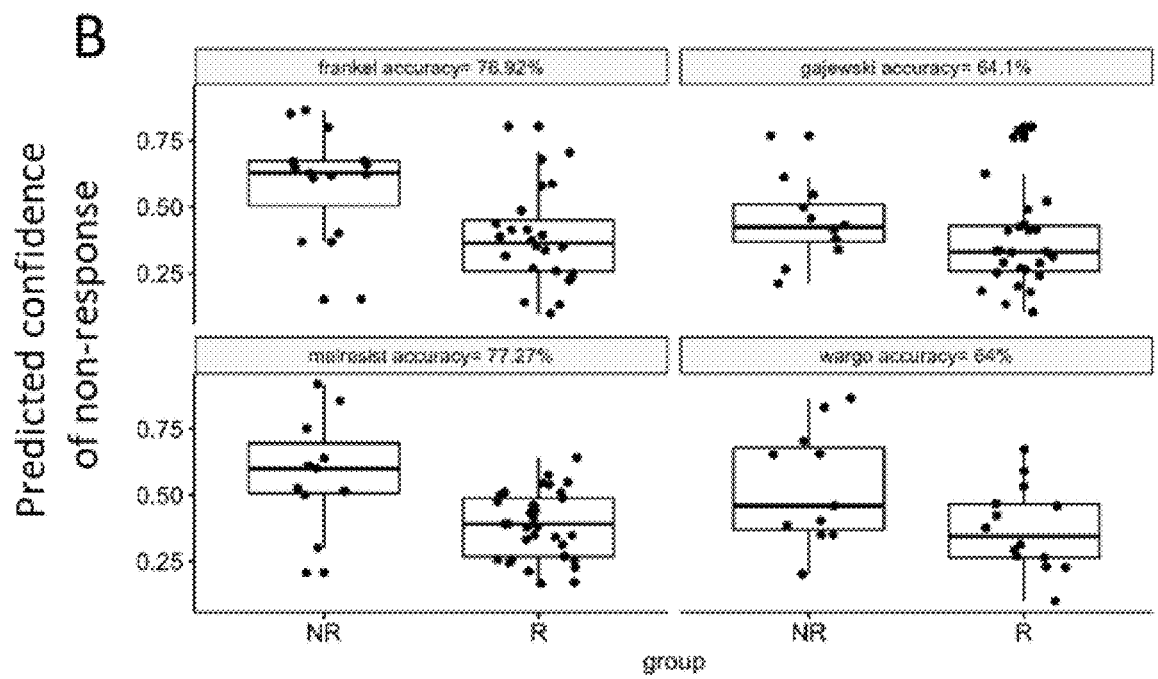
Figure 5:
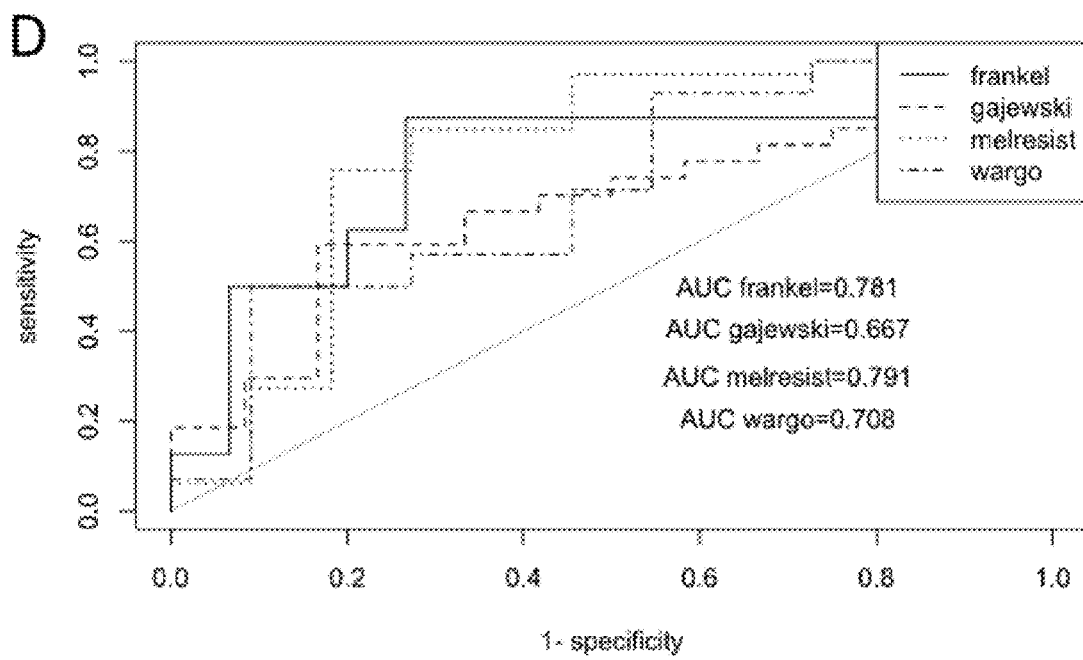
Figure 6:
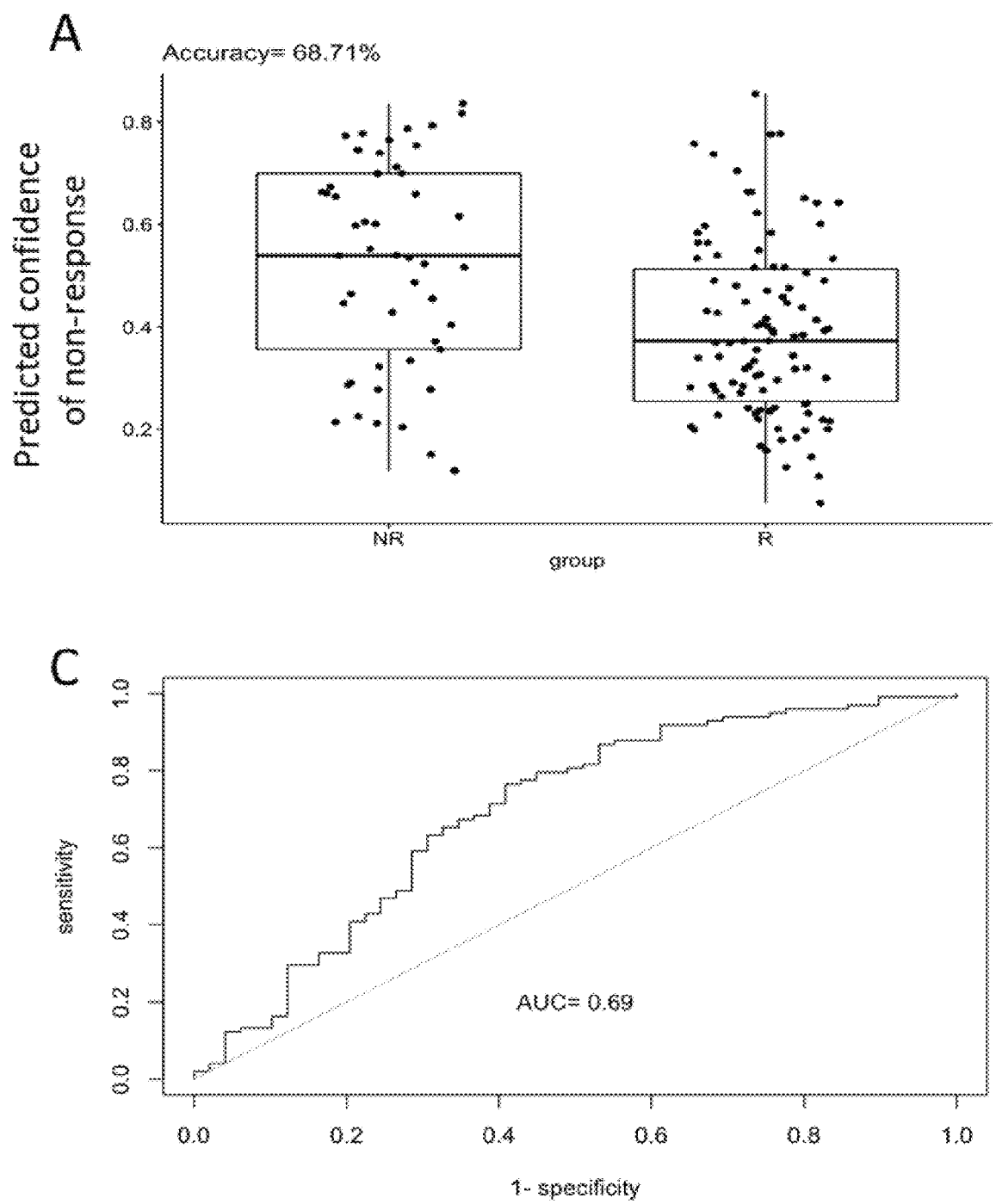
FIG. 6. A) All 147 patients from the four melanoma studies were divided into responders and non-responders according to clinical outcome. The probability of not responding to immunotherapy was predicted from the baseline faecal sample based on machine learning predictions that used the abundance of the 9 bacteria in consortium 5. A cut off of 0.5 was used to determine the accuracy of the prediction. Accuracy was 68.71%. B) As A except each study is considered separately. frankel accuracy 71.79%; gajewski accuracy 58.97%; melresist accuracy 70.45%; wargo accuracy 76%. C) Receiver Operating Characteristic (ROC) curve of the combined melanoma dataset showing False Positive Rate as a function of True Positive Rate based on machine learning predictions based on consortium 3. AUC=0.69. D) As C but each study is considered separately. Random forest out-of-bag error was used to prevent overoptimistic performance and improve generalizability. AUC frankel 0.75; AUC gajewski 0.596; AUC melresist 0.766; AUC wargo 0.675.
Figure 6:
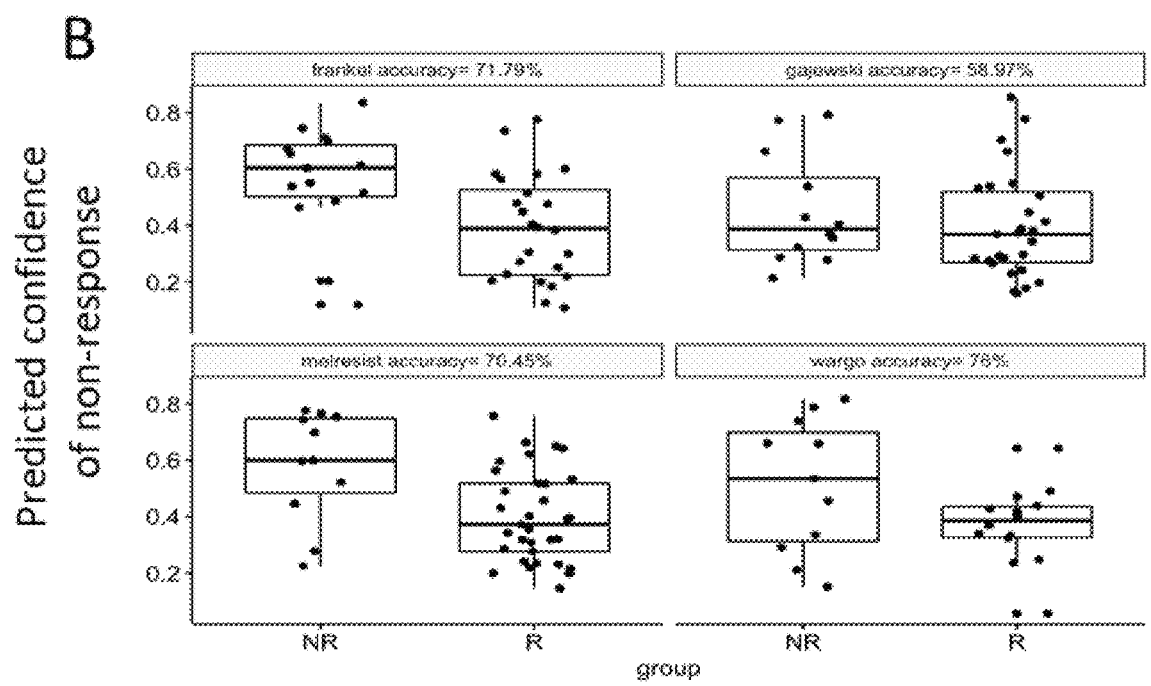
Figure 6:
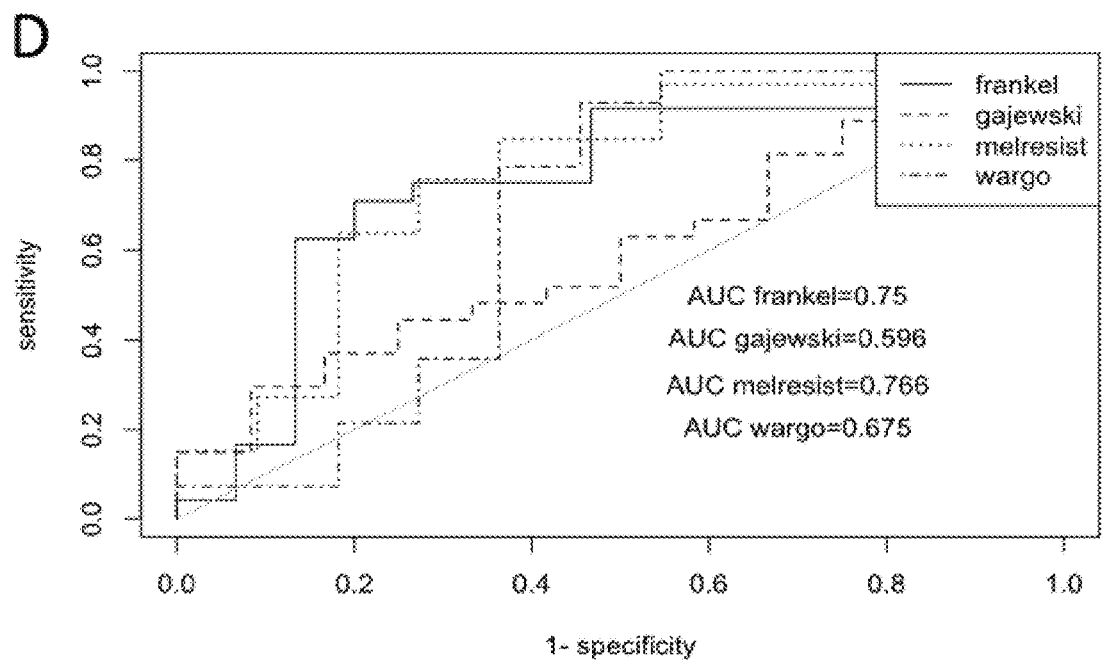
Figure 7:
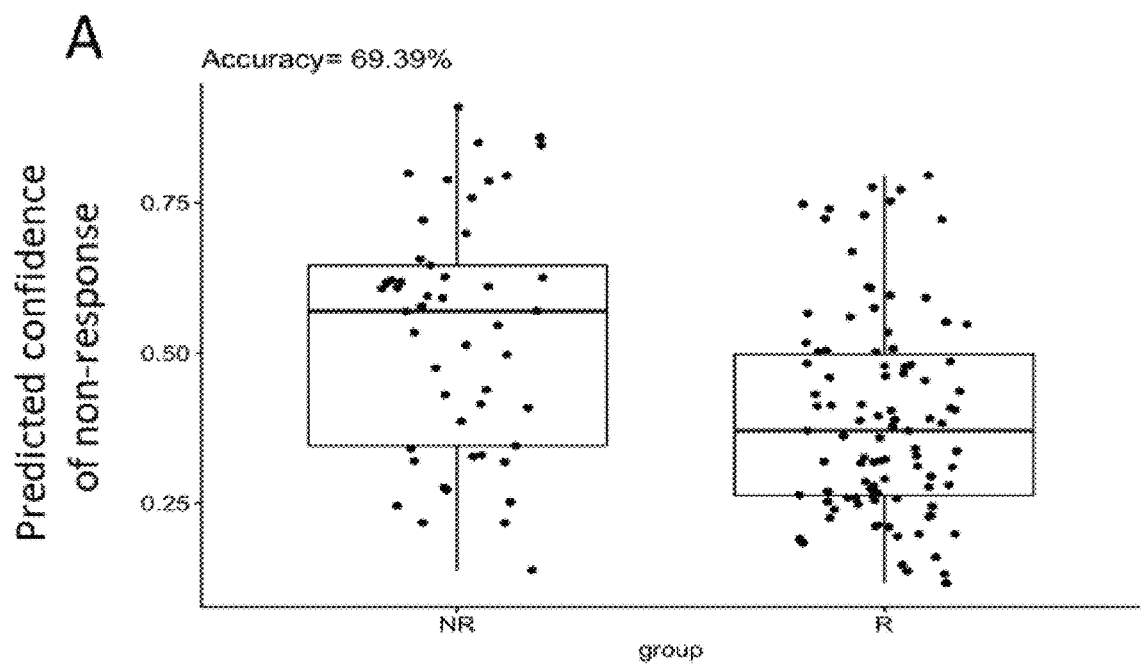
FIG. 7. A) All 147 patients from the four melanoma studies were divided into responders and non-responders according to clinical outcome. The probability of not responding to immunotherapy was predicted from the baseline faecal sample based on machine learning predictions that used the abundance of the 9 bacteria in consortium 6. A cut off of 0.5 was used to determine the accuracy of the prediction. Accuracy was 69.39%. B) As A except each study is considered separately. frankel accuracy 69.23%; gajewski accuracy 58.97%; melresist accuracy 77.27%; wargo accuracy 72%. C) Receiver Operating Characteristic (ROC) curve of the combined melanoma dataset showing False Positive Rate as a function of True Positive Rate based on machine learning predictions based on consortium 3. AUC=0.71. D) As C but each study is considered separately. Random forest out-of-bag error was used to prevent overoptimistic performance and improve generalizability. AUC frankel 0.767; AUC gajewski 0.577; AUC melresist 0.81; AUC wargo 0.708.
Figure 7:
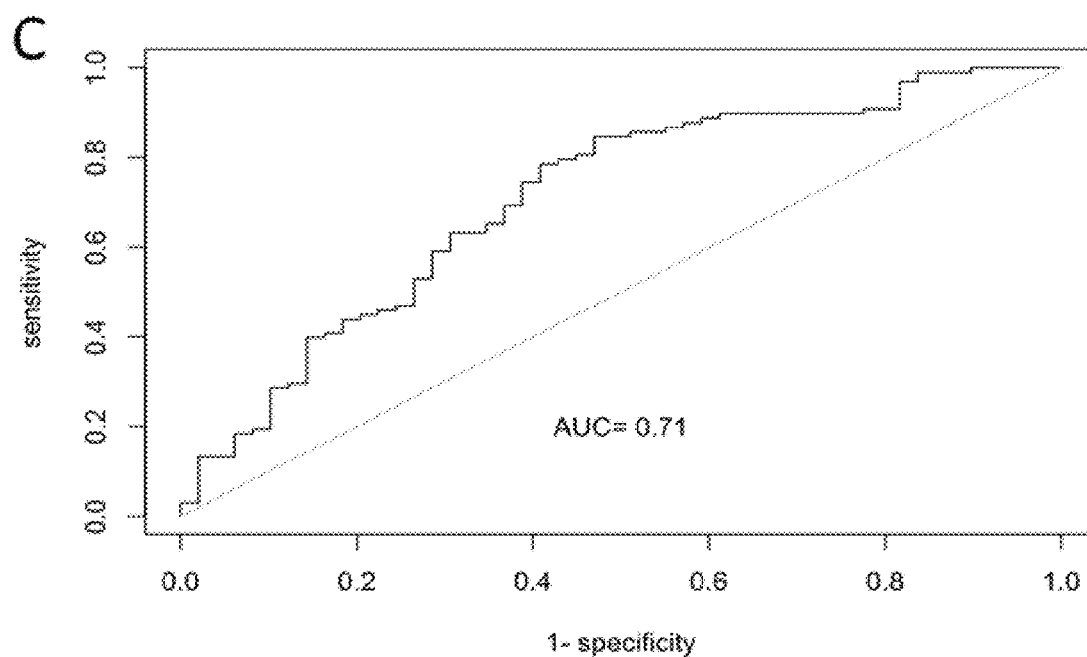
Figure 7:
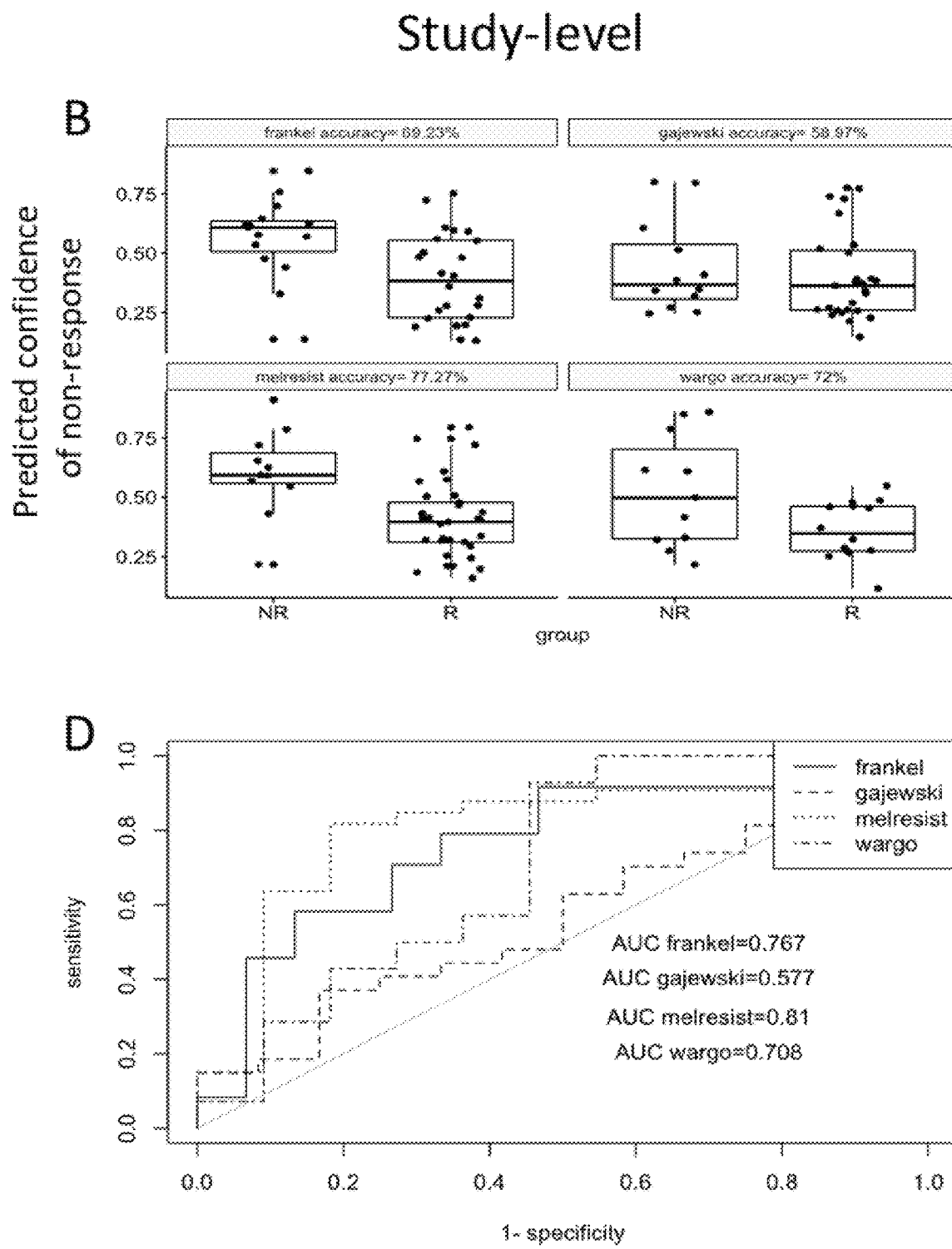

The entire analysis was repeated from the start but excluding patients with stable disease, where possible, to focus on bacteria linked to a better clinical response. This reanalysis overlapped considerably with the first thereby validating it and was used to refine the final list of species. These analyses produced a list of 15 bacterial species, consortium 1, all increased in abundance in melanoma patients that subsequently responded to immune checkpoint inhibitor therapy across multiple studies (see Table 1 and 3). The robustness of this reduced signature was demonstrated by repeating the test as a biomarker in the combined dataset, and it predicted whether a patient would respond to therapy with an accuracy of 77% (FIG. 2A). The Receiver Operating Characteristic (ROC) curve of this analysis gave an area under the curve (AUC) of 0.8 (FIG. 2C) thereby confirming how highly predictive this signature is. Importantly, the signature was 67-84% accurate when tested against the studies individually (FIG. 2B), and the ROC gave AUCs from 0.73 to 0.88 (FIG. 2D). Six additional consortia 2, 3, 4, 5, 6 and 10 composed of 9 or 12 species (Table 3) from the 15 were also tested as biomarkers, and had good predictivity of response both in the combined dataset and the individual studies (FIGS. 3-7 and 17).

Thus, the results show that the bacteria identified can be used as predictive biomarker for response to anti-PD1 therapy in melanoma patients and also as a bacterial co-therapy to increase the proportion of melanoma patients responding to checkpoint inhibitors.

Figure 8:
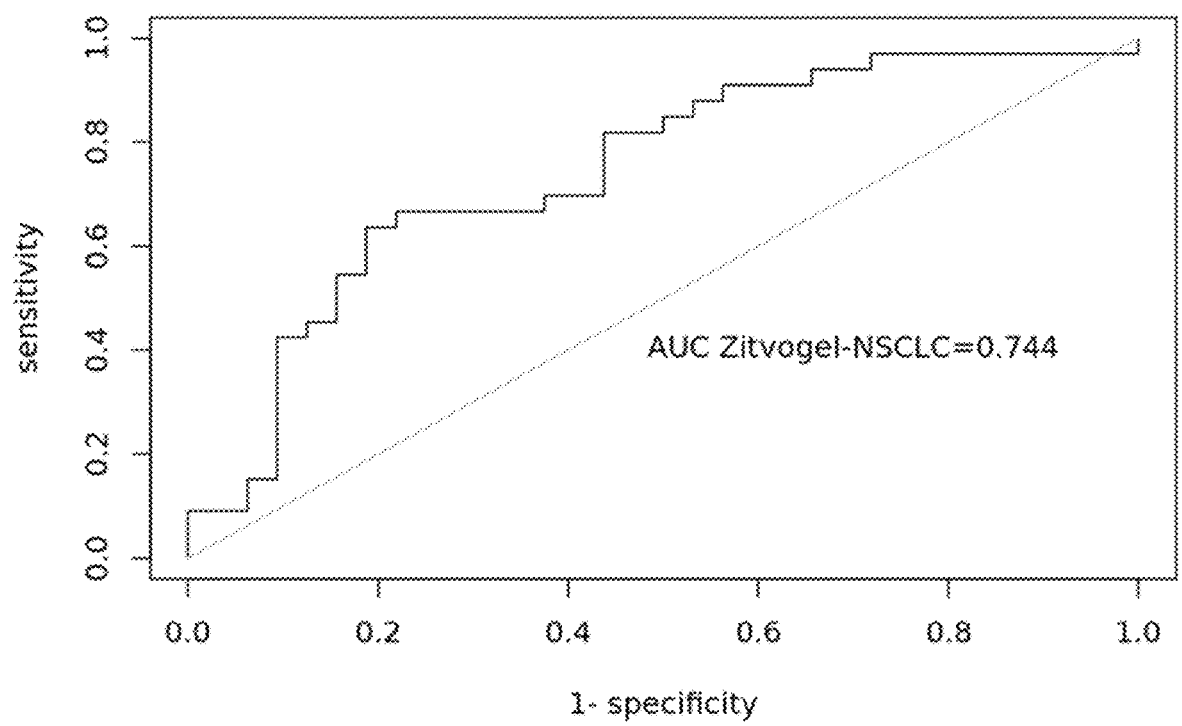
FIG. 8. Receiver Operating Characteristic (ROC) curve of a NSCLC cohort showing False Positive Rate as a function of True Positive Rate based on machine learning predictions based on consortium 1. NSCLC dataset is metagenomic sequence from Routy and Zitvogel et al (2018 Science 359:91-97) classified using the Microbiotica high-precision platform. Random forest out-of-bag error was used to prevent overoptimistic performance and improve generalizability. AUC=0.744.

To understand if the bacteria could have utility in other cancer indications where checkpoint inhibitors are used, the inventors analysed the predictive value of the full signature in a Non-Small Cell Lung Cancer (NSCLC) patient cohort (Routy et al 2018 Science 359:91-97). The study sampled patients stool prior to anti-PD1 based therapy, and subjected it to shotgun metagenomic sequencing. This was reanalysed using the Microbiotica high-precision platform. The fifteen species in consortium 1 were predictive of whether NSCLC patients would respond to anti-PD1 therapy (ROC AUC=0.722; FIG. 8). Therefore, the bacteria described herein and discovered in melanoma patients are also linked to response in NSCLC. This shows that the bacteria described herein can be used as predictive biomarkers in another cancer indication. Moreover, this also suggests that the bacteria described herein can be used as a bacterial co-therapy in other cancer indications.

1.3 Selection of Bacterial Isolates

The reference-based metagenomic analysis using genomes from cultured isolates enables the identified bacteria to be linked back to isolates of the specific strains and/or closely related strains in the associated culture collection. All available strains representing the species in table 1 underwent in silico characterisation to select for strains with a desirable developability and safety profile. The primary selection criteria consisted of anti-microbial resistance, bacteriophage production, and sporulation. Strains with a good profile were selected for further testing. These were expanded, cell banks generated, and growth characterised to enable testing in in vitro assays and in vivo models. In addition, each strain has undergone full developability and safety testing by laboratory testing and in silico analysis. For each genome assembly, 16S rDNA regions were identified in two ways. Firstly, using barmap (https://github.com/tseemann/barmap), and secondly by extracting, in silico, sequences of the desired length (between 1200 and 1800 bp) by searching for DNA matches to the 7F (5'-AGAGTTTGATYMTGGCTCAG-3') (SEQ ID NO. 30) 1510R (5'-ACGGYTACCTTGTTACGACTT-3') (SEQ ID NO. 31) universal 16S primers. Where multiple overlapping 16S sequences were extracted from an assembly, the longest was retained.

1.4 Host Interaction

The lead bacteria have been selected based on a strong association with clinical response across multiple studies, and, therefore, are considered suitable candidates for inclusion in a Live Bacterial Therapeutic. To understand the mechanism of action, the bacteria have been profiled individually, as a complete consortium and as sub-consortia in several in vitro assays with human cells. Cytotoxic T Lymphocytes (CTLs) are a significant effector cell in anti-tumour immune responses by directly lysing tumour cells via granzyme B and perforin release and production of cytokines such as IFNγ. CTLs can express co-stimulatory and co-inhibitory receptors. Immune checkpoint inhibitor therapies block the suppression of CTL activity by blocking the interaction between co-inhibitory receptor (eg PD-1) and their ligands (eg PD-L1). The later can be expressed by tumour cells as a mechanism to escape immune-mediated depletion, which is reversed by checkpoint inhibitor therapy. CTLs are activated and educated by dendritic cells, which are a sentinel innate immune cells that have many receptors to sense and respond to bacteria. Therefore, the bacteria identified (individually or as consortia) were tested for an ability to stimulate dendritic cells (DCs), and then if these DCs activate CTLs.

Figure 9:
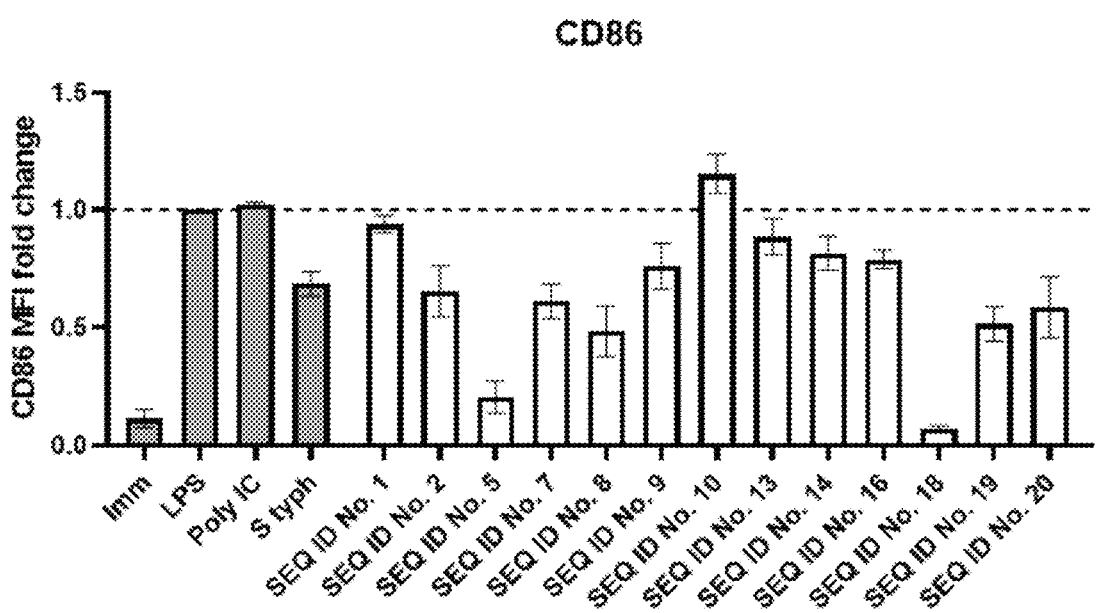
FIG. 9. Isolated bacteria induce dendritic cell maturation and cytokine production. The ability of the isolated bacteria to activate dendrdtic cells (DCs) was determined by co-culturing with human monocyte-derived Dendritic cells in anaerobic conditions at multiplicity of infection (MOI) of approximately 10:1. Subsequent maturation of the dendritic cells was determined by expression levels of the maturation markers CD86 (A) and CD83 (B) as determined by flow cytometry. Data is displayed as fold change of mean fluorescence intensity (MFI), compared to the LPS control to normalise across different donors and experiments. The DC expression of CD86 (C) and CD83 (D) following treatment with consortium 5 (MOI of approximately 10:1) was similarly determined by flow cytometry. The MFIs of those markers following stimulation with consortium 5 are displayed in white bars. The DC expression of CD86 (E) and CD83 (F) following treatment with consortia 6, 7, 8 and 9 was determined by flow cytometry. The MFIs of those markers are displayed in white bars. (G) IL-12 and IL-10 production by DCs following treatment with isolated bacteria alone (MOI of approximately 10:1) or as consortia 5 and 6 (MOI of approximately 10:1) were determined by ELISA. MOI 10 N=5 (5 donors in 5 independent experiments). Data are displayed as ratio of IL-12 to IL-10. LPS (10 ng/ml), Poly I:C (20 µg/ml) and *Salmonella typhimurium* (MOI of approximately 10:1) are strong inducers of DC activation and used as positive controls for all assays (grey bars). Unstimulated or immature (Imm) DCs are shown for comparison (grey bars). Results are the mean±SEM of 5 (A and B), 2 (C, D, E and F) and 3 (G) independent experiments.
Figure 9:
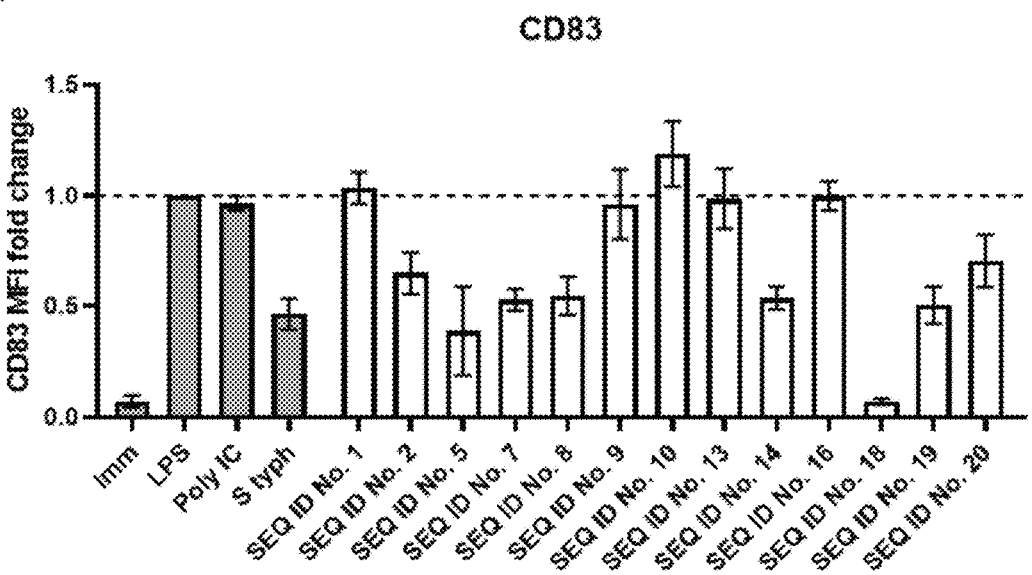
Figure 9:
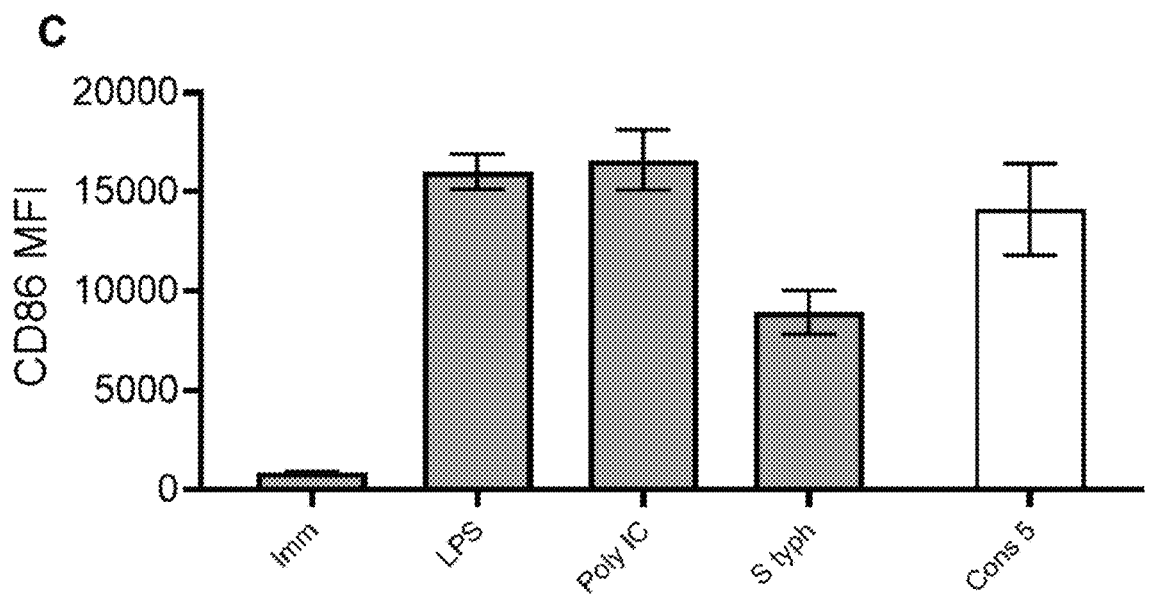
Figure 9:
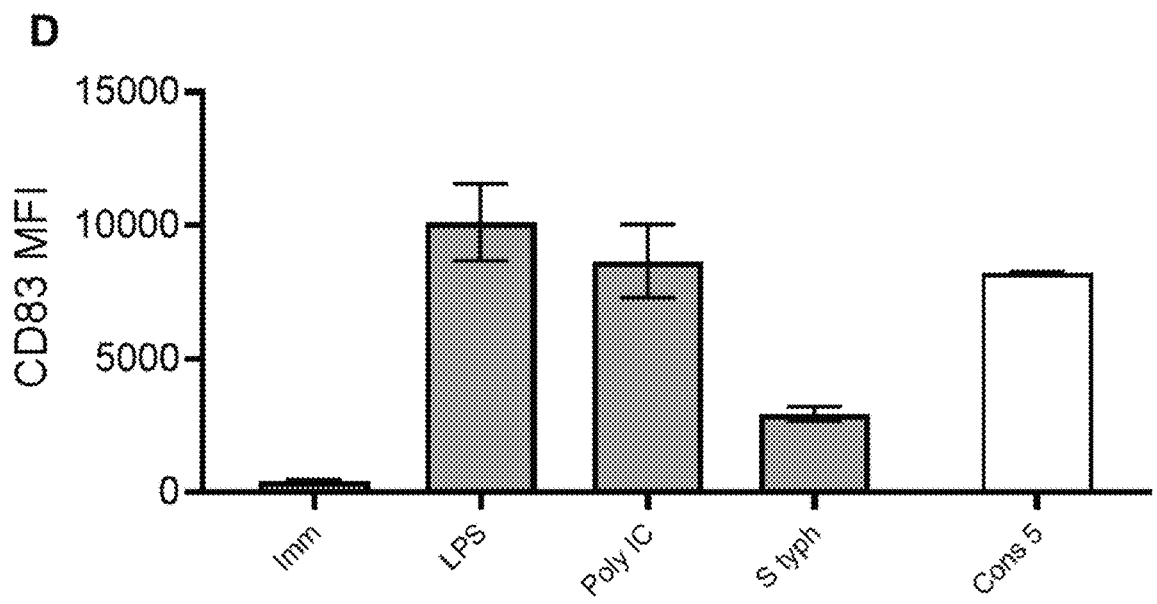
Figure 9:
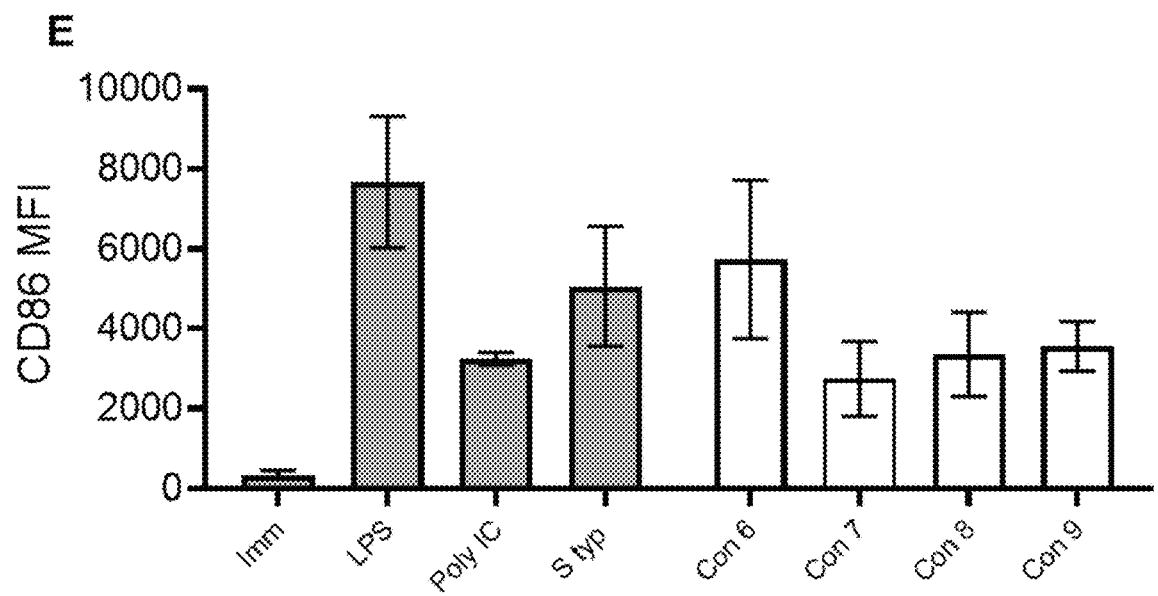
Figure 9:
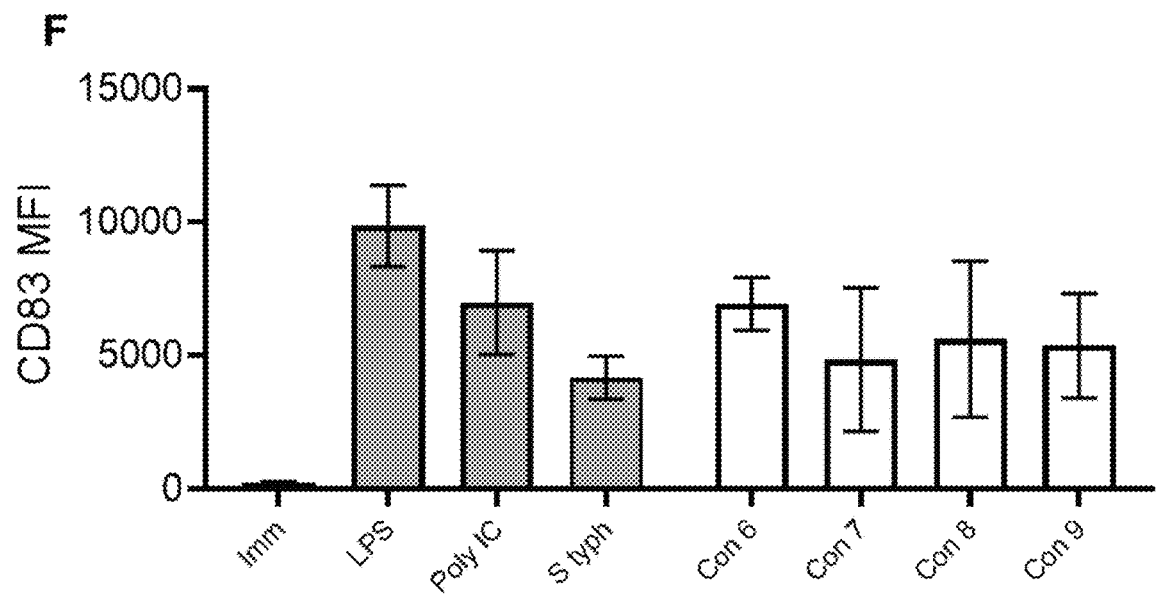
Figure 9:
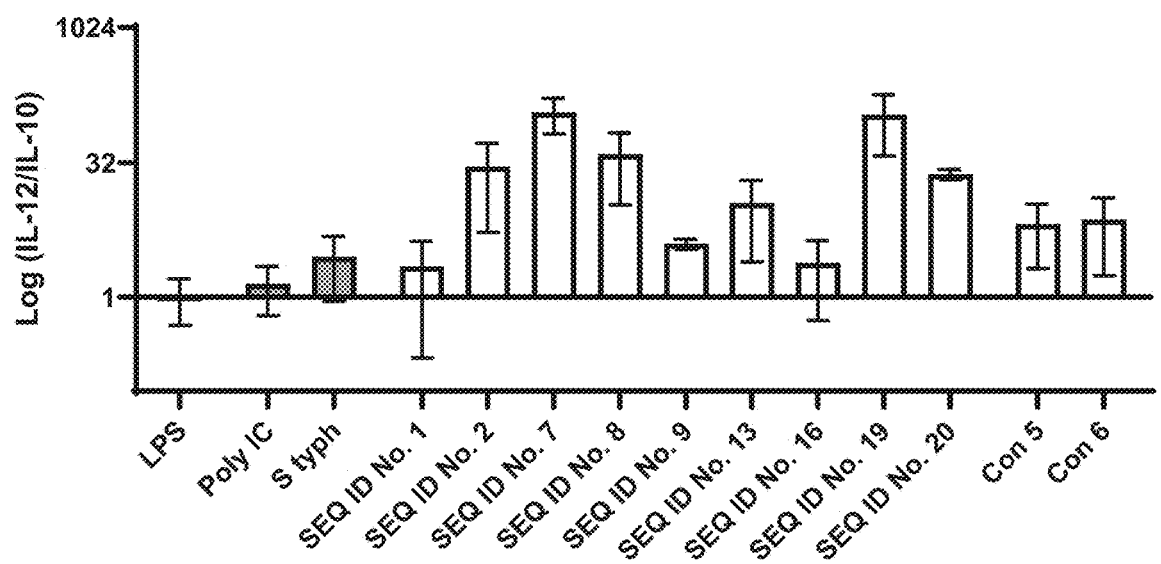

Bacterial strains representing thirteen of the fifteen species were identified and grown in bacterial media. These were washed and added in co-cultured with human monocyte-derived DCs in anaerobic conditions. Antibiotics were then added and the DCs cultured in an aerobic environment. The activation of DCs was measured by upregulation of the maturation markers CD86 (a co-stimulatory ligand) and CD83. Eleven of the thirteen species robustly induced expression of both markers with *Gordonibacter urolithinfaciens* and *Alistipes indictincus* being poor activators of DC maturation (FIGS. 9A and 9B). Indeed, many induced a similar level of CD86 and CD83 express as the positive controls, lipopolysaccharide (LPS), Poly I:C and *Salmonella typhimurium*, all of which are known to be very potent activators of DCs. Two consortia of nine species (Consortia 5 and 6), as well as sub-consortia of consortium 6 containing six, three and two species all also triggered DC maturation as measured by CD86 and CD83 upregulation (FIG. 9B-9E). The bacteria also triggered cytokine release from the DCs. IL-12 is a very important cytokine for the priming of a CTL response, and IL-10 is associated with suppression of T cell response. Therefore, the ratio of IL-12 to IL-10 was used to measure whether the DCs could be a strong inducer of a positive CTL response. The nine of the ten species tested and Consortia 5 and 6 triggered higher levels of IL-12 than IL-10 even when compared to strong inflammatory stimuli like LPS and Poly I:C (FIG. 9G). The data from *Gordonibacter urolithinfaciens* is not shown because the levels of cytokines released was too low to make a ratio meaningful. These data indicate that the bacteria identified as being associated with response to immune checkpoint inhibitor therapy are by enlarge potent activators of DC maturation, and release cytokines that could direct an enhanced T cell response.

Figure 10:
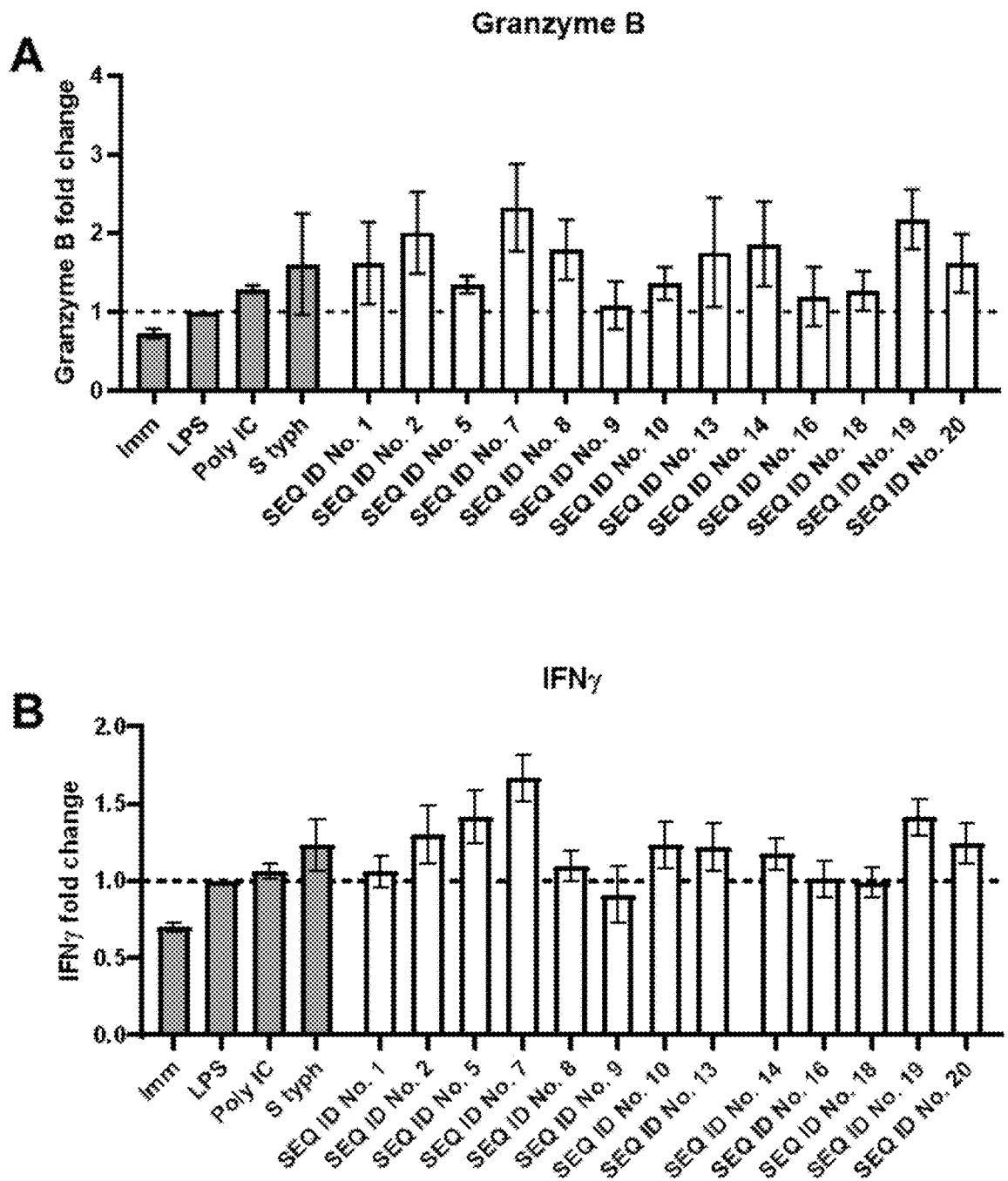
FIG. 10. Dendritic cells treated with isolated bacteria activate Cytotoxic CD8+ T Lymphocytes (CTLs). Following co-culture with isolated bacteria or control stimuli as in FIG. 9, human monocyte-derived DCs were washed and co-cultured with purified allogenic CD8+ T cells for 6 days. CTL activation was determined by analysing the expression of Granzyme B (A). IFN-γ (B) and Perforin (C) using intracellular staining and flow cytometry. Data is displayed as fold change of the percentage of positive cells, compared to the LPS control to normalise across different donors and experiments. LPS (10 ng/ml), Poly I:C (20 µg/ml) and *Salmonella typhimurium* (MOI of approximately 10:1) are strong inducers of DC activation and used as positive controls for all assays (grey bars). Unstimulated or immature (Imm) DCs are shown for comparison (grey bars). Results are the mean±SEM of 7 donors in 4 independent experiments.
Figure 10:
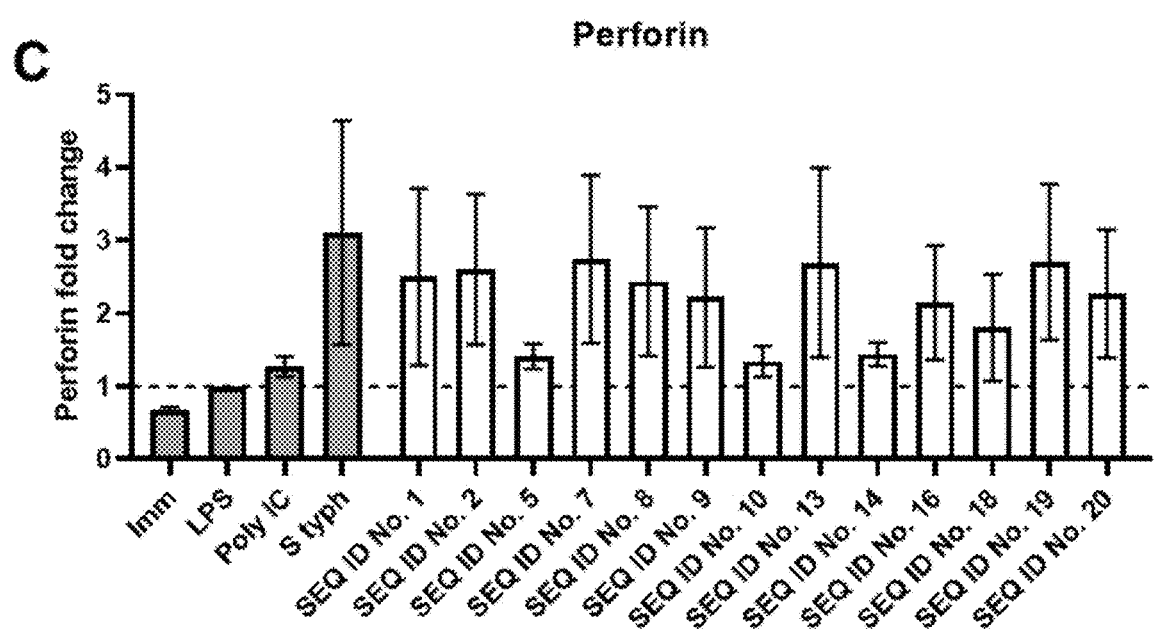
Figure 11:
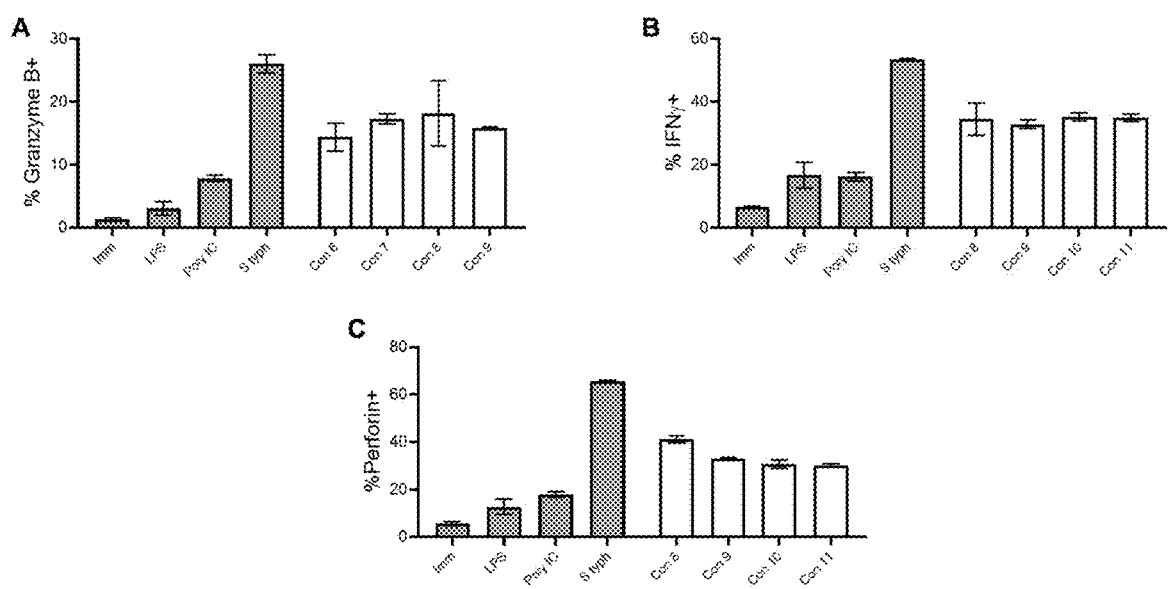
FIG. 11. Dendritic cells treated with consortia 6, 7, 8 and 9 activate Cytotoxic CD8+ T Lymphocytes (CTLs). Following co-culture with consortia 6, 7, 8 and 9 or control stimuli as in FIG. 9, human monocyte-derived DCs were washed and co-cultured with purified allogenic CD8+ T cells for 6 days. CTL activation was determined by analysing the expression of Granzyme B (A), IFN-γ (B) and Perforin (C) using intracellular staining and flow cytometry. Data is displayed as the percentage of positive cells. LPS (10 ng/ml), Poly I:C (20 µg/ml) and *Salmonella typhimurium* (MOI of approximately 10:1) are strong inducers of DC activation and used as positive controls for all assays (grey bars). Unstimulated or immature (Imm) DCs are shown for comparison (grey bars). Results are the mean±SEM of a duplicate of a single representative experiment.
Figure 12:
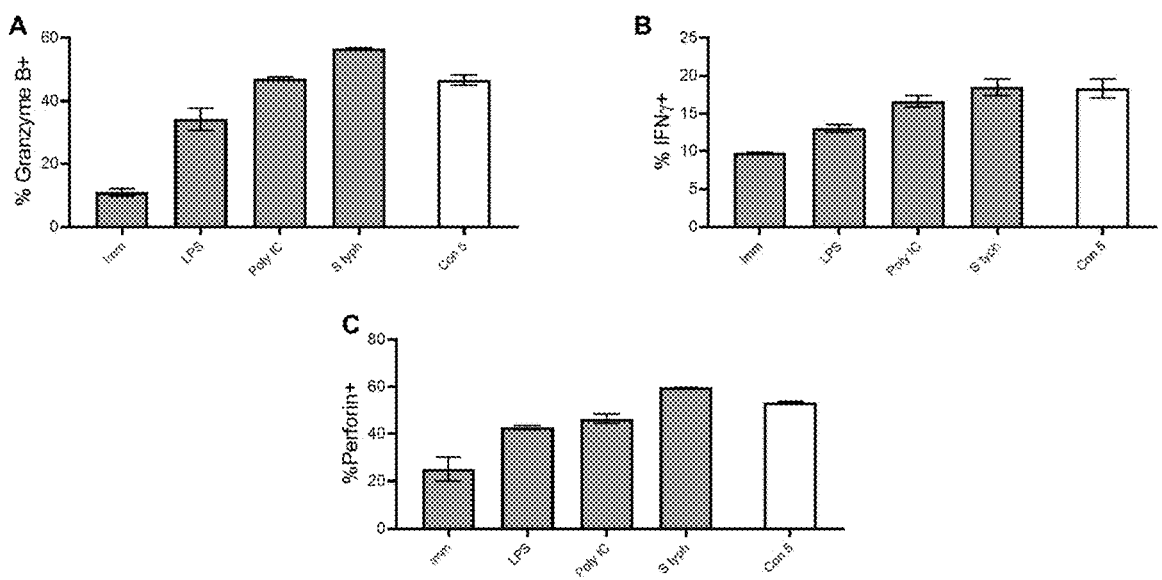
FIG. 12. Dendritic cells treated with consortium 5 activate Cytotoxic CD8+ T Lymphocytes (CTLs). Following co-culture with consortium 5 or control stimuli as in FIG. 11, human monocyte-derived DCs were washed and co-cultured with purified allogenic CD8+ T cells for 6 days. CTL activation was determined by analysing the expression of Granzyme B (A), IFN-γ (B) and Perforin (C) using intracellular staining and flow cytometry. Data is displayed as the percentage of positive cells. LPS (10 ng/ml), Poly I:C (20 µg/ml) and *Salmonella typhimurium* (MOI of approximately 10:1) are strong inducers of DC activation and used as positive controls for all assays (grey bars). Unstimulated or immature (Imm) DCs are shown for comparison (grey bars). Results are the mean±SEM of a duplicate of a single representative experiment.

To understand how effective these DCs were at stimulating CTLs, the mature DCs were co-cultured with allogenic CD8 expressing T cells (CTLs) for 6 days. CTLs activation was quantified by upregulation of Granzyme B, perforin and IFNγ. Thirteen of the bacterial species were tested, and all were shown to induce DCs that can potentially activate CTLs (FIG. 10). The level of activation was comparable to or better than the strong inflammatory stimuli LPS, Poly I:C and *Salmonella typhimurium*. Interesting, even *Gordonibacter urolithinfaciens* and *Alistipes indictincus* were shown to lead to robust CTLs activation despite being poor stimulators of CD86 and CD83 expression by DCs. The consortia tested (5, 6, 7, 8 and 9) also all induced strong CTL activation (FIGS. 11 and 12). These data demonstrate that the bacteria identified as being associated with response to immune checkpoint inhibitor therapy are potent activators of a CTL response via stimulation of DCs. This is true of the individual species and of consortia of two to nine species. This induction of CTL activation could be a key mechanism by which the raised abundance of these bacteria leads to enhanced anti-tumour immunity in the presence of anti-PD1. It could also indicate that a therapeutic composition comprising these bacteria could enhance a vaccine response and/or anti-viral immunity.

Figure 13:
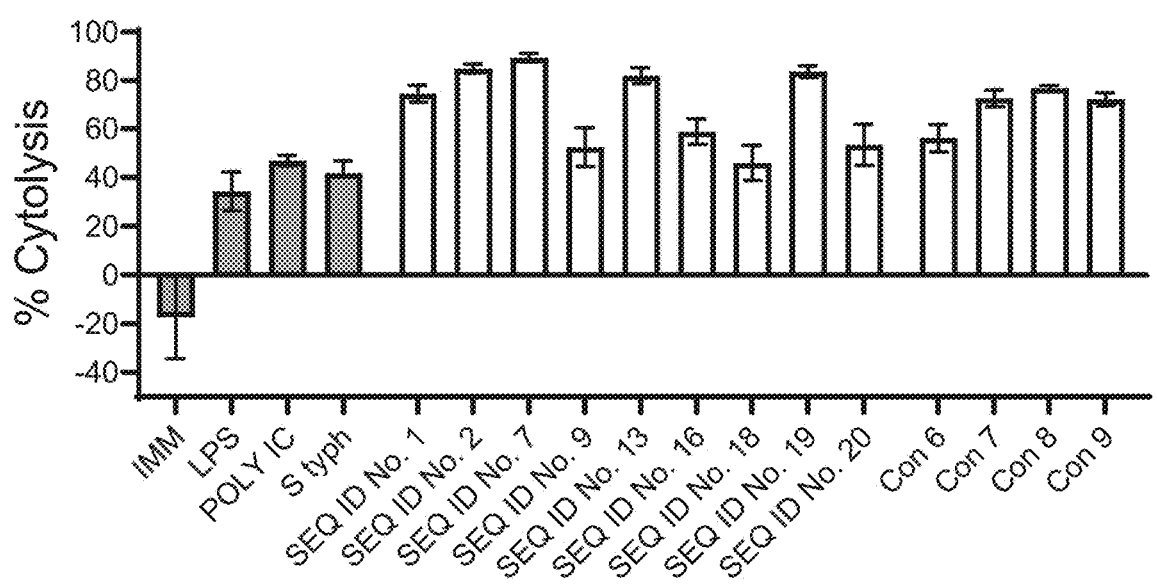
FIG. 13. Isolated bacteria and consortia 6, 7, 8 and 9 endow the induced CTLs with tumor killing capacity. CD8+ T cells primed by bacteria/consortia-treated DCs (as in FIGS. 10 and 11) were assessed for their capacity to kill SKOV-3 cells. Cytolysis is determined by measuring the decreasing electric impedance of the SKOV-3 cells. Data is displayed as the percentage of cytolysis of SKOV-3 cells, 72 hours following co-culture with CD8+ T cells. LPS (10 ng/ml), Poly I:C (20 µg/ml) and *Salmonella typhimurium* (MOI of approximately 10:1) are strong inducers of DC activation and used as positive controls for all assays (grey bars). Unstimulated or immature (Imm) DCs are shown for comparison (grey bars). Results are the mean±SEM of 3 independent experiments.
Figure 14:
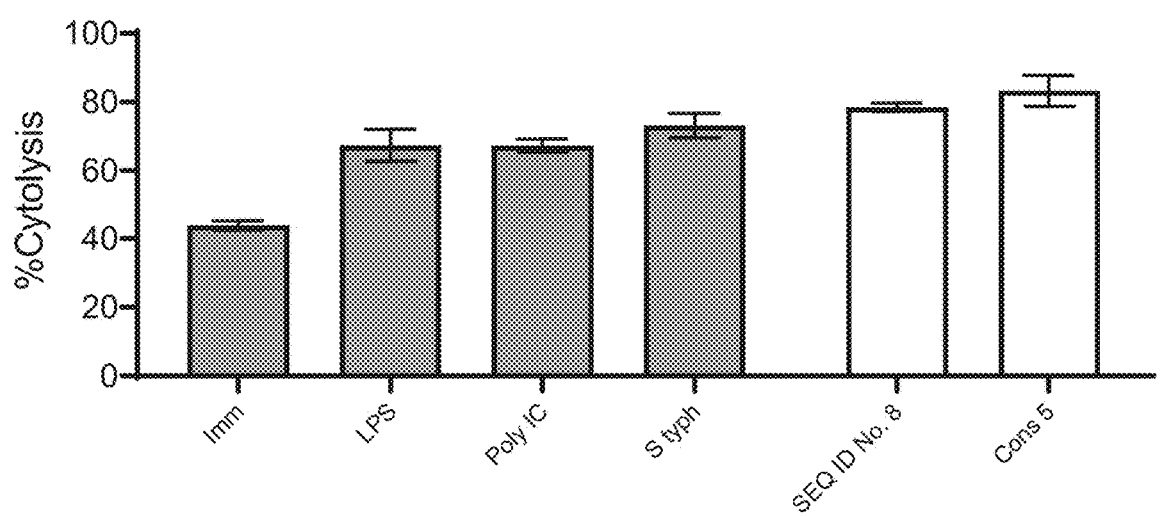
FIG. 14. Consortium 5 and *Blautia* sp. endow the induced CTLs with tumor killing capacity. CD8+ T cells primed by consortium 5- or *Blautia* sp.-treated DCs (as in FIG. 12) were assessed for their capacity to kill SKOV-3 cells. Cytolysis is determined by measuring the decreasing electric impedance of the SKOV-3 cells. Data is displayed as the percentage of cytolysis of SKOV-3 cells, 72 hours following co-culture with CD8+ T cells. LPS (10 ng/ml), Poly I:C (20 µg/ml) and *Salmonella typhimurium* (MOI of approximately 10:1) are strong inducers of DC activation and used as positive controls for all assays (grey bars). Unstimulated or immature (Imm) DCs are shown for comparison (grey bars). Results are the mean±SEM of a duplicate of a single representative experiment.

The bacteria lead to potent CTL activation, so their ability to kill tumour cells was tested next. In this assay, the CTLs activated by bacteria-stimulated DCs were co-cultured with the tumour cell line SKOV-3 cells. All ten of the species tested led to potent cytolysis of the tumour cells by CTLs as measured by a decrease in electric impedance. The level of tumour cell killing compared favourably to the other known strong innate stimuli. The consortia tested (5, 6, 7, 8 and 9) also led to high levels of tumour cell killing (FIGS. 13 and 14). These data demonstrate that the bacteria identified as being associated with response to immune checkpoint inhibitor therapy are potent activators of an immune-mediated tumour cell killing. This is true of the individual species tested and of consortia of two to nine species.

In total, the above data show that the bacterial species identified as being associated anti-PD-1 response are able to stimulate DCs to trigger CTLs activation and tumour cell killing. This mechanism is likely to explain, at least in part, why these bacteria are associated with response to anti-PD-1 based therapy in melanoma. This mechanism is associated with immune checkpoint inhibitor efficacy in multiple tumours indicating that the bacteria described herein can be used as a bacterial co-therapy in other cancer indications. Indeed, the bacteria described herein are likely to be an effective co-therapy with any immunotherapy that enhances CTL response for example adoptive T cell transfer therapy and CAR-T cell therapy. Interestingly, two of the strains tested (*Gordonibacter urolithinfaciens* and *Alistipes indictincus*) did not induce classical markers of DC activation (CD86 and CD83), but the DCs still induced CTL activation.

Figure 15:
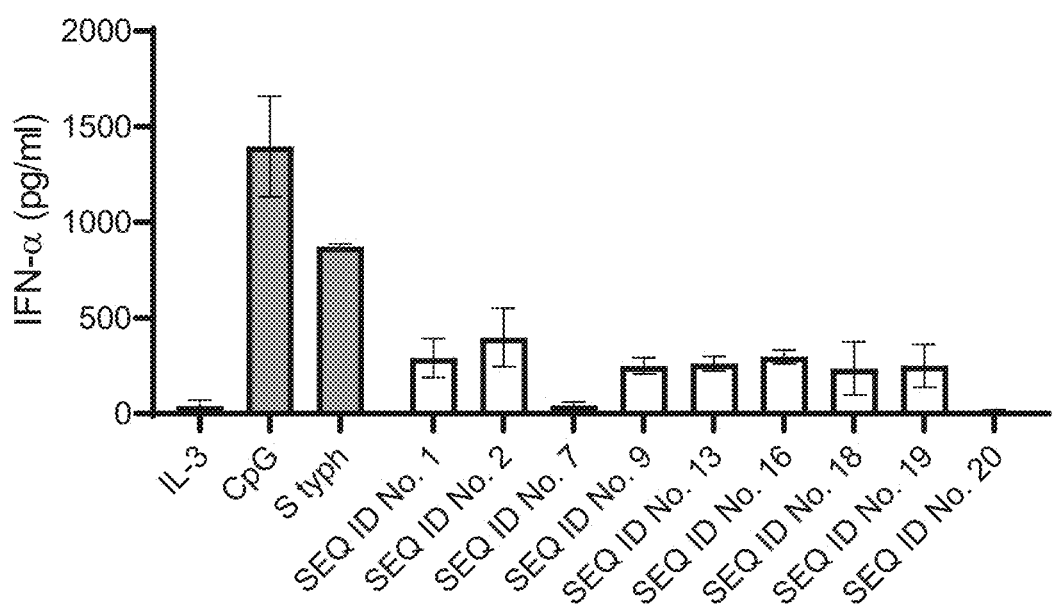
FIG. 15. Isolated bacteria possess a variable capacity to induce IFN-α production by plasmacytoid dendritic cells. IFN-α production by plasmacytoid dendritic cells (pDCs) was determined by ELISA following an overnight incubation with heat-killed bacteria (moimoi of approximately 10:1). 10 ng/ml IL-3 and 10 µg/ml CpG (grey bars) were taken along as a negative and positive controls, respectively. Results are the mean±SEM of 3 donors in 2 independent experiments.

The type 1 Interferons (IFNs), IFNα and IFNβ, are potent inducers of CTL immunity and can have direct anti-tumour effects. Plasmacytoid dendritic cells are capable of producing very high levels of IFNα and IFNβ. To test if the isolated bacteria associated with anti-PD-1 response induced IFNα release, plasmacytoid dendritic cells were stimulated with strains representing nine of the species. Plasmacytoid dendritic cells did not tolerate anaerobic conditions, so heat-killed bacteria were used in an aerobic environment. Seven of the nine strain induced IFNα release from plasmacytoid DCs (FIG. 15). This could be another potential mechanism by which these bacteria enhance anti-tumour immune responses. Interesting a tonic type 1 Interferon signal from the microbiome has been implicated in enhancing anti-viral responses in the lung (Bradley et al 2019 Cell Reports 28:245-256). Therefore, the species identified may also potential drive an anti-viral response and/or anti-viral vaccine efficacy.

Figure 16:
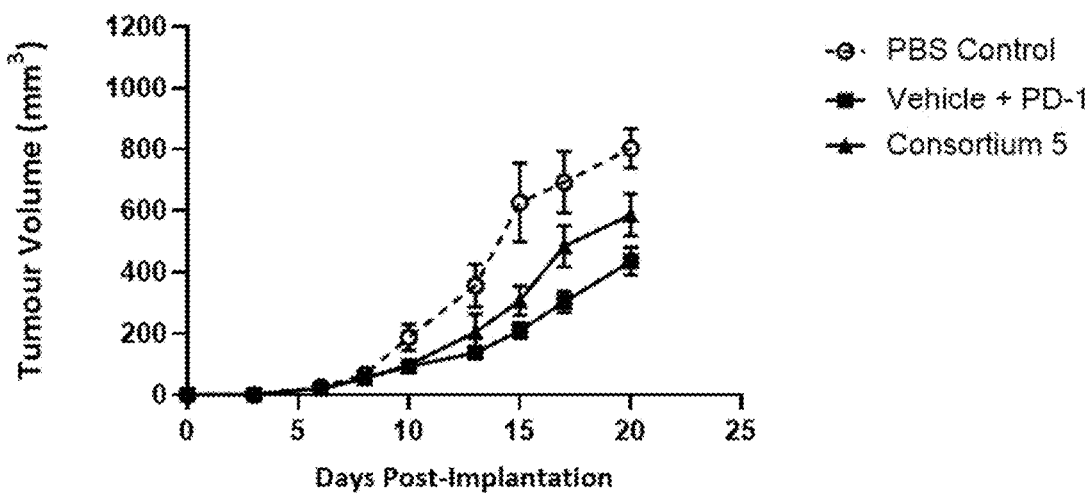
FIG. 16. In vivo efficacy in a murine cancer model Prior to tumour implantation, SPF C57BL/6N female mice were administered antibiotics in drinking water (kanamycin (0.4 mg/ml), colistin (850 U/ml), metronidazole (0.215 mg/m), vancomycin (0.045 mg/ml), gentamycin (0.035 mg/ml)) for 7 days (day −9 to day −2). Subsequently, mice were reconstituted with human donor stool from a melanoma patient (20 mg) by oral gavage on day −1. $5 \times 10^5$ MCA-205 murine fibrosarcoma cells were implanted subcutaneously in the flank on day 0. Consortium 5 (n=8) and consortium 6 (n=8) were administered by oral gavage twice weekly from day −1 for 3 weeks (approximate total of $1 \times 10^9$ CFU/dose) and compared to animals treated with vehicle controls. Anti-PD-1 antibody (RMP1-14) was administered (10 mg/kg intraperitoneal) thrice weekly for 2 weeks from day 6. Plots show tumour growth, as measured by volume, over time in response to vehicle control, anti-PD1 and Consortium 5 (A) or consortium 6 (B). Data are mean±SEM tumour size, and representatives of at least three (A) and two (B) experiments.
Figure 16:
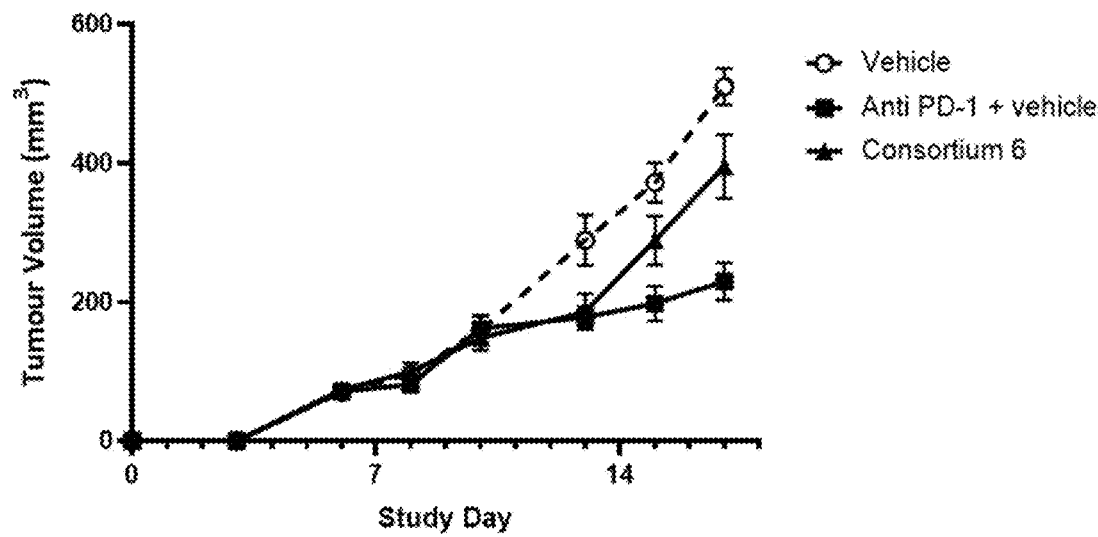
Figure 17:
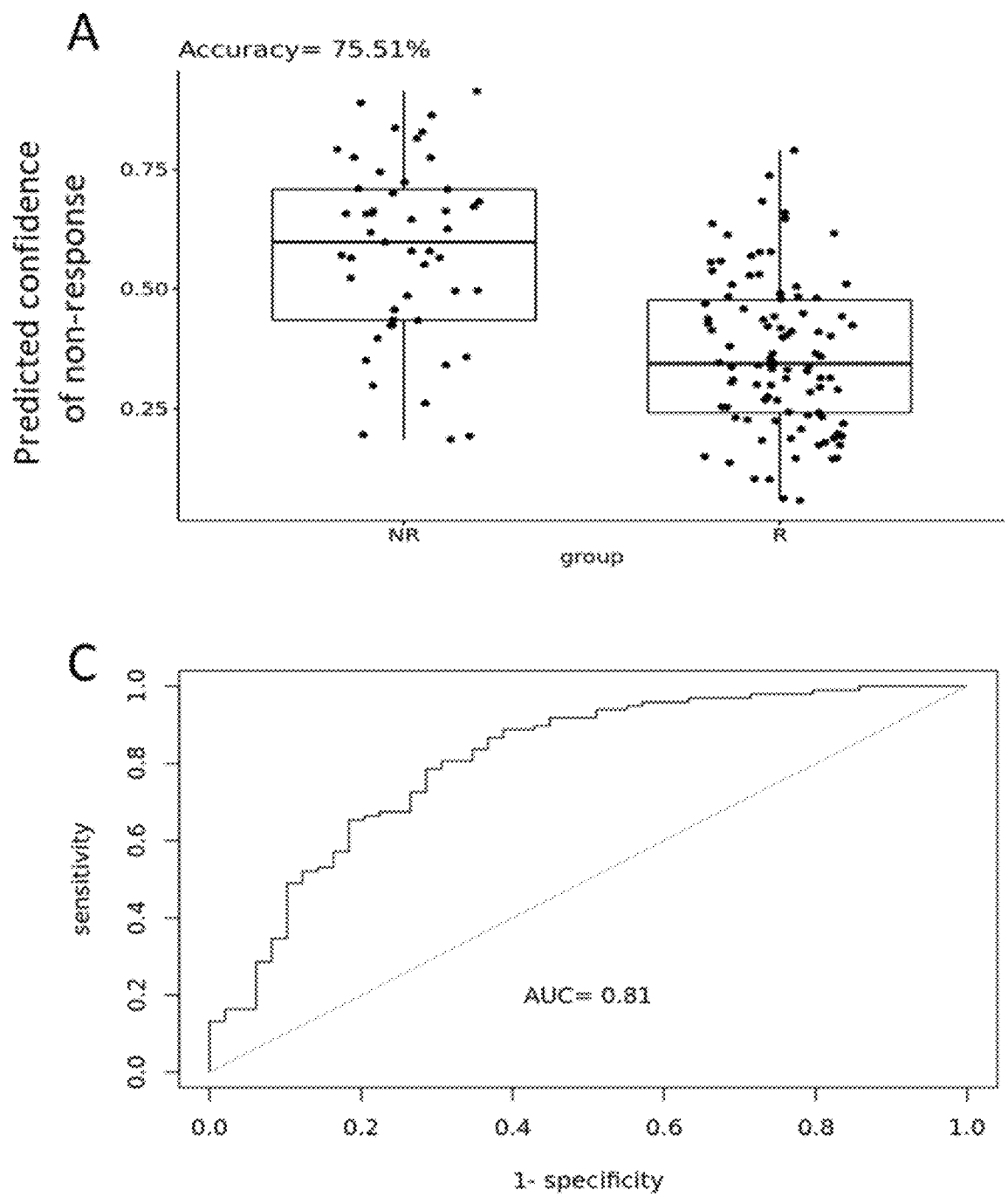
FIG. 17. A) All 147 patients from the four melanoma studies were divided into responders and non-responders according to clinical outcome. The probability of not responding to immunotherapy was predicted from the baseline faecal sample based on machine learning predictions that used the abundance of the 9 bacteria in consortium 10. A cut off of 0.5 was used to determine the accuracy of the prediction. Accuracy was 75.51%. B) As A except each study is considered separately. frankel accuracy 74.38%; gajewski accuracy 71.79%; melresist accuracy 77.27%; wargo accuracy. C) Receiver Operating Characteristic (ROC) curve of the combined melanoma dataset showing False Positive Rate as a function of True Positive Rate based on machine learning predictions based on consortium 3. AUC=0.81. D) As C but each study is considered separately. Random forest out-of-bag error was used to prevent overoptimistic performance and improve generalizability. AUC frankel 0.85; AUC gajewski 0.725; AUC melresist 0.826; AUC wargo 0.805.
Figure 17:
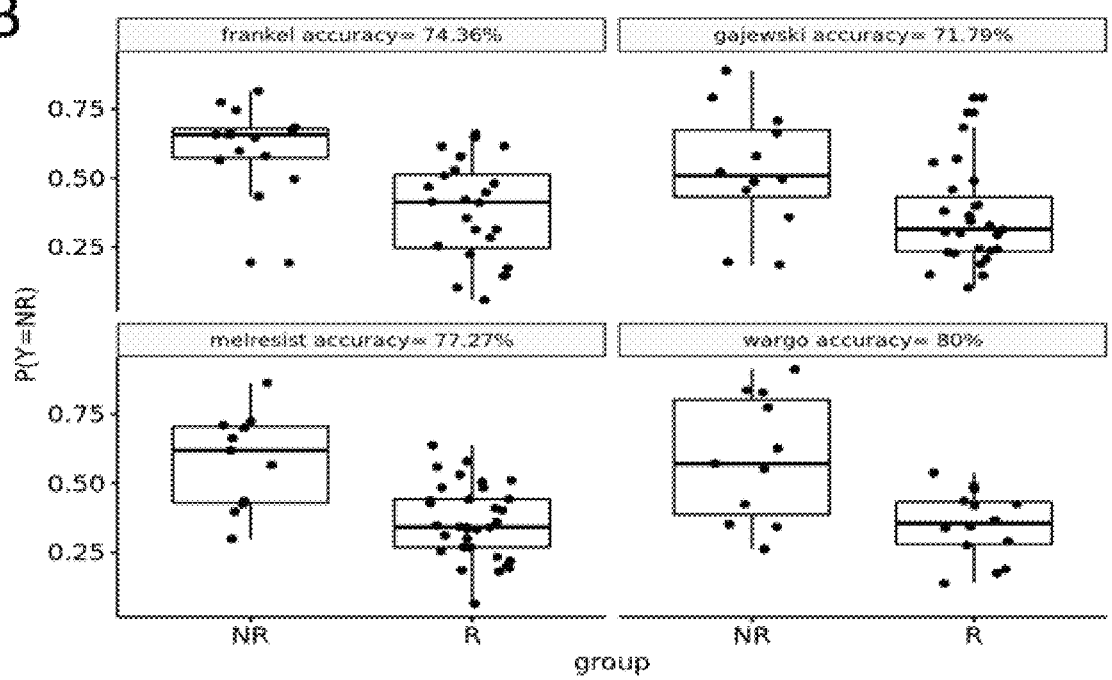
Figure 17:
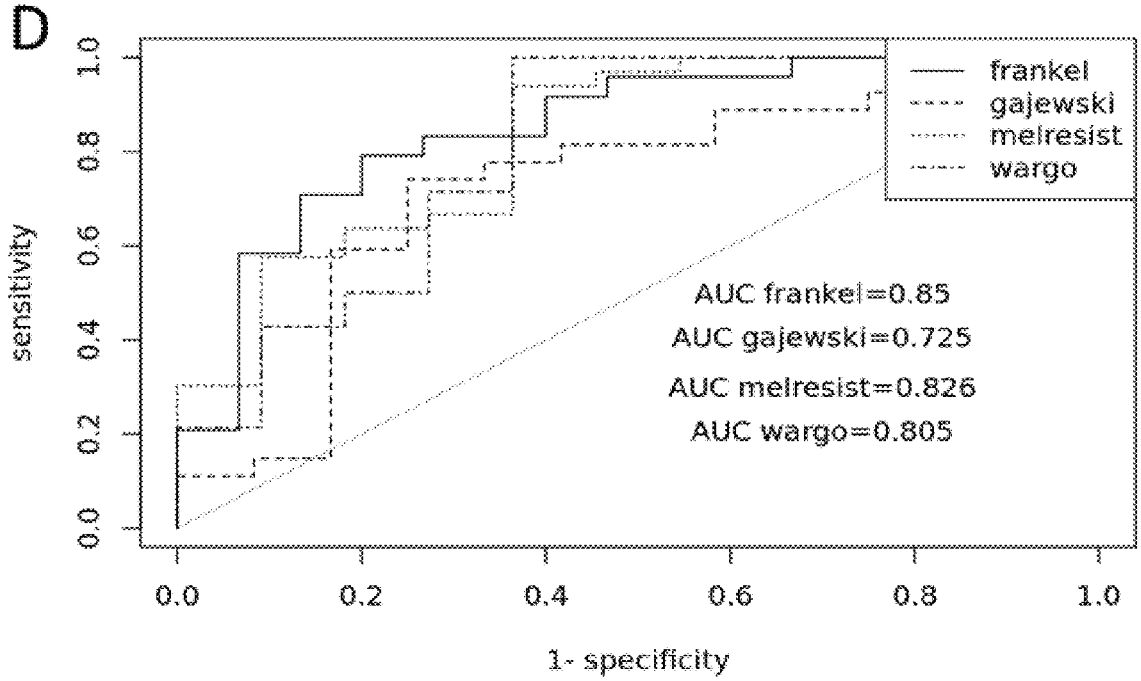

In addition, to the above mechanistic assays two selected consortia were tested for efficacy in a syngeneic model of cancer. SPF mice were treated with antibiotics before engrafting the microbiome of a melanoma patient one day prior to implanting MCA205 tumour cells. Dosing consortium 5 or 6 by oral gavage induce tumour growth inhibition (FIG. 16) although not to the same degree as the positive control (anti-PD1). This shows the anti-tumour potential of these consortia, and validates the selection of these species by association with improved clinical outcome. MCA-205 is a fibrosarcoma cell lines, which further demonstrates that the bacteria described herein have potential in cancer indications beyond melanoma. Together the data presented here shows we have identified bacterial species predictive of response to checkpoint inhibitor therapy in multiple melanoma studies and in NSCLC. These species are able to stimulate DCs leading to the activation of CTLs and tumour cell killing. Two consortia of these species are further validated in an in vivo cancer model.

TABLE 2

| Sequences | |
|---|---|
| SEQ ID | 16S rDNA Sequence |
| SEQ ID No. 1 | AGAGAGTTTGATCCTGGCTCAGGATGAACGCTGGCGGCGTGCCTAACACATGCAAGT CGAACGGAGTTATGCAGAGGAAGTTTTCGGATGGAATCGGCGTAACTTAGTGGCGGA CGGGTGAGTAACGCGTGGGAAACCTGCCCTGTACCGGGGGATAACACTTAGAAATAG GTGCTAATACCGCATAAGCGCACAGCTTCACATGAGGCAGTGTGAAAAACTCCGGTGG TACAGGATGGTCCCGCGTCTGATTAGCCAGTTGGCAGGGTAACGGCCTACCAAAGCG ACGATCAGTAGCCGGCCTGAGAGGGTGAACGGCCACATTGGGACTGAGACACGGCC CAAACTCCTACGGGAGGCAGCAGTGGGGAATATTGCACAATGGGGGAAACCCTGATG CAGCGACGCCGCGTGAGTGAAGAAGTATTTCGGTATGTAAAGCTCTATCAGCAGGGAA GAAAATGACGGTACCTGACTAAGAAGCCCCGGCTAACTACGTGCCAGCAGCCGCGGT AATACGTAGGGGGCAAGCGTTATCCGGATTTACTGGGTGTAAAGGGAGCGTAGACGG CATGACAAGCCAGATGTGAAAACCCAGGGCTCAACCCTGGGACTGCATTTGGAACTG CCAGGCTGGAGTGCAGGAGAGGTAAGCGGAATTCCTAGTGTAGCGGTGAAATGCGTA GATATTAGGAGGAACACCAGTGGCGAAGGCGGCTTACTGGACTGTAACTGACGTTGA GGCTCGAAAGCGTGGGGAGCAAACAGGATTAGATACCCTGGTAGTCCACGCGGTAAA CGATGATTGCTAGGTGTAGGTGGGTATGGACCCATCGGTGCCGCAGCTAACGCAATA AGCAATCCACCTGGGGAGTACGTTCGCAAGAATGAAACTCAAAGGAATTGACGGGGA CCCGCACAAGCGGTGGAGCATGTGGTTTAATTCGAAGCAACGCGAAGAACCTTACCAA GTCTTGACATCCCAATGACGTGTCCGTAACGGGGCATTCTCTTCGGAGCATTGGAGAC AGGTGGTGCATGGTTGTCGTCAGCTCGTGTCGTGAGATGTTGGGTTAAGTCCCGCAA CGAGCGCAACCCTTATCCTTAGTAGCCAGCAGGTAGAGCTGGGCACTCTAGGGAGAC TGCCGGGGATAACCCGGAGGAAGGCGGGGATGACGTCAAATCATCATGCCCCTTATG ATTTGGGCTACACACGTGCTACAATGGCGTAAACAAAGGGAAGCGAGACAGTGATGTT GAGCAAATCCCAGAAATAACGTCTCAGTTCGGATTGTAGTCTGCAACTCGACTACATG AAGCTGGAATCGCTAGTAATCGCGAATCAGCATGTCGCGGTGAATACGTTCCCGGGTC TTGTACACACCGCCCGTCACACCATGGGAGTTGGAAATGCCCGAAGCCTGTGACCTAA CCGCAAGGGAGGAGCAGTCGAAGGCAGGTCTAATAACTGGGGTGAAGTCGTAACAAG GTAGCCGTATCGGAAGGTGCGGCTGGATCACCTCCTTT |
| SEQ ID No. 2 | TTTAGAGAGTTTGATCCTGGCTCAGGATGAACGCTGGCGGCGTGCCTAACACATGCAA GTCGAACGGAGTTATTTTGGAAATCTCTTCGGGGATGGAATTCATAACTTAGTGGCGG ACGGGTGAGTAACGCGTGAGCAATCTGCCCTTAGGTGGGGGATAACAGCCGGAAACG GCTGCTAATACCGCATAACACATTGAAGCCGCATGGTTTTGATGTCAAAGATTATTGC CTTTGGATGAGCTCGCGTCTGATTAGCTGGTTGGCGGGGTAACGGCCCACCAAGGCG ACGATCAGTAGCCGGACTGAGAGGTTGAACGGCCACATTGGGACTGAGACACGCCC AGACTCCTACGGGAGGCAGCAGTGGGGAATATTGCGCAATGGGGGAAACCCTGACGC AGCAACGCCGCGTGATTGAAGAAGGCCTTCGGGTTGTAAAGATCTTTAATTGGGGACG AATTTTGACGGTACCCAAAGAATAAGCTCCGGCTAACTACGTGCCAGCAGCCGCGGTA ATACGTAGGGAGCAAGCGTTATCCGGATTTACTGGGTGTAAAGGGCGAGTAGGCGGG CTGGCAAGTTGGGAGTGAAATCCCGGGGCTTAACCCCGGAACTGCTTTCAAAACTGCT GGTCTTGAGTGATGGAGAGGCAGGCGGAATTCCGTGTGTAGCGGTGAAATGCGTAGA TATACGGAGGAACACCAGTGGCGAAGGCGGCCTGCTGGACATTAACTGACGCTGAGG AGCGAAAGCGTGGGGAGCAAACAGGATTAGATACCCTGGTAGTCCACGCCGTAAACG ATGGATACTAGGTGTGGGAGGTATTGACCCCTTCCGTGCCGGAGTTAACACAATAAGT ATCCCACCTGGGGAGTACGGCCGCAAGGTTGAAACTCAAAGGAATTGACGGGGGCCC GCACAAGCAGTGGAGTATGTGGTTTAATTCGAAGCAACGCGAAGAACCTTACCAGGTC TTGACATCCCTCTGACCGCCCTAGAGATAGGGTTTCCCTTCGGGGACAGAGGTGACAG GTGGTGCATGGTTGTCGTCAGCTCGTGTCGTGAGATGTTGGGTTAAGTCCCGCAACG AGCGCAACCCTTACGGTTAGTTGATACGAAAGATCACTCTAGCCGGACTGCCGTTGAC AAAACGGAGGAAGGTGGGGACGACGTCAAATCATCATGCCCCTTATGACCTGGGCTA CACACGTACTACAATGGCAGTCATACAGAGGGAAGCAAAACAGTGATGTGGAGCAAAT CCCTAAAAGCTGTCCCAGTTCAGATTGCAGGCTGCAACTCGCCTGCATGAAGTCGGAA TTGCTAGTAATCGCGGATCAGCATGCCGCGGTGAATACGTTCCCGGGCCTTGTACACA CCGCCCGTCACACCATGAGAGCCGGTAATACCCGAAGTCCGTAGCCTAACCGCAAGG AGGGCGCGGCCGAAGGTAGGACTGGTAATTAGGGTGAAGTCGTAACAAGGTAGCCGT ATCGGAAGGTGCGGCTGGATCACCTCCTTT |
| SEQ ID No. 3 | TTTAAGAGTTTGATCCTGGCTCAGGACGAACGCTGGCGGCGTGCCTAACACATGCAAG TCGAACGAAGCTTGATTTCTGATTTTTTCGGAATGACGAATGATATGACTGAGTGGCGG ACGGGTGAGTAACGCGTGAGCAACCTGCCCTTCGGAACGGGATAGTGTCTGGAAACG GACAGTAATACCGTATAATATATATTGATCGCATGGTTGATATATCAAAACTGAGGTGC CGAAGGATGGGCTCGCGTCTGATTAGATAGTTGGTGGGGTAACGGCCTACCAAGTCG ACGATCAGTAGCCGGACTGAGAGGTTGAACGGCCACATTGGGACTGAGACACGGCCC AGACTCCTACGGGAGGCAGCAGTGGGGAATATTGCACAATGGGGGAAACCCTGATGC AGCAACGCCGCGTGAAGGAAGACGGTTTTCGGATTGTAAACTTCTGTTCTTAGTGAAG AATAATGACGGTAGCTAAGGAGCAAGCCACGGCTAACTACGTGCCAGCAGCCGCGGT AATACGTAGGTGGCAAGCGTTGTCCGGAATTACTGGGTGTAAAGGGAGCGTAGGCGG GATGCCAAGTCAGCTGTGAAAACTATGGGCTTAACTTGTAGACTGCAGTTGAAACTGG TATTCTTGAGTGAAGTAGAGGTTGGCGGAATTCCGAGTGTAGCGGTGAAATGCGTAGA TATTCGGAGGAACACCGGTGGCGAAGGCGGCCAACTGGGCTTTAACTGACGCTGAGG CTCGAAAGTGTGGGGAGCAAACAGGATTAGATACCCTGGTAGTCCACACTGTAAACGA TGATAACTAGGTGTGGGGGTCTGACCCCTTCCGTGCCGCAGCTAACGCAATAAGTTA TCCACCTGGGGAGTACGACCGCAAGGTTGAAACTCAAAGGAATTGACGGGGACCCGC ACAAGCAGTGGATTATGTGGTTTAATTCGAAGCAACGCGAAGAACCTTACCAGCACTT GACATCCGACTAACGAAGTAGAGATACATTAGGTGCCCTTCGGGGAAAGTCGAGACA GGTGGTGCATGGTTGTCGTCAGCTCGTGTCGTGAGATGTTGGGTTAAGTCCCGCAAC GAGCGCAACCCCTGCCATTAGTTGCTACGCAAGAGCACTCTAATGGGACCGCTACCG |

TABLE 2-continued

Sequences

| SEQ ID | 16S rDNA Sequence |
|---|---|
| | ACAAGGTGGAGGAAGGTGGGGACGACGTCAAATCATCATGCCCCTTATGTGCTGGGC<br>TACACACGTAATACAATGGCCATCAACAAAGAGAAGCAATACCGCGAGGTGGAGCAAA<br>ACTATAAAAATGGTCTCAGTTCGGACTGCAGGCTGCAACCCGCCTGCACGAAGTTGGA<br>ATTGCTAGTAATCGTGGATCAGCATGCCACGGTGAATACGTTCCCGGGTCTTGTACAC<br>ACCGCCCGTCACACCATGGGAGTTGGTAACACCCGAAGTCAGTAGTCTAACCGCAAG<br>GAGGACGCTGCCGAAGGTGGGATTGACGACTGGGGTGAAGTCGTAACAAGGTAGCC<br>GTATCAGAAGGTGCGGCTGGATCACCTCCTTT |
| SEQ ID No. 4 | ATGGAGAGTTTGATCCTGGCTCAGGATGAACGCTAGCGGCAGGCTTAACACATGCAA<br>GTCGAGGGGCAGCATAATGGTAGCAATACTATTGATGGCGACCGGCGGACGGGTGCGG<br>TAACGCGTATGCAACCTACCCTTTACAGGGGGATAACACTGAGAAATCGGTACTAATA<br>CCCCATAATATTCTGGGAGGCATCTTCGGAGTTGAAAGCTTTGGTGGTAAAGGATGG<br>GCATGCGTTGTATTAGCTAGTTGGTAAGGTAACGGCTTACCAAGGCGACGATACATAG<br>GGGGACTGAGAGGTTAACCCCCCACATTGGTACTGAGACACGGACCAAACTCCTACG<br>GGAGGCAGCAGTGAGGAATATTGGTCAATGGACGGAAGTCTGAACCAGCCATGCCGC<br>GTGCAGGAAGACGGCTCTATGAGTTGTAAACTGCTTTTGTACGAGGGTAAACGCAGAT<br>ACGTGTATCTGCCTGAAAGTATCGTACGAATAAGGATCGGCTAACTCCGTGCCAGCAG<br>CCGCGGTAATACGGAGGATCCAAGCGTTATCCGGATTTATTGGGTTTAAAGGGTGCGT<br>AGGCGGTTTAGTAAGTCAGCGGTGAAATTTTGGTGCTTAACACCAAACGTGCCGTTGA<br>TACTGCTGGGCTAGAGAGTAGTTGCGGTAGGCGGAATGTATGGTGTAGCGGTGAAAT<br>GCTTAGAGATCATACAGAACACCGATTGCGAAGGCAGCTTACTAAACTATATCTGACG<br>TTGAGGCACGAAAGCGTGGGGAGCAAACAGGATTAGATACCCTGGTAGTCCACGCAG<br>TAAACGATGATAGCTCGTTGTCGGCGATACACAGTCGGTGACTAAGAGAAATCGATAA<br>GCTATCCACCTGGGGAGTACGTTCGCAAGAATGAAACTCAAAGGAATTGACGGGGGC<br>CCGCACAAGCGGAGGAACATGTGGTTTAATTCGATGATACGCGAGGAACCTTACCCG<br>GGCTTGAAAGTTACTGACGATTCTGGAAACAGGATTTCCCTTCGGGGCAGGAAACTAG<br>GTGCTGCATGGTTGTCGTCAGCTCGTGCCGTGAGGTGTCGGGTTAAGTCCCATAACG<br>AGCGCAACCCCTACTGATAGTTGCCATCAGAGCGTTTGAGCGATCAAACAAGCTGGGC<br>ACTCTATCGGGACTGCCGGTGTAAGCCGAGAGGAAGGTGGGGATGACGTCAAATCAG<br>CACGGCCCTTACGTCCGGGGCGACACACGTGTTACAATGGTAGGTACAGAGGGCAGC<br>CACCCAGTGATGGGGAGCGAATCTCGAAAGCCTATCTCAGTTCGGATTGGAGGCTGA<br>AACTCGCCTCCATGAAGTTGGATTCGCTAGTAATCGCGCATCAGCCATGGCGCGGTGA<br>ATACGTTCCCGGGCCTTGTACACACCGCCCGTCAAGCCATGGGAGTTGGGGGTGCCT<br>GAAGTTCGTGACCGAAAGGAGCGACCTAGGGCAAAACCGATGACTGGGGCTAAGTCG<br>TAACAAGGTAGCCGTACCGGAAGGTGCGGCTGGAACACCTCCTTT |
| SEQ ID No. 5 | ATGGAGAGTTTGATCCTGGCTCAGGATAAACGCTAGCGGCAGGCCTAACACATGCAA<br>GTCGAGGGGCAGCGGGTGGAGTATTTCGGTACTTCCTGCCGGCGACCGGCGCACGGG<br>TGCGTAACGCGTATGCAACCTACCTTTAACAGGGGGATAATCCGAAGAAATTTGGTCT<br>AATACCCCATAATATCATTTAAGGCATCTTAGATGGTTGAAAATTCCGATGGTTAGAGA<br>TGGGCATGCGTTGTATTAGCTAGTTGGTGAGGTAACGGCTCACCAAGGCTACGATACA<br>TAGGGGGACTGAGAGGTTTTCCCCCCACACTGGTACTGAGACACGGACCAGACTCCT<br>ACGGGAGGCAGCAGTGAGGAATATTGGTCAATGGACGCAAGTCTGAACCAGCCATGC<br>CGCGTGCAGGATGAAGGTGCTATGCATTGTAAACTGCTTTTGTACGAGGGTAAATGCA<br>GGTACGTGTACCTGTTTGAAAGTATCGTACGAATAAGGGTCGGCTAACTCCGTGCCAG<br>CAGCCGCGGTAATACGGAGGACCCGAGCGTTATCCGGATTTATTGGGTTTAAAGGGT<br>GCGTAGGCGGATTAGTAAGTTAGAGGTGAAAGCTCGATGCTCAACATCGAAATTGCCT<br>CTGATACTGTTAGTCTAGAGTATAGTTGCGGAAGGCGGAATGTGTGGTGTAGCGGTGA<br>AATGCTTAGATATCACACAGAACACCGATTGCGAAGGCAGCTTTCCAAGCTATTACTGA<br>CGCTGATGCACGAAAGCGTGGGGAGCGAACAGGATTAGATACCCTGGTAGTCCACGC<br>CGTAAACGATGATAACTCGTTGCAGGCGATACACAGTCTGTGACTTAGCGAAAGCGTT<br>AAGTTATCCACCTGGGGAGTACGTTCGCAAGAATGAAACTCAAAGGAATTGACGGGGG<br>CCCGCACAAGCGGAGGAACATGTGGTTTAATTCGATGATACGCGAGGAACCTTACCC<br>GGGCTTGAAAGTTAGCGACGGATCCTGAAAGGGGTCTTCTCTTCGGAGCGCGAAACT<br>AGGTGCTGCATGGTTGTCGTCAGCTCGTGCCGTGAGGTGTCGGGTTAAGTCCCATAA<br>CGAGCGCAACCCCTACTGTTAGTTACCAGCACGTCAAGGTGGGCACTCTAGCAGGAC<br>TGCCGGTGTAAGCCGAGAGGAAGGTGGGGATGACGTCAAATCAGCACGGCCCTTACG<br>TCCGGGGCGACACACGTGTTACAATGGTCGGTACAGAGGGTCGCTACCCCGTGAGGG<br>GATGCCAATCTCGAAAGCCGATCTCAGTTCGGATTGGAGGCTGAAACTCGCCTCCATG<br>AAGTTGGATTCGCTAGTAATCGCGCATCAGCCATGGCGCGGTGAATACGTTCCCGGG<br>CCTTGTACACACCGCCCGTCAAGCCATGGGAGTGGGGGTGCCTGAAGTACGTGACC<br>GCAAGGAGCGTCCTAGGGCAAAACCGATGACTGGGGCTAAGTCGTAACAAGGTAGCC<br>GTACCGGAAGGTGCGGCTGGAACACCTCCTT |
| SEQ ID No. 6 | ACGGAGAGTTTGATCCTGGCTCAGGATGAACGCTGGCGGCGTGCCTAACACATGCAA<br>GTCGAACGGTTAAGGCGCTTCGGGCGCGAATAGAGTGGCGAACGGGTGAGTAACAC<br>GTGACCAACCTGCCCCCCTCCCCGGGATAACGCGAGGAAACCCGCTAATACCGGA<br>TACTCGCCCCTCCCGCATGGGAGGGCGGGAAAGCCCCGACGGAGGGGGATGGG<br>GTCGCGGCCCATTAGGTAGACGGCGGGGCAACGGCCCACCGTGCCTGCGATGGGTA<br>GCCGGGTTGAGAGACCGACCGGCCACATTGGGACTGAGATACGCCCAGACTCCTAC<br>GGGAGGCAGCAGTGGGGAATTTTGCGCAATGGGGGAACCCTGACGCAGCAAGCC<br>GCGTGCGGGACGAAGGCCTTCGGGTTGTAAACCGCTTTCAGCAGGGAAGAAGTTGAC<br>GGTACCTGCAGAAGAAGCCCCGGCTAACTACGTGCCAGCAGCCGCGGTAATACGTAG<br>GGGGCGAGCGTTATCCGGATTCATTGGGCGTAAAGCGCGCGTAGGCGGCCCGTCAA<br>GCGGAACCTCTAACCCGAGGGCTCAACCCCCGGCCGGGTTCCGAACTGGCAGGCTC<br>GAGTTTGGTAGAGGAAGATGGAATTCCCGGTGTAGCGGTGGAATGCGCAGATATCGG |

TABLE 2-continued

Sequences

| SEQ ID | 16S rDNA Sequence |
|---|---|
| | GAAGAACACCGATGGCGAAGGCAGTCTTCTGGGCCATCAACTGACGCTGAGGCGCGA |
| | AAGCTGGGGAGCGAACAGGATTAGATACCCTGGTAGTCCCAGCCGTAAACGATGGG |
| | TGCTAGGTGTGGGGGGATCATCCCTCCGTGCCGCAGCCAACGCATTAAGCACCCCGC |
| | CTGGGGAGTACGGCCGCAAGGCTAAAACTCAAAGGAATTGACGGGGGCCCGCACAA |
| | GCAGCGGAGCATGTGGCTTAATTCGAAGCAACGCGAAGAACCTTACCAGGGCTTGAC |
| | ATGCTGGTGAAGCCGGGGAAACCCGGTGGCCGAGAGGAGCCAGCGCAGGTGGTGCA |
| | TGGCTGTCGTCAGCTCGTGTCGTGAGATGTTGGGTTAAGTCCCGCAACGAGCGCAAC |
| | CCCTGCCCATATGTTGCCAGCATTCAGTTGGGGACTCATATGGGACTGCCGGCGTCAA |
| | GCCGGAGGAAGGTGGGGACGACGTCAAGTCATCATGCCCTTTATGCCCTGGGCTGCA |
| | CACGTGCTACAATGGCCGGTACAACGGGCCGCGACCTGGCGACAGGAAGCGAATCC |
| | CTCAAAGCCGGCCCCAGTTCGGATCGGAGGCTGCAACCCGCCTCCGTGAAGTCGGA |
| | GTTGCTAGTAATCGCGGATCAGCATGCCGCGGTGAATACGTTCCCGGGCCTTGTACA |
| | CACCGCCCGTCACACCACCCGAGTCGTCTGCACCCGAAGCCGCCGGCCGAACCCGC |
| | AAGGGGCGGAGGCGTCGAAGGTGTGGAGGGTAAGGGGGGTGAAGTCGTAACAAGGT |
| | AGCCGTACCGGAAGGTGCGGCTGGATCACCTCCTTT |
| SEQ ID No. 7 | ATGGAGAGTTTGATCCTGGCTCAGGATGAACGCTGGCGGCATGCCTAATACATGCAAG |
| | TCGAACGAAGTCTTTAGGAAGCTTGCTTCCAAAGAGACTTAGTGGCGAACGGGTGAGT |
| | AACACGTAGGTAACCTGCCCATGTGCCCGGGATAACTGCTGGAAACGGTAGCTAAAAC |
| | CGGATAGGTATGAGGGAGGCATCTTCCTCATATTAAAGCACCTTCGGGTGTGAACATG |
| | GATGGACCTGCGGCGCATTAGCTGGTTGGTGAGGTAACGGCCCACCAAGGCGATGAT |
| | GCGTAGCCGACCTGAGAGGGTGAACGGCCACATTGGGACTGAGACACGGCCCAAACT |
| | CCTACGGGAGGCAGCAGTAGGGAATTTTCGTCAATGGGGGGAACCCTGAACGAGCAA |
| | TGCCGCGTGTGTGAAGAAGGTCTTCGGATCGTAAAGCACTGTTGTAAGTGAAGAATGC |
| | CATATAGAGGAAATGCTATGTGGGTGACGGTAGCTTACCAGAAAGCCACGGCTAACTA |
| | CGTGCCAGCAGCCGCGGTAATACGTAGGTGGCAAGCGTTATCCGGAATCATTGGGCG |
| | TAAAGGGTGCGTAGGTGGCACGATAAGTCTGAAGTAAAAGGCAACAGCTCAACTGTTG |
| | TATGCTTTGGAAACTGTCGAGCTAGAGTGCAGAAGAGGGCGATGGAATTCCATGTGTA |
| | GCGGTAAAATGCGTAGATATATGGAGGAACACCAGTGGCGAAGGCGGTCGCCTGGTC |
| | TGTAACTGACACTGATGCACGAAAGCGTGGGGAGCAAATAGGATTAGATACCCTAGTA |
| | GTCCACGCCGTAAACGATGAGAACTAAGTGTTGGAGAGATTCAGTGCTGCAGTTAACG |
| | CAATAAGTTCTCCGCCTGGGGAGTATGCACGCAAGTGTGAAACTCAAAGGAATTGACG |
| | GGGGCCCGCACAAGCGGTGGAGTATGTGGTTTAATTCGAAGCAACGCGAAGAACCTT |
| | ACCAGGCCTTGACATGGATATAAATGTTCTAGAGATAGAAAGATAGCTATATATCACAC |
| | AGGTGGTGCATGGTTGTCGTCAGCTCGTGTCGTGAGATGTTGGGTTAAGTCCCGCAA |
| | CGAGCGCAACCCTTGTCTTCTGTTACCAGCATTAAGTTGGGGACTCAGGAGAGACTGC |
| | CGGTGACAAACCGGAGGAAGGTGGGGATGACGTCAAATCATCATGCCCCTTATGGCC |
| | TGGGCTACACACGTACTACAATGGCGCCTACAAAGAGCAGCGACACCGCGAGGTGGA |
| | GCGAATCTCATAAAGGGCGTCTCAGTTCGGATTGAAGTCTGCAACTCGACTTCATGAA |
| | GTCGGAATCGCTAGTAATCGCAGATCAGCATGCTGCGGTGAATACGTTCTCGGGCCTT |
| | GTACACACCGCCCGTCAAACCATGGGAGTTGGTAATACCCGAAGCCGGTGGCATAAC |
| | CGCAAGGAGTGAGCCGTCGAAGGTAGGACCGATGACTGGGGTTAAGTCGTAACAAGG |
| | TATCCCTACGGGAACGTGGGGATGGATCACCTCCTTT |
| SEQ ID No. 8 | TCAGAGAGTTTGATCCTGGCTCAGGATGAACGCTGGCGCGTGCTTAACACATGCAA |
| | GTCGAGCGAAGCACTTAAGTGGATCTCTTCGGATTGAAACTTATTTGACTGAGCGGCG |
| | GACGGGTGAGTAACGCGTGGGTAACCTGCCTCATACAGGGGGATAACAGTTAGAAAT |
| | GGCTGCTAATACCGCATAAGCGCACAGGACCGCATGGTCTGGTGTGAAAAACTCCGG |
| | TGGTATGAGATGGACCCGCGTCTGATTAGCTAGTTGGAGGGGTAACGGCCCACCAAG |
| | GCGACGATCAGTAGCCGGCCTGAGAGGGTGAACGGCCACATTGGGACTGAGACACG |
| | GCCCAGACTCCTACGGGAGGCAGCAGTGGGGAATATTGCACAATGGGGGAAACCCTG |
| | ATGCAGCGACGCCGCGTGAAGGAAGAAGTATCTCGGTATGTAAACTTCTATCAGCAGG |
| | GAAGAAAATGACGGTACCTGACTAAGAAGCCCCGGCTAACTACGTGCCAGCAGCCGC |
| | GGTAATACGTAGGGGGCAAGCGTTATCCGGATTTACTGGGTGTAAAGGGAGCGTAGA |
| | CGGAAGAGCAAGTCTGATGTGAAAGGCTGGGGCTTAACCCCAGGACTGCATTGGAAA |
| | CTGTTTTTCTAGAGTGCCGGAGAGGTAAGCGGAATTCCTAGTGTAGCGGTGAAATGCG |
| | TAGATATTAGGAGGAACACCAGTGGCGAAGGCGGCTTACTGGACGGTAACTGACGTT |
| | GAGGCTCGAAAGCGTGGGGAGCAAACAGGATTAGATACCCTGGTAGTCCCACGCCGTA |
| | AACGATGAATACTAGGTGTCGGGTGGCAAAGCCATTCGGTGCCGCAGCAAACGCAAT |
| | AAGTATTCCACCTGGGGAGTACGTTCGCAAGAATGAAACTCAAAGGAATTGACGGGGA |
| | CCCGCACAAGCGGTGGAGCATGTGGTTTAATTCGAAGCAACGCGAAGAACCTTACCAA |
| | GTCTTGACATCCCTCTGACCGGCCCGTAACGGGCCTTCCCTTCGGGGCAGAGGAGA |
| | CAGGTGGTGCATGGTTGTCGTCAGCTCGTGTCGTGAGATGTTGGGTTAAGTCCCGCA |
| | ACGAGCGCAACCCCTATCCTTAGTAGCCAGCAGGTAGAGCTGGGCACTCTAGGGAGA |
| | CTGCCGGGGATAACCCGGAGGAAGGCGGGGACGACGTCAAATCATCATGCCCCTTAT |
| | GATTTGGGCTACACACGTGCTACAATGGCGTAAACAAAGGGAAGCGAGACAGCGATG |
| | TTGAGCAAATCCCAAAAATAACGTCCCAGTTCGGACTGCAGTCTGCAACTCGACTGCA |
| | CGAAGCTGGAATCGCTAGTAATCGCGAATCAGAATGTCGCGGTGAATACGTTCCCGG |
| | GTCTTGTACACACCGCCCGTCACACCATGGGAGTCAGTAACGCCCGAAGTCAGTGAC |
| | CCAACCTTACAGGAGGGAGCTGCCGAAGGCGGGACCGATAACTGGGGTGAAGTCGTA |
| | ACAAGGTAGCCGTATCGGAAGGTGCGGCTGGATCACCTCCTTT |
| SEQ ID No. 9 | CGAAGAGTTTGATCCTGGCTCAGGATGAACGCTAGCGACAGGCCTAACACATGCAAGT |
| | CGAGGGGCAGCGGAGAGGTAGCAATACCTTTGCCGGCGACCGGCGCACGGGTGAGT |
| | AACACGTATGCAATCCACCTGTAACAGGGGGATAACCCGGAGAAATCCGGACTAATAC |
| | CCCATAATATGGGCGCTCCGCATGGAGAGTCCATTAAAGAGAGCAATTTTGGTTACAG |

TABLE 2-continued

Sequences

| SEQ ID | 16S rDNA Sequence |
|---|---|
| | ACGAGCATGCGCTCCATTAGCCAGTTGGCGGGGTAACGGCCCACCAAAGCGACGATG<br>GATAGGGGTTCTGAGAGGAAGGTCCCCCACATTGGAACTGAGACACGGTCCAAACTC<br>CTACGGGAGGCAGCAGTGAGGAATATTGGTCAATGGTCGGCAGACTGAACCAGCCAA<br>GTCGCGTGAGGGAAGACGGCCCTACGGGTTGTAAACCTCTTTTGTCGGAGAGTAAAG<br>TACGCTACGTGTAGTGTATTGCAAGTATCCGAAGAAAAAGCATCGGCTAACTCCGTGC<br>CAGCAGCCGCGGTAATACGGAGGATGCGAGCGTTATCCGGATTTATTGGGTTTAAAG<br>GGTGCGTAGGCGGCACGCCAAGTCAGCGGTGAAATTTCCGGGCTCAACCCGGACTGT<br>GCCGTTGAAACTGGCGAGCTAGAGTGCACAAGAGGCAGGCGGAATGCGTGGTGTAG<br>CGGTGAAATGCATAGATATCACGCAGAACCCCGATTGCGAAGGCAGCCTGCTAGGGT<br>GCGACAGACGCTGAGGCACGAAAGCGTGGGTATCGAACAGGATTAGATACCCTGGTA<br>GTCCACGCAGTAAACGATGAATACTAACTGTTTGCGATACAATGTAAGCGGTACAGCG<br>AAAGCGTTAAGTATTCCACCTGGGGAGTACGCCGGCAACGGTGAAACTCAAAGGAATT<br>GACGGGGGCCCGCACAAGCGGAGGAACATGTGGTTTAATTCGATGATACGCGAGGAA<br>CCTTACCCGGGCTCAAACGCAGGGGAATGCCGGTGAAAGTCGGCAGCTAGCAATAG<br>TCACCTGCGAGGTGCTGCATGGTTGTCGTCAGCTCGTGCCGTGAGGTGTCGGCTTAA<br>GTGCCATAACGAGCGCAACCCCTATGGACAGTTACTAACGGGTGAAGCCGAGGACTC<br>TGTCTAGACTGCCGGCGCAAGCCGCGAGGAAGGTGGGGATGACGTCAAATCAGCAC<br>GGCCCTTACGTCCGGGGCGACACACGTGTTACAATGGCAGGTACAGAAGGCAGCCAG<br>TCAGCAATGACGCGCGAATCCCGAAAACCTGTCTCAGTTCGGATTGGAGTCTGCAACC<br>CGACTCCATGAAGCTGGATTCGCTAGTAATCGCGCATCAGCCATGGCGCGGTGAATA<br>CGTTCCCGGGCCTTGTACACACCGCCCGTCAAGCCATGGAAGCCGGGAGTACCTGAA<br>GCATGCAACCGCAAGGAGCGTACGAAGGTAATACCGGTAACTGGGGCTAAGTCGTAA<br>CAAGGTAGCCGTACCGGAAGGTGCGGCTGGAACACCTCCTTT |
| SEQ ID<br>No. 10 | ATGGAGAGTTTGATCCTGGCTCAGGATGAACGCTAGCGGCAGGCCTAACACATGCAA<br>GTCGAGGGGCAGCGGGATTGAAGCTTGCTTCAATCGCCGGCGACCGGCGCACGGGT<br>GCGTAACGCGTATGCAACCTACCCAGAACAGGGGGATAACACTGAGAAATTGGTACTA<br>ATATCCCATAACATCATAAGGGGCATCCCTTTTGGTTGAAAACTCCGGTGGTTCTGGAT<br>GGGCATGCGTTGTATTAGCTAGTTGGTGAGGTAACGGCTCACCAAGGCAACGATACAT<br>AGGGGGACTGAGAGGTTAACCCCCCACATTGGTACTGAGACACGGACCAAACTCCTA<br>CGGGAGGCAGCAGTGAGGAATATTGGTCAATGGACGCAAGTCTGAACCAGCCATGCC<br>GCGTGCAGGAAGACGGCTCTATGAGTTGTAAACTGCTTTTGTACTAGGGTAAACTCAG<br>ATACGTGTATCTGACTGAAAGTATAGTACGAATAAGGATCGGCTAACTCCGTGCCAGC<br>AGCCGCGGTAATACGGAGGATTCAAGCGTTATCCGGATTTATTGGGTTTAAAGGGTGC<br>GTAGGCGGTTTGATAAGTTAGAGGTGAAATACCGGTGCTTAACACCGGAACTGCCTCT<br>AATACTGTTGAGCTAGAGAGTAGTTGCGGTAGGCGGAATGTATGGTGTAGCGGTGAAA<br>TGCTTAGAGATCATACAGAACACCGATTGCGAAGGCAGCTTACCAAACTATATCTGAC<br>GTTGAGGCACGAAAGCGTGGGGAGCAAACAGGATTAGATACCCTGGTAGTCCACGCA<br>GTAAACGATGATAACTCGCTGTCGGCGATACACAGTCGGTGGCTAAGCGAAAGCGATA<br>AGTTATCCACCTGGGGAGTACGTTCGCAAGAATGAAACTCAAAGGAATTGACGGGGG<br>CCCGCACAAGCGGAGGAACATGTGGTTTAATTCGATGATACGCGAGGAACCTTACCC<br>GGGCTTGAAAGTTAGTGACGGATCTGGAAACAGGTCTTCCCTTCGGGGCGCGAAACT<br>AGGTGCTGCATGGTTGTCGTCAGCTCGTGCCGTGAGGTGTCGGGTTAAGTCCCATAA<br>CGAGCGCAACCCCTACCGTTAGTTGCCATCAGGTCAAGCTGGGCACTCTGACGGGAC<br>TGCCGGTGTAAGCCGAGAGGAAGGTGGGGATGACGTCAAATCAGCACGGCCCTTACG<br>TCCGGGGCCACACACGTGTTACAATGGTAGGTACAGAGGGCAGCTACCCAGCGATGG<br>GATGCGAATCTCGAAAGCCTATCTCAGTTCGGATCGGAGGCTGAAACCCGCCTCCGT<br>GAAGTTGGATTCGCTAGTAATCGCGCATCAGCCATGGCGCGGTGAATACGTTCCCGG<br>GCCTTGTACACACCGCCCGTCAAGCCATGGAAGCTGGGGGTGCCTGAAGTTCGTGAC<br>CGCAAGGAGCGACCTAGGGCAAAACCGGTGACTGGGGCTAAGTCGTAACAAGGTAGC<br>CGTACCGGAAGGTGCGGCTGGAACACCTCCTTT |
| SEQ ID<br>No. 11 | TCAGAGAGTTTGATCCTGGCTCAGGATGAACGCTGGCGGCGTGCTTAACACATGCAA<br>GTCGAGCGAAGCACTTGCCATTGACTCTTCGGAAGATTTGGCATTTGACTGAGCGGCG<br>GACGGGTGAGTAACGCGTGGGTAACCTGCCTCATACAGGGGAATAACAGTTAGAAAT<br>GGCTGCTAATGCCGCATAAGCGCACAGGACCGCATGGTCTGGTGTGAAAAACTGAGG<br>TGGTATGAGATGGGCCCGCGTCTGATTAGGTAGTTGGCGGGGTAACGGCCCACCAAG<br>CCGACGATCAGTAGCCGACCTGAGAGGGTGACCGGCCACATTGGGACTGAGACACG<br>GCCCAGACTCCTACGGGAGGCAGCAGTGGGGAATATTGCACAATGGAGGAAACTCTG<br>ATGCAGCGACGCCGCGTGAAGGAAGAAGTATCTCGGTATGTAAACTTCTATCAGCAGG<br>GAAGAAAATGACGGTACCTGACTAAGAAGCCCCGGCTAACTACGTGCCAGCAGCCGC<br>GGTAATACGTAGGGGGCAAGCGTTATCCGGATTTACTGGGTGTAAAGGGAGCGTAGA<br>CGGACGGGCAAGTCTGATGTGAAAGCCCGGGGCTTAACCCCGGGACTGCATTGGAAA<br>CTGTCCATCTTGAGTGCCGGAGAGGTAAGCGGAATTCCTAGTGTAGCGGTGAAATGC<br>GTAGATATTAGGAGGAACACCAGTGGCGAAGGCGGCTTACTGGACGGTAACTGACGT<br>TGAGGCTCGAAAGCGTGGGGAGCAAACAGGATTAGATACCCTGGTAGTCCACGCCGT<br>AAACGATGAATACTAGGTGTCGGGTTGCAAAGCAATCCGGTGCCGCAGCAAACGCAG<br>TAAGTATTCCACCTGGGGAGTACGTTCGCAAGAATGAAACTCAAAGGAATTGACGGGG<br>ACCCGCACAAGCGGTGGAGCATGTGGTTTAATTCGAAGCAACGCGAAGAACCTTACCA<br>AGTCTTGACATCTGCCTGACCGTTCCTTAACCGGAACTTTCCTTCGGGACAGGCAAGA<br>CAGGTGGTGCATGGTTGTCGTCAGCTCGTGTCGTGAGATGTTGGGTTAAGTCCCGCAA<br>ACGAGCGCAACCCCTGTCCTTAGTAGCCAGCAGTCCGGCTGGGCACTCTAGGGAGAC<br>TGCCGGGGATAACCCGGAGGAAGGCGGGGACGACGTCAAATCATCATGCCCCTTATG<br>ATTTGGGCTACACACGTGCTACAATGGCGTAAACAAAGGGAAGCGGAGTGGTGACAC<br>TGAGCAAATCTCAAAAATAACGTCCCAGTTCGGACTGCAGTCTGCAACTCGACTGCAC<br>GAAGCTGGAATCGCTAGTAATCGCGAATCAGAATGTCGCGGTGAATACGTTCCCGGGT |

TABLE 2-continued

Sequences

| SEQ ID | 16S rDNA Sequence |
|---|---|
| | CTTGTACACACCGCCCGTCACACCATGGGAGTCAGTAACGCCCGAAGTCAGTGACCT<br>AACCGCAAGGGAGGAGCTGCCGAAGGCGGGACCGATAACTGGGGTGAAGTCGTAAC<br>AAGGTAGCCGTATCGGAAGGTGCGGCTGGATCACCTCCTTT |
| SEQ ID No. 12 | TTATGAGAGTTTGATCCTGGCTCAGGATGAACGCTGGCGGCGTGCTTAACACATGCAA<br>GTCGAACGAAGCATTTAAGACGGATTCTTTCGGGATGAAGACTTTTATGACTGAGTGG<br>CGGACGGGTGAGTAACGCGTGGGTAACCTGCCTCACACAGGGGGATAGCAGTTGGAA<br>ACGGCTGATAATACCGCATAAGCGCACAGTACCGCATGGTACAGTGTGAAAAACTCCG<br>GTGGTGTGAGATGGACCCGCGTCTGATTAGCTTGTTGGCAGGGTAACGGCCTACCAA<br>GGCAACGATCAGTAGCCGACCTGAGAGGGTGACCGGCCACATTGGGACTGAGACAC<br>GGCCCAGACTCCTACGGGAGGCAGCAGTGGGGAATATTGCACAATGGAGGAAACTCT<br>GATGCAGCGACGCCGCGTGAGTGAAGAAGTAATTCGTTATGTAAAGCTCTATCAGCAG<br>GGAAGATAGTGACGGTACCTGACTAAGAAGCTCCGGCTAAATACGTGCCAGCAGCCG<br>CGGTAATACGTATGGAGCAAGCGTTATCCGGATTTACTGGGTGTAAAGGGAGTGTAGG<br>TGGCATCACAAGTCAGAAGTGAAAGCCCGGGGCTCAACCCCGGGACTGCTTTTGAAA<br>CTGTGGAGCTGGAGTGCAGGAGAGGCAAGTGGAATTCCTAGTGTAGCGGTGAAATGC<br>GTAGATATTAGGAGGAACACCAGTGGCGAAGGCGGCTTGCTGGACTGTAACTGACAC<br>TGAGGCTCGAAAGCGTGGGGAGCAAACAGGATTAGATACCCTGGTAGTCCACGCCGT<br>AAACGATGAATACTAGGTGTCGGGGCTCATAAGAGCTTCGGTGCCGCAGCAAACGCA<br>ATAAGTATTCCACCTGGGGAGTACGTTCGCAAGAATGAAACTCAAAGGAATTGACGGG<br>GACCCGCACAAGCGGTGGAGCATGTGGTTTAATTCGAAGCAACGCGAAGAACCTTAC<br>CAAGTCTTGACATCCTCTTGACCGGTCAGTAATGTGACCTTTTCTTCGGAACAAGAGTG<br>ACAGGTGGTGCATGGTTGTCGTCAGCTCGTGTCGTGAGATGTTGGGTTAAGTCCCGC<br>AACGAGCGCAACCCCTATTCTTAGTAGCCAGCATTTAAGGTGGGCACTCTAGGAAGAC<br>TGCCAGGGATAACCTGGAGGAAGGTGGGGATGACGTCAAATCATCATGCCCCTTATG<br>ACTTGGGCTACACACGTGCTACAATGGCGTAAACAAAGTGAAGCGAGAGTGTGAGCTT<br>AAGCAAATCACAAAAATAACGTCTCAGTTCGGATTGTAGTCTGCAACTCGACTACATGA<br>AGCTGGAATCGCTAGTAATCGCGAATCAGAATGTCGCGGTGAATACGTTCCCGGGTCT<br>TGTACACACCGCCCGTCACACCATGGGAGTCGGAAATGCCCGAAGTCGGTGACCTAA<br>CGAAAGAAGGAGCCGCCGAAGGCAGGTCTGATAACTGGGGTGAAGTCGTAACAAGGT<br>AGCCGTATCGGAAGGTGCGGCTGGATCACCTCCTTT |
| SEQ ID No. 13 | TAAAGAGTTTGATCCTGGCTCAGGACGAACGCTGGCGGCACGCTTAACACATGCAAGT<br>CGAACGGAGAATATCGAAGCTTGCTTTGATATTCTTAGTGGCGGACGGGTGAGTAACA<br>CGTGAGTAACCTGCCTCTGAGAGTGGGATAGCTTCTGGAAACGGATGGTAATACCGCA<br>TGAAATCATAGTATCGCATGGTACAATGATCAAAGATTTATCGCTCAGAGATGGACTCG<br>CGTCTGATTAGCTAGTTGGTAAGGTAACGGCTTACCAAGGCGACGATCAGTAGCCGGA<br>CTGAGAGGTTGATCGGCCACATTGGGACTGAGACACGGCCCAGACTCCTACGGGAGG<br>CAGCAGTGGGGAATATTGCACAATGGGGGAAACCCTGATGCAGCGATGCCGCGTGGA<br>GGAAGAAGGTTTTCGGATTGTAAACTCCTGTTGAAGAGGACGATAATGACGGTACTCT<br>TTTAGAAAGCTCCGGCTAACTACGTGCCAGCAGCCGCGGTAATACGTAGGGAGCGAG<br>CGTTGTCCGGAATTACTGGGTGTAAAGGGAGCGTAGGCGGGACGGCAAGTCAGATGT<br>GAAAACTATGGGCTCAACCCATAGACTGCATTTGAAACTGTTGTTCTTGAGTGAGGTAG<br>AGGTAAGCGGAATTCCTGGTGTAGCGGTGAAATGCGTAGAGATCAGGAGGAACATCG<br>GTGGCGAAGGCGGCTTACTGGGCCTTTACTGACGCTGAGGCTCGAAAGCGTGGGGA<br>GCAAACAGGATTAGATACCCTGGTAGTCCACGCCGTAAACGATGATTACTAGGTGTGG<br>GGGGACTGACCCCTTCCGTGCCGCAGTTAACACAATAAGTAATCCACCTGGGGAGTA<br>CGGCCGCAAGGTTGAAACTCAAAGGAATTGACGGGGGCCCGCACAAGCAGTGGAGTA<br>TGTGGTTTAATTCGAAGCAACGCGAAGAACCTTACCAGGTCTTGACATCGAGTGACGT<br>ACCTAGAGATAGGTATTTCTTCGGAACACAAAGACAGGTGGTGCATGGTTGTCGTCA<br>GCTCGTGTCGTGAGATGTTGGGTTAAGTCCCGCAACGAGCGCAACCCTTACCATTAGT<br>TGCTACGCAAGAGCACTCTAATGGGACTGCCGTTGACAAAACGGAGGAAGGTGGGGA<br>TGACGTCAAATCATCATGCCCCTTATGACCTGGGCTACACACGTACTACAATGGCAATA<br>TAACAGAGGGAAGCAATACAGCGATGTGGAGCAAATCCCCAAAAATTGTCCCAGTTCA<br>GATTCAGGCTGCAACTCGCCTGCATGAAGTCGGAATTGCTAGTAATCGCAGATCAGC<br>ATGCTGCGGTGAATACGTTCCCGGGCCTTGTACACACCGCCCGTCACACCATGGGAG<br>TCGGTAACACCCAAAGCCGGTCGTCTAACCTTCGGGAGGACGCCGTCTAAGGTGGGA<br>TTGATGACTGGGGTGAAGTCGTAACAAGGTAGCCGTATCGGAAGGTGCGGCTGGATC<br>ACCTCCTTT |
| SEQ ID No. 14 | ATGAGAGTTTGATCCTGGCTCAGGATGAACGCTGGCGGCGTGCTTAACACATGCAAGT<br>CGAACGAAGCACTCTATTTGATTTTCTTCGGAAATGAAGATTTTGTGACTGAGTGGCGG<br>ACGGGTGAGTAACGCGTGGGTAACCTGCCTCATACAGGGGGATAACAGTTGGAAACG<br>ACTGCTAATACCGCATAAGCGCACAGGATCGCATGGTCCGGTGTGAAAAACTCCGGT<br>GGTATGAGATGGACCCGCGTCTGATTAGCTAGTTGGCAGGGTAACGGCCTACCAAAG<br>CGACGATCAGTAGCCGACCTGAGAGGGTGACCGGCCACATTGGGACTGAGACACGG<br>CCCAAACTCCTACGGGAGGCAGCAGTGGGGAATATTGCACAATGGGGGAAACCCTGA<br>TGCAGCGACGCCGCGTGAGCGAAGAAGTATTTCGGTATGTAAAGCTCTATCAGCAGG<br>GAAGAAGAATGACGGTACCTGACTAAGAAGCACCGGCTAAATACGTGCCAGCAGCCG<br>CGGTAATACGTATGGTGCAAGCGTTATCCGGATTTACTGGGTGTAAAGGGAGCGCAG<br>GCGGTGCGGCAAGTCTGATGTGAAAGCCCGGGGCTCAACCCCGGGTACTCATTGAA<br>ACTGTCGTACTAGAGTGTCGGAGGGGTAAGTGGAATTCCTAGTGTAGCGGTGAAATGC<br>GTAGATATTAGGAGGAACACCAGTGGCGAAGGCGGCTTACTGGACGATAACTGACGC<br>TGAGGCTCGAAAGCGTGGGGAGCAAACAGGATTAGATACCCTGGTAGTCCACGCCGT<br>AAACGATGAATACTAGGTGTCGGGAGCATTGCTCTTCGGTGCCGCAGCAAACGCAAT<br>AAGTATTCCACCTGGGGAGTACGTTCGCAAGAATGAAACTCAAAGGAATTGACGGGGA |

TABLE 2-continued

Sequences

| SEQ ID | 16S rDNA Sequence |
|---|---|
| | CCCGCACAAGCGGTGGAGCATGTGGTTTAATTCGAAGCAACGCGAAGAACCTTACCAA
GTCTTGACATCCCGATGACAGAGTATGTAATGTACTTTCTCTTCGGAGCATCGGTGACA
GGTGGTGCATGGTTGTCGTCAGCTCGTGTCGTGAGATGTTGGGTTAAGTCCCGCAAC
GAGCGCAACCCCTGTTCTTAGTAGCCAGCGGTTCGGCCGGGCACTCTAGGGAGACTG
CCAGGGATAACCTGGAGGAAGGCGGGGATGACGTCAAATCATCATGCCCCTTATGAC
TTGGGCTACACACGTGCTACAATGGCGTAAACAAAGGGAAGCGGAGCCGTGAGGCCG
AGCAAATCTCAAAAATAACGTCTCAGTTCGGACTGTAGTCTGCAACCCGACTACACGA
AGCTGGAATCGCTAGTAATCGCAGATCAGAATGCTGCGGTGAATACGTTCCCGGGTCT
TGTACACACCGCCCGTCACACCATGGGAGTTGGAAATGCCCGAAGTCAGTGACCCAA
CCGCAAGGAGGGAGCTGCCGAAGGCAGGTTCGATAACTGGGGTGAAGTCGTAACAAG
GTAGCCGTATCGGAAGGTGCGGCTGGATCACCTCCTTT |
| SEQ ID No. 15 | AGAGTTTGATCCTGGCTCAGGACGAACGCTGGCGGCGCGCCTAACACATGCAAGTCG
AACGAGAGAGAGGGAGCTTGCTTCCTTGATCGAGTGGCGAACGGGTGAGTAACGCGT
GAGGAACCTGCCTCAAAGAGGGGGACAACAGTTGGAAACGACTGCTAATACCGCATA
AGCCCACGACCCGGCATCGGGAAGAGGGAAAAGGAGCAATCCGCTTTGAGATGGCCT
CGCGTCCGATTAGCTAGTTGGTGAGGTAACGGCCCACCAAGCGACGATCGGTAGCCG
GACTGAGAGGTTGAACGGCCACATTGGGACTGAGACACGGCCCAGACTCCTACGGGA
GGCAGCAGTGGGGAATATTGCACAATGGGGGAAACCCTGATGCAGCGACGCCGCGT
GGAGGAAGAAGGTCTTCGGATTGTAAACTCCTGTTGTTGAGGAAGATAATGACGGTAC
TCAACAAGGAAGTGACGGCTAACTACGTGCCAGCAGCCGCGGTAAAACGTAGGTCAC
AAGCGTTGTCCGGAATTACTGGGTGTAAAGGGAGCGCAGGCGGGCGATCAAGTTGGA
AGTGAAATCCATGGGCTCAACCCATGAACTGCTTTCAAAACTGGTCGTCTTGAGTAGT
GCAGAGGTAGGCGGAATTCCCGGTGTAGCGGTGGAATGCGTAGATATCGGGAGGAAC
ACCAGTGGCGAAGGCGGCCTACTGGGCACCAACTGACGCTGAGGCTCGAAAGTGTG
GGTAGCAAACAGGATTAGATACCCTGGTAGTCCACACCGTAAACGATGATTACTAGGT
GTTGGGAGATTGACCCTCTCAGTGCCGCAGTTAACACAATAAGTAATCCACCTGGGGA
GTACGACCGCAAGGTTGAAACTCAAAGGAATTGACGGGGGCCCGCACAAGCAGTGGA
GTATGTGGTTTAATTCGACGCAACGCGAAGAACCTTACCAAGTCTTGACATCCCTTGAC
GATGCTGGAAACAGTATTTCTCTTCGGAGCAAGGAGACAGGTGGTGCATGGTTGTCGT
CAGCTCGTGTCGTGAGATGTTGGGTTAAGTCCCGCAACGAGCGCAACCCTTATGGTCA
GTTACTACGCAAGAGGACTCTGGCCAGACTGCCGTTGACAAAACGGAGGAAGGTGGG
GATGACGTCAAATCATCATGCCCTTTATGACTTGGGCTACACACGTACTACAATGGCGT
TAAACAAAGAGAAGCAAGACCGCGAGGTGGAGCAAAACTCAGAAACAACGTCCCAGTT
CGGACTGCAGGCTGCAACTCGCCTGCACGAAGTCGGAATTGCTAGTAATCGTGGATC
AGCATGCCACGGTGAATACGTTCCCGGGCCTTGTACACACCGCCCGTCACACCATGA
GAGCCGGGGGACCCGAAGTCGGTAGTCTAACCGCAAGGAGGACGCCGCCGAAGGT
AAAACTGGTGATTGGGGTGAAGTCGTAACAAGGTAGCCGT |
| SEQ ID No. 16 | ATGGAGAGTTTGATCCTGGCTCAGGATGAACGCTAGCGGCAGGCTTAACACATGCAA
GTCGAGGGGCAGCATAATGGTAGTAATACTATTGATGGCGACCGGCGGACGGGTGCG
TAACGCGTATGCAACCTACCCCTTTACAGGGGATAACACTGAGAAATCGGTACTAATA
CCCCATAATATTCTGGGAGGCATCTTTCGGAGTTGAAAGCTTTGGTGGTAAAGGATGG
GCATGCGTTGTATTAGCTAGTTGGTAAGGTAACGGCTTACCAAGGCGACGATACATAG
GGGGACTGAGAGGTTAACCCCCCACATTGGTACTGAGACACGGACCAAACTCCTACG
GGAGGCAGCAGTGAGGAATATTGGTCAATGGACGGAAGTCTGAACCAGCCATGCCGC
GTGCAGGAAGACGGCTCTATGAGTTGTAAACTGCTTTTGTACGAGGGTAAACGCAGAT
ACGTGTATCTGCCTGAAAGTATCGTACGAATAAGGATCGGCTAACTCCGTGCCAGCAG
CCGCGGTAATACGGAGGATCCAAGCGTTATCCGGATTTATTGGGTTTAAAGGGTGCGT
AGGCGGTTTAGTAAGTCAGCGGTGAAATTTTGGTGCTTAACACCAAACGTGCCGTTGA
TACTGCTGGGCTAGAGAGTAGTTGCGGTAGGCGGAATGTATGGTGTAGCGGTGAAAT
GCTTAGAGATCATACAGAACACCGATTGCGAAGGCAGCTTACCAAACTATATCTGACG
TTGAGGCACGAAAGCGTGGGGAGCAAACAGGATTAGATACCCTGGTAGTCCACGCAG
TAAACGATGATAGCTCGTTGTCGGCGATACACAGTCGGTGACTAAGAGAAATCGATAA
GCTATCCACCTGGGGAGTACGTTCGCAAGAATGAAACTCAAAGGAATTGACGGGGGC
CCGCACAAGCGGAGGAACATGTGGTTTAATTCGATGATACGCGAGGAACCTTACCCG
GGCTTGAAAGTTACTGACGATTCTGGAAACAGGATTTCCCTTCGGGGCAGGAAACTAG
GTGCTGCATGGTTGTCGTCAGCTCGTGCCGTGAGGTGTCGGGTTAAGTCCCATAACG
AGCGCAACCCCTACTGATAGTTGCCATCAGAGCGTTTGAGCGATCAAACAAGCTGGGC
ACTCTATCGGGACTGCCGGTGTAAGCCGAGAGGAAGGTGGGGATGACGTCAAATCAG
CACGGCCCTTACGTCCGGGGCGACACACGTGTTACAATGGTAGGTACAGAGGGCAGC
CACCCAGTGATGGGGAGCGAATCTCGAAAGCCTATCTCAGTTCGGATTGGAGGCTGA
AACTCGCCTCCATGAAGTTGGATTCGCTAGTAATCGCATCAGCCATGGCGCGGTGA
ATACGTTCCCGGGCCTTGTACACACCGCCCGTCAAGCCATGGGAGTTGGGGTGCCT
GAAGTTCGTGACCGAAAGGAGCGACCTAGGGCAAAACCGATGACTGGGGCTAAGTCG
TAACAAGGTAGCCGTACCGGAAGGTGCGGCTGGAACACCTCCTTT |
| SEQ ID No. 17 | TTTAGAGTTTGATCCTGGCTCAGGATGAACGCTGGCGGCGTGCCTAACACATGCAA
GTCGAACGGAGTTATTTTGGAAATCTCTTCGGAGATGGAATTCATAACTTAGTGGCGG
ACGGGTGAGTAACGCGTGAGCAATCTGCCCTTAGGTGGGGGATAACAGCCGGAAACG
GCTGCTAATACCGCATAACACATTGAAGCCGCATGGTTTTGATGTCAAAGATTTATTGC
CTTTGGATGAGCTCGCGTCTGATTAGCTGGTTGGCGGGTAACGGCCCACCAAGGCG
ACGATCAGTAGCCGGACTGAGAGGTTGAACGGCCACATTGGGACTGAGACACGGCCC
AGACTCCTACGGGAGGCAGCAGTGGGGAATATTGCGCAATGGGGGAAACCCTGACGC
AGCAACGCCGCGTGATTGAAGAAGGCCTTCGGGTTGTAAAGATCTTTAATTGGGGACG
AAAAATGACGGTACCCAAAGAATAAGCTCCGGCTAACTACGTGCCAGCAGCCGCGGT |

TABLE 2-continued

Sequences

| SEQ ID | 16S rDNA Sequence |
|---|---|
| | AATACGTAGGGAGCAAGCGTTATCCGGATTTACTGGGTGTAAAGGGCGAGTAGGCGG<br>GCTGGCAAGTTGGGAGTGAAATCCCGGGGCTTAACCCCGGAACTGCTTTCAAAACTG<br>CTGGTCTTGAGTGATGGAGAGGCAGGCGGAATTCCGTGTGTAGCGGTGAAATGCGTA<br>GATATACGGAGGAACACCAGTGGCGAAGGCGGCCTGCTGGACATTAACTGACGCTGA<br>GGAGCGAAAGCGTGGGGAGCAAACAGGATTAGATACCCTGGTAGTCCACGCCGTAAA<br>CGATGGATACTAGGTGTGGGAGGTATTGACCCCTTCCGTGCCGGAGTTAACACAATAA<br>GTATCCCACCTGGGGAGTACGGCCGCAAGGTTGAAACTCAAAGGAATTGACGGGGGC<br>CCGCACAAGCAGTGGAGTATGTGGTTTAATTCGAAGCAACGCGAAGAACCTTACCAGG<br>TCTTGACATCCCTCTGACCGCCCTAGAGATAGGGTTTCCCTTCGGGGCAGAGGTGACA<br>GGTGGTGCATGGTTGTCGTCAGCTCGTGTCGTGAGATGTTGGGTTAAGTCCCGCAAC<br>GAGCGCAACCCTTACGGTTAGTTGATACGCAAGATCACTCTAGCCGGACTGCCGTTGA<br>CAAAACGGAGGAAGGTGGGGACGACGTCAAATCATCATGCCCCTTATGACCTGGGCT<br>ACACACGTACTACAATGGCAGTCATACAGAGGGAAGCAAAACAGTGATGTGGAGCAAA<br>TCCCTAAAAGCTGTCCCAGTTCAGATTGCAGGCTGCAACTCGCCTGCATGAAGTCGGA<br>ATTGCTAGTAATCGCGGATCAGCATGCCGCGGTGAATACGTTCCCGGGCCTTGTACAC<br>ACCGCCCGTCACACCATGAGAGCCGGTAATACCCGAAGTCCGTAGCCTAACCGCAAG<br>GAGGGCGCGGCCGAAGGTAGGACTGGTAATTAGGGTGAAGTCGTAACAAGGTAGCC<br>GTATCGGAAGGTGCGGCTGGATCACCTCCTTT |
| SEQ ID<br>No. 18 | ACGGAGAGTTTGATCCTGGCTCAGGATGAACGCTGGCGGCGTGCCTAACACATGCAA<br>GTCGAACGGTTAAGGCGCCTTCGGGCGCGAATAGAGTGGCGAACGGGTGAGTAACAC<br>GTGACCAACCTGCCCCCCTCCCGGGATAACGCGAGGAAACCCGCGCTAATACCGGA<br>TACTCCGCCCCTCCCGCATGGGAGGGCGGGAAAGCCCCGACGGAGGGGATGGG<br>GTCGCGGCCCATTAGGTAGACGGCGAGGCAACGCCCACCGTGCCTGCGATGGGTA<br>GCCGGGTTGAGAGACCGACCGGCCACATTGGGACTGAGATACGGCCCAGACTCCTAC<br>GGGAGGCAGCAGTGGGGAATTTTGCGCAATGGGGGAACCCTGACGCAGCAACGCC<br>GCGTGCGGGACGAAGGCCTTCGGGTTGTAAACCGCTTTCAGCAGGGAAGAAGTTGAC<br>GGTACCTGCAGAAGAAGCCCCGGCTAACTACGTGCCAGCAGCCGCGGTAATACGTAG<br>GGGGCGAGCGTTATCCGGATTCATTGGGCGTAAAGCGCGCGTAGGCGGCCCGTCAA<br>GeGGAACCTCTAACCCGAGGGCTCAACCCCCGGCCGGGTTCCGAACTGGCAGGCTC<br>GAGTTTGGTAGAGGAAGATGGAATTCCCGGTGTAGCGGTGGAATGCGCAGATATCGG<br>GAAGAACACCGATGGCGAAGGCAGTCTTCTGGGCCATCAACTGACGCTGAGGCGCGA<br>AAGCTGGGGGAGCGAACAGGATTAGATACCCTGGTAGTCCCAGCCGTAAACGATGGG<br>TGCTAGGTGTGGGGGATCATCCCTCCGTGCCGCAGCCAACGCATTAAGCACCCCGC<br>CTGGGGAGTACGGCCGCAAGGCTAAAACTCAAAGGAATTGACGGGGGCCCGCACAA<br>GCAGCGGAGCATGTGGCTTAATTCGAAGCAACGCGAAGAACCTTACCAGGGCTTGAC<br>ATGCTGGTGAAGCCGGGGAAACCCGGTGGCCGAGAGGAGCCAGCGCAGGTGGTGCA<br>TGGCTGTCGTCAGCTCGTGTCGTGAGATGTTGGGTTAAGTCCCGCAACGAGCGCAAC<br>CCCTGCCATATGTTGCCAGCATTCAGTTGGGGACTCATATGGGACTGCCGGCGTCAA<br>GCCGGAGGAAGGTGGGGACGACGTCAAGTCATCATGCCCTTTATGCCCTGGGCTGCA<br>CACGTGCTACAATGGCCGGTACAACGGGCCGCGACCTGGCGACAGGAAGCGAATCC<br>CTCAAAGCCGGCCCCAGTTCGGATCGGAGGCTGCAACCCGCCTCCGTGAAGTCGGA<br>GTTGCTAGTAATCGCGGATCAGCATGCCGCGGTGAATACGTTCCCGGGCCTTGTACA<br>CACCGCCCGTCACACCACCCGAGTCGTCTGCACCCGAAGCCGCCGGCCGAACCCGC<br>AAGGGGCGGAGGCGTCGAAGGTGTGGAGGGTAAGGGGGGTGAAGTCGTAACAAGGT<br>AGCCGTACCGGAAGGTGCGGCTGGATCACCTCCTTT |
| SEQ ID<br>No. 19 | TCAGAGAGTTTGATCCTGGCTCAGGATGAACGCTGGCGGCGTGCTTAACACATGCAA<br>GTCGAGCGAAGCACTTGCCATTGACTCTTCGGAAGATTTGGCATTTGACTGAGCGGCG<br>GACGGGTGAGTAACGCGTGGGTAACCTGCCTCATACAGGGGAATAACAGTTAGAAAT<br>GGCTGCTAATGCCGCATAAGCGCACAGGACCGCATGGTCTGGTGTGAAAAACTGAGG<br>TGGTATGAGATGGGCCCGCGTCTGATTAGGTAGTTGGCGGGTAACGGCCCACCAAG<br>CCGACGATCAGTAGCCGACCTGAGAGGGTGACCGGCCACATTGGGACTGAGACACG<br>GCCCAGACTCCTACGGGAGGCAGCAGTGGGGAATATTGCACAATGGAGGAAACTCTG<br>ATGCAGCGACGCCGCGTGAAGGAAGAAGTATCTCGGTATGTAAACTTCTATCAGCAGG<br>GAAGAAAATGACGGTACCTGACTAAGAAGCCCCGGCTAACTACGTGCCAGCAGCCGC<br>GGTAATACGTAGGGGGCAAGCGTTATCCGGATTTACTGGGTGTAAAGGGAGCGTAGA<br>CGGACGGGCAAGTCTGATGTGAAAGCCCGGGGCTTAACCCCGGGACTGCATTGGAAA<br>CTGTCCATCTTGAGTGCCGGAGAGGTAAGCGGAATTCCTAGTGTAGCGGTGAAATGC<br>GTAGATATTAGGAGGAACACCAGTGGCGAAGGCGGCTTACTGGACGGTAACTGACGT<br>TGAGGCTCGAAAGCGTGGGGAGCAAACAGGATTAGATACCCTGGTAGTCCACGCCGT<br>AAACGATGAATACTAGGTGTCGGGTTGCAAAGCAATCCGGTGCCGCAGCAAACGCAG<br>TAAGTATTCCACCTGGGGAGTACGTTCGCAAGAATGAAACTCAAAGGAATTGACGGGG<br>ACCCGCACAAGCGGTGGAGCATGTGGTTTAATTCGAAGCAACGCGAAGAACCTTACCA<br>AGTCTTGACATCTGCCTGACCGTTCCTTAACCGGAACTTTCCTTCGGGACAGGCAAGA<br>CAGGTGGTGCATGGTTGTCGTCAGCTCGTGTCGTGAGATGTTGGGTTAAGTCCCGCA<br>ACGAGCGCAACCCCTGTCCTTAGTAGCCAGCAGTCCGGCTGGGCACTCTAGGGAGAC<br>TGCCGGGGATAACCCGGAGGAAGGCGGGGACGACGTCAAATCATCATGCCCCTTATG<br>ATTTGGGCTACACACGTGCTACAATGGCGTAAACAAAGGGAAGCGGGAGTGGTGACAC<br>TGAGCAAATCTCAAAAATAACGTCCCAGTTCGGACTGCAGTCTGCAACTCGACTGCAC<br>GAAGCTGGAATCGCTAGTAATCGCGAATCAGAATGTCGCGGTGAATACGTTCCCGGGT<br>CTTGTACACACCGCCCGTCACACCATGGGAGTCAGTAACGCCCGAAGTCAGTGACCT<br>AACCGCAAGGGAGGAGCTGCCGAAGGCGGGACCGATAACTGGGGTGAAGTCGTAAC<br>AAGGTAGCCGTATCGGAAGGTGCGGCTGGATCACCTCCTTT |

TABLE 2-continued

Sequences

| SEQ ID | 16S rDNA Sequence |
|---|---|
| SEQ ID No. 20 | TTATGAGAGTTTGATCCTGGCTCAGGATGAACGCTGGCGGCGTGCTTAACACATGCAA<br>GTCGAACGAAGCATTTAAGACGGATTCTTTCGGGATGAAGACTTTTATGACTGAGTGG<br>CGGACGGGTGAGTAACGCGTGGGTAACCTGCCTCACACAGGGGGATAGCAGTTGGAA<br>ACGGCTGATAATACCGCATAAGCGCACAGTACCGCATGGTACAGTGTGAAAAACTCCG<br>GTGGTGTGAGATGGACCCGCGTCTGATTAGCTTGTTGGCAGGGTAACGGCCTACCAA<br>GGCAACGATCAGTAGCCGACCTGAGAGGGTGACCGGCCACATTGGGACTGAGACAC<br>GGCCCAGACTCCTACGGGAGGCAGCAGTGGGGAATATTGCACAATGGAGGAAACTCT<br>GATGCAGCGACGCCGCGTGAGTGAAGAAGTAATTCGTTATGTAAAGCTCTATCAGCAG<br>GGAAGATAGTGACGGTACCTGACTAAGAAGCTCCGGCTAAATACGTGCCAGCAGCCG<br>CGGTAATACGTATGGAGCAAGCGTTATCCGGATTTACTGGGTGTAAAGGGAGTGTAGG<br>TGGCATCACAAGTCAGAAGTGAAAGCCCGGGGCTCAACCCCGGGACTGCTTTTGAAA<br>CTGTGGAGCTGGAGTGCAGGAGAGGCAAGTGGAATTCCTAGTGTAGCGGTGAAATGC<br>GTAGATATTAGGAGGAACACCAGTGGCGAAGGCGGCTTGCTGGACTGTAACTGACAC<br>TGAGGCTCGAAAGCGTGGGGAGCAAACAGGATTAGATACCCTGGTAGTCCACGCCGT<br>AAACGATGAATACTAGGTGTCGGGGCTCATAAGAGCTTCGGTGCCGCAGCAAACGCA<br>ATAAGTATTCCACCTGGGGAGTACGTTCGCAAGAATGAAACTCAAAGGAATTGACGGG<br>GACCCGCACAAGCGGTGGAGCATGTGGTTTAATTCGAAGCAACGCGAAGAACCTTAC<br>CAAGTCTTGACATCCTCTTGCCCGGTCAGTAATGTGACCTTTTCTTCGGAACAAGAGTG<br>ACAGGTGGTGCATGGTTGTCGTCAGCTCGTGTCGTGAGATGTTGGGTTAAGTCCCGC<br>AACGAGCGCAACCCCTATTCTTAGTAGCCAGCATATAAGGTGGGCACTCTAGGAAGAC<br>TGCCAGGGATAACCTGGAGGAAGGTGGGGATGACGTCAAATCATCATGCCCCTTATG<br>ACTTGGGCTACACACGTGCTACAATGGCGTAAACAAAGTGAAGCGAGAGTGTGAGCTT<br>AAGCAAATCACAAAAATAACGTCTCAGTTCGGATTGTAGTCTGCAACTCGACTACATGA<br>AGCTGGAATCGCTAGTAATCGCGAATCAGAATGTCGCGGTAATACGTTCCCGGGTCT<br>TGTACACACCGCCCGTCACACCATGGGAGTCGGAAATGCCCGAAGTCGGTGACCTAA<br>CGAAAGAAGGAGCCGCCGAAGGCAGGTCTGATAACTGGGGTGAAGTCGTAACAAGGT<br>AGCCGTATCGGAAGGTGCGGCTGGATCACCTCCTTT |
| SEQ ID NO. 21 | AGAGAGTTTGATCCTGGCTCAGGATGAACGCTGGCGGCGTGCCTAACACATGCAAGT<br>CGAACGGAGTTATGCAGAGGAAGTTTTCGGATGGAATCGGCGTAACTTAGTGGCGGA<br>CGGGTGAGTAACGCGTGGGAAACCTGCCCTGTACCGGGGATAACACTTAGAAATAG<br>GTGCTAATACCGCATAAGCGCACAGCTTCACATGARGCAGTGTGAAAAACTCCGGTGG<br>TACAGGATGGTCCCGCGTCTGATTAGCCAGTTGGCAGGGTAAYGGCCTACCAAAGCG<br>ACGATCAGTAGCCGGCCTGAGAGGGTGAACGGCCACATTGGGACTGAGACACGCC<br>CAAACTCCTACGGGAGGCAGCAGTGGGGAATATTGCACAATGGGGGAAACCCTGATG<br>CAGCGACGCCGCGTGAGTGAAGAAGTATTTCGGTATGTAAAGCTCTATCAGCAGGGAA<br>GAAAATGACGGTACCTGACTAAGAAGCCCCGGCTAACTACGTGCCAGCAGCCGCGGT<br>AATACGTAGGGGGCAAGCGTTATCCGGATTTACTGGGTGTAAAGGGAGCGTAGACGG<br>CATGACAAGCCAGATGTGAAAACCCAGGGCTCAACCCTGGGACTGCATTTGGAACTG<br>CCAGGCTGGAGTGCAGGAGAGGTAAGCGGAATTCCTAGTGTAGCGGTGAAATGCGTA<br>GATATTAGGAGGAACACCAGTGGCGAAGGCGGCTTACTGGACTGTAACTGACGTTGA<br>GGCTCGAAAGCGTGGGGAGCAAACAGGATTAGATACCCTGGTAGTCCACGCCGGTAAA<br>CGATGATTGCTAGGTGTAGGTGGGTATGGACCCATCGGTGCCGCAGCTAACGCAATA<br>AGCAATCCACCTGGGGAGTACGTTCGCAAGAATGAAACTCAAAGGAATTGACGGGGA<br>CCCGCACAAGCGGTGGAGCATGTGGTTTAATTCGAAGCAACGCGAAGAACCTTACCAA<br>GTCTTGACATCCCAATGACGTGTCCGTAACGGGGCATTCTCTTCGGAGCATTGGAGAC<br>AGGTGGTGCATGGTTGTCGTCAGCTCGTGTCGTGAGATGTTGGGTTAAGTCCCGCAA<br>CGAGCGCAACCCTTATCCTTAGTAGCCAGCAGGTARAGCTGGGCACTCTAGGGAGAC<br>TGCCGGGGATAACCCGGAGGAAGGCGGGGAYGACGTCAAATCATCATGCCCCTTATG<br>ATTTGGGCTACACACGTGCTACAATGGCGTAAACAAAGGGAAGCGAGACAGTGATGT<br>GAGCAAATCCCAGAAATAACGTCTCAGTTCGGATTGTAGTCTGCAACTCGACTACATG<br>AAGCTGGAATCGCTAGTAATCGCGAATCAGCATGTCGCGGTGAATACGTTCCCGGGTC<br>TTGTACACACCGCCCGTCACACCATGGGAGTTGGAAATGCCCGAAGCCTGTGACCTAA<br>CCGCAAGGGAGGAGCAGTCGAAGGCAGGTCTAATAACTGGGGTGAAGTCGTAACAAG<br>GTAGCCGTATCGGAAGGTGCGGCTGGATCACCTCCTTT |
| SEQ ID NO. 22 | TTTAGAGAGTTTGATCCTGGCTCAGGATGAACGCTGGCGGCGTGCCTAACACATGCAA<br>GTCGAACGGAGTTATTTTGGAAATCTCTTCGGGGATGGAATTCATAACTTAGTGGCGG<br>ACGGGTGAGTAACGCGTGAGCAATCTGCCCTTAGGTGGGGGATAACAGCCGGAAACG<br>GCTGCTAATACCGCATAACACATTGAAGCCGCATGGTTTTGATGTCAAAGATTTATTGC<br>CTTTGGATGAGCTCGCGTCTGATTAGCTGGTTGGCGGGTAACGGCCCACCAAGGCG<br>ACGATCAGTAGCCGGACTGAGAGGTTGAACGGCCACATTGGGACTGAGACACGGCCC<br>AGACTCCTACGGGAGGCAGCAGTGGGGAATATTGCACAATGGGGGAAACCCTGACGC<br>AGCAACGCCGCGTGATTGAAGAAGGCCTTCGGGTTGTAAAGATCTTTAATTGGGGACG<br>AAWWWTGACGGTACCCAAAGAATAAGCTCCGGCTAACTACGTGCCAGCAGCCGCGG<br>TAATACGTAGGGAGCAAGCGTTATCCGGATTTACTGGGTGTAAAGGGCGAGTAGGCG<br>GCTGGCAAGTTGGGAGTGAAATCCCGGGGCTTAACCCCGGAACTGCTTTCAAAACT<br>GCTGGTCTTGAGTGATGGAGAGGCAGGCGGAATTCCGTGTGTAGCGGTGAAATGCGT<br>AGATATACGGAGGAACACCAGTGGCGAAGGCGGCCTGCTGGACATTAACTGACGCTG<br>AGGAGCGAAAGCGTGGGGAGCAAACAGGATTAGATACCCTGGTAGTCCACGCCGTAA<br>ACGATGGATACTAGGTGTGGGAGGTATTGACCCCTTCCGTGCCGGAGTTAACACAATA<br>AGTATCCCACCTGGGGAGTACGACCGCAAGGTTGAAACTCAAAGGAATTGACGGGGG<br>CCCGCACAAGCAGTGGAGTATGTGGTTTAATTCGAAGCAACGCGAAGAACCTTACCAG<br>GTCTTGACATCCCTCTGACCGCCCTAGAGATAGGGTTTCCCTTCGGGGCAGAGGTGA<br>CAGGTGGTGCATGGTTGTCGTCAGCTCGTGTCGTGAGATGTTGGGTTAAGTCCCGCA<br>ACGAGCGCAACCCTTACGGTTAGTTGATACGAAAGATCACTCTAGCCGGACTGCCGTT |

TABLE 2-continued

Sequences

| SEQ ID | 16S rDNA Sequence |
|---|---|
| | GACAAAACGGAGGAAGGTGGGGACGACGTCAAATCATCATGCCCCTTATGACCTGGG<br>CTACACACGTACTACAATGGCAGTCATACAGAGGGAAGCAAAACAGTGATGTGGAGCA<br>AATCCCTAAAAGCTGTCCCAGTTCAGATTGCAGGCTGCAACTCGCCTGCATGAAGTCG<br>GAATTGCTAGTAATCGCGGATCAGCATGCCGCGGTGAATACGTTCCCGGGCCTTGTAC<br>ACACCGCCCGTCACACCATGAGAGCCGGTAATACCCGAAGTCCGTAGCCTAACCGCA<br>AGGAGGGCGCGGCCGAAGGTAGGACTGGTAATTAGGGTGAAGTCGTAACAAGGTAGC<br>CGTATCGGAAGGTGCGGCTGGATCACCTCCTTT |
| SEQ ID NO. 23 | ACGGAGAGTTTGATCCTGGCTCAGGATGAACGCTGGCGGCGTGCCTAACACATGCAA<br>GTCGAACGGTTAAGGCGCCTTCGGGCGCGAATAGAGTGGCGAACGGGTGAGTAACAC<br>GTGACCAACCTGCCCCCCTCCCCGGGATAACGCGAGGAAACCCGCGCTAATACCGGA<br>TACTCCGCCCCTCCCGCATGGGAGGGGCGGGAAAGCCCCGACGGAGGGGATGGG<br>GTCGCGGCCCATTAGGTAGACGGCGGGGCAACGGCCCACCGTGCCTGCGATGGGTA<br>GCCGGGTTGAGAGACCGACCGGCCACATTGGGACTGAGATACGGCCCAGACTCCTAC<br>GGGAGGCAGCAGTGGGGAATTTTGCGCAATGGGGGGAACCCTGACGCAGCAACGCC<br>GCGTGCGGGACGAAGGCCTTCGGGTTGTAAACCGCTTTCAGCAGGGAAGAAGTTGAC<br>GGTACCTGCAGAAGAAGCCCCGGCTAACTACGTGCCAGCAGCCGCGGTAATACGTAG<br>GGGGCGAGCGTTATCCGGATTCATTGGGCGTAAAGCGCGCGTAGGCGGCCCGTCAA<br>GCGGAACCTCTAACCCGAGGGCTCAACCCCCGGCCGGGTTCCGAACTGGCAGGCTC<br>GAGTTTGGTAGAGGAAGATGGAATTCCCGGTGTAGCGGTGGAATGCGCAGATATCGG<br>GAAGAACACCGATGGCGAAGGCAGTCTTCTGGGCCATCAACTGACGCTGAGGCGCGA<br>AAGCTGGGGGAGCGAACAGGATTAGATACCCTGGTAGTCCCAGCCGTAAACGATGGG<br>YGCTAGGTGTGGGGGGATCATCCCTCCGTGCCGCAGCCAACGCATTAAGCRCCCCGC<br>CTGGGGAGTACGGCCGCAAGGCTAAAACTCAAAGGAATTGACGGGGGCCCGCACAA<br>GCAGCGGAGCATGTGGCTTAATTCGAAGCAACGCGAAGAACCTTACCAGGGCTTGAC<br>ATGCTGGTGAAGCGGGGAAACCCGGTGGCCGAGAGGAGCCAGCGCAGGTGGTGCA<br>TGGCTGTCGTCAGCTCGTGTCGTGAGATGTTGGGTTAAGTCCCGCAACGAGCGCAAC<br>CCCTGCCATATGTTGCCAGCATTCAGTTGGGGACTCATATGGGACTGCCGGCGTCAA<br>GCCGGAGGAAGGTGGGGACGACGTCAAGTCATCATGCCCTTTATGCCCTGGGCTGCA<br>CACGTGCTACAATGGCCGGTACAACGGGCCGCGACCTGGCGACAGGAAGCGAATCC<br>CTCAAAGCCGGCCCCAGTTCGGATCGGAGGCTGCAACCCGCCTCCGTGAAGTCGGA<br>GTTGCTAGTAATCGCGGATCAGCATGCCGCGGTGAATACGTTCCCGGGCCTTGTACA<br>CACCGCCCGTCACACCACCCGAGTCGTCTGCACCCGAAGCCGCCGGCCGAACCCGC<br>AAGGGGCGGAGGCGTCGAAGGTGTGGAGGGTAAGGGGGGTGAAGTCGTAACAAGGT<br>AGCCGTACCGGAAGGTGCGGCTGGATCACCTCCTTT |
| SEQ ID NO. 24 | ATGGAGAGTTTGATCCTGGCTCAGGATGAACGCTGGCGGCATGCCTAATACATGCAAG<br>TCGAACGAAGTCTTTAGGAAGCTTGCTTCCAAAGAGACTTAGTGGCGAACGGGTGAGT<br>AACACGTAGGTAACCTGCCCATGTGCCCGGGATAACTGCTGGAAACGGTAGCTAAAAC<br>CGGATAGGTATGAGGGAGGCATCTTCCTCATATTAAAGCACCTTCGGGTGTGAACATG<br>GATGGACCTGCGGCGCATTAGCTGGTTGGTGAGGTAACGGCCCACCAAGGCGATGAT<br>GCGTAGCCGACCTGAGAGGGTGAACGGCCACATTGGGACTGAGACACGGCCCAAACT<br>CCTACGGGAGGCAGCAGTAGGGAATTTTCGTCAATGGGGGGAACCCTGAACGAGCAA<br>TGCCGCGTGTGTGAAGAAGGTCTTCGGATCGTAAAGCACTGTTGTAAGTGAAGAATGC<br>CATATAGAGGAAATGCTATGTGGGTGACGGTAGCTTACCAGAAAGCCACGGCTAACTA<br>CGTGCCAGCAGCCGCGGTAATACGTAGGTGGCAAGCGTTATCCGGAATCATTGGGC<br>TAAAGGGTGCGTAGGTGGCACGATAAGTCTGAAGTAAAAGGCAACAGCTCAACTGTTG<br>TATGCTTTGGAAACTGTCGAGCTAGAGTGCAGAAGAGGGCGATGGAATTCCATGTGTA<br>GCGGTAAAATGCGTAGATATATGGAGGAACACCAGTGGCGAAGGCGGTCGCCTGGTC<br>TGTAACTGACACTGATGCACGAAAGCGTGGGGAGCAAATAGGATTAGATACCCTAGTA<br>GTCCACGCCGTAAACGATGAGAACTAAGTGTTGGAGAGATTCAGTGCTGCAGTTAACG<br>CAATAAGTTCTCCGCCTGGGGAGTATGCACGCAAGTGTGAAACTCAAAGGAATTGACG<br>GGGGCCCGCACAAGCGGTGGAGTATGTGGTTTAATTCGAAGCAACGCGAAGAACCTT<br>ACCAGGCCTTGACATGGATATAAATGTTCTAGAGATAGAAAGATAGCTATATATCACAC<br>AGGTGGTGCATGGTTGTCGTCAGCTCGTGTCGTGAGATGTTGGGTTAAGTCCCGCAA<br>CGAGCGCAACCCTTGTCTTCGTTACCAGCATTAAGTTGGGGACTCAGGAGAGACTGC<br>CGGTGACAAACGGAGGAAGGTGGGGATGACGTCAAATCATCATGCCCCTTATGGCC<br>TGGGCTACACACGTACTACAATGGCGCCTACAAAGAGCAGCACCGCGAGGTGGA<br>GCGAATCTCATAAAGGGCGTCTCAGTTCGGATTGAAGTCTGCAACTCGACTTCATGAA<br>GTCGGAATCGCTAGTAATCGCAGATCAGCATGCTGCGGTGAATACGTTCTCGGGCCTT<br>GTACACACCGCCCGTCAAACCATGGGAGTTGGTAATACCCGAAGCCGGTGGCATAAC<br>CGCAAGGAGTGAGCCGTCGAAGGTAGGACCGATGACTGGGGTTAAGTCGTAACAAGG<br>TATCCCTACGGGAACGTGGGGATGGATCACCTCCTTT |
| SEQ ID NO. 25 | TCAGAGAGTTTGATCCTGGCTCAGGATGAACGCTGGCGGCGTGCTTAACACATGCAA<br>GTCGAGCGAAGCRCTTRARYGGATCTCTTCGGATTGAAARYTTWTKTGACTGAGCGGC<br>GGACGGGTGAGTAACGCGTGGGTAACCTGCCTCATACAGGGGGATAACAGTTAGAAA<br>TGGCTGCTAATACCGCATAAGCGCACAGGACCGCATGGTCTGGTGTGAAAAACTCCG<br>GTGGTATGAGATGGACCCGCGTCTGATTAGCTAGTTGGAGGGGTAACGGCCCACCAA<br>GGCGACGATCAGTAGCCGGCCTGAGAGGGTGAACGGCCACATTGGGACTGAGACAC<br>GGCCCAGACTCCTACGGGAGGCAGCAGTGGGGAATATTGCACAATGGGGGAAACCCT<br>GATGCAGCGACGCCGCGTGAAGGAAGAAGTATCTCGGTATGTAAACTTCTATCAGCAG<br>GGAAGAAAATGACGGTACCTGACTAAGAAGCCCCGGCTAACTACGTGCCAGCAGCCG<br>CGGTAATACGTAGGGGGCAAGCGTTATCCGGATTTACTGGGTGTAAAGGGAGCGTAG<br>ACGGAAGAGCAAGTCTGATGTGAAAGGCTGGGGCTTAACCCCAGGACTGCATTGGAA<br>ACTGTTTTTCTAGAGTGCCGGAGAGGTAAGCGGAATTCCTAGTGTAGCGGTGAAATGC |

TABLE 2-continued

Sequences

| SEQ ID | 16S rDNA Sequence |
|---|---|
| | GTAGATATTAGGAGGAACACCAGTGGCGAAGGCGGCTTACTGGACGGTAACTGACGT<br>TGAGGCTCGAAAGCGTGGGGAGCAAACAGGATTAGATACCCTGGTAGTCCACGCCGT<br>AAACGATGAATACTAGGTGTCGGGTGGCAAAGCCATTCGGTGCCGCAGCAAACGCAA<br>TAAGTATTCCACCTGGGGAGTACGTTCGCAAGAATGAAACTCAAAGGAATTGACGGGG<br>ACCCGCACAAGCGGTGGAGCATGTGGTTTAATTCGAAGCAACGCGAAGAACCTTACCA<br>AGTCTTGACATCCCTCTGACCGGCCCGTAACGGGGCCTTCCCTTCGGGGCAGAGGAG<br>ACAGGTGGTGCATGGTTGTCGTCAGCTCGTGTCGTGAGATGTTGGGTTAAGTCCCGC<br>AACGAGCGCAACCCCTATCCTTAGTAGCCAGCAGGTRRAGCTGGGCACTCTAGGGAG<br>ACTGCCGGGGATAACCCGGAGGAAGGCGGGGACGACGTCAAATCATCATGCCCCTTA<br>TGATTTGGGCTACACACGTGCTACAATGGCGTAAACAAAGGGAAGCGAGACAGCGAT<br>GTTGAGCAAATCCCAAAAATAACGTCCCAGTTCGGACTGCAGTCTGCAACTCGACTGC<br>ACGAAGCTGGAATCGCTAGTAATCGCGAATCAGAATGTCGCGGTGAATACGTTCCCGG<br>GTCTTGTACACACCGCCCGTCACACCATGGGAGTCAGTAACGCCCGAAGTCAGTGAC<br>CCAACCTTAYAGGAGGGAGCTGCCGAAGGCGGGACCGATAACTGGGGTGAAGTCGTA<br>ACAAGGTAGCCGTATCGGAAGGTGCGGCTGGATCACCTCCTTT |
| SEQ ID NO. 26 | CGAAGAGTTTGATCCTGGCTCAGGATGAACGCTAGCGACAGGCCTAACACATGCAAGT<br>CGAGGGGCAGCGGRGAGGYAGCAATACCTTTGCCGGCGACCGGCGCACGGGTGAGT<br>AACACGTATGCAATCCACCTGTAACAGGGGGATAACCCGGAGAAATCCGGACTAATAC<br>CCCATAATATGGGCGCTCCGCATGGAGRGTCCATTAAAGAGAGCAATTTTGGTTACAG<br>ACGAGCATGCGCTCCATTAGCCAGTTGGCGGGGTAACGGCCCACCAAAGCGACGATG<br>GATAGGGGTTCTGAGAGGAAGGTCCCCCACATTGGAACTGAGACACGGTCCAAACTC<br>CTACGGGAGGCAGCAGTGAGGAATATTGGTCAATGGTCGGCAGACTGAACCAGCCAA<br>GTCGCGTGAGGGAAGACGGCCCTACGGGTTGTAAACCTCTTTTGTCGGAGAGTAAAG<br>TRCGCTACGTGTAGYGTATTGCAAGTATCCGAAGAAAAAGCATCGGCTAACTCCGTGC<br>CAGCAGCCGCGGTAATACGGAGGATGCGAGCGTTATCCGGATTTATTGGGTTTAAAG<br>GGTGCGTAGGCGGCACGCCAAGTCAGCGGTGAAATTTCCGGGCTCAACCCGGACTGT<br>GCCGTTGAAACTGGCGAGCTAGAGTGCACAAGAGGCAGGCGGAATGCGTGGTGTAG<br>CGGTGAAATGCATAGATATCACGCAGAACCCCGATTGCGAAGGCAGCCTGCTAGGGT<br>GCGACAGACGCTGAGGCACGAAAGCGTGGGTATCGAACAGGATTAGATACCCTGGTA<br>GTCCACGCAGTAAACGATGAATACTAACTGTTTGCGATACAATGTAAGCGGTACAGCG<br>AAAGCGTTAAGTATTCCACCTGGGGAGTACGCCGGCAACGGTGAAACTCAAAGGAATT<br>GACGGGGGCCCGCACAAGCGGCGGAGGAACATGTGGTTTAATTCGATGATACGCGAGGAA<br>CCTTACCCGGGCTCAAACGCAGGGGAATGCCGGTGAAAGTCGGCAGCTAGCAATAG<br>TCACCTGCGAGGTGCTGCATGGTTGTCGTCAGCTCGTGCCGTGAGGTGTCGGCTTAA<br>GTGCCATAACGAGCGCAACCCCTATGGACAGTTACTAACGGGTGAAGCCGAGGACTC<br>TGTCTAGACTGCCGGCGCAAGCCGCGAGGAAGGTGGGGATGACGTCAAATCAGCAC<br>GGCCCTTACGTCCGGGGCGACACACGTGTTACAATGGCAGGTACAGAAGGCAGCCAG<br>TCAGCAATGACGCGCGAATCCCGAAAACCTGTCTCAGTTCGGATTGGAGTCTGCAACC<br>CGACTCCATGAAGCTGGATTCGCTAGTAATCGCGCATCAGCCATGCGCGGTGAATA<br>CGTTCCCGGGCCTTGTACACACCGCCCGTCAAGCCATGGAAGCCGGGAGTACCTGAA<br>GCATGCAACCGCAAGGAGCGTACGAAGGTAATACCGGTAACTGGGGCTAAGTCGTAA<br>CAAGGTAGCCGTACCGGAAGGTGCGGCTGGAACACCTCCTTT |
| SEQ ID NO. 27 | TCAGAGAGTTTGATCCTGGCTCAGGATGAACGCTGGCGGCGTGCTTAACACATGCAA<br>GTCGAGCGAAGCACTTRYYATTGAMTCTTCGGARGATTTRGCATKTGACTGAGCGGCG<br>GACGGGTGAGTAACGCGTGGGTAACCTGCCTCATACAGGGGAATAACAGTTAGAAAT<br>GGCTGCTAATGCCGCATAAGCGCACAGGRCCGCATGGTCYGGTGTGAAAAACTSMGG<br>TGGTATGAGATGGRCCCGCGTCTGATTAGGTAGTTGGCGGGGTAACGGCCCACCAAG<br>CCGACGATCAGTAGCCGACCTGAGAGGGTGACCGGCCACATTGGGACTGAGACACG<br>GCCCAGACTCCTACGGGAGGCAGCAGTGGGGAATATTGCACAATGGAGGAAACTCTG<br>ATGCAGCGACGCCGCGTGAAGGAAGAAGTATCTCGGTATGTAAACTTCTATCAGCAGG<br>GAAGAAAATGACGGTACCTGACTAAGAAGCCCCGGCTAACTACGTGCCAGCAGCCGC<br>GGTAATACGTAGGGGGCAAGCGTTATCCGGATTTACTGGGTGTAAAGGGAGCGTAGA<br>CGGACGGGCAAGTCTGATGTGAAAGCCCGGGGCTTAACCCCGGGACTGCATTGGAAA<br>CTGTCCATCTTGAGTGCCGGAGAGGTAAGCGGAATTCCTAGTGTAGCGGTGAAATGC<br>GTAGATATTAGGAGGAACACCAGTGGCGAAGGCGGCTTACTGGACGGTAACTGACGT<br>TGAGGCTCGAAAGCGTGGGGAGCAAACAGGATTAGATACCCTGGTAGTCCACGCCGT<br>AAACGATGAATACTAGGTGTCGGGTTGCAAAGCAATCCGGTGCCGCAGCAAACGCAG<br>TAAGTATTCCACCTGGGGAGTACGTTCGCAAGAATGAAACTCAAAGGAATTGACGGGG<br>ACCCGCACAAGCGGTGGAGCATGTGGTTTAATTCGAAGCAACGCGAAGAACCTTACCA<br>AGTCTTGACATCTGCCTGACCGTTCCTTAACCGGAACTTTCCTTCGGGACAGGCAAGA<br>CAGGTGGTGCATGGTTGTCGTCAGCTCGTGTCGTGAGATGTTGGGTTAAGTCCCGCA<br>ACGAGCGCAACCCCTGTCCTTAGTAGCCAGCAGTCCGGCTGGGCACTCTAGGGAGAC<br>TGCCGGGGATAACCCGGAGGAAGGCGGGGACGACGTCAAATCATCATGCCCCTTATG<br>ATTTGGGCTACACACGTGCTACAATGGCGTAAACAAAGGGAAGCGGAGTGGTGACAC<br>TGAGCAAATCTCAAAAATAACGTCCCAGTTCGGACTGCAGTCTGCAACTCGACTGCAC<br>GAAGCTGGAATCGCTAGTAATCGCGAATCAGAATGTCGCGGTGAATACGTTCCCGGGT<br>CTTGTACACACCGCCCGTCACACCATGGGAGTCAGTAACGCCCGAAGTCAGTGACCT<br>AACCGCAAGGGAGGAGCTGCCGAAGGCGGGACCGATAACTGGGGTGAAGTCGTAAC<br>AAGGTAGCCGTATCGGAAGGTGCGGCTGGATCACCTCCTTT |
| SEQ ID NO. 28 | TTATGAGAGTTTGATCCTGGCTCAGGATGAACGCTGGCGGCGTGCTTAACACATGCAA<br>GTCGAACGAAGCATTTGMGACRGATTYYTTCGGRWTGAAGACTTTTATGACTGAGTGG<br>CGGACGGGTGAGTAACGCGTGGGTAACCTGCCTCACACAGGGGGATAGCAGTTGGAA<br>ACGGCTGATAATACCGCATAAGCGCACAGTACCGCATGGTACAGTGTGAAAAACTCCG |

TABLE 2-continued

Sequences

| SEQ ID | 16S rDNA Sequence |
|---|---|
| | GTGGTGTGAGATGGACCCGCGTCTGATTAGCTTGTTGGCRGGGTAACGGCCYACCAA<br>GGCAACGATCAGTAGCCGACCTGAGAGGGTGACCGGCCACATTGGGACTGAGACAC<br>GGCCCAGACTCCTACGGGAGGCAGCAGTGGGGAATATTGCACAATGGAGGAAACTCT<br>GATGCAGCGACGCCGCGTGAGTGAAGAAGTAATTCGTTATGTAAAGCTCTATCAGCAG<br>GGAAGATAGTGACGGTACCTGACTAAGAAGCTCCGGCTAAATACGTGCCAGCAGCCG<br>CGGTAATACGTATGGAGCAAGCGTTATCCGGATTTACTGGGTGTAAAGGGAGTGTAGG<br>TGGCATCACAAGTCAGAAGTGAAAGCCCGGGGCTCAACCCCGGGACTGCTTTTGAAA<br>CTGTGTGGAGCTGGAGTGCAGGAGAGGCAAGTGGAATTCCTAGTGTAGCGGTGAAATGC<br>GTAGATATTAGGAGGAACACCAGTGGCGAAGGCGGCTTGCTGGACTGTAACTGACAC<br>TGAGGCTCGAAAGCGTGGGGAGCAAACAGGATTAGATACCCTGGTAGTCCACGCCGT<br>AAACGATGAATACTAGGTGTCGGGGCTCATAAGAGCTTCGGTGCCGCAGCAAACGCA<br>ATAAGTATTCCACCTGGGGAGTACGTTCGCAAGAATGAAACTCAAAGGAATTGACGGG<br>GACCCGCACAAGCGGTGGAGCATGTGGTTTAATTCGAAGCAACGCGAAGAACCTTAC<br>CAAGTCTTGACATCCTCTTGRCCGGTCAGTAATGTGRYCTTTTCTTCGGAACAAGAGTG<br>ACAGGTGGTGCATGGTTGTCGTCAGCTCGTGTCGTGAGATGTTGGGTTAAGTCCCGC<br>AACGAGCGCAACCCCTATTCTTAGTAGCCAGCATTTAAGRTGGGCACTCTAGGAAGAC<br>TGCCAGGGATAACCTGGAGGAAGGTGGGGATGACGTCAAATCATCATGCCCCTTATG<br>ACTTGGGCTACACACGTGCTACAATGGCGTAAACAAAGTGAAGCGAGAGTGTGAGCTT<br>AAGCAAATCACAAAAATAACGTCTCAGTTCGGATTGTAGTCTGCAACTCGACTACATGA<br>AGCTGGAATCGCTAGTAATCGCGAATCAGAATGTCGCGGTGAATACGTTCCCGGGTCT<br>TGTACACACCGCCCGTCACACCATGGGAGTCGGAAATGCCCGAAGTCGGTGACCTAA<br>CGAAAGAAGGAGCCGCCGAAGGCAGGTCTGATAACTGGGGTGAAGTCGTAACAAGGT<br>AGCCGTATCGGAAGGTGCGGCTGGATCACCTCCTTT |
| SEQ ID<br>NO. 29 | ATGAGAGTTTGATCCTGGCTCAGGATGAACGCTGGCGGCGTGCTTAACACATGCAAGT<br>CGAACGAAGCACTCTATTTGATTTTCTTCGGRAATGAAGATTTTGTGACTGAGTGGCGG<br>ACGGGTGAGTAACGCGTGGGTAACCTGCCTCATACAGGGGGATAACAGTTGGAAACG<br>ACTGCTAATACCGCATAAGCGCACAGGATYGCATGRTCCGGTGTGAAAAACTCCGGTG<br>GTATGRGATGGACCCGCGTCTGATTAGCCAGTTGGCAGGGTAACGGCCTACCAAAGC<br>GACGATCAGTAGCCGACCTGAGAGGGTGACCGGCCACATTGGGACTGAGACACGGC<br>CCAAACTCCTACGGGAGGCAGCAGTGGGGAATATTGCACAATGGGGGAAACCCTGAT<br>GCAGCGACGCCGCGTGAGCGAAGAAGTATTTCGGTATGTAAAGCTCTATCAGCAGGG<br>AAGAAGAATGACGGTACCTGACTAAGAAGCACCGGCTAAATACGTGCCAGCAGCCGC<br>GGTAATACGTATGGTGCAAGCGTTATCCGGATTTACTGGGTGTAAAGGGAGCGCAGG<br>CGGTGCGGCAAGTCTGATGTGAAAGCCCGGGGCTCAACCCCGGTACTGCATTGGAAA<br>CTGTCGTACTAGAGTGTCGGAGGGGTAAGTGGAATTCCTAGTGTAGCGGTGAAATGC<br>GTAGATATTAGGAGGAACACCAGTGGCGAAGGCGGCTTACTGGACGATAACTGACGC<br>TGAGGCTCGAAAGCGTGGGGAGCAAACAGGATTAGATACCCTGGTAGTCCACGCCGT<br>AAACGATGAATACTAGGTGTCGGGGAGCATTGCTCTTCGGTGCCGCAGCAAACGCAAT<br>AAGTATTCCACCTGGGGAGTACGTTCGCAAGAATGAAACTCAAAGGAATTGACGGGGA<br>CCCGCACAAGCGGTGGAGCATGTGGTTTAATTCGAAGCAACGCGAAGAACCTTACCAA<br>GTCTTGACATCCCGATGACAGAGTATGTAATGTASYYTCYCTTCGGRGCATCGGTGAC<br>AGGTGGTGCATGGTTGTCGTCAGCTCGTGTCGTGAGATGTTGGGTTAAGTCCCGCAA<br>CGAGCGCAACCCCTGTYCTTAGTAGCCAGCGGTTCGGCCGGGCACTCTAGGGAGACT<br>GCCAGGGATAACCTGGAGGAAGGCGGGGATGACGTCAAATCATCATGCCCCTTATGA<br>CTTGGGCTACACACGTGCTACAATGGCGTAAACAAAGGGAAGCRRAGCCGTGAGGCC<br>GAGCAAATCTCAAAAATAACGTCTCAGTTCGGACTGTAGTCTGCAACCCGACTACACG<br>AAGCTGGAATCGCTAGTAATCGCAGATCAGAATGCTGCGGTGAATACGTTCCCGGGTC<br>TTGTACACACCGCCCGTCACACCATGGGAGTTGGAAATGCCCGAAGTCAGTGACCCA<br>ACCGCAAGGAGGGAGCTGCCGAAGGCAGGTTCGATAACTGGGGTGAAGTCGTAACAA<br>GGTAGCCGTATCGGAAGGTGCGGCTGGATCACCTCCTTT |

TABLE 3

| No | Taxonomy | 16S rDNA sequence identifier | Consortium |||||||||| |
|---|---|---|---|---|---|---|---|---|---|---|---|---|
| | | | 1 | 2 | 3 | 4 | 5 | 6 | 7 | 8 | 9 | 10 |
| B1 | *Eisenbergiella sp.* | SEQ ID No. 1 | X | X | X | X | X | X | X | X | X | X |
| B2 | *Butyricicoccus sp.* | SEQ ID No. 2 | X | X | X | X | | X | X | X | X | X |
| B3 | *Clostridiales sp.* | SEQ ID No. 3 | X | X | X | X | | | | | | X |
| B4 | *Alistipes obesi* | SEQ ID No. 4 | X | X | | | | | | | | |
| B5 | *Alistipes indistinctus* | SEQ ID No. 5 | X | X | | | | | | | | X |
| B6 | *Gordonibacter urolithinfaciens* | SEQ ID No. 6 | X | X | X | X | | | | | | |
| B7 | *Faecalitalea sp.* | SEQ ID No. 7 | X | X | X | X | X | X | X | | | X |
| B8 | *Blautia sp.* | SEQ ID No. 8 | X | X | X | X | X | | | | | |
| B9 | *Barnesiella intestinihominis* | SEQ ID No. 9 | X | X | X | X | X | X | X | | | |
| B10 | *Alistipes timonensis* | SEQ ID No. 10 | X | | | | | | | | | X |
| B11 | *Blautia sp.* | SEQ ID No. 11 | X | | X | X | | | | | | X |
| B12 | *Lachnospira sp.* | SEQ ID No. 12 | X | | X | | | | | | | |

TABLE 3-continued

|    |                          | 16S rDNA sequence | Consortium |   |   |   |   |   |   |   |   |    |
|----|--------------------------|-------------------|------------|---|---|---|---|---|---|---|---|----|
| No | Taxonomy                 | identifier        | 1 | 2 | 3 | 4 | 5 | 6 | 7 | 8 | 9 | 10 |
| B13 | *Ruminococcus callidus* | SEQ ID No. 13    | X |   | X |   | X | X |   |   |   | X  |
| B14 | *Roseburia faecis*      | SEQ ID No. 14    | X |   | X | X |   |   |   |   |   | X  |
| B15 | *Faecalibacterium prausnitzii* | SEQ ID No. 15 | X |   | X |   |   |   |   |   |   |    |
| B4 | *Alistipes obesi*        | SEQ ID No. 16    |   |   |   |   | X | X |   |   |   |    |
| B2 | *Butyricicoccus sp.*     | SEQ ID No. 17    |   |   |   |   | X |   |   |   |   |    |
| B6 | *Gordonibacter urolithinfaciens* | SEQ ID No. 18 |   |   |   |   | X | X | X |   |   |    |
| B11 | *Blautia sp.*           | SEQ ID No. 19    |   |   |   |   |   | X | X |   |   |    |
| B12 | *Lachnospira sp.*       | SEQ ID No. 20    |   |   |   |   | X | X |   |   |   |    |
|    | Number of bacteria       |                   | 15 | 9 | 12 | 9 | 9 | 9 | 6 | 3 | 2 | 9 |

The invention claimed is:

1. A method for identifying and treating a subject that will respond to therapy with an immune checkpoint inhibitor comprising determining the abundance of bacteria from at least 9 different species in a biological sample from said subject that comprises gut flora wherein said bacteria comprise a 16S rDNA sequence selected from SEQ ID NOs: 1 to 15 or a sequence having at least 98.7% sequence identity with a nucleic acid sequence selected from SEQ ID NOs: 1 to 15 wherein said abundance is indicative of a response of a subject to therapy with an anti-PD-1 antibody or an anti-PD-L1 antibody; and administering to the subject an immune checkpoint inhibitor therapy if the subject is identified as a subject that will respond to therapy with an anti-PD-1 antibody or an anti-PD-L1 antibody, thereby treating the subject;

wherein the subject is a cancer patient and the cancer is selected from melanoma, urothelial cancer, breast cancer, non-small cell lung cancer, lymphoma, renal cancer, colorectal cancer, cancer of the esophagus, cancer of the head and neck or gastric cancer.

2. The method for identifying a subject that will respond to therapy with an immune checkpoint inhibitor according to claim 1, the method comprising:
   a) determining the abundance of the bacteria in a biological sample obtained from the subject and
   b) comparing the abundance to a reference level from cancer patients that do not respond to therapy with an immune checkpoint inhibitor or cancer patients that respond to therapy with an immune checkpoint inhibitor;
   wherein if the reference level is from cancer patients that do not respond to therapy with an immune checkpoint inhibitor, then an increase in the abundance of each of the bacteria compared to the reference level, is indicative that the subject will respond to therapy with an immune checkpoint inhibitor or
   wherein if the reference level is from cancer patients that do respond to therapy with an immune checkpoint inhibitor, then the same or substantially the same or an increase in abundance of each of the bacteria, is indicative that the subject will respond to therapy with an immune checkpoint inhibitor.

3. The method for identifying a subject that will respond to therapy with an immune checkpoint inhibitor according to claim 1, the method comprising:
   a) determining the abundance of the bacteria in a biological sample obtained from the subject;
   b) comparing the abundance to a reference level from cancer patients and
   c) applying random forest analysis.

4. The method according to claim 1 wherein the bacterial species comprise a 16S rDNA sequence selected from SEQ ID NO: 1 or 2 or a 16S rDNA sequence having at least 98.7% sequence identity thereto.

5. The method according to claim 1, wherein the method comprises determining the abundance of bacteria from 10, 11, 12, 13, 14 or 15 species wherein said bacteria comprise a 16S rDNA sequence selected from SEQ ID NOs: 1 to 15 or a sequence having at least 98.7% sequence identity with a nucleic acid sequence selected from SEQ ID NOs: 1 to 15.

6. The method according to claim 1, wherein the antibody inhibits PD-1 or PD-L1 activity.

7. The method according to claim 1, wherein the anti PD-1 or PD-L1 antibody is selected from nivolumab, pembrolizumab, cemiplimab, avelumab, durvalumab, atezolizumab, spartalizumab, camrelizumab, cintilimab, tislelizumab, pidilizumab, or toripalimab.

8. The method according to claim 1, wherein the abundance determined is the abundance of the bacterium in the sample as a proportion of the total microbiota in the sample.

9. The method according to a claim 1, further comprising the step of obtaining the biological sample that comprises gut flora from said subject.

10. The method according to claim 1, wherein the sample is a faecal sample.

11. The method according to claim 1, further comprising the step of identifying the subject as a subject in need of treatment with the immune checkpoint inhibitor.

12. The method according to claim 1, wherein said subject has not received previous treatment with an anti-PD-1 antibody or an anti-PD-L1 antibody.

13. The method according to claim 1, wherein the melanoma is Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma, subungual melanoma, cutaneous melanoma, uveal/intraocular melanoma, superficial spreading melanoma, or cutaneous or intraocular malignant melanoma.

14. The method according to claim 1, wherein the lymphoma is Hodgkin's disease or Hodgkin's disease.

15. The method according to claim 1, wherein the anti-PD-1 antibody or anti-PD-L1 antibody is administered in combination with another anti-cancer antibody therapy that targets an immune checkpoint inhibitor, wherein said antibody therapy is selected from an anti-CTLA-4 antibody, an anti-TIM-3 antibody or an anti-LAG-3 antibody.

16. The method according to claim 15, wherein the anti-CTLA-4 antibody is selected from ipilimumab or tremelimumab.

* * * * *

UNITED STATES PATENT AND TRADEMARK OFFICE
CERTIFICATE OF CORRECTION

PATENT NO. : 11,376,285 B2
APPLICATION NO. : 17/324899
DATED : July 5, 2022
INVENTOR(S) : Robinson et al.

It is certified that error appears in the above-identified patent and that said Letters Patent is hereby corrected as shown below:

On the Title Page

Item (30) Foreign Application Priority Data: Please correct "2007452" to read --2007452.2--

In the Specification

Column 2, Line 56: Please correct "Invention Is" to read --invention is--

Column 4, Line 34: Please correct "98% 98.7%" to read --98%, 98.7%--

Column 4, Line 38: Please correct "98% 98.7%" to read --98%, 98.7%--

Column 4, Line 45: Please correct "98% 98.7%" to read --98%, 98.7%--

Column 10, Line 4: Please correct "(0.215 mg/m)" to read --(0.215 mg/ml)--

Column 18, Line 49: Please correct "Identity" to read --identity--

Column 18, Line 61: Please correct "Identity" to read --identity--

Column 18, Line 64: Please correct "Identity" to read --identity--

Column 20, Line 43: Please correct "Identity" to read --identity--

Column 20, Line 52: Please correct "Identity" to read --identity--

Column 20, Line 67: Please correct "Identity" to read --identity--

Column 21, Line 61: Please correct "Identity" to read --identity--

Signed and Sealed this
Twenty-fourth Day of January, 2023

Katherine Kelly Vidal
*Director of the United States Patent and Trademark Office*

CERTIFICATE OF CORRECTION (continued)
U.S. Pat. No. 11,376,285 B2

Column 22, Line 3: Please correct "Identity" to read --identity--

Column 22, Line 8: Please correct "Identity" to read --identity--

Column 22, Line 11: Please correct "Identity" to read --identity--

Column 22, Line 14: Please correct "Identity" to read --identity--

Column 22, Line 36: Please correct "Identity" to read --identity--

Column 22, Line 39: Please correct "Identity" to read --identity--

Column 22, Line 48: Please correct "Identity" to read --identity--

Column 22, Line 50: Please correct "Identity" to read --identity--

Column 22, Line 53: Please correct "Identity" to read --identity--

Column 22, Line 56: Please correct "Identity" to read --identity--

Column 28, Line 24: Please correct "Tremellmumab" to read --Tremelimumab--

Column 32, Line 61: Please correct "injection/Infusion" to read --injection/infusion--

Column 32, Line 62: Please correct "Intramuscular" to read --intramuscular--

Column 32, Line 64: Please correct "Inhibitors" to read --inhibitors--

Column 36, Line 59: Please correct "anti-viralS" to read --anti-virals--

Column 38, Lines 40-41: Please remove the paragraph break between "inhibitor." and "As used"

Column 39, Lines 41-42: Please remove the paragraph break between "or" and "wherein"

Column 45, Line 48: Please correct "=In" to read --In--

Column 51, Line 45: Please correct "melanoma. S91" to read --melanoma, S91--

In the Claims

Column 132, Line 41, Claim 14: Please correct "Hodgkin's disease or Hodgkin's disease." to read --Hodgkin's disease or non-Hodgkin's disease.--